US012358992B2

(12) United States Patent
Schurpf et al.

(10) Patent No.: US 12,358,992 B2
(45) Date of Patent: Jul. 15, 2025

(54) LTBP COMPLEX-SPECIFIC INHIBITORS OF TGF-BETA 1 AND USES THEREOF

(71) Applicant: Scholar Rock, Inc., Cambridge, MA (US)

(72) Inventors: Thomas Schurpf, Cambridge, MA (US); Christopher Littlefield, Marblehead, MA (US); Gregory J. Carven, Maynard, MA (US); Abhishek Datta, Boston, MA (US)

(73) Assignee: Scholar Rock, Inc., Cambridge, MA (US)

( * ) Notice: Subject to any disclaimer, the term of this patent is extended or adjusted under 35 U.S.C. 154(b) by 0 days.

(21) Appl. No.: 16/634,336

(22) PCT Filed: Jul. 27, 2018

(86) PCT No.: PCT/US2018/044216
§ 371 (c)(1),
(2) Date: Jan. 27, 2020

(87) PCT Pub. No.: WO2019/023661
PCT Pub. Date: Jan. 31, 2019

(65) Prior Publication Data
US 2020/0231682 A1    Jul. 23, 2020

Related U.S. Application Data

(60) Provisional application No. 62/585,148, filed on Nov. 13, 2017, provisional application No. 62/538,476, filed on Jul. 28, 2017.

(51) Int. Cl.
| C07K 16/28 | (2006.01) |
| A61K 39/00 | (2006.01) |
| C07K 16/22 | (2006.01) |
| G01N 33/531 | (2006.01) |
| G01N 33/537 | (2006.01) |

(52) U.S. Cl.
CPC .......... *C07K 16/2863* (2013.01); *C07K 16/22* (2013.01); *G01N 33/531* (2013.01); *G01N 33/537* (2013.01); *A61K 2039/545* (2013.01); *C07K 2317/10* (2013.01); *C07K 2317/21* (2013.01); *C07K 2317/24* (2013.01); *C07K 2317/31* (2013.01); *C07K 2317/33* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 2015/0361421 A1* | 12/2015 | Schurpf | A61P 3/10 |
| | | | 530/387.3 |
| 2018/0207267 A1* | 7/2018 | Schurpf | A61P 35/04 |
| 2019/0071493 A1* | 3/2019 | Schurpf | A61P 21/00 |

FOREIGN PATENT DOCUMENTS

| CA | 3128042 A1 | 8/2020 |
| WO | 2014/182676 A2 | 11/2014 |
| WO | 2015/171691 A2 | 11/2015 |
| WO | 2017/156500 A1 | 9/2017 |
| WO | 2018/129329 A1 | 7/2018 |

OTHER PUBLICATIONS

Abe et al., Anal Biochem, 216(2):276-84, 1994.*
Meng et al., TGF-beta: the master regulator of fibrosis. Nat Rev Nephrol. 2016;12(6):325-338.
Robertson et al., Latent TGF-beta-binding proteins. Matrix Biol. 2015;47:44-53.
Tsumura et al., Generation of recombinant human large latent transforming growth factor-beta 1 and monoclonal antibodies to it. Biosci Biotechnol Biochem. 2000;64(1):17-23.
Wakefield et al., Latent transforming growth factor-beta from human platelets. A high molecular weight complex containing precursor sequences. J Biol Chem. 1988;263(16):7646-7654.
Yu et al., TGF-beta isoforms in renal fibrogenesis. Kidney Int. 2003;64(3):844-856.
International Search Report and Written Opinion for Application No. PCT/US2018/044216, dated Oct. 10, 2018, 13 pages.

* cited by examiner

*Primary Examiner* — Marianne P Allen
(74) *Attorney, Agent, or Firm* — McCarter & English, LLP; Marcie B. Clarke, Esq.

(57) ABSTRACT

Disclosed herein are inhibitors, such as antibodies, and antigen binding portions thereof, that selectively bind complexes of LTBP1-TGFβ1 and/or LTBP3-TGFβ1. The application also provides methods of use of these inhibitors for, for example, inhibiting TGFβ1 activation, and treating subjects suffering from TGFβ1-related disorders, such as fibrotic conditions. Methods of selecting a context-dependent or context-independent isoform-specific TGFβ1 inhibitor for a subject in need thereof are also provided.

4 Claims, 14 Drawing Sheets
Specification includes a Sequence Listing.

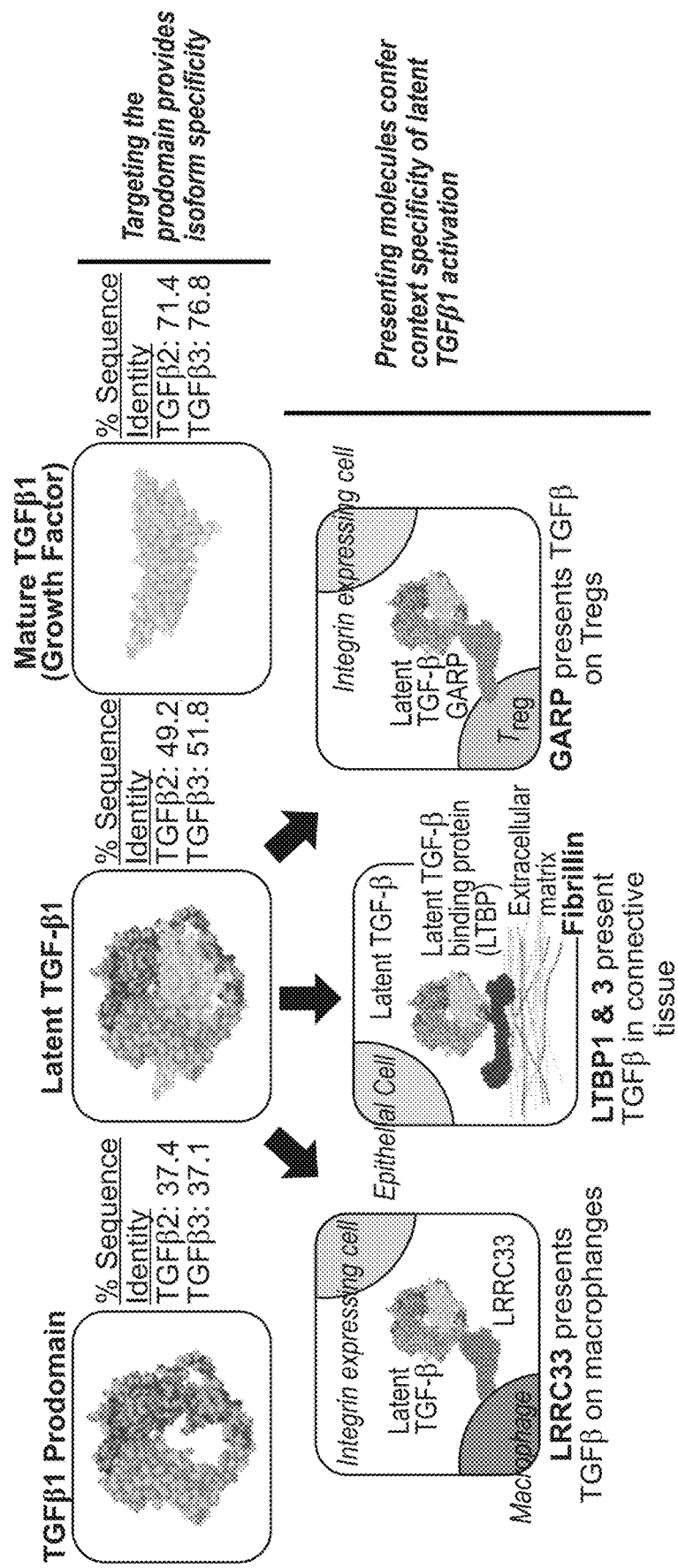
FIG. 1: Targeting the latent form of TGFβ1 provides isoform and context specificity

FIG. 2A: Identification of isoform-specific and LTBP-specific binders of latent TGFβ1 – SR-AB1 Binds latent TGFβ1 independent of presenting molecule

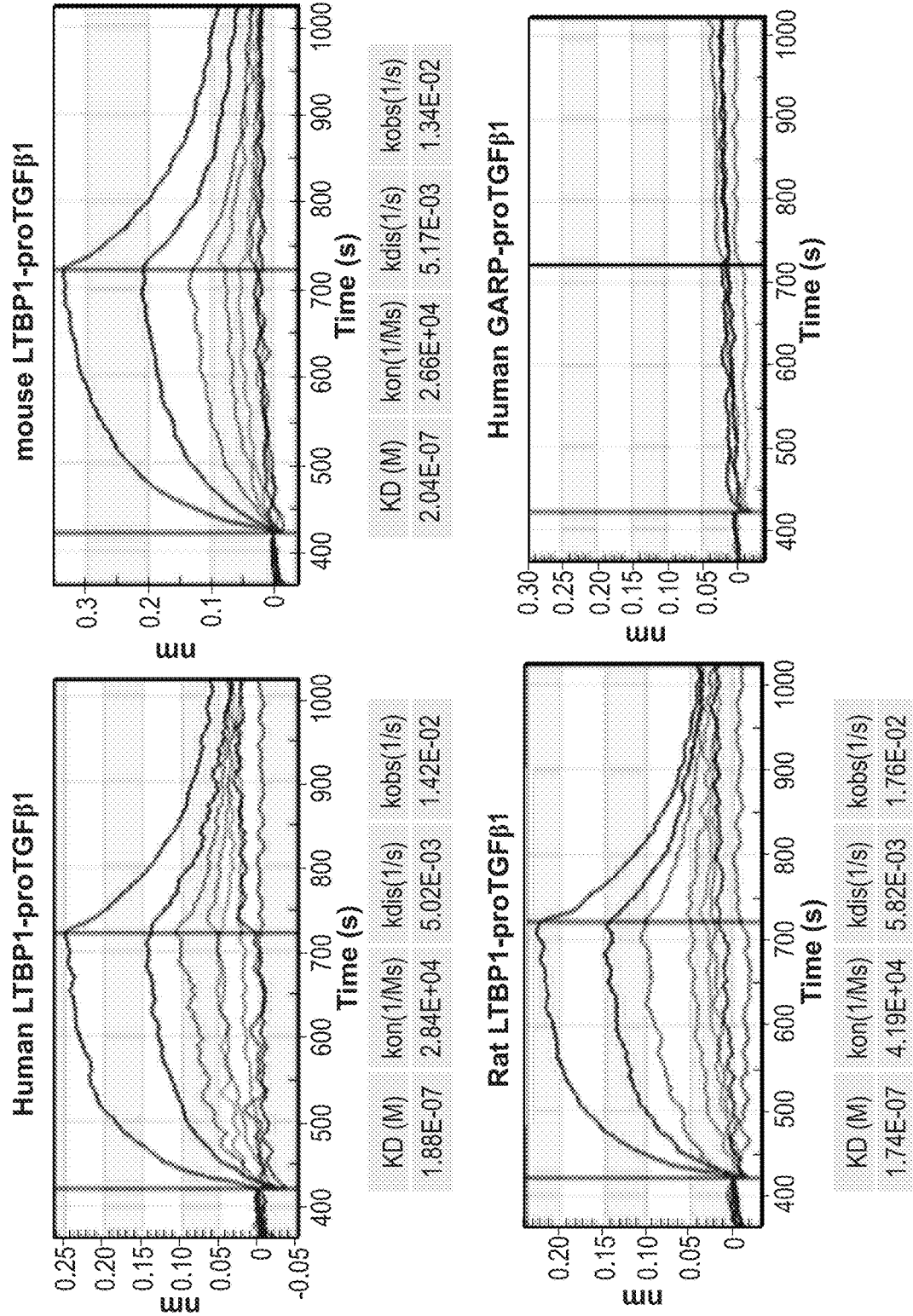

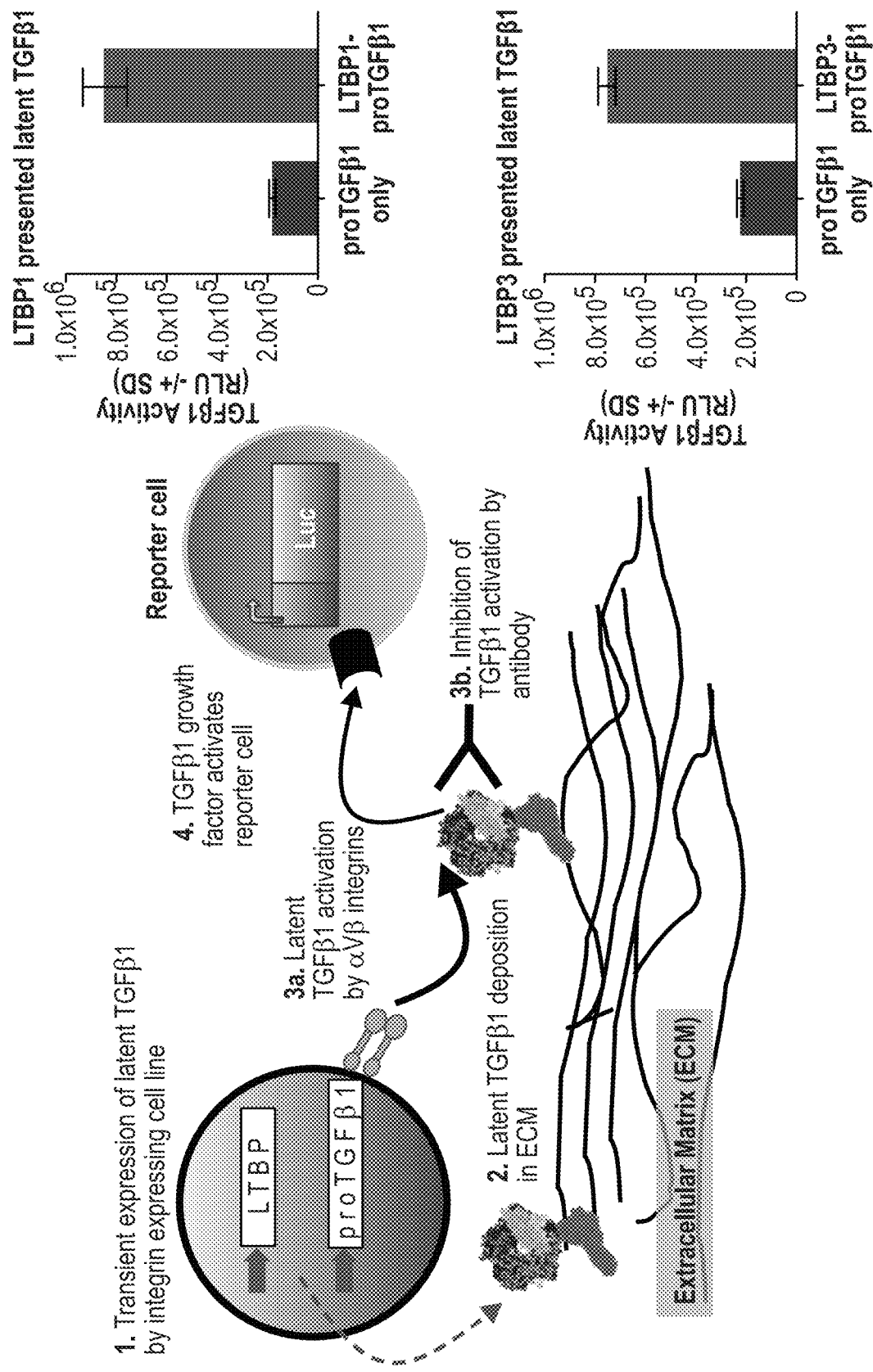
FIG. 3A: Functional Assay to detect the inhibition of activated recombinant latent TGFβ1 - Activation of latent TGFβ1 deposited in ECM

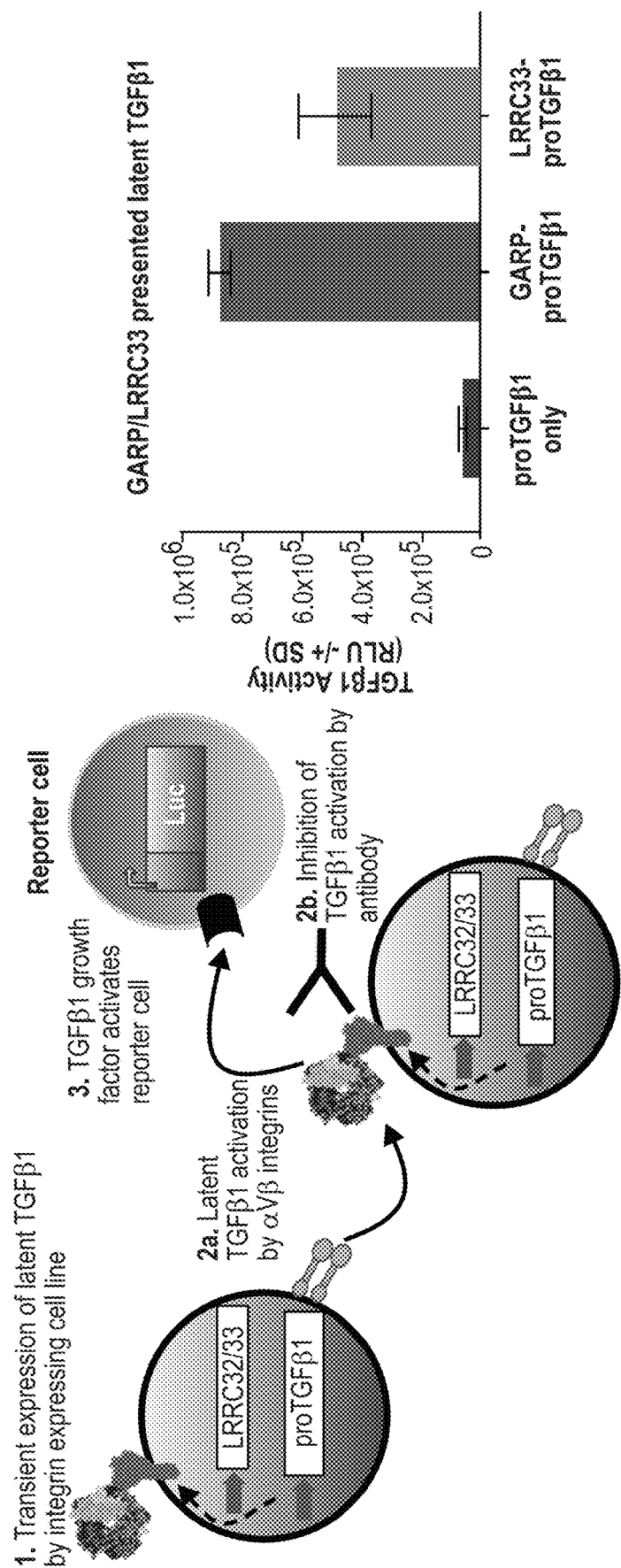
FIG. 3B: Functional Assay to detect the inhibition of activated recombinant latent TGFβ1 – Activation of latent TGFβ1 presented on cell surface FIG. 4: Optimization of recombinant functional assay

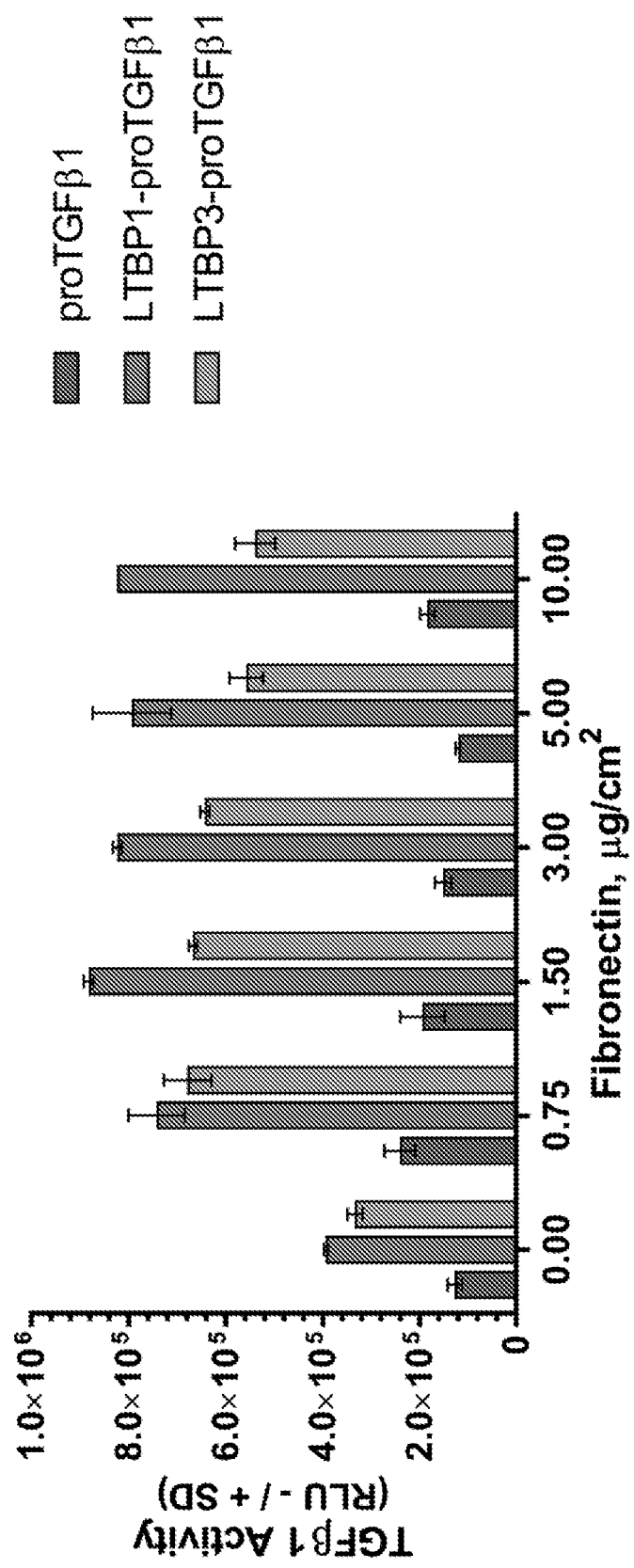
FIG. 5: Fibronectin promotes integrin activation of LTBP-presented latent TGFβ1

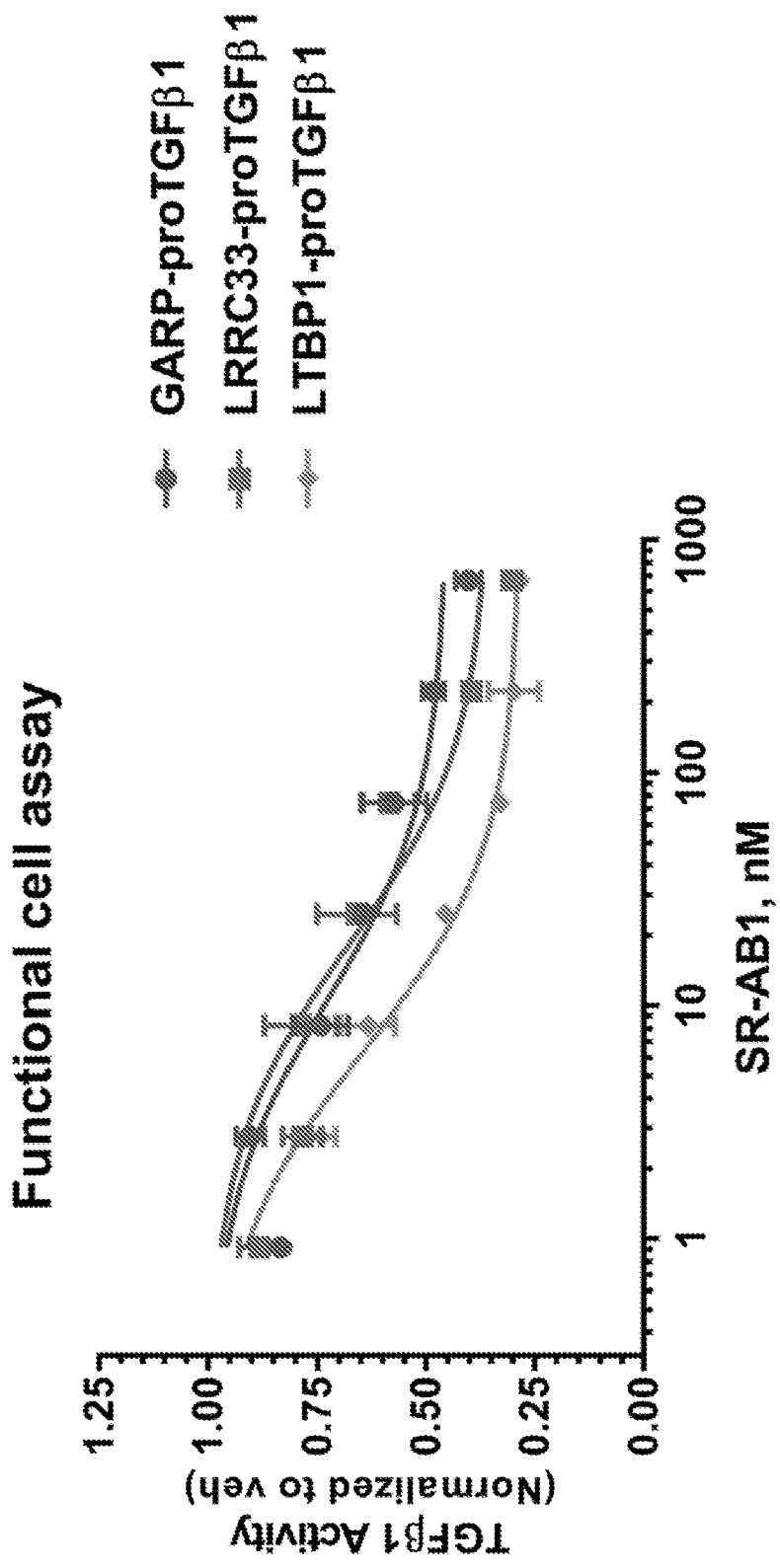
FIG. 6: SR-AB1 is a context-independent inhibitor TGFβ1 LLC activation by integrin

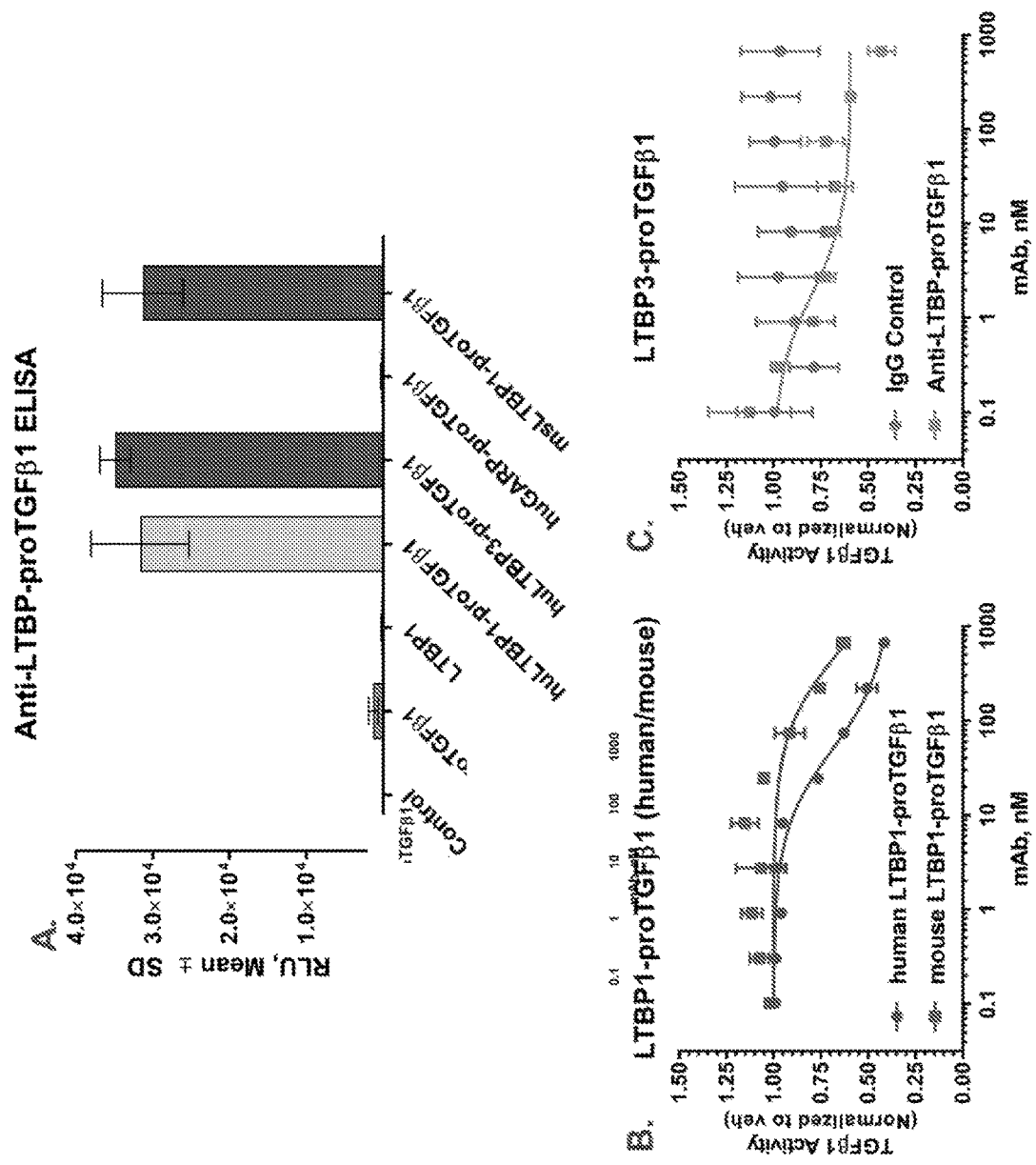
FIG. 7: Validation of a LTBP-specific inhibitor of TGFβ1 LLC activation by integrin

FIG. 8: SR-AB2 Variable Region Sequence

VH:

QVQLVQSGAEVKKPGASVKVSCKASG<u>YTFTSYGIS</u>WVRQAPGQGLEWMGWISAY<u>NGNTNYAQKLQ</u>GRVTMTDTSTSTAYMELRSLRSDDTAVYYCARAP<u>LGNFDSW</u>GQGTMVTVSS (CDRH1: YTFTSYGIS, CDRH2: NGNTNYAQKLQ, CDRH3: LGNFDSW)

VLambda:

NFMLTQPHSVSESPGKTVTISCTRSSGSI<u>ASNYVQ</u>WYQQRPGSSPTTVIYED<u>NQRPSG</u>VPDRFSGSIDSSSNSASLTISGLKTEDEADYYCQ<u>SYDSSNHPVV</u>FGGGTKLTVL (CDRL1: ASNYVQ, CDRL2: NQRPSG, CDRL3: SYDSSNHPVV)

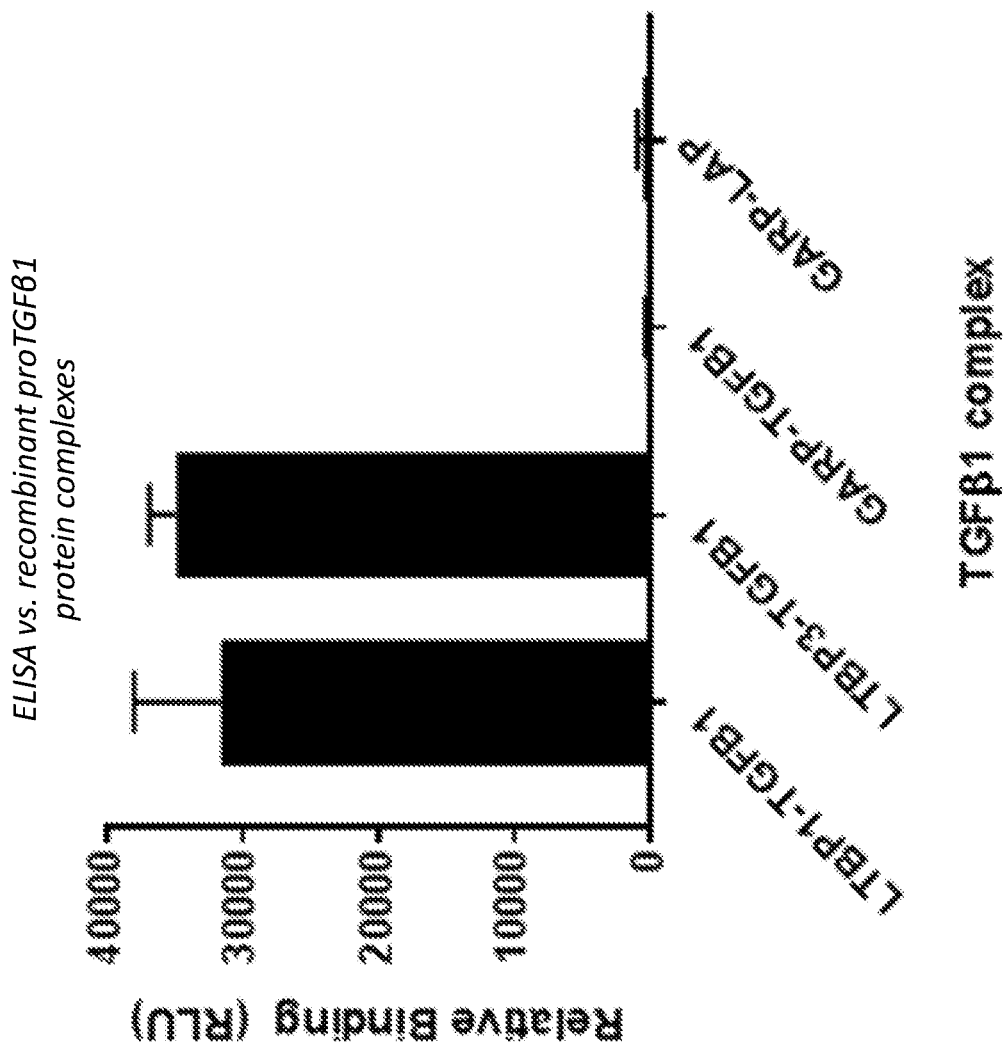
FIG. 9: SR-AB2 Specifically Binds to proTGFβ1:LTBP1 & 3 Complexes

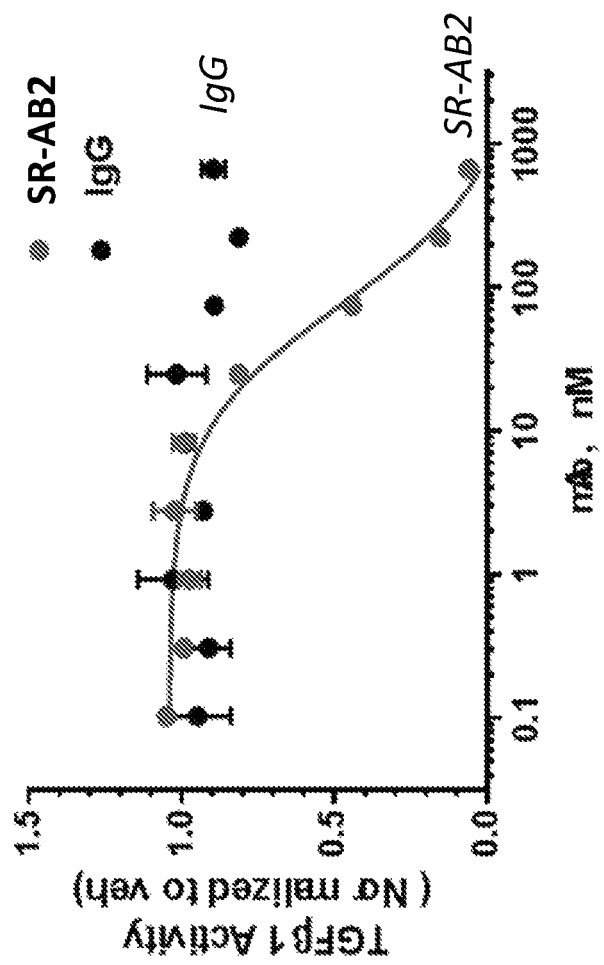
FIG. 10A: SR-AB2 Inhibits LTBP-proTGFβ1 Signaling, But Does Not Affect GARP-proTGFβ1

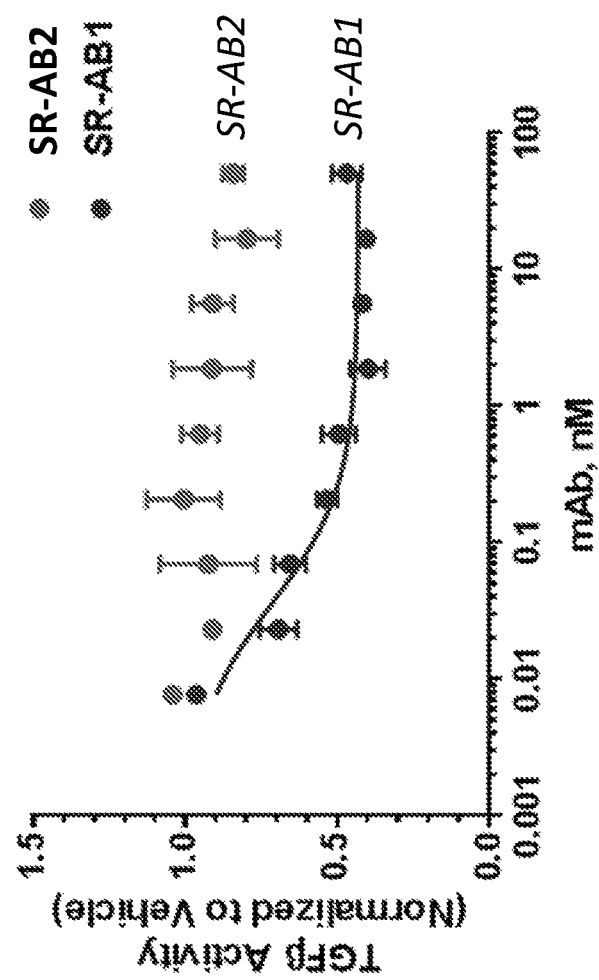
FIG. 10B: SR-AB2 Inhibits LTBP-proTGFβ1 Signaling, But Does Not Affect GARP-proTGFβ1

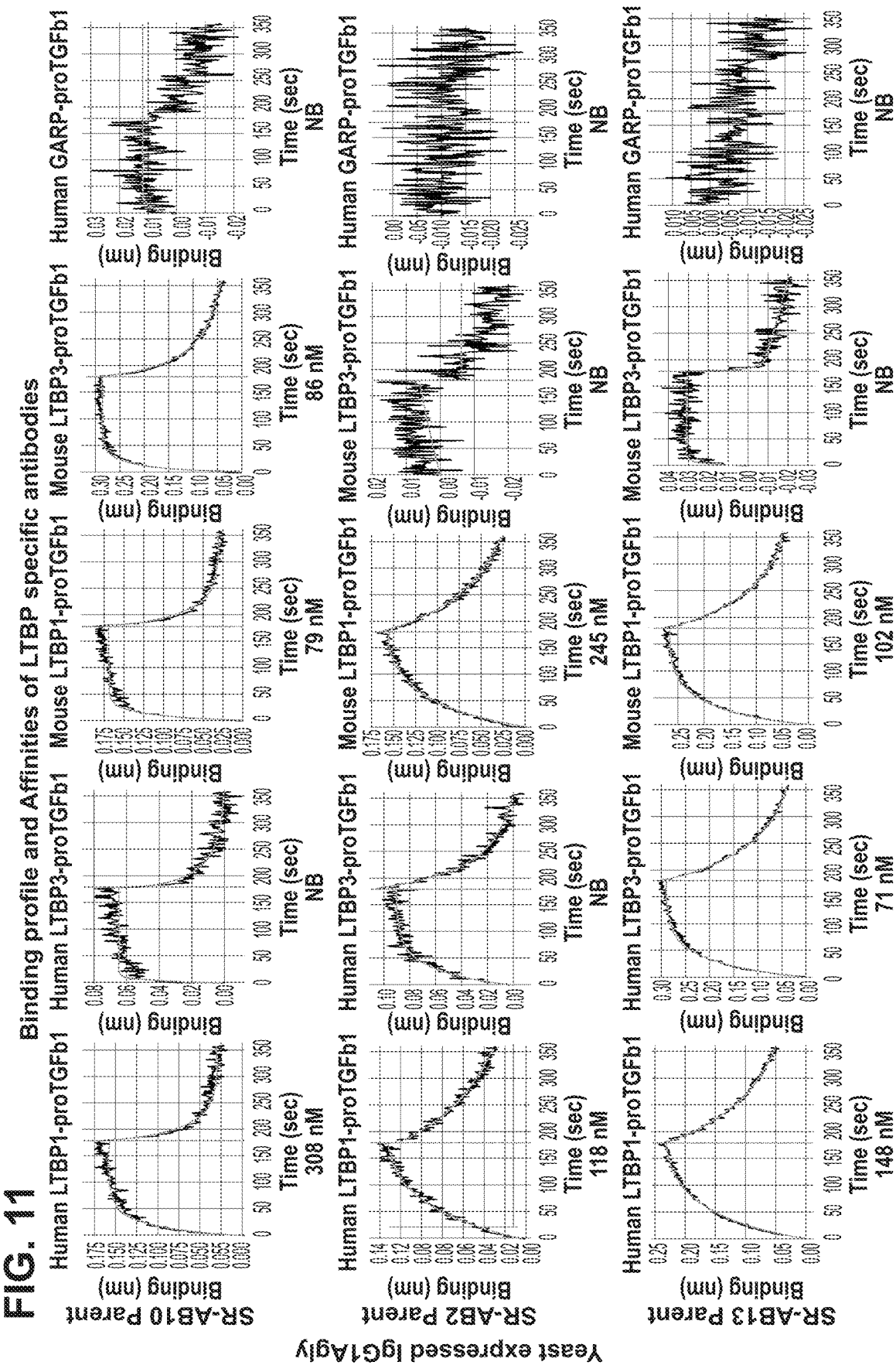
FIG. 11 Binding profile and Affinities of LTBP specific antibodies

LTBP COMPLEX-SPECIFIC INHIBITORS OF TGF-BETA 1 AND USES THEREOF

CROSS REFERENCE TO RELATED APPLICATIONS

This International Application claims priority and benefit under 35 U.S.C. § 119(e) of U.S. Provisional Application No. 62/538,476 filed on Jul. 28, 2017 and U.S. Provisional Application No. 62/585,148 filed on Nov. 13, 2017, the contents of each of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Jul. 26, 2018, is named 127036-02120_SL.txt and is 218,803 bytes in size.

BACKGROUND

Transforming growth factor beta (TGFβ) superfamily of growth factors are involved in a number of signaling cascades that regulate diverse biological processes including, but not limited to: inhibition of cell growth, tissue homeostasis, extracellular matrix (ECM) remodeling, endothelial to mesenchymal transition, cell migration and invasion, and immune modulation/suppression, as well as mesenchymal to epithelial transition. In relation to ECM remodeling, TGFβ signaling may increase fibroblast populations and ECM deposition (e.g., collagen). In the immune system, TGFβ ligand modulates T regulatory cell function and maintenance of immune precursor cell growth and homeostasis. In normal epithelial cells, TGFβ is a potent growth inhibitor and promoter of cellular differentiation. However, as tumors develop and progress, they frequently lose their negative growth response to TGFβ. In this setting, TGFβ may become a promoter of tumor development due to its ability to stimulate angiogenesis, alter the stromal environment, and induce local and systemic immunosuppression. For these and other reasons, TGFβ has been a therapeutic target for a number of clinical indications. Despite much effort made to date by a number of groups, clinical development of a TGFβ therapeutic has been challenging.

Observations from preclinical studies, including in rats and dogs, have revealed certain toxicities associated with inhibition of TGFβ in vivo. Moreover, although several TGFβ inhibitors have been developed to date, most clinical programs targeting TGFβ have been discontinued due to side effects or risk of toxicity.

For example, Anderton et al. (Toxicology Pathology, 39: 916-24, 2011) reported that small molecule inhibitors of TGFβ type I (ALK5) receptor induced heart valve lesions characterized by hemorrhage, inflammation, degeneration and proliferation of valvular interstitial cells in a preclinical animal model. The toxicity was observed in all heart valves at all doses tested. Frazier et al. (Toxicology Pathology, 35: 284-295, 2007) reported that administration of the small molecule inhibitor of TGFβ type I (ALK5) receptor GW788388 induced physeal dysplasia in rats.

Stauber et al. (J. Clin. Practice 4:3, 2014) reported that a chronic (≥3 months) administration of the inhibitor of TGFβ receptor I kinase, LY2157299, which is being investigated for certain cancer treatments, caused multiple organ toxicities involving the cardiovascular, gastrointestinal, immune, bone/cartilage, reproductive, and renal systems, in rats and dogs.

Fresolimumab (GC1008), a "pan" TGFβ antibody capable of neutralizing all human isoforms of TGFβ, has been reported to induce an epithelial hyperplasia of the gingiva, bladder, and of the nasal turbinate epithelium after multiple administrations in studies with cynomolgus macaques (Lonning et al., Current Pharmaceutical Biotechnology 12: 2176-89, 2011). Similarly, a variety of skin rashes/lesions, gingival bleeding and fatigue have been reported in clinical trials after administration of multiple doses of the drug. The most notable adverse reaction to fresolimumab includes the induction of cutaneous keratoacanthomas and/or squamous cell carcinomas in human cancer patients (see, for example: Lacouture et al., 2015, Cancer Immunol Immunother, 64: 437-46; Stevenson et al., 2013, OncoImmunology, 2:8, e26218; and Lonning et al., 2011). Additional evidence from a clinical trial suggests that in some cases this antibody may accelerate tumor progression (Stevenson et al., 2013, OncoImmunology, 2:8, e26218).

Thus, new methods and compositions for modulating TGFβ signaling are necessary that can be used to effectively and safely treat diseases and disorders involving TGFβ, including, for example, cancer, fibrosis and inflammation.

More recently, Applicant described isoform-selective TGFβ1 inhibitors which were demonstrated to be both safe and efficacious in animal models (see, for example: WO 2017/156500 and WO 2018/129329, incorporated by reference), supporting the notion that selectively targeting the TGFβ1 isoform, as opposed to broadly antagonizing all TGFβ isoforms, may provide an advantageous approach to achieving efficacy with acceptable toxicity.

Whilst the observed safety profile achieved by selective inhibition of TGFβ1 at doses that were shown efficacious in vivo is a promising step towards developing a TGFβ1 inhibitor for clinical applications, identification of TGFβ1 inhibitors that are capable of selectively affecting a defined subset of TGFβ1 effects has been elusive.

SUMMARY OF THE INVENTION

The present disclosure relates to selective inhibition of a subset of biological effects mediated by TGFβ1. Thus, the invention relates to agents that are capable of selectively inhibiting TGFβ1 signaling only in certain biological contexts. In particular, given that TGFβ1 is implicated in both extracellular matrix-associated effects and immune response, it is desirable to develop an isoform-selective antibody that is capable of inhibiting only one of these processes. Antibodies that are aimed to selectively affect TGFβ1 signaling that is associated with a particular biological context are referred to as "context-dependent" or "context-specific" TGFβ1 antibodies.

Both the TGFβ ligand and its receptors are widely expressed in a number of cell types and tissues throughout the body during development and in adults. This means that traditional antagonists that directly target the ligand itself (mature growth factor) or its receptors will systemically inhibit TGFβ activities without discriminating the various biological contexts of TGFβ1 function. On the other hand, the latent (inactive) TGFβ1 complex (proTGFβ1), which is the precursor (pro-protein) of the growth factor, is anchored to its respective biological niche via so-called "presenting molecules." Because these presenting molecules are expressed in a tissue- or cell-type-specific manner, by specifically targeting this latent pro-form in association with particular presenting molecules, it is possible to achieve context-selective inhibition of TGFβ1 signaling.

With this premise, the inventors of the instant application sought to develop monoclonal antibodies that can selectively inhibit matrix-associated TGFβ1 signaling, without materially affecting immune cell-associated TGFβ1 signaling.

Within the TGFβ1 isoform axis, there are several "contexts" by which TGFβ1 exerts differential biological effects. It is contemplated that such regulation is at least in part achieved by associations with different "presenting molecules" that are differentially expressed in various biological niches, cell types, activation or disease status or contexts, thereby conferring signaling selectivity. Briefly, transforming growth factor beta 1 (TGFβ1) is expressed as a pro-protein, which forms a latent (inactive) homodimer referred to as a proTGFβ complex. During the activation process, this latent complex is proteolytically cleaved into a C-terminal growth factor portion and an N-terminal prodomain portion. After cleavage, the prodomain remains noncovalently associated with the growth factor, preventing receptor binding. This latent TGFβ1 forms a larger complex through disulfide bonds that link the prodomain to presenting molecules in the extracellular matrix (ECM) or on the cell surface. These presenting molecules provide an anchor for αV integrins to exert traction force on latent TGFβ1, thus releasing the growth factor from the complex to allow signaling.

Four TGFβ1 presenting proteins have been identified: Latent TGFβ Binding Protein-1 (LTBP1) and Latent TGFβ Binding Protein-3 (LTBP3) are deposited in the extracellular matrix (i.e., components of the ECM), while Glycoprotein-A Repetitions Predominant (GARP; also known as Leucine-Rich Repeat-Containing Protein 32 or /LRRC32) and Leucine-Rich Repeat-Containing Protein 33 (LRRC33) present latent TGFβ1 on the surface of certain cells, such as immune cells. Biochemical evidence suggests that at least some, if not all, of these presenting molecules are capable of "presenting" all three TGFβ isoforms. Thus, targeting a specific presenting molecule per se is unlikely to be sufficient to produce isoform-selectivity. The TGFβ1 isoform alone has been implicated in a number of biological processes in both normal and disease situations. These include, but are not limited to, maintenance of tissue homeostasis, inflammation response, ECM reorganization such as wound healing, and regulation of immune responses, as well as organ fibrosis, cancer, and autoimmunity.

Conventional inhibitors of TGFβ are neither isoform-specific, nor context-specific. Applicant of the present disclosure previously characterized TGFβ1 isoform-specific inhibitors, which demonstrated improved safety profiles in vivo, as compared to conventional pan-TGF inhibitors that did not discriminate among the three isoforms (see WO 2017/156500, contents of which are incorporated herein by reference). The work described herein further builds upon the improved selectivity achieved by targeting inactive, latent pro-TGFβ1 complex, in lieu of mature growth factors, and provides inhibitors of TGFβ1, which preferentially or selectively target matrix (e.g., ECM)-associated TGFβ1 signaling, while maintaining isoform-selectivity. These inhibitors bind and inhibit LTBP1- and/or LTBP3-presented proTGFβ1 but do not bind and inhibit GARP- and/or LRRC33-presented proTGFβ1. Thus, these inhibitors can selectively inhibit activation of TGFβ1 in an isoform-specific, and context-dependent manner, such that they selectively bind, thereby inhibiting a subset, but not all, of the TGFβ1 signaling axis. In particular, the present disclosure includes selective inhibitors of matrix-associated (e.g., LTBP1 and/or LTBP3-associated) TGFβ1 activation. In some embodiments, such inhibitors do not inhibit activation of TGFβ1 associated with immune cell function, mediated by GARP and/or LRRC33. Rationale for the therapeutic use of a TGFβ1 inhibitor that does not target the GARP-proTGFβ1 complex on regulatory T cells is at least three-fold:

First, regulatory T cells play a crucial role in maintaining immune tolerance to self-antigens and in preventing autoimmune disease. Since Tregs generally suppress, dampen or downregulate induction and proliferation of effector T cells, systemic inhibition of this function may lead to overactive or exaggerated immune responses in the host by disabling the "break" that is normally provided by Treg cells. Thus, the approach taken here (e.g., TGFβ1 inhibition without disabling Treg function) is aimed to avoid the risk of eliciting autoimmunity. Furthermore, patients who already have a propensity for developing over-sensitive immune responses or autoimmunity may be particularly at risk of triggering or exacerbating such conditions, without the availability of normal Treg function; and therefore, the inhibitors that selectively target the matrix TGFβ1 may advantageously minimize such risk.

Second, evidence suggests that an alteration in the Th17/Treg ratio leads to an imbalance in pro-fibrotic Th17 cytokines, which correlate with severity of fibrosis, such as liver fibrosis (see, for example, Shoukry et al. (2017) J Immunol 198 (1 Supplement): 197.12). The present inventors reasoned that perturbation of the GARP arm of TGFβ1 function may directly or indirectly exacerbate fibrotic conditions.

Third, regulatory T cells are indispensable for immune homeostasis and the prevention of autoimmunity. It was reasoned that, particularly for a TGFβ1 inhibition therapy intended for a long-term or chronic administration, it would be desirable to avoid potential side effects stemming from perturbation of normal Treg function in maintaining innune homeostasis (reviewed in, for example, Richert-Spuhler and Lund (2015) Prog Mol Biol Transl Sci. 136: 217-243). This strategy is at least in part aimed to preserve normal immune function, which is required, inter alia, for combatting infections.

To this end, the inventors of the present disclosure set out to generate isoform-specific, context-selective inhibitors of TGFβ1 that selectively target matrix-associated TGFβ1 activation but not immune cell-associated TGFβ1 activation.

Technical challenges that exist to date include limited ability to discern and selectively modulate these subpools of TGFβ1 present in various contexts in vivo.

In an effort to address this challenge, the present inventors have identified isoform-specific monoclonal antibodies that bind the latent TGFβ1 prodomain, with no detectable binding to latent TGFβ2 or TGFβ3, and that inhibit integrin-mediated activation of latent TGFβ1 in vitro with the context-dependency as described herein. The discovery and characterization of such antibodies was made possible, at least in part, by the development of context-dependent cell-based assays of TGFβ1 activation. In the process of this novel assay development and validation, it was demonstrated that, like the αVβ6 integrin, αVβ8 can also activate LTBP1-proTGFβ1. It was further demonstrated that, similar to the LTBP1 complex, LTBP3-proTGFβ1 can be activated by αVβ6. Antibodies discovered by screening in these assays revealed a class of antibodies that binds and inhibits TGFβ1 only when presented by LTBP1 or LTBP3. Such LTBP-specific antibodies do not inhibit TGFβ1 in the context of the immune-associated TGFβ1 presenters GARP and LRRC33. Such antibodies are therapeutic candidates for the treatment of disorders including, e.g., fibrotic conditions, and could allow chronic dosing that would avoid TGFβ-related immune system activation. Methods of selecting a context-specific or context-independent TGFβ1 inhibitor for various fibrotic conditions are also provided herein.

Accordingly, in one aspect, the invention provides isoform-specific TGFβ1 antibodies, or antigen binding fragments thereof, characterized in that they bind selectively to an LTBP1-TGFβ1 complex and/or a LTBP3-TGFβ1 complex. In one embodiment, the invention provides an isolated antibody, or antigen-binding portion thereof, that selectively binds to a LTBP1-proTGFβ1 complex and a LTBP3-proTGFβ1 complex, wherein the antibody, or antigen-binding portion thereof, does not bind to one or more of the following targets: (a) LTBP1 alone; (b) proTGFβ1 alone; (c) a GARP-proTGFβ1 complex; and (d) a LRRC33-proTGFβ1 complex.

In one aspect, the invention provides inhibitors of extracellular matrix-associated TGFβ1 activation, which selectively bind a LTBP1/3-presented proTGFβ1 latent complex. In one embodiment, the inhibitor does not inhibit immune cell-associated TGFβ1 activation, for example, immune cell-associated TGFβ1 activation that results from activation of a GARP-presented proTGFβ1 latent complex. In exemplary embodiments, the inhibitor is an antibody, or antigen-binding portion thereof.

In other aspects, the invention provides isoform-specific TGFβ1 antibodies, or antigen binding fragments thereof, characterized in that they bind selectively to an LTBP1-TGFβ1 complex and/or a LTBP3-TGFβ1 complex.

In one aspect, the invention provides an isolated antibody, or antigen-binding portion thereof, that selectively binds an LTBP1-proTGFβ1 latent complex and/or an LTBP3-proTGFβ1 latent complex, thereby modulating release of mature TGFβ1 growth factor from the latent complex, wherein the antibody, or antigen-binding portion thereof, does not bind mature TGFβ1 alone or a GARP-proTGFβ1 latent complex. In one embodiment, the antibody, or antigen-binding portion thereof, does not bind an LRRC33-proTGFβ1 latent complex. Alternatively, in one embodiment, the antibody, or antigen-binding portion thereof, binds an LRRC33-proTGFβ1 latent complex.

In some embodiments, the antibody, or antigen-binding portion thereof, is specific to an LTBP1-proTGFβ1 latent complex. In other embodiments, the antibody, or antigen-binding portion thereof, is specific to an LTBP3-proTGFβ1 latent complex. In one embodiment, the antibody, or antigen-binding portion thereof, binds an LTBP1-proTGFβ1 complex and/or a LTBP3-proTGFβ1 complex with a dissociation constant ($K_D$) of at least about $10^{-6}$ M.

In one aspect, the invention provides an antibody, or antigen-binding fragment thereof, for use in a method for treating a fibrotic disorder in a subject, wherein the antibody, or antigen-binding fragment thereof, specifically binds a human LTBP1-proTGFβ1 complex and/or a human LTBP3-proTGFβ1 complex, and does not bind a human GARP-proTGFβ1 complex; wherein the antibody, or antigen-binding fragment thereof, is an isoform-specific TGFβ1 inhibitor; and, wherein: a) the fibrotic disorder comprises chronic inflammation; b) the subject benefits from immune suppression; c) the subject has or is at risk of developing an autoimmune disease; d) the subject is a candidate for or has received an allograft transplant; e) the subject has an elevated Th17/Treg ratio; and/or, f) the subject is in need of a long-term or chronic administration of the TGFβ1 inhibitor.

In another aspect, the invention provides a method for making a composition comprising an antibody, or antigen-binding fragment thereof, that specifically binds a human LTBP1-proTGFβ1 complex and/or a human LTBP3-proTGFβ1 complex, and does not bind a human GARP-proTGFβ1 complex; wherein the antibody, or antigen-binding fragment thereof, inhibits TGFβ1 but does not inhibit TGFβ2 or TGFβ3, the method comprising steps of i) providing at least one antigen comprising LTBP1-proTGFβ1 and/or LTBP3-proTGFβ1, ii) selecting a first pool of antibodies, or antigen-binding fragments thereof, that specifically bind the at least one antigen of step (i) so as to provide specific binders of LTBP1-proTGFβ1 and/or LTBP3-proTGFβ1; iii) selecting a second pool of antibodies, or antigen-binding fragments thereof, that inhibit activation of TGFβ1, so as to generate specific inhibitors of TGFβ1 activation; iv) formulating an antibody, or antigen-binding fragment thereof, that is present in the first pool of antibodies and the second pool of antibodies into a pharmaceutical composition, thereby making the composition comprising the antibody, or antigen-binding fragment thereof.

In one embodiment, the method further comprises a step of removing from the first pool of antibodies, or antigen-binding fragments thereof, any antibodies, or antigen-binding fragments thereof, that bind GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3, mature TGFβ3, or any combinations thereof. In one embodiment, the method further comprises a step of determining or confirming isoform-specificity of the antibodies, or antigen-binding fragments thereof, selected in steps (ii) and/or (iii). In one embodiment, the method further comprises a step of selecting for antibodies, or antigen-binding fragments thereof, that are cross-reactive to human and rodent antigens. In one embodiment, the method further comprises a step of generating a fully human or humanized antibody, or antigen-binding fragment thereof, of the antibody, or antigen-binding fragment thereof, that is present in the first pool of antibodies and the second pool of antibodies. In one embodiment, the method further comprises a step of subjecting the antibody, or antigen-binding fragment thereof, that is present in the first pool of antibodies and the second pool of antibodies to affinity maturation and/or optimization, so as to provide an affinity matured and/or optimized antibody or fragment thereof.

BRIEF DESCRIPTION OF THE FIGURES

FIG. 1 graphically depicts that targeting of the latent form of TGFβ1 provides isoform and context specificity.

FIGS. 2A-2B demonstrate the identification of isoform-specific and LTBP-specific binders of latent TGFβ1. FIG. 2A demonstrates that SR-AB1 binds latent TGFβ1, independent of the presenting molecule. SR-AB1 is a human monoclonal antibody that was discovered by yeast display, which selectively binds latent TGFβ1, without detectable binding to latent TGFβ2, TGFβ3, or mature TGFβ1. SR-AB1 cross-reacts with mouse, rat, and cynomolgus monkey proteins and binds to all four latent TGFβ1 complexes. FIG. 2B demonstrates that SR-AB2, an anti-LTBP1-proTGFβ1 antibody, does not bind GARP-proTGFβ1 or mature TGFβ1. SR-AB2 cross-reacts with rodent LTBP1-proTGFβ1.

FIGS. 3A-3B demonstrate functional assays (potency assays) to detect the inhibition of activated recombinant latent TGFβ1. FIG. 3A depicts the activation of latent TGFβ1 deposited in the extracellular matrix (ECM). In this assay, presenting molecules are co-transfected with proTGFβ1 in integrin-expressing cells. Transiently transfected cells are seeded in assay plates in the presence of inhibitors. Latent LTBP-proTGFβ1 complex is embedded in the ECM. TGFβ reporter cells are then added to the system; free growth factor (released by integrin) signals and is detected by luciferase assay. FIG. 3B depicts the activation of latent TGFβ1 presented on the cell surface. Presenting molecules are co-transfected with proTGFβ1 in integrin-expressing cells. Latent TGFβ1 is expressed on the cell surface by GARP or LRRC33. TGFβ reporter cells and inhibitors are then added to the system; free growth factor (released by integrin) signals and is detected by luciferase assay.

FIG. 4A depicts the relative contribution of presenting molecule and/or proTGFβ1 activation upon co-transfection of presenting molecule and proTGFβ1. FIG. 4B depicts the optimization of co-transfection: the ratio of plasmid DNAs for presenting molecule and proTGFβ1. Equivalent amounts of each plasmid were optimal for co-transfection.

FIG. 5 demonstrates that fibronectin promotes integrin activation of LTBP-presented latent TGFβ1. Assay plates were pre-coated with fibronectin purified from human plasma. Fibronectin increases integrin-mediated activation of latent TGFβ1 presented by LTBP1 and/or LTBP3.

FIG. 6 is a graph demonstrating that SR-AB1 is a context-independent inhibitor of TGFβ1 large latent complex (LLC) by integrin. SR-AB1 was shown to inhibit integrin activation of TGFβ1 independent of the presenting molecule.

FIGS. 7A-7C depict the validation of a LTBP-specific inhibitor of TGFβ1 large latent complex (LLC) by integrin. FIG. 7A demonstrates that SR-AB2 only binds LTBP-proTGFβ1 complex; it does not bind proTGFβ1 or LTBP1 alone. SR-AB2 also does not bind GARP-proTGFβ1. FIG. 7B depicts that SR-AB2 inhibits integrin activation of LTBP1-proTGFβ1 (human and mouse complexes). FIG. 7C depicts that R-AB2 inhibits integrin activation of LTBP3-proTGFβ1.

FIG. 8 presents the heavy chain and light chain variable region sequences of SR-AB2 (SEQ ID NOS 7-8, respectively, in order of appearance). Complementary determining regions (CDRs) are underlined.

FIG. 9 is a graph demonstrating that SR-AB2 specifically binds to proTGFβ1:LTBP1 & 3 complexes.

FIGS. 10A-10B are graphs that demonstrate SR-AB2 inhibits LTBP-proTGFβ1 signaling, but does not affect GARP-proTGFβ1. FIG. 10A demonstrates that SR-AB2 inhibits LTBP-proTGFβ. proTGFβ1 is presented by endogenous LTBP1/3. This assay was performed in LN229 cells, which express high LTBP1 & 3, undetectable GARP and LRRC33. TGFβ1 activity, normalized to vehicle, is shown on the y-axis. FIG. 10B demonstrates that SR-AB2 does not inhibit GARP-proTGFβ. SR-AB1 binds latent TGBβ1 independent of the presenting molecule. proTGFβ1 is presented by overexpressed GARP. This assay was performed in LN229 cells, which express high LTBP1 & 3, undetectable GARP and LRRC33. TGFβ1 activity, normalized to vehicle, is shown on the y-axis.

FIG. 11 presents binding profile and affinity data for LTBP-specific antibodies SR-AB10, SR-AB2, and SR-AB13.

DETAILED DESCRIPTION OF CERTAIN EMBODIMENTS

Figure 4B:
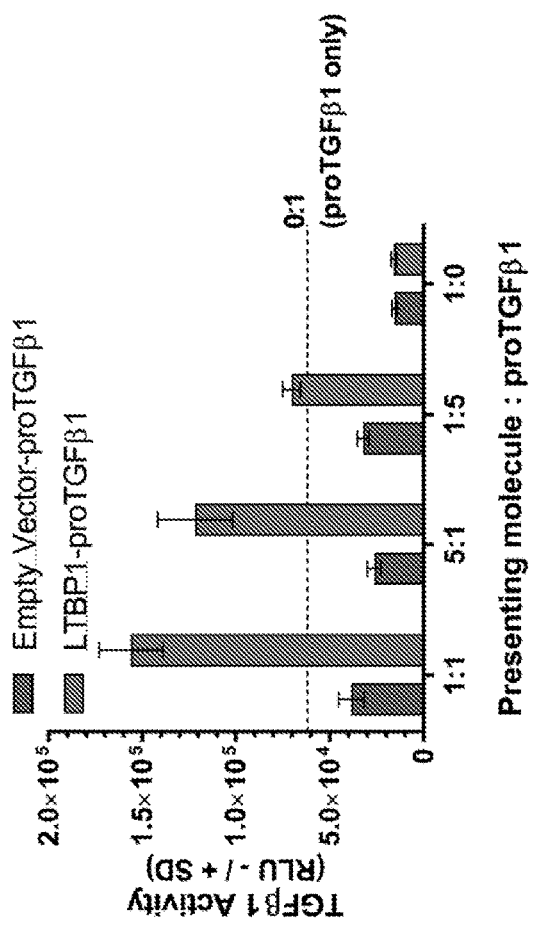
FIGS. 4A-4B depict the optimization of the recombinant functional assays.

The present invention provides compositions that are useful for reducing activation of TGFβ1. Inhibitors that target latent proTGFβ1 complexes, upstream of growth factor-receptor interaction, are generally referred to as activation inhibitors of TGFβ1.

To date, four presenting molecules for TGFβ have been identified: latent TGF beta-binding protein 1 ("LTBP1"), latent TGF beta-binding protein 3 ("LTBP3"), glycoprotein A repetitions predominant ("GARP") and leucine-rich repeat-containing protein 33 ("LRRC33"). Each of these presenting molecules can form disulfide bonds with a homodimeric pro-protein complex of the TGFβ1 precursor, i.e., proTGFβ1. The proTGFβ1 complex remains dormant (latent) in the respective extracellular niche (e.g., ECM and immune cell surface) until activation events trigger the release of soluble growth factor from the complex.

As compared to the TGFβ growth factors and the receptors, which are expressed broadly, the presenting molecules show more restricted or selective (e.g., tissue-specific) expression patterns, giving rise to functional compartmentalization of TGFβ1 activities by virtue of association. The four presenting molecule-proTGFβ1 complexes, namely, LTBP1-proTGFβ1, LTBP3-proTGFβ1, GARP-proTGFβ1 and LRRC33-proTGFβ1, therefore, provide discrete "contexts" of TGFβ1 signaling within the tissue in which the presenting molecules are expressed. These contexts may be divided into two broad categories: i) TGFβ1 signaling associated with the ECM (e.g., matrix-associated TGFβ1 function); and ii) TGFβ1 signaling associated with cells (particularly certain immune cell function). The LTBP1-proTGFβ1 and LTBP3-proTGFβ1 complexes fall under the first category, while GARP-proTGFβ1 and LRRC33-proTGFβ1 complexes fall under the second category. Thus, disclosed herein are isoform-selective inhibitors of TGFβ1 that are capable of selectively inhibiting the activation of TGFβ1 that is associated with the ECM.

In exemplary embodiments, the compositions described herein are useful for selectively reducing activation of TGFβ1 in the context of an LTBP protein, e.g., a LTBP1 and/or a LTBP3 protein. Such compositions advantageously inhibit activation of extracellular matrix-associated TGFβ1, without inhibiting TGFβ1 in the context of the immune-associated TGFβ1 presenting molecules GARP and LRRC33. The compositions described herein are useful for treating disorders associated with TGFβ1 activation, e.g., fibrotic disorders. Accordingly, in embodiments, the invention provides compositions for reducing activation of TGFβ1, methods of use thereof, methods of manufacture, and treatment methods. Methods of selecting a TGFβ1 inhibitor for subjects exhibiting symptoms of a fibrotic disorder are also provided.

Definitions

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

Affinity: Affinity is the strength of binding of a molecule (such as an antibody) to its ligand (such as an antigen). It is typically measured and reported by the equilibrium dissociation constant (KD). KD is the ratio of the antibody dissociation rate ("off rate" or $K_{off}$), how quickly it dissociates from its antigen, to the antibody association rate ("on rate" or $K_{on}$) of the antibody, how quickly it binds to its antigen. For example, an antibody with an affinity of <1 μM has a KD value that is 1 μM or lower (i.e., 1 μM or higher affinity) determined by a suitable in vitro binding assay. Suitable in vitro assays, such as Biolayer Interferometry (e.g., Octet) or surface plasmon resonance (e.g., Biacore System) can be used to assess affinities, as measured by KD values based on well-known methods.

Affinity maturation: Affinity maturation is a process of improving the affinity of an antibody or a fragment to its antigen and typically involves making one or more changes to the amino acid sequence of the antibody or the fragment to achieve greater affinity. Typically, a parental antibody and an affinity matured counterpart retain the same epitope.

Antibody: The term "antibody" encompasses any naturally-occurring, recombinant, modified or engineered immunoglobulin or immunoglobulin-like structure or antigen-binding fragment or portion thereof, or derivative thereof, as further described elsewhere herein. Thus, the term refers to an immunoglobulin molecule that specifically binds to a target antigen, and includes, for instance, chimeric, humanized, fully human, and bispecific antibodies.

Antigen: The term "antigen" broadly includes any molecules comprising an antigenic determinant within a binding region(s) to which an antibody or a fragment specifically binds. An antigen can be a single-unit molecule (such as a protein monomer or a fragment) or a complex comprised of multiple components. An antigen provides an epitope, e.g., a molecule or a portion of a molecule, or a complex of molecules or portions of molecules, capable of being bound by a selective binding agent, such as an antigen binding protein (including, e.g., an antibody). Thus, a selective binding agent may specifically bind to an antigen that is formed by two or more components in a complex. In some embodiments, the antigen is capable of being used in an animal to produce antibodies capable of binding to that antigen. An antigen can possess one or more epitopes that are capable of interacting with different antigen binding proteins, e.g., antibodies.

Antigen-binding portion/fragment: The terms "antigen-binding portion" or "antigen-binding fragment" of an antibody, as used herein, refers to one or more fragments of an antibody that retain the ability to specifically bind to an antigen (e.g., LTBP1-proTGFβ1 and LTBP3-proTGFβ1).

Advanced fibrosis: As used herein, a subject suffers from advanced fibrosis if s/he has an advanced stage of a fibrotic disorder, particularly organ fibtosis, which renders the patient a candidate for receiving, or in need of, an allograft transplant.

Biolayer Interferometry (BLI): BLI is a label-free technology for optically measuring biomolecular interactions, e.g., between a ligand immobilized on the biosensor tip surface and an analyte in solution. BLI provides the ability to monitor binding specificity, rates of association and dissociation, or concentration, with precision and accuracy. BLI platform instruments are commercially available, for example, from ForteBio and are commonly referred to as the Octet® System. BLI can be employed in carrying out in vitro binding assays as described herein.

Autoimmune disease: An autoimmune disease is a condition arising from an abnormal or overactive immune response to a normal body part Immunostimulating agents administered to such patients with autoimmune conditions may exacerbate the condition.

Cell-associated proTGFβ1: The term refers to TGFβ1 or its signaling complex (e.g., pro/latent TGFβ1) that is membrane-bound (e.g., tethered to cell surface). Typically, such cell is an immune cell. TGFβ1 that is presented by GARP or LRRC33 is a cell-associated TGFβ1. GARP and LRRC33 are transmembrane presenting molecules that are expressed on cell surface of certain cells. GARP-proTGFβ1 and LRRC33-proTGFβ1 may be collectively referred to as "cell-associated" (or "cell-surface") proTGFβ1 complexes, that mediate cell-associated (e.g., immune cell-associated) TGFβ1 activation/signaling.

Chronic inflammation: In the context of the present disclosure, fibrotic disorders that involve chronic inflammation are characterized by continuous or persistent injury to a tissue such that it does not resolve in normal healing after an initial injury. Chronic inflammation refers to a prolonged inflammatory response that involves a progressive change in the type of cells present at the site of inflammation (e.g., fibrotic tissues). It is characterized by the simultaneous destruction and repair of the tissue from the inflammatory process. It can follow an acute form of inflammation or be a prolonged low-grade form.

Clinical benefit: As used herein, the term "clinical benefits" is intended to include both efficacy and safety of a therapy. Thus, therapeutic treatment that achieves a desirable clinical benefit is both efficacious and safe (e.g., with tolerable or acceptable toxicities or adverse events).

Combinatory or combinatorial epitope: A combinatorial epitope is an epitope that is recognized and bound by a combinatorial antibody at a site (i.e., antigenic determinant) formed by non-contiguous portions of a component or components of an antigen, which, in a three-dimensional structure, come together in close proximity to form the epitope. Thus, antibodies of the invention may bind an epitope formed by two or more components (e.g., portions or segments) of a pro/latent TGFβ1 complex. A combinatory epitope may comprise amino acid residue(s) from a first component of the complex, and amino acid residue(s) from a second component of the complex, and so on. Each component may be of a single protein or of two or more proteins of an antigenic complex. A combinatory epitope is formed with structural contributions from two or more components (e.g., portions or segments, such as amino acid residues) of an antigen or antigen complex.

Complementary determining region: As used herein, the term "CDR" refers to the complementarity determining region within antibody variable sequences. There are three CDRs in each of the variable regions of the heavy chain and the light chain, which are designated CDR1, CDR2 and CDR3, for each of the variable regions.

Conformational epitope: A conformational epitope is an epitope that is recognized and bound by a conformational antibody in a three-dimensional conformation, but not in an unfolded peptide of the same amino acid sequence. A conformational epitope may be referred to as a conformation-specific epitope, conformation-dependent epitope, or conformation-sensitive epitope. A corresponding antibody or fragment thereof that specifically binds such an epitope may be referred to as conformation-specific antibody, conformation-selective antibody, or conformation-dependent antibody. Binding of an antigen to a conformational epitope depends on the three-dimensional structure (conformation) of the antigen or antigen complex.

Context-specific: Context-specific (or context-selective) antibodies of the invention (as opposed to "context-independent" antibodies) are capable of binding selectively to a subset, but not all, of proTGFβ1 complexes associated with a particular biological context. For example, matrix-selective targeting enables specific inhibition of TGFβ1 function associated with the ECM. ECM-selective inhibition can be achieved by the use of antibodies or fragments thereof that selectively target the ECM components, LTBP1-proTGFβ1 and/or LTBP3-proTGFβ1. Antibodies and fragments disclosed herein therefore represent a class of context-specific antibodies. LTBP1-specific and LTBP3-specific inhibitors of TGFβ1 activation are also context-specific antibodies.

Cross-block/cross-blocking: a first antibody or antigen-binding portion thereof and a second antibody or antigen-binding portion thereof cross-block with each other with respect to the same antigen, for example, as assayed by as measured by Biolayer Interferometry (such as Octet) or surface plasmon resonance (such as Biacore System), using standard test conditions, e.g., according to the manufacturer's instructions (e.g., binding assayed at room temperature, 20-25° C.). The first antibody or fragment thereof and the second antibody or fragment thereof may have the same epitope; may have non-identical but overlapping epitopes; or, may have separate (different) epitopes which are in close proximity in a three-dimensional space, such that antibody binding is cross-blocked via steric hinderance. "Cross-block" means that binding of the first antibody to an antigen prevents binding of the second antibody to the same antigen, and similarly, binding of the second antibody to an antigen prevents binding of the first antibody to the same antigen.

Dosage: As used herein, typical therapeutic dosage of an antibody of the present invention ranges between about 1-30 mg/kg per dose.

ECM-associated (or "matrix-associated") TGFβ1: The term refers to TGFβ1 or its signaling complex (e.g., pro/latent TGFβ1) that is a component of (e.g., deposited into) the extracellular matrix. TGFβ1 that is presented by LTBP1 or LTBP3 is an ECM-associated TGFβ1.

Effective amount: An "effective amount" (or therapeutically effective amount) is a dosage or dosing regimen that achieves statistically significant clinical benefits in a patient population.

Fibrotic disorder: The term "fibrosis" or "fibrotic condition/disorder" refers to the process or manifestation characterized by the pathological accumulation of extracellular matrix (ECM) components, such as collagens, within a tissue or organ. Fibrosis can include primary fibrosis, as well as secondary fibrosis that are associated with a disease or disorder.

GARP-proTGFβ1: As used herein, the term "GARP-proTGFβ1" refers to a protein complex comprising a pro-protein form or latent form of a transforming growth factor-β1 (TGFβ1) protein associated with a glycoprotein-A repetitions predominant protein (GARP) or fragment or variant thereof. The proTGFβ1 homodimer is capable of forming covalent association with a single molecule of GARP via disulfide bonds. The term "GARP-TGFβ1" may be used interchangeably. GARP-proTGFβ1 expression is limited to certain cell types, such as regulatory T cells (Treg).

Human antibody: The term "human antibody," as used herein, is intended to include antibodies having variable and constant regions derived from human germline immunoglobulin sequences. The human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3.

Humanized antibody: The term "humanized antibody" refers to antibodies, which comprise heavy and light chain variable region sequences from a non-human species (e.g., a mouse) but in which at least a portion of the VH and/or VL sequence has been altered to be more "human-like," i.e., more similar to human germline variable sequences. One type of humanized antibody is a CDR-grafted antibody.

Immune suppression/immunosuppression: The term immunosuppressin refers to suppression or reduction of the strength of the body's immune system. Patients who "benefit from immunosuppression" include those who have advanced stages of organ fibrosis and are candidates for, being considered for, or have undergone transplantation.

Isoform-specific: The term "isoform specificity" refers to an agent's ability to discriminate one isoform over other structurally related isoforms (i.e., selectivity). An isoform-specific TGFβ inhibitor exerts its inhibitory activity towards one isoform of TGFβ but not the other isoforms of TGFβ at a given concentration. For example, an isoform-specific TGFβ1 antibody selectively binds TGFβ1. A TGFβ1-specific inhibitor (antibody) preferentially targets (binds thereby inhibits) the TGFβ1 isoform over TGFβ2 or TGFβ3 with substantially greater affinity. For example, the selectivity in this context may refer to at least a 500-1000-fold difference in respective affinities as measured by an in vitro binding assay such as Octet and Biacor. In some embodiments, the selectivity is such that the inhibitor when used at a dosage effective to inhibit TGFβ1 in vivo does not inhibit TGFβ2 and TGFβ3. Context-specific inhibitors of the present disclosure are also isoform-specific.

Isolated: An "isolated" antibody as used herein, refers to an antibody that is substantially free of other antibodies having different antigenic specificities. In some embodiments, an isolated antibody is substantially free of other unintended cellular material and/or chemicals.

Long-term or chronic administration: As used herein, a therapeutic regimen that involves over six months of treatment is considered long-term. In some patient populations, long-term therapeutic resiments involve administration of a drug (such as context-selective TGFβ1 inhibitors) for an indefinite duration of time.

LRRC33-proTGFβ1: As used herein, the term "LRRC33-TGFβ1 complex" refers to a complex between a pro-protein form or latent form of transforming growth factor-β1 (TGFβ1) protein and a Leucine-Rich Repeat-Containing Protein 33 (LRRC33; also known as Negative Regulator Of Reactive Oxygen Species or NRROS) or fragment or variant thereof. In some embodiments, a LRRC33-TGFβ1 complex comprises LRRC33 covalently linked with pro/latent TGFβ1 via one or more disulfide bonds. In other embodiments, a LRRC33-TGFβ1 complex comprises LRRC33 non-covalently linked with pro/latent TGFβ1. In some embodiments, a LRRC33-TGFβ1 complex is a naturally-occurring complex, for example a LRRC33-TGFβ1 complex in a cell.

LTBP1-proTGFβ1: As used herein, the term "LTBP1-TGFβ1 complex" refers to a protein complex comprising a pro-protein form or latent form of transforming growth factor-β1 (TGFβ1) protein and a latent TGF-beta binding protein 1 (LTBP1) or fragment or variant thereof. In some embodiments, a LTBP1-TGFβ1 complex comprises LTBP1 covalently linked with pro/latent TGFβ1 via one or more disulfide bonds. In other embodiments, a LTBP1-TGFβ1 complex comprises LTBP1 non-covalently linked with pro/latent TGFβ1. In some embodiments, a LTBP1-TGFβ1 complex is a naturally-occurring complex, for example a LTBP1-TGFβ1 complex in a cell. An exemplary LTBP1-TGFβ1 complex is shown in FIG. 3.

LTBP3-proTGFβ1: As used herein, the term "LTBP3-TGFβ1 complex" refers to a protein complex comprising a pro-protein form or latent form of transforming growth factor-β1 (TGFβ1) protein and a latent TGF-beta binding protein 3 (LTBP3) or fragment or variant thereof. In some embodiments, a LTBP3-TGFβ1 complex comprises LTBP3 covalently linked with pro/latent TGFβ1 via one or more disulfide bonds. In other embodiments, a LTBP3-TGFβ1 complex comprises LTBP1 non-covalently linked with pro/latent TGFβ1. In some embodiments, a LTBP3-TGFβ1 complex is a naturally-occurring complex, for example a LTBP3-TGFβ1 complex in a cell. An exemplary LTBP3-TGFβ1 complex is shown in FIG. 3.

Macrophages: Macrophages are a type of white blood cells of the immune system and includes heterogeneous, phenotypically diverse subpopulations of myeloid cells. Some macrophages differentiate from bone marrow-derived, circulating monocytes, while others are tissue-specific macrophages that reside within particular anatomical or tissue locations ("resident" macrophages). Tissue-specific macrophages include but are not limited to: Adipose tissue macrophages; Kupffer cells (Liver); Sinus histiocytes (Lymph nodes); Alveolar macrophages (or dust cells, Pulmonary alveoli of lungs); Tissue macrophages (histiocytes) leading to giant cells (Connective tissue); Langerhans cells (Skin and mucosa); Microglia (Central nervous system); Hofbauer cells (Placenta); Intraglomerular mesangial cells (Kidney); Osteoclasts (Bone); Epithelioid cells (Granulomas); Red pulp macrophages (or Sinusoidal lining cells, Red pulp of spleen); Peritoneal macrophages (Peritoneal cavity); and, LysoMac (Peyer's patch). Macrophages, e.g., bone-marrow derived monocytes, can be activated by certain stimuli (such as cytokines) resulting in polarized phenotypes, e.g., M1 and M2. M2-biased activated macrophages are further classified into several phenotypically distinct subtypes, such as M2a, M2b, M2c (e.g., pro-fibrotic) and M2d (pro-tumor or TAM-like).

Matrix-associated proTGFβ1: LTBP1 and LTBP3 are presenting molecules that are components of the extracellular matrix (ECM). LTBP1-proTGFβ1 and LTBP3-proTGFβ1 may be collectively referred to as "ECM-associated" (or "matrix-associated") proTGFβ1 complexes, that mediate ECM-associated TGFβ1 activation/signaling.

Pan-TGFβ inhibitor/pan-inhibition of TGFβ: The term "pan-TGFβ inhibitor" refers to any agent that is capable of inhibiting or antagonizing all three isoforms of TGFβ. Such an inhibitor may be a small molecule inhibitor of TGFβ isoforms. The term includes pan-TGFβ antibody which refers to any antibody capable of binding to each of TGFβ isoforms, i.e., TGFβ1, TGFβ2, and TGFβ3. In some embodiments, a pan-TGFβ antibody binds and neutralizes activities of all three isoforms, i.e., TGFβ1, TGFβ2, and TGFβ3 activities.

Potency: The term "potency" as used herein refers to activity of a drug, such as an functional antibody (or fragment) having inhibitory activity, with respect to concentration or amount of the drug to produce a defined effect. For example, an antibody capable of producing certain effects at a given dosage is more potent than another antibody that requires twice the amount (dosage) to produce equivalent effects. Potency may be measured in cell-based assays, such as TGFβ activation/inhibition assays. Typically, antibodies with higher affinities tend to show higher potency than antibodies with lower affinities.

Presenting molecule: Presenting molecules are proteins that form covalent bonds with latent pro-proteins (e.g., proTGFβ1) and "present" the inactive complex in an extracellular niche (such as ECM or immune cell surface) thereby maintaining its latency until an activation event occurs. Known presenting molecules for proTGFβ1 include: LTBP1, LTBP3, GARP and LRRC33, which can form presenting molecule-proTGFβ1 complexes, namely, LTBP1-proTGFβ1, LTBP3-proTGFβ1, GARP-proTGFβ1 and LRRC33-proTGFβ1, respectively. LTBP1 and LTBP3 are components of the extracellular matrix (ECM); therefore, LTBP1-proTGFβ1 and LTBP3-proTGFβ1 may be collectively referred to as "ECM-associated" (or "matrix-associated") proTGFβ1 complexes, that mediate ECM-associated TGFβ1 signaling/activities. GARP and LRRC33, on the other hand, are transmembrane proteins expressed on cell surface of certain cells; therefore, GARP-proTGFβ1 and LRRC33-proTGFβ1 may be collectively referred to as "cell-associated" (or "cell-surface") proTGFβ1 complexes, that mediate cell-associated (e.g., immune cell-associated) TGFβ1 signaling/activities.

ProTGFβ1: The term "proTGFβ1" as used herein is intended to encompass precursor forms of inactive TGFβ1 complex that comprises a prodomain sequence of TGFβ1 within the complex. Thus, the term can include the pro-, as well as the latent-forms of TGFβ1. The expression "pro/latent TGFβ1" may be used interchangeably.

Regulatory T cell (Treg): "Regulatory T cells," or Tregs, are a type of immune cells characterized by the expression of the biomarkers, CD4, forkhead box P3 (FOXP3), and CD25, as well as STATS. Tregs are sometimes referred to as suppressor T cells and represent a subpopulation of T cells that modulate the immune system, maintain tolerance to self-antigens, and prevent autoimmune disease. Tregs are immunosuppressive and generally suppress or downregulate induction and proliferation of effector T (Teff) cells. Tregs can develop in the thymus (so-called CD4+ Foxp3+"natural" Tregs) or differentiate in the periphery upon priming of naïve CD4+ T cells by antigen-presenting cells (APCs), for example, following exposure to TGFβ or retinoic acid. Treg cells produce and secrete cytokines including IL-10 and TGFβ1. Generally, differentiation of Treg and Th17 cells is negatively correlated.

Specific binding: As used herein, the term "specific binding" or "specifically binds" means that the interaction of the antibody, or antigen binding portion thereof, with an antigen is dependent upon the presence of a particular structure (e.g., an antigenic determinant or epitope). For example, the antibody, or antigen binding portion thereof, binds to a specific protein rather than to proteins generally. In some embodiments, an antibody, or antigen binding portion thereof, specifically binds to a target, e.g., TGFβ1, if the antibody has a KD for the target of at least about $10^{-6}$ M. More preferably, the measured KD values of such antibody range between 40-400 nM.

Subject: The term "subject" in the context of therapeutic applications refers to an individual who receives clinical care or intervention, such as treatment, diagnosis, etc. Suitable subjects include vertebrates, including but not limited to mammals (e.g., human and non-human mammals) Where the subject is a human subject, the term "patient" may be used interchangeably. In a clinical context, the term "a patient population" or "patient subpopulation" is used to refer to a group of individuals that falls within a set of criteria, such as clinical criteria (e.g., disease presentations, disease stages, susceptibility to certain conditions, responsiveness to therapy, etc.), medical history, health status, gender, age group, genetic criteria (e.g., carrier of certain mutation, polymorphism, gene duplications, DNA sequence repeats, etc.) and lifestyle factors (e.g., smoking, alcohol consumption, exercise, etc.).

TGFβ inhibitor: The term "TGFβ inhibitor" refers to any agent capable of antagonizing biological activities or function of TGFβ growth factor (e.g., TGFβ1, TGFβ2 and/or TGFβ3). The term is not intended to limit its mechanism of action and includes, for example, neutralizing inhibitors, receptor antagonists, soluble ligand traps, and activation inhibitors of TGFβ.

T helper 17 cell: T helper 17 cells (Th17) are a subset of pro-inflammatory T helper cells characterized by the markers STAT3 and RORγt and the production of cytokines including interleukin 17 (IL-17A/F) and IL-22. Th17 cells are differentiated when naive T cells are exposed to TGFβ and IL-6. Th17 cells are generally associated with tissue inflammation, autoimmunity and clearance of certain pathogens. The differentiation of Th17 cells and Treg cells is generally inversely related. Imbalance in Th17-to-Treg ratios (e.g., "Th17/Treg") has been implicated in a number of pathologies, such as fibrotic conditions and autoimmune conditions.

Th17/Treg ratio: Th17-to-Treg ratios refer to measured ratios (relative proportions) of the number of Th17 cells versus the number of Treg cells in a tissue or sample of interest. Typically, known cell markers are used to identify, sort or isolate the cell types. Such markers include cell-surface molecules expressed on the particular cell type; a cytokine or a panel of cytokines produced (e.g., secreted) by the particular cell type, and/or mRNA expression of certain gene markers that serve as a signature/profile of the particular cell type. For example, the Th17/Treg ratio of one (1) means that there is an equal or equivalent number of each of the cell types within the tissue or sample being evaluated. The Th17/Treg ratio of two (2) means that there is approximately twice the number of Th17 cells as compared to Treg cells in the tissue or sample. An elevated Th17/Treg ratio may arise from an increased number of Th17 cells, a decreased number of Treg cells, or combination thereof.

Toxicity: As used herein, the term "toxicity" or "toxicities" refers to unwanted in vivo effects in patients associated with a therapy administered to the patients, such as undesirable side effects and adverse events. "Tolerability" refers to a level of toxicities associated with a therapy or therapeutic regimen, which can be reasonably tolerated by patients, without discontinuing the therapy due to the toxicities (i.e., acceptable level of toxicities).

Treat/treatment: The term "treat" or "treatment" includes therapeutic treatments, prophylactic treatments, and applications in which one reduces the risk that a subject will develop a disorder or other risk factor. Thus the term is intended to broadly mean: causing therapeutic benefits in a patient by, for example, enhancing or boosting the body's immunity; reducing or reversing immune suppression; reducing, removing or eradicating harmful cells or substances from the body; reducing disease burden (e.g., tumor burden); preventing recurrence or relapse; prolonging a refractory period, and/or otherwise improving survival. Treatment does not require the complete curing of a disorder and encompasses embodiments in which one reduces symptoms or underlying risk factors. In the context of combination therapy, the term may also refer to: i) the ability of a second therapeutic to reduce the effective dosage of a first therapeutic so as to reduce side effects and increase tolerability; ii) the ability of a second therapy to render the patient more responsive to a first therapy; and/or iii) the ability to effectuate additive or synergistic clinical benefits.

Variable region: The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

TGFβ1

In mammals, the transforming growth factor-beta (TGFβ) superfamily is comprised of at least 33 gene products. These include the bone morphogenetic proteins (BMPs), activins, growth and differentiation factors (GDFs), and the three isoforms of the TGFβ family TGFβ1, TGFβ2, and TGFβ3. The TGFβs are thought to play key roles in diverse processes, such as inhibition of cell proliferation, extracellular matrix (ECM) remodeling, and immune homeostasis. The importance of TGFβ1 for T cell homeostasis is demonstrated by the observation that TGFβ1−/− mice survive only 3-4 weeks, succumbing to multiorgan failure due to massive immune activation (Kulkarni, A. B., et al., Proc Natl Acad Sci USA, 1993. 90(2): p. 770-4; Shull, M. M., et al., Nature, 1992. 359(6397): p. 693-9). The roles of TGFβ2 and TGFβ3 are less clear. Whilst the three TGFβ isoforms have distinct temporal and spatial expression patterns, they signal through the same receptors, TGFβRI and TGFβRII, although in some cases, for example for TGFβ2 signaling, type III receptors such as betaglycan are also required (Feng, X. H. and R. Derynck, Annu Rev Cell Dev Biol, 2005. 21: p. 659-93; Massague, J., Annu Rev Biochem, 1998. 67: p. 753-91). Ligand-induced oligomerization of TGFβRI/II triggers the phosphorylation of SMAD transcription factors, resulting in the transcription of target genes, such as Col1a1, Col3a1, ACTA2, and SERPINE1 (Massague, J., J. Seoane, and D. Wotton, Genes Dev, 2005. 19(23): p. 2783-810). SMAD-independent TGFβ signaling pathways have also been described, for example in cancer or in the aortic lesions of Marfan mice (Derynck, R. and Y. E. Zhang, Nature, 2003. 425(6958): p. 577-84; Holm, T. M., et al., Science, 2011. 332(6027): p. 358-61).

The biological importance of the TGFβ pathway in humans has been validated by genetic diseases. Camurati-Engelman disease results in bone dysplasia due to an autosomal dominant mutation in the TGFβ1 gene, leading to constitutive activation of TGFβ1 signaling (Janssens, K., et al., J Med Genet, 2006. 43(1): p. 1-11). Patients with Loeys/Dietz syndrome carry autosomal dominant mutations in components of the TGFβ signaling pathway, which cause aortic aneurism, hypertelorism, and bifid uvula (Van Laer, L., H. Dietz, and B. Loeys, Adv Exp Med Biol, 2014. 802: p. 95-105). As TGFβ pathway dysregulation has been implicated in multiple diseases, several drugs that target the TGFβ pathway have been developed and tested in patients, but with limited success. Most TGFβ inhibitors described to date lack isoform specificity as briefly summarized below.

Fresolimumab, a humanized monoclonal antibody that binds and inhibits all three isoforms of TGFβ has been tested clinically in patients with focal segmental glomerulosclerosis, malignant melanoma, renal cell carcinoma, and systemic sclerosis (Rice, L. M., et al., J Clin Invest, 2015. 125(7): p. 2795-807; Trachtman, H., et al., Kidney Int, 2011. 79(11): p. 1236-43; Morris, J. C., et al., PLoS One, 2014. 9(3): p. e90353). Additional companies have developed monoclonal antibodies against the TGFβ growth factors with varying degrees of selectivity for TGFβ isoforms. Such agents likely elicit toxicities in vivo through residual activity against other TGFβ family members besides TGFβ1. This lack of isoform specificity may be due to the high degree of sequence identity between isoforms.

Other approaches to target the TGFβ pathway include ACE-1332, a soluble TGFβRII-Fc ligand trap from Acceleron (Yung, L. M., et al., A Am J Respir Crit Care Med, 2016. 194(9): p. 1140-1151), or small molecule inhibitors of the ALK5 kinase, such as Eli Lilly's galunisertib. ACE-1332 binds TGFβ1 and TGFβ3 with equally high affinity (Yung, L. M., et al., Am J Respir Crit Care Med, 2016. 194(9): p. 1140-1151), and ALK5 inhibitors block the activity of all growth factors that signal through TGFR1. Substantial toxicities have been found in preclinical studies using ALK5 inhibitors (Anderton, M. J., et al., Toxicol Pathol, 2011. 39(6): p. 916-24; Stauber, A., et al., Clinical Toxicology, 2014. 4(3): p. 1-10), and sophisticated clinical dosing schemes are required to maintain efficacy while reducing adverse events (Herbertz, S., et al., Drug Des Devel Ther, 2015. 9: p. 4479-99). In fact, the question of TGFβ signaling specificity and its possible effect on toxicity observed with the known TGFβ inhibitors has not been raised in most, if not all, of the candidate drugs that attempted to block TGFβ. For example, how much of the toxicities are due to inhibition of TGFβ1 versus TGFβ2 and/or TGFβ3 has not been addressed. Similarly, modes of TGFβ activation have not been taken into account in designing or developing ways to antagonize TGFβ signaling.

Recent structural insights into the activation mechanism of TGFβ1 (Shi, M., et al., Nature, 2011. 474(7351): p. 343-9) have enabled more specific approaches to TGFβ inhibition (see, e.g., PCT/US2017/21972, the entire contents of which are incorporated herein by reference). Unlike other cytokines, TGFβ superfamily members are not secreted as active growth factors, but as dimeric pro-proteins which consist of an N-terminal prodomain and a C-terminal growth factor domain Cleavage of proTGFβ1 by furin proteases separates the homodimeric growth factor domain from its prodomain, also referred to as latency associated peptide (LAP). However, the growth factor and LAP remain non-covalently associated, forming a latent complex which is unable to bind its receptors and induce signaling. During translation, latent TGFβ1, also called the small latent complex (SLC), becomes linked to "presenting molecules" via disulfide bridges, forming the large latent complex (LLC). These molecules allow proTGFβ1 to be presented in specific cellular or tissue contexts. Two cysteines near the N-terminus of the latent TGFβ1 link to appropriately positioned cysteines on the presenting molecule. The identity of the presenting molecule depends on the environment and cell type producing latent TGFβ1. For example, fibroblasts secrete latent TGFβ1 tethered to latent TGFβ-binding proteins (LTBPs), which then associate with proteins in the extracellular matrix (ECM) (i.e., fibronectin, fibrillin-1) to link latent TGFβ to the ECM (Robertson et al. Matrix Biol 47: 44-53 (2015) (FIG. 2A). On the surface of activated regulatory T cells latent TGFβ1 is covalently linked to the transmembrane protein GARP (glycoprotein-A repetitions predominant protein (GARP), and a protein closely related to GARP, LRRC33 (leucine-rich repeat-containing protein 33), serves as a presenting molecule for TGFβ1 on the surface of monocytes, macrophages and microglia (Wang, R., et al., Mol Biol Cell, 2012. 23(6): p. 1129-39 and T. A. Springer, Int. BMP Conference 2016).

A number of studies have shed light on the mechanisms of TGFβ1 activation. Three integrins, αVβ6, αVβ8, and αVβ1 have been demonstrated to be key activators of latent TGFβ1 (Reed, N. I., et al., Sci Transl Med, 2015. 7(288): p. 288ra79; Travis, M. A. and D. Sheppard, Annu Rev Immunol, 2014. 32: p. 51-82; Munger, J. S., et al., Cell, 1999. 96(3): p. 319-28). αV integrins bind the RGD sequence present in TGFβ1 and TGFβ1 LAPs with high affinity (Dong, X., et al., Nat Struct Mol Biol, 2014. 21(12): p. 1091-6). Transgenic mice with a mutation in the TGFβ1 RGD site that prevents integrin binding, but not secretion, phenocopy the TGFβ1−/− mouse (Yang, Z., et al., J Cell Biol, 2007. 176(6): p. 787-93). Mice that lack both β6 and β8 integrins recapitulate all essential phenotypes of TGFβ1 and TGFβ3 knockout mice, including multiorgan inflammation and cleft palate, confirming the essential role of these two integrins for TGFβ1 activation in development and homeostasis (Aluwihare, P., et al., J Cell Sci, 2009. 122(Pt 2): p. 227-32). Key for integrin-dependent activation of latent TGFβ1 is the covalent tether to presenting molecules; disruption of the disulfide bonds between GARP and TGFβ1 LAP by mutagenesis does not impair complex formation, but completely abolishes TGFβ1 activation by αVβ6 (Wang, R., et al., Mol Biol Cell, 2012. 23(6): p. 1129-39). The recent structure of latent TGFβ1 illuminates how integrins enable release of active TGFβ1 from the latent complex: the covalent link of latent TGFβ1 to its presenting molecule anchors latent TGFβ1, either to the ECM through LTBPs, or to the cytoskeleton through GARP or LRRC33. Integrin binding to the RGD sequence results in a force-dependent change in the structure of LAP, allowing active TGFβ1 to be released and bind nearby receptors (Shi, M., et al., Nature, 2011. 474(7351): p. 343-9). The importance of integrin-dependent TGFβ1 activation in disease has also been well validated. A small molecular inhibitor of αVβ1 protects against bleomycin-induced lung fibrosis and carbon tetra-chloride-induced liver fibrosis (Reed, N. I., et al., Sci Transl Med, 2015. 7(288): p. 288ra79), and αVβ6 blockade with an antibody or loss of integrin β6 expression suppresses bleomycin-induced lung fibrosis and radiation-induced fibrosis (Munger, J. S., et al., Cell, 1999. 96(3): p. 319-28); Horan, G. S., et al., Am J Respir Crit Care Med, 2008. 177(1): p. 56-65). In addition to integrins, other mechanisms of TGFβ1 activation have been implicated, including thrombospondin-1 and activation by proteases such as matrix metallo-proteinases (MMPs), cathepsin D or kallikrein. However, the majority of these studies were performed in vitro using purified proteins; there is less evidence for the role of these molecules from in vivo studies. Knockout of thrombospondin-1 recapitulates some aspects of the TGFβ1−/− phenotype in some tissues, but is not protective in bleomycin-induced lung fibrosis, known to be TGFβ-dependent (Ezzie, M. E., et al., Am J Respir Cell Mol Biol, 2011. 44(4): p. 556-61). Additionally, knockout of candidate proteases did not result in a TGFβ1 phenotype (Worthington, J. J., J. E. Klementowicz, and M. A. Travis, Trends Biochem Sci, 2011. 36(1): p. 47-54). This could be explained by redundancies or by these mechanisms being critical in specific diseases rather than development and homeostasis.

TGFβ has been implicated in a number of biological processes, including fibrosis, immune-modulation and cancer progression. TGFβ1 was the first identified member of the TGFβ superfamily of proteins. Like other members of the TGFβ superfamily, TGFβ1 and the isoforms TGFβ2 and TGFβ3, are initially expressed as inactive precursor pro-protein forms (termed proTGFβ). TGFβ proteins (e.g., TGFβ1, TGFβ2 and TGFβ3) are proteolytically cleaved by proprotein convertases (e.g., furin) to yield the latent form (termed latent TGFβ). In some embodiments, a pro-protein form or latent form of a TGFβ protein (e.g., TGFβ1, TGFβ2 and TGFβ3) may be referred to as "pro/latent TGFβ protein". TGFβ1 may be presented to other molecules in complex with multiple molecules including, for example, GARP (to form a GARP-TGFβ1 complex), LRRC33 (to form a LRRC33-TGFβ1 complex), LTBP1 (to form a LTBP1-TGFβ1 complex), and/or LTBP3 (to form a LTBP3-TGFβ1 complex). The TGFβ1 present in these complexes may be in either latent form (latent TGFβ1) or in precursor form (proTGFβ1).

Latent TGFβ-Binding Proteins (LTBPs)

In mammals there are four known LTBPs, LTBP1-4, each with multiple splice variants (Robertson, I. B., et al., Matrix Biol, 2015. 47: p. 44-53). LTBP2 is the only LTBP that does not associate with latent TGFβ (Saharinen, J. and J. Keski-Oja, Mol Biol Cell, 2000. 11(8): p. 2691-704). While the association between LTBP1 or LTBP3 and latent TGFβ1 has been well validated, the role of LTBP4 in TGFβ presentation is less clear. The complex with LTBP4 and latent TGFβ1 appears to form much less efficiently, potentially due to the absence of several negatively charged residues in the TGFβ-binding domain of LTBP4 (Saharinen, J. and J. Keski-Oja, Mol Biol Cell, 2000. 11(8): p. 2691-704; Chen, Y., et al., J Mol Biol, 2005. 345(1): p. 175-86). Both LTBP4S-/- mice and Urban-Rifkin-Davis syndrome patients, who have null mutations in LTBP4, suffer from disrupted elastic fiber assembly (Urban, Z., et al., Am J Hum Genet, 2009. 85(5): p. 593-605; Dabovic, B., et al., J Cell Physiol, 2015. 230(1): p. 226-36). Additionally, while LTBP4S-/- mice have a lung septation and an elastogenesis defect, transgenic mice with an LTBP4 that cannot form a complex with latent TGFβ1 have no obvious phenotype (Dabovic, B., et al., J Cell Physiol, 2015. 230(1): p. 226-36). Whether LTBP4 is directly involved in regulation of latent TGFβ1 by functioning as a presenting molecule is unclear; LTBP4 may instead be required for proper formation of elastic fibrils in the ECM and its loss indirectly affect latent TGFβ1 activation through defects in the ECM.

In one aspect, the present invention is directed to inhibitors, e.g., immunoglobulins, e.g., antibodies, or antigen binding portions thereof, that selectively bind to a complex containing a TGFβ pro-protein and a LTBP protein (e.g., LTBP1 or LTBP3). In a preferred embodiment, the TGFβ protein is TGFβ1. In some embodiments, the binding molecules disclosed herein bind selectively to a complex containing pro/latent TGFβ1 and LTBP1 or LTBP3. Such binding molecules can allow TGFβ1 activity to be selectively modulated in a context-dependent manner, i.e., by modulating TGFβ1 in the context of a LTPB protein, without modulating the activity of TGFβ1 complexed with other presenting molecules (e.g., GARP and/or LRRC33).

Inhibitors that Selectively Bind to a LTBP-TGFβ1 Complex

The present invention provides novel, TGFβ1 inhibitors that selectively target matrix- or ECM-associated TGFβ1 activities. More specifically, such inhibitors include iso-form-specific, context-selective inhibitors of TGFβ1 activation that specifically bind latent forms of TGFβ1 (e.g., proTGFβ1 complex) within the ECM environment and prevent release of mature growth factor from the complex at the niche. Such matrix-targeting inhibitors are context-specific in that they selectively bind proTGFβ1 associated with ECM presenting molecules, namely, LTBP1 and/or LTBP3. Thus, disclosed herein are monoclonal antibodies and fragments thereof capable of binding an epitope present in an LTBP1-proTGFβ1 complex and/or LTBP3-proTGFβ1 complex, whereas the epitope is not present in a GARP-proTGFβ1 complex and/or LRRC33-proTGFβ1 complex.

In some embodiments, the context-selective inhibitors of the present disclosure are capable of specifically binding both a human LTBP1-proTGFβ1 complex and a human LTBP3-proTGFβ1 complex, with affinities of at least 350 nM (measured KD values) in a suitable in vitro binding assay, such as Octet. On the other hand, these context-specific antibodies do not show any detectable binding to a human GARP-proTGFβ1 complex or a human LRRC33-proTGFβ1 complex under the same assay conditions.

In some embodiments, the context-selective inhibitors of the present disclosure are capable of specifically binding either a human LTBP1-proTGFβ1 complex or a human LTBP3-proTGFβ1 complex. Neither shows any detectable binding to a human GARP-proTGFβ1 complex or a human LRRC33-proTGFβ1 complex under the same assay conditions.

The TGFβ1 present in these complexes may be in either latent form (latent TGFβ1) or in precursor form (proTGFβ1). In one embodiment, the inhibitors do not significantly bind to LTBP1 alone (e.g., when not complexed with TGFβ1). In another embodiment, the inhibitors do not significantly bind to LTBP3 alone (e.g., when not complexed with TGFβ1). In another embodiment, the inhibitors do not significantly bind to TGFβ1 alone (e.g., pro or latent TGFβ1 not complexed with LTBP1 or LTBP3, or mature TGFβ1). In another embodiment, the inhibitors that selectively bind a LTBP1-TGFβ1 complex and/or a LTBP3-TGFβ1 complex do not significantly bind to a complex containing TGFβ1 and another presenting molecule, e.g., a GARP-TGFβ1 complex (e.g., GARP complexed to pro- or latent TGFβ1) and/or a LRRC33-TGFβ1 complex (e.g., LRRC33 complexed to pro- or latent TGFβ1). In one embodiment, the inhibitors that selectively bind LTBP1/3-TGFβ1 do not significantly bind one or more (e.g., two or more, three or more, or all four) of the following: LTBP1 alone, TGFβ1 alone, a GARP-TGFβ1 complex, and a LRRC33-TGFβ1 complex. In addition, in some embodiments, the inhibitors do not significantly bind LTBP3 alone.

As used herein, the term "inhibitor" refers to any agent capable of blocking or antagonizing TGFβ1 signaling. Such agents may include small molecule antagonists of TGFβ1 and biologic antagonists of TGFβ1 (e.g., protein fragments and antibodies). In some embodiments, the inhibitor may be an antibody (including fragments thereof, such as Domain Antibodies (dAbs) as described in, for example, U.S. Pat. Nos. 6,291,158; 6,582,915; 6,593,081; 6,172,197; and 6,696,245), a small molecule inhibitor, an Adnectin, an Affibody, a DARPin, an Anticalin, an Avimer, a Versabody or a gene therapy. Use of inhibitors encompassed by the present invention also includes antibody mimetics, such as monobodies and single-domain antibodies. Monobodies are synthetic binding proteins that typically employ a fibronectin type III domain (FN3) as a molecular scaffold. Monobodies include Adnectins™ which are based on the 10th fibronectin type III domain.

In some aspects, the inhibitors, e.g., antibodies, or antigen binding portions thereof, selectively bind to an epitope present on a LTBP1/3-TGFβ1 complex, that is not present on a GARP-TGFβ1 complex and/or a LRRC33-TGFβ1 complex. In some embodiments, the epitope is available due to a conformational change in LTBP1/3 and/or TGFβ1 that occurs when LTBP1/3 and TGFβ1 form a complex. In this embodiment, the epitope is not present in LTBP1/3 or TGFβ1 when the proteins are not associated in a complex. In one embodiment, the epitope is present on TGFβ1, when TGFβ1 is in a complex with LTBP1 or LTBP3. In another embodiment, the epitope is present on LTBP1, when LTBP1 is in a complex with TGFβ1. In another embodiment, the epitope is present on LTBP3, when LTBP3 is in a complex with TGFβ1. In another embodiment, the epitope comprises residues from both LTBP1 and TGFβ1. In another embodiment, the epitope comprises residues from both LTBP3 and TGFβ1.

In some embodiments, the inhibitors, e.g., antibodies, or antigen binding portions thereof, are selective for the TGFβ1 isoform. In such embodiments, the inhibitors, e.g., antibodies, or antigen binding portions thereof, do not bind to TGFβ2 and/or TGFβ3. For example, in one embodiment, the inhibitors, e.g., antibodies, or antigen-binding portions thereof, selectively bind a LTBP1/3-TGFβ1 complex, but do not bind TGFβ2, or a complex containing TGFβ2. In another embodiment, the inhibitors, e.g., antibodies, or antigen-binding portions thereof, selectively bind a LTBP1/3-TGFβ1 complex, but do not bind TGFβ3, or a complex containing TGFβ3.

In some embodiments, the inhibitors, e.g., antibodies, or antigen binding portions thereof, do not prevent TGFβ1 from binding to integrin. For example, in some embodiments, the inhibitors, e.g., antibodies, or antigen binding portions thereof, do not mask the integrin-binding site of TGFβ1.

In one aspect, the invention provides functional inhibitors, e.g., antibodies, that modulate TGFβ1 activity. In exemplary embodiments, the antibodies described herein are inhibitory antibodies, which inhibit the function or activity of TGFβ1. In some embodiments, the antibodies, or antigen binding portions thereof, inhibit the activation (release) of TGFβ1 from a LTBP1-TGFβ1 complex and/or a LTBP3-TGFβ1 complex. The present disclosure provides, in exemplary embodiments, "context-specific" or "context-selective" inhibitors of TGFβ1 activation. Such inhibitors can bind a LTBP1/3-TGFβ1 complex and inhibit activation of TGFβ1 that is presented by LTBP1 or LTBP3, without inhibiting the activation of TGFβ1 presented by GARP and/or LRRC33. Accordingly, in some embodiments, the antibodies, or antigen binding portions thereof, described herein inhibit the release of mature TGFβ1 from a LTBP1-TGFβ1 complex and/or a LTBP3-TGFβ1 complex, but do not inhibit the release of mature TGFβ1 from a GARP-TGFβ1 complex and/or a LRRC33-TGFβ1 complex. Due to the differential localization of LTBP, GARP, and LRRC33, the context-specific inhibitors of TGFβ1 provided by the present invention can block a particular subset of TGFβ1 activity in vivo. In one embodiment, the context-specific antibodies provided herein that inhibit LTBP1/3-TGFβ1 but do not inhibit GARP-TGFβ1 or LRRC33-TGFβ1 can be used to inhibit TGFβ1 localized to the extracellular matrix. In another embodiment, the context-specific antibodies can inhibit TGFβ1 without modulating TGFβ1-associated immune activity or immune response. In another embodiment, the context-specific antibodies can be used to inhibit TGFβ1 activity associated with the extracellular matrix without modulating TGFβ1 activity associated with hematopoietic cells. Accordingly, the context-specific antibodies can be used to inhibit LTBP1/3-associated TGFβ1 activity in applications in which TGFβ1 activation in the context of GARP and/or LRRC33 is undesirable, as described herein.

In some embodiments, the TGFβ1 comprises a naturally occurring mammalian amino acid sequence. In some embodiment, the TGFβ1 comprises a naturally occurring human amino acid sequence. In some embodiments, the TGFβ1 comprises a human, a monkey, a rat or a mouse amino acid sequence.

In some embodiments, an antibody, or antigen binding portion thereof, described herein selectively binds to a complex comprising a TGFβ1 protein comprising the amino acid sequence set forth in SEQ ID NO: 9, and LTBP1 or LTBP3. In some embodiments, an antibody, or antigen binding portion thereof, described herein selectively binds to a LTBP1/3-TGFβ1 complex which comprises a non-naturally-occurring TGFβ1 amino acid sequence (otherwise referred to herein as a non-naturally-occurring TGFβ1). For example, a non-naturally-occurring TGFβ1 may comprise one or more recombinantly generated mutations relative to a naturally-occurring TGFβ1 amino acid sequence.

In some embodiments, an antibody, or antigen binding portion thereof, described herein does not bind TGFβ2 and/or TGFβ3, or to protein complexes containing TGFβ2 and/or TGFβ3. Exemplary TGFβ2 and TGFβ3 amino acid sequences are set forth in SEQ ID NOs: 10 and 11, respectively. In some embodiments, a TGFβ1, TGFβ2, or TGFβ3 amino acid sequence comprises an amino acid sequence as set forth in SEQ ID NOs: 12-23, as shown in Table 1. In some embodiments, a TGFβ1 amino acid sequence comprises an amino acid sequence as set forth in SEQ ID NOs: 24-31, as shown in Table 2.

TGFβ1

(SEQ ID NO: 9)
LSTCKTIDMELVKRKRIEAIRGQILSKLRLASPPSQGEVPPGPLPEAVLA

LYNSTRDRVAGESAEPEPEPEADYYAKEVTRVLMVETHNEIYDKFKQSTH

SIYMFFNTSELREAVPEPVLLSRAELRLLRLKLKVEQHVELYQKYSNNSW

RYLSNRLLAPSDSPEWLSFDVTGVVRQWLSRGGEIEGFRLSAHCSCDSRD

NTLQVDINGFTTGRRGDLATIHGMNRPFLLLMATPLERAQHLQSSRHRRA

LDTNYCFSSTEKNCCVRQLYIDFRKDLGWKWIHEPKGYHANFCLGPCPYI

WSLDTQYSKVLALYNQHNPGASAAPCCVPQALEPLPIVYYVGRKPKVEQL

SNMIVRSCKCS

TGFβ2

(SEQ ID NO: 10)
SLSTCSTLDMDQFMRKRIEAIRGQILSKLKLTSPPEDYPEPEEVPPEVIS

IYNSTRDLLQEKASRRAAACERERSDEEYYAKEVYKIDMPPFFPSENAIP

PTFYRPYFRIVRFDVSAMEKNASNLVKAEFRVFRLQNPKARVPEQRIELY

QILKSKDLTSPTQRYIDSKVVKTRAEGEWLSFDVTDAVHEWLHHKDRNLG

FKISLHCPCCTFVPSNNYIIPNKSEELEARFAGIDGTSTYTSGDQKTIKS

TRKKNSGKTPHLLLMLLPSYRLESQQTNRRKKRALDAAYCFRNVQDNCCL

RPLYIDFKRDLGWKWIHEPKGYNANFCAGACPYLWSSDTQHSRVLSLYNT

INPEASASPCCVSQDLEPLTILYYIGKTPKIEQLSNMIVKSCKCS

TGFβ3

(SEQ ID NO: 11)
SLSLSTCTTLDFGHIKKKRVEAIRGQILSKLRLTSPPEPTVMTHVPYQVL

ALYNSTRELLEEMHGEREEGCTQENTESEYYAKEIHKFDMIQGLAEHNEL

AVCPKGITSKVFRFNVSSVEKNRTNLFRAEFRVLRVPNPSSKRNEQRIEL

FQILRPDEHIAKQRYIGGKNLPTRGTAEWLSFDVTDTVREWLLRRESNLG

LEISIHCPCHTFQPNGDILENIHEVMEIKFKGVDNEDDHGRGDLGRLKKQ

KDHHNPHLILMMIPPHRLDNPGQGGQRKKRALDTNYCFRNLEENCCVRPL

YIDFRQDLGWKWVHEPKGYYANFCSGPCPYLRSADTTHSTVLGLYNTLNP

EASASPCCVPQDLEPLTILYYVGRTPKVEQLSNMVVKSCKCS

TABLE 1

Exemplary TGFβ1, TGFβ2, and TGFβ3 amino acid sequences

| Protein | Sequence | SEQ ID NO |
|---|---|---|
| proTGFβ1 | LSTCKTIDMELVKRKRIEAIRGQILSKLRLASPPSQGEVPPGP<br>LPEAVLALYNSTRDRVAGESAEPEPEPEADYYAKEVTRVL<br>MVETHNEIYDKFKQSTHSIYMFFNTSELREAVPEPVLLSRA<br>ELRLLRLKLKVEQHVELYQKYSNNSWRYLSNRLLAPSDSP<br>EWLSFDVTGVVRQWLSRGGEIEGFRLSAHCSCDSRDNTLQ<br>VDINGFTTGRRGDLATIHGMNRPFLLLMATPLERAQHLQSS<br>RHRRALDTNYCFSSTEKNCCVRQLYIDFRKDLGWKWIHEP<br>KGYHANFCLGPCPYIWSLDTQYSKVLALYNQHNPGASAAP<br>CCVPQALEPLPIVYYVGRKPKVEQLSNMIVRSCKCS | 12 |
| proTGFβ1 C4S | LSTSKTIDMELVKRKRIEAIRGQILSKLRLASPPSQGEVPPGP<br>LPEAVLALYNSTRDRVAGESAEPEPEPEADYYAKEVTRVL<br>MVETHNEIYDKFKQSTHSIYMFFNTSELREAVPEPVLLSRA<br>ELRLLRLKLKVEQHVELYQKYSNNSWRYLSNRLLAPSDSP<br>EWLSFDVTGVVRQWLSRGGEIEGFRLSAHCSCDSRDNTLQ<br>VDINGFTTGRRGDLATIHGMNRPFLLLMATPLERAQHLQSS<br>RHRRALDTNYCFSSTEKNCCVRQLYIDFRKDLGWKWIHEP<br>KGYHANFCLGPCPYIWSLDTQYSKVLALYNQHNPGASAAP<br>CCVPQALEPLPIVYYVGRKPKVEQLSNMIVRSCKCS | 13 |
| proTGFβ1 D2G | LSTCKTIDMELVKRKRIEAIRGQILSKLRLASPPSQGEVPPGP<br>LPEAVLALYNSTRDRVAGESAEPEPEPEADYYAKEVTRVL<br>MVETHNEIYDKFKQSTHSIYMFFNTSELREAVPEPVLLSRA<br>ELRLLRLKLKVEQHVELYQKYSNNSWRYLSNRLLAPSDSP<br>EWLSFDVTGVVRQWLSRGGEIEGFRLSAHCSCDSRDNTLQ<br>VDINGFTTGRRGDLATIHGMNRPFLLLMATPLERAQHLQSS<br>RHGALDTNYCFSSTEKNCCVRQLYIDFRKDLGWKWIHEPK<br>GYHANFCLGPCPYIWSLDTQYSKVLALYNQHNPGASAAPC<br>CVPQALEPLPIVYYVGRKPKVEQLSNMIVRSCKCS | 14 |
| proTGFβ1 C4S D2G | LSTSKTIDMELVKRKRIEAIRGQILSKLRLASPPSQGEVPPGP<br>LPEAVLALYNSTRDRVAGESAEPEPEPEADYYAKEVTRVL<br>MVETHNEIYDKFKQSTHSIYMFFNTSELREAVPEPVLLSRA<br>ELRLLRLKLKVEQHVELYQKYSNNSWRYLSNRLLAPSDSP<br>EWLSFDVTGVVRQWLSRGGEIEGFRLSAHCSCDSRDNTLQ<br>VDINGFTTGRRGDLATIHGMNRPFLLLMATPLERAQHLQSS<br>RHGALDTNYCFSSTEKNCCVRQLYIDFRKDLGWKWIHEPK<br>GYHANFCLGPCPYIWSLDTQYSKVLALYNQHNPGASAAPC<br>CVPQALEPLPIVYYVGRKPKVEQLSNMIVRSCKCS | 15 |
| proTGFβ2 | SLSTCSTLDMDQFMRKRIEAIRGQILSKLKLTSPPEDYPEPE<br>EVPPEVISIYNSTRDLLQEKASRRAAACERERSDEEYYAKE<br>VYKIDMPPFFPSENAIPPTFYRPYFRIVRFDVSAMEKNASNL<br>VKAEFRVFRLQNPKARVPEQRIELYQILKSKDLTSPTQRYID<br>SKVVKTRAEGEWLSFDVTDAVHEWLHHKDRNLGFKISLH<br>CPCCTFVPSNNYIIPNKSEELEARFAGIDGTSTYTSGDQKTIK<br>STRKKNSGKTPHLLLMLLPSYRLESQQTNRRKKRALDAAY<br>CFRNVQDNCCLRPLYIDFKRDLGWKWIHEPKGYNANFCA<br>GACPYLWSSDTQHSRVLSLYNTINPEASASPCCVSQDLEPL<br>TILYYIGKTPKIEQLSNMIVKSCKCS | 16 |
| proTGFβ2 C5S | SLSTSSTLDMDQFMRKRIEAIRGQILSKLKLTSPPEDYPEPEE<br>VPPEVISIYNSTRDLLQEKASRRAAACERERSDEEYYAKEV<br>YKIDMPPFFPSENAIPPTFYRPYFRIVRFDVSAMEKNASNLV<br>KAEFRVFRLQNPKARVPEQRIELYQILKSKDLTSPTQRYIDS<br>KVVKTRAEGEWLSFDVTDAVHEWLHHKDRNLGFKISLHC<br>PCCTFVPSNNYIIPNKSEELEARFAGIDGTSTYTSGDQKTIKS<br>TRKKNSGKTPHLLLMLLPSYRLESQQTNRRKKRALDAAYC<br>FRNVQDNCCLRPLYIDFKRDLGWKWIHEPKGYNANFCAG<br>ACPYLWSSDTQHSRVLSLYNTINPEASASPCCVSQDLEPLTI<br>LYYIGKTPKIEQLSNMIVKSCKCS | 17 |
| proTGFβ2 C5S D2G | SLSTSSTLDMDQFMRKRIEAIRGQILSKLKLTSPPEDYPEPEE<br>VPPEVISIYNSTRDLLQEKASRRAAACERERSDEEYYAKEV<br>YKIDMPPFFPSENAIPPTFYRPYFRIVRFDVSAMEKNASNLV<br>KAEFRVFRLQNPKARVPEQRIELYQILKSKDLTSPTQRYIDS<br>KVVKTRAEGEWLSFDVTDAVHEWLHHKDRNLGFKISLHC<br>PCCTFVPSNNYIIPNKSEELEARFAGIDGTSTYTSGDQKTIKS<br>TRKKNSGKTPHLLLMLLPSYRLESQQTNRRKKGALDAAYCF<br>RNVQDNCCLRPLYIDFKRDLGWKWIHEPKGYNANFCAGA<br>CPYLWSSDTQHSRVLSLYNTINPEASASPCCVSQDLEPLTIL<br>YYIGKTPKIEQLSNMIVKSCKCS | 18 |

TABLE 1-continued

Exemplary TGFβ1, TGFβ2, and TGFβ3 amino acid sequences

| Protein | Sequence | SEQ ID NO |
|---|---|---|
| proTGFβ2 D2G | SLSTCSTLDMDQFMRKRIEAIRGQILS KLKLTSPPEDYPEPE EVPPEVISIYNSTRDLLQEKASRRAAACERERSDEEYYAKE VYKIDMPPFFPSENAIPPTFYRPYFRIVRFDVSAMEKNASNL VKAEFRVFRLQNPKARVPEQRIELYQILKSKDLTSPTQRYID SKVVKTRAEGEWLSFDVTDAVHEWLHHKDRNLGFKISLH CPCCTFVPSNNYIIPNKSEELEARFAGIDGTSTYTSGDQKTIK STRKKNSGKTPHLLLMLLPSYRLESQQTNRRKGALDAAYC FRNVQDNCCLRPLYIDFKRDLGWKWIHEPKGYNANFCAG ACPYLWSSDTQHSRVLSLYNTINPEASASPCCVSQDLEPLTI LYYIGKTPKIEQLSNMIVKSCKCS | 19 |
| proTGFβ3 | SLSLSTCTTLDFGHIKKKRVEAIRGQILSKLRLTSPPEPTVMT HVPYQVLALYNSTRELLEEMHGEREEGCTQENTESEYYAK EIHKFDMIQGLAEHNELAVCPKGITSKVFRFNVSSVEKNRT NLFRAEFRVLRVPNPSSKRNEQRIELFQILRPDEHIAKQRYI GGKNLPTRGTAEWLSFDVTDTVREWLLRRESNLGLEISIHC PCHTFQPNGDILENIHEVMEIKFKGVDNEDDHGRGDLGRL KKQKDHHNPHLILMMIPPHRLDNPGQGGQRKKRALDTNY CFRNLEENCCVRPLYIDFRQDLGWKWVHEPKGYYANFCS GPCPYLRSADTTHSTVLGLYNTLNPEASASPCCVPQDLEPL TILYYVGRTPKVEQLSNMVVKSCKCS | 20 |
| proTGFβ3 C7S | SLSLSTSTTLDFGHIKKKRVEAIRGQILSKLRLTSPPEPTVMT HVPYQVLALYNSTRELLEEMHGEREEGCTQENTESEYYAK EIHKFDMIQGLAEHNELAVCPKGITSKVFRFNVSSVEKNRT NLFRAEFRVLRVPNPSSKRNEQRIELFQILRPDEHIAKQRYI GGKNLPTRGTAEWLSFDVTDTVREWLLRRESNLGLEISIHC PCHTFQPNGDILENIHEVMEIKFKGVDNEDDHGRGDLGRL KKQKDHHNPHLILMMIPPHRLDNPGQGGQRKKRALDTNY CFRNLEENCCVRPLYIDFRQDLGWKWVHEPKGYYANFCS GPCPYLRSADTTHSTVLGLYNTLNPEASASPCCVPQDLEPL TILYYVGRTPKVEQLSNMVVKSCKCS | 21 |
| proTGFβ3 C7S D2G | SLSLSTSTTLDFGHIKKKRVEAIRGQILSKLRLTSPPEPTVMT HVPYQVLALYNSTRELLEEMHGEREEGCTQENTESEYYAK EIHKFDMIQGLAEHNELAVCPKGITSKVFRFNVSSVEKNRT NLFRAEFRVLRVPNPSSKRNEQRIELFQILRPDEHIAKQRYI GGKNLPTRGTAEWLSFDVTDTVREWLLRRESNLGLEISIHC PCHTFQPNGDILENIHEVMEIKFKGVDNEDDHGRGDLGRL KKQKDHHNPHLILMMIPPHRLDNPGQGGQRKGALDTNYC FRNLEENCCVRPLYIDFRQDLGWKWVHEPKGYYANFCSGP CPYLRSADTTHSTVLGLYNTLNPEASASPCCVPQDLEPLTIL YYVGRTPKVEQLSNMVVKSCKCS | 22 |
| proTGFβ3 D2G | SLSLSTCTTLDFGHIKKKRVEAIRGQILSKLRLTSPPEPTVMT HVPYQVLALYNSTRELLEEMHGEREEGCTQENTESEYYAK EIHKFDMIQGLAEHNELAVCPKGITSKVFRFNVSSVEKNRT NLFRAEFRVLRVPNPSSKRNEQRIELFQILRPDEHIAKQRYI GGKNLPTRGTAEWLSFDVTDTVREWLLRRESNLGLEISIHC PCHTFQPNGDILENIHEVMEIKFKGVDNEDDHGRGDLGRL KKQKDHHNPHLILMMIPPHRLDNPGQGGQRKGALDTNYC FRNLEENCCVRPLYIDFRQDLGWKWVHEPKGYYANFCSGP CPYLRSADTTHSTVLGLYNTLNPEASASPCCVPQDLEPLTIL YYVGRTPKVEQLSNMVVKSCKCS | 23 |

TABLE 2

Exemplary non-human TGFFβ1 amino acid sequences

| Protein | Species | Sequence | SEQ ID NO |
|---|---|---|---|
| proTGFβ1 | Mouse | LSTCKTIDMELVKRKRIEAIRGQILSKLRLASPPSQGEVPP GPLPEAVLALYNSTRDRVAGESADPEPEPEADYYAKEV TRVLMVDRNNAIYEKTKDISHSIYMFFNTSDIREAVPEPP LLSRAELRLQRLKSSVEQHVELYQKYSNNSWRYLGNRL LTPTDTPEWLSFDVTGVVRQWLNQGDGIQGFRFSAHCS CDSKDNKLHVEINGISPKRRGDLGTIHDMNRPFLLLMAT PLERAQHLHSSRHRRALDTNYCFSSTEKNCCVRQLYIDF RKDLGWKWIHEPKGYHANFCLGPCPYIWSLDTQYSKVL | 24 |

TABLE 2-continued

Exemplary non-human TGFβ1 amino acid sequences

| Protein | Species | Sequence | SEQ ID NO |
|---|---|---|---|
| | | ALYNQHNPGASASPCCVPQALEPLPIVYYVGRKPKVEQ<br>LSNMIVRSCKCS | |
| proTGFβ1 | Cyno | LSTCKTIDMELVKRKRIEAIRGQILSKLRLASPPSQGEVPP<br>GPLPEAVLALYNSTRDRVAGESAEPEPEPEADYYAKEVT<br>RVLMVETHNEIYDKFKQSTHSIYMFFNTSELREAVPEPV<br>LLSRAELRLLRLKLKVEQHVELYQKYSNNSWRYLSNRL<br>LAPSDSPEWLSFDVTGVVRQWLSRGGEIEGFRLSAHCSC<br>DSKDNTLQVDINGFTTGRRGDLATIHGMNRPFLLLMAT<br>PLERAQHLQSSRHRRALDTNYCFSSTEKNCCVRQLYIDF<br>RKDLGWKWIHEPKGYHANFCLGPCPYIWSLDTQYSKVL<br>ALYNQHNPGASAAPCCVPQALEPLPIVYYVGRKPKVEQ<br>LSNMIVRSCKCS | 25 |
| TGFβ1 LAP C4S | Mouse | LSTSKTIDMELVKRKRIEAIRGQILSKLRLASPPSQGEVPP<br>GPLPEAVLALYNSTRDRVAGESADPEPEPEADYYAKEV<br>TRVLMVDRNNAIYEKTKDISHSIYMFFNTSDIREAVPEPP<br>LLSRAELRLQRLKSSVEQHVELYQKYSNNSWRYLGNRL<br>LTPTDTPEWLSFDVTGVVRQWLNQGDGIQGFRFSAHCS<br>CDSKDNKLHVEINGISPKRRGDLGTIHDMNRPFLLLMAT<br>PLERAQHLHSSRHRR | 26 |
| TGFβ1 LAP C4S | Cyno | LSTSKTIDMELVKRKRIEAIRGQILSKLRLASPPSQGEVPP<br>GPLPEAVLALYNSTRDRVAGESAEPEPEPEADYYAKEVT<br>RVLMVETHNEIYDKFKQSTHSIYMFFNTSELREAVPEPV<br>LLSRAELRLLRLKLKVEQHVELYQKYSNNSWRYLSNRL<br>LAPSDSPEWLSFDVTGVVRQWLSRGGEIEGFRLSAHCSC<br>DSKDNTLQVDINGFTTGRRGDLATIHGMNRPFLLLMAT<br>PLERAQHLQSSRHRR | 27 |
| proTGFβ1 C4S D2G | Mouse | LSTSKTIDMELVKRKRIEAIRGQILSKLRLASPPSQGEVPP<br>GPLPEAVLALYNSTRDRVAGESADPEPEPEADYYAKEV<br>TRVLMVDRNNAIYEKTKDISHSIYMFFNTSDIREAVPEPP<br>LLSRAELRLQRLKSSVEQHVELYQKYSNNSWRYLGNRL<br>LTPTDTPEWLSFDVTGVVRQWLNQGDGIQGFRFSAHCS<br>CDSKDNKLHVEINGISPKRRGDLGTIHDMNRPFLLLMAT<br>PLERAQHLHSSRHGALDTNYCFSSTEKNCCVRQLYIDFR<br>KDLGWKWIHEPKGYHANFCLGPCPYIWSLDTQYSKVLA<br>LYNQHNPGASASPCCVPQALEPLPIVYYVGRKPKVEQLS<br>NMIVRSCKCS | 28 |
| proTGFβ1 C4S | Mouse | LSTSKTIDMELVKRKRIEAIRGQILSKLRLASPPSQGEVPP<br>GPLPEAVLALYNSTRDRVAGESADPEPEPEADYYAKEV<br>TRVLMVDRNNAIYEKTKDISHSIYMFFNTSDIREAVPEPP<br>LLSRAELRLQRLKSSVEQHVELYQKYSNNSWRYLGNRL<br>LTPTDTPEWLSFDVTGVVRQWLNQGDGIQGFRFSAHCS<br>CDSKDNKLHVEINGISPKRRGDLGTIHDMNRPFLLLMAT<br>PLERAQHLHSSRHRRALDTNYCFSSTEKNCCVRQLYIDF<br>RKDLGWKWIHEPKGYHANFCLGPCPYIWSLDTQYSKVL<br>ALYNQHNPGASASPCCVPQALEPLPIVYYVGRKPKVEQ<br>LSNMIVRSCKCS | 29 |
| proTGFβ1 C4S | Cyno | LSTSKTIDMELVKRKRIEAIRGQILSKLRLASPPSQGEVPP<br>GPLPEAVLALYNSTRDRVAGESAEPEPEPEADYYAKEVT<br>RVLMVETHNEIYDKFKQSTHSIYMFFNTSELREAVPEPV<br>LLSRAELRLLRLKLKVEQHVELYQKYSNNSWRYLSNRL<br>LAPSDSPEWLSFDVTGVVRQWLSRGGEIEGFRLSAHCSC<br>DSKDNTLQVDINGFTTGRRGDLATIHGMNRPFLLLMAT<br>PLERAQHLQSSRHRRALDTNYCFSSTEKNCCVRQLYIDF<br>RKDLGWKWIHEPKGYHANFCLGPCPYIWSLDTQYSKVL<br>ALYNQHNPGASAAPCCVPQALEPLPIVYYVGRKPKVEQ<br>LSNMIVRSCKCS | 30 |
| proTGFβ1 C4S D2G | Cyno | LSTSKTIDMELVKRKRIEAIRGQILSKLRLASPPSQGEVPP<br>GPLPEAVLALYNSTRDRVAGESAEPEPEPEADYYAKEVT<br>RVLMVETHNEIYDKFKQSTHSIYMFFNTSELREAVPEPV<br>LLSRAELRLLRLKLKVEQHVELYQKYSNNSWRYLSNRL<br>LAPSDSPEWLSFDVTGVVRQWLSRGGEIEGFRLSAHCSC<br>DSKDNTLQVDINGFTTGRRGDLATIHGMNRPFLLLMAT<br>PLERAQHLQSSRHGALDTNYCFSSTEKNCCVRQLYIDFR<br>KDLGWKWIHEPKGYHANFCLGPCPYIWSLDTQYSKVLA<br>LYNQHNPGASAAPCCVPQALEPLPIVYYVGRKPKVEQL<br>SNMIVRSCKCS | 31 |

In some embodiments, an antibody, or antigen binding portion thereof, as described herein, is capable of selectively binding to a LTBP-TGFβ1 complex. In some embodiments, antigenic protein complexes (e.g., a LTBP-TGFβ1 complex) may comprise one or more LTBP proteins (e.g., LTBP1, LTBP2, LTBP3, and LTBP4).

In some embodiments, the antibody, or antigen binding portion thereof, selectively binds a LTBP1-TGFβ1 complex. In some embodiments, the LTBP1 protein is a naturally-occurring protein. In some embodiments, the LTBP1 protein is a non-naturally occurring protein. In some embodiments, the LTBP1 protein is a recombinant protein. Such recombinant LTBP1 protein may comprise LTBP1, alternatively spliced variants thereof, and/or fragments thereof. Recombinant LTBP1 proteins may also be modified to comprise one or more detectable labels. In some embodiments, the LTBP1 protein comprises a leader sequence (e.g., a native or non-native leader sequence). In some embodiments, the LTBP1 protein does not comprise a leader sequence (i.e., the leader sequence has been processed or cleaved). Such detectable labels may include, but are not limited to biotin labels, polyhistidine tags, myc tags, HA tags and/or fluorescent tags. In some embodiments, the LTBP1 protein is a mammalian LTBP1 protein. In some embodiments, the LTBP1 protein is a human, a monkey, a mouse, or a rat LTBP1 protein. In some embodiments, the LTBP1 protein comprises an amino acid sequence as set forth in SEQ ID NO: 32 in Table 3. In some embodiments, the LTBP1 protein comprises an amino acid sequence as set forth in SEQ ID NOs: 33 or SEQ ID NO: 34 in Table 3.

In some embodiments, an antibody, or antigen binding portion thereof, as described herein, is capable of binding to a LTBP3-TGFβ1 complex. In some embodiments, the LTBP3 protein is a naturally-occurring protein. In some embodiments, the LTBP3 protein is a non-naturally occurring protein. In some embodiments, the LTBP3 protein is a recombinant protein. Such recombinant LTBP3 protein may comprise LTBP3, alternatively spliced variants thereof and/or fragments thereof. In some embodiments, the LTBP3 protein comprises a leader sequence (e.g., a native or non-native leader sequence). In some embodiments, the LTBP3 protein does not comprise a leader sequence (i.e., the leader sequence has been processed or cleaved). Recombinant LTBP3 proteins may also be modified to comprise one or more detectable labels. Such detectable labels may include, but are not limited to biotin labels, polyhistidine tags, myc tags, HA tags and/or fluorescent tags. In some embodiments, the LTBP3 protein is a mammalian LTBP3 protein. In some embodiments, the LTBP3 protein is a human, a monkey, a mouse, or a rat LTBP3 protein. In some embodiments, the LTBP3 protein comprises an amino acid sequence as set forth in SEQ ID NO: 35. In some embodiments, the LTBP3 protein comprises an amino acid sequence as set forth in SEQ ID NOs: 36 or 37.

TABLE 3

Exemplary LTBP amino acid sequences.

| Protein | Species | Sequence | SEQ ID NO |
|---|---|---|---|
| LTBP1S | Human | NHTGRIKVVFTPSICKVTCTKGSCQNSCEKGNTTTL ISENGHAADTLTATNFRVVICHLPCMNGGQCSSRD KCQCPPNFTGKLCQIPVHGASVPKLYQHSQQPGKA LGTHVIHSTHTLPLTVTSQQGVKVKFPPNIVNIHVK HPPEASVQIHQVSRIDGPTGQKTKEAQPGQSQVSY QGLPVQKTQTIHSTYSHQQVIPHVYPVAAKTQLGR CFQETIGSQCGKALPGLSKQEDCCGTVGTSWGFNK CQKCPKKPSYHGYNQMMECLPGYKRVNNTFCQDI NECQLQGVCPNGECLNTMGSYRCTCKIGFGPDPTF SSCVPDPPVISEEKGPCYRLVSSGRQCMHPLSVHLT KQLCCCSVGKAWGPHCEKCPLPGTAAFKEICPGG MGYTVSGVHRRRPIHHHVGKGPVFVKPKNTQPVA KSTHPPPLPAKEEPVEALTFSREHGPGVAEPEVATA PPEKEIPSLDQEKTKLEPGQPQLSPGISTIHLHPQFPV VIEKTSPPVPVEVAPEASTSSASQVIAPTQVTEINEC TVNPDICGAGHCINLPVRYTCICYEGYRFSEQQRKC VDIDECTQVQHLCSQGRCENTEGSFLCICPAGFMAS EEGTNCIDVDECLRPDVCGEGHCVNTVGAFRCEYC DSGYRMTQRGRCEDIDECLNPSTCPDEQCVNSPGS YQCVPCTEGFRGWNGQCLDVDECLEPNVCANGDC SNLEGSYMCSCHKGYTRTPDHKHCRDIDECQQGN LCVNGQCKNTEGSFRCTCGQGYQLSAAKDQCEDI DECQHRHLCAHGQCRNTEGSFQCVCDQGYRASGL GDHCEDINECLEDKSVCQRGDCINTAGSYDCTCPD GFQLDDNKTCQDINECEHPGLCGPQGECLNTEGSF HCVCQQGFSISADGRTCEDIDECVNNTVCDSHGFC DNTAGSFRCLCYQGFQAPQDGQGCVDVNECELLS GVCGEAFCENVEGSFLCVCADENQEYSPMTGQCR SRTSTDLDVDVDQPKEEKKECYYNLNDASLCDNV LAPNVTKQECCCTSGVGWGDNCEIFPCPVLGTAEF TEMCPKGKGFVPAGESSSEAGGENYKDADECLLFG QEICKNGFCLNTRPGYECYCKQGTYYDPVKLQCFD MDECQDPSSCIDGQCVNTEGSYNCFCTHPMVLDAS EKRCIRPAESNEQIEETDVYQDLCWEHLSDEYVCS RPLVGKQTTYTECCCLYGEAWGMQCALCPLKDSD DYAQLCNIPVTGRRQPYGRDALVDFSEQYTPEADP YFIQDRFLNSFEELQAEECGILNGCENGRCVRVQEG YTCDCFDGYHLDTAKMTCVDVNECDELNNRMSL CKNAKCINTDGSYKCLCLPGYVPSDKPNYCTPLNT ALNLEKDSDLE | 32 |

TABLE 3-continued

Exemplary LTBP amino acid sequences.

| Protein | Species | Sequence | SEQ ID NO |
|---|---|---|---|
| LTBP1S | Cyno | NHTGRIKVVFTPSICKVTCTKGSCQNSCEKGNTTTL ISENGHAADTLTATNFRVVLCHLPCMNGGQCSSRD KCQCPPNFTGKLCQIPVHGASVPKLYQHSQQPGKA LGTHVIHSTHTLPLTVTSQQGVKVKFPPNIVNIHVK HPPEASVQIHQVSRIDGPTGQKTKEAQPGQS QVSY QGLPVQKTQTIHSTYSHQQVIPHVYPVAAKTQLGR CFQETIGSQCGKALPGLSKQEDCCGTVGTSWGFNK CQKCPKKPSYHGYNQMMECLPGYKRVNNTFCQDI NECQLQGVCPNGECLNTMGSYRCTCKIGFGPDPTF SSCVPDPPVISEEKGPCYRLVSSGRQCMHPLSVHLT KQLCCCSVGKAWGPHCEKCPLPGTAAFKEICPGG MGYTVSGVHRRRPIHHHVGKGPVFVKPKNTQPVA KSTHPPPLPAKEEPVEALTFSREHGPGVAEPEVATA PPEKEIPSLDQEKTKLEPGQPQLSPGISTIHLHPQFPV VIEKTSPPVPVEVAPEASTSSASQVIAPTQVTEINEC TVNPDICGAGHCINLPVRYTCICYEGYKFSEQQRKC VDIDECTQVQHLCSQGRCENTEGSFLCICPAGFMAS EEGTNCIDVDECLRPDVCGEGHCVNTVGAFRCEYC DSGYRMTQRGRCEDIDECLNPSTCPDEQCVNSPGS YQCVPCTEGFRGWNGQCLDVDECLEPNVCTNGDC SNLEGSYMCSCHKGYTRTPDHKHCKDIDECQQGN LCVNGQCKNTEGSFRCTCGQGYQLSAAKDQCEDI DECQHHHLCAHGQCRNTEGSFQCVCDQGYRASGL GDHCEDINECLEDKSVCQRGDCINTAGSYDCTCPD GFQLDDNKTCQDINECEHPGLCGPQGECLNTEGSF HCVCQQGFSISADGRTCEDIDECVNNTVCDSHGFC DNTAGSFRCLCYQGFQAPQDGQGCVDVNECELLS GVCGEAFCENVEGSFLCVCADENQEYSPMTGQCR SRTSTDLDVEQPKEEKKECYYNLNDASLCDNVLAP NVTKQECCCTSGAGWGDNCEIFPCPVLGTAEFTEM CPKGKGFVPAGESSSEAGGENYKDADECLLFGQEI CKNGFCLNTRPGYECYCKQGTYYDPVKLQCFDMD ECQDPSSCIDGQCVNTEGSYNCFCTHPMVLDASEK RCIRPAESNEQIEETDVYQDLCWEHLSDEYVCSRPL VGKQTTYTECCCLYGEAWGMQCALCPMKDSDDY AQLCNIPVTGRRQPYGRDALVDFSEQYAPEADPYFI QDRFLNSFEELQAEECGILNGCENGRCVRVQEGYT CDCFDGYHLDTAKMTCVDVNECDELNNRMSLCK NAKCINTEGSYKCLCLPGYVPSDKPNYCTPLNTAL NLEKDSDLE | 33 |
| LTBP1S | mouse | NHTGRIKVVFTPSICKVTCTKGNCQNSCQKGNTTT LISENGHAADTLTATNFRVVICHLPCMNGGQCSSR DKCQCPPNFTGKLCQIPVLGASMPKLYQHAQQQG KALGSHVIHSTHTLPLTMTSQQGVKVKFPPNIVNIH VKHPPEASVQIHQVSRIDSPGGQKVKEAQPGQSQV SYQGLPVQKTQTVHSTYSHQQLIPHVYPVAAKTQL GRCFQETIGSQCGKALPGLSKQEDCCGTVGTSWGF NKCQKCPKKQSYHGYTQMMECLQGYKRVNNTFC QDINECQLQGVCPNGECLNTMGSYRCSCKMGFGP DPTFSSCVPDPPVISEEKGPCYRLVSPGRHCMHPLS VHLTKQICCCSVGKAWGPHCEKCPLPGTAAFKEIC PGGMGYTVSGVHRRRPIHQHIGKEAVYVKPKNTQ PVAKSTHPPPLPAKEEPVEALTSSWEHGPRGAEPEV VTAPPEKEIPSLDQEKTRLEPGQPQLSPGVSTIHLHP QFPVVVEKTSPPVPVEVAPEASTSSASQVIAPTQVT EINECTVNPDICGAGHCINLPVRYTCICYEGYKFSE QLRKCVDIDECAQVRHLCSQGRCENTEGSFLCVCP AGFMASEEGTNCIDVDECLRPDMCRDGRCINTAGA FRCEYCDSGYRMSRRGYCEDIDECLKPSTCPEEQC VNTPGSYQCVPCTEGFRGWNGQCLDVDECLQPKV CTNGSCTNLEGSYMCSCHRGYSPTPDHRHCQDIDE CQQGNLCMNGQCRNTDGSFRCTCGQGYQLSAAK DQCEDIDECEHHHLCSHGQCRNTEGSFQCVCNQG YRASVLGDHCEDINECLEDSSVCQGGDCINTAGSY DCTCPDGFQLNDNKGCQDINECAQPGLCGSHGECL NTQGSFHCVCEQGFSISADGRTCEDIDECVNNTVC DSHGFCDNTAGSFRCLCYQGFQAPQDGQGCVDVN ECELLSGVCGEAFCENVEGSFLCVCADENQEYSPM TGQCRSRVTEDSGVDRQPREEKKECYYNLNDASL CDNVLAPNVTKQECCCTSGAGWGDNCEIFPCPVQ GTAEFTEMCPRGKGLVPAGESSYDTGGENYKDAD ECLLFGEEICKNGYCLNTQPGYECYCKQGTYYDPV KLQCFDMDECQDPNSCIDGQCVNTEGSYNCFCTHP | 34 |

TABLE 3-continued

Exemplary LTBP amino acid sequences.

| Protein | Species | Sequence | SEQ ID NO |
|---|---|---|---|
| | | MVLDASEKRCVQPTESNEQIEETDVYQDLCWEHLS EEYVCSRPLVGKQTTYTECCCLYGEAWGMQCALC PMKDSDDYAQLCNIPVTGRRRPYGRDALVDFSEQ YGPETDPYFIQDRFLNSFEELQAEECGILNGCENGR CVRVQEGYTCDCFDGYHLDMAKMTCVDVNECSE LNNRMSLCKNAKCINTEGSYKCLCLPGYIPSDKPN YCTPLNSALNLDKESDLE | |
| LTBP3 | Human | GPAGERGAGGGGALARERFKVVFAPVICKRTCLK GQCRDSCQQGSNMTLIGENGHSTDTLTGSGFRVVV CPLPCMNGGQCSSRNQCLCPPDFTGRFCQVPAGGA GGGTGGSGPGLSRTGALSTGALPPLAPEGDSVASK HAIYAVQVIADPPGPGEGPPAQHAAFLVPLGPGQIS AEVQAPPPVVNVRVHHPPEASVQVHRIESSNAESA APSQHLLPHPKPSHPRPPTQKPLGRCFQDTLPKQPC GSNPLPGLTKQEDCCGSIGTAWGQSKCHKCPQLQY TGVQKPGPVRGEVGADCPQGYKRLNSTHCQDINE CAMPGVCRHGDCLNNPGSYRCVCPPGHSLGPSRT QCIADKPEEKSLCFRLVSPEHQCQHPLTTRLTRQLC CCSVGKAWGARCQRCPTDGTAAFKEICPAGKGYH ILTSHQTLTIQGESDFSLFLHPDGPPKPQQLPESPSQ APPPEDTEEERGVTTDSPVSEERSVQQSHPTATTTP ARPYPELISRPSPPTMRWFLPDLPPSRSAVEIAPTQV TETDECRLNQNICGHGECVPGPPDYSCHCNPGYRS HPQHRYCVDVNECEAEPCGPGRGICMNTGGSYNC HCNRGYRLHVGAGGRSCVDLNECAKPHLCGDGGF CINFPGHYKCNCYPGYRLKASRPPVCEDIDECRDPS SCPDGKCENKPGSFKCIACQPGYRSQGGGACRDVN ECAEGSPCSPGWCENLPGSFRCTCAQGYAPAPDGR SCLDVDECEAGDVCDNGICSNTPGSFQCQCLSGYH LSRDRSHCEDIDECDFPAACIGGDCINTNGSYRCLC PQGHRLVGGRKCQDIDECSQDPSLCLPHGACKNLQ GSYVCVCDEGFTPTQDQHGCEEVEQPHHKKECYL NFDDTVFCDSVLATNVTQQECCCSLGAGWGDHCE IYPCPVYSSAEFHSLCPDGKGYTQDNNIVNYGIPAH RDIDECMLFGSEICKEGKCVNTQPGYECYCKQGFY YDGNLLECVDVDECLDESNCRNGVCENTRGGYRC ACTPPAEYSPAQRQCLSPEEMDVDECQDPAACRPG RCVNLPGSYRCECRPPWVPGPSGRDCQLPESPAER APERRDVCWSQRGEDGMCAGPLAGPALTFDDCCC RQGRGWGAQCRPCPPRGAGSHCPTSQSESNSFWD TSPLLLGKPPRDEDSSEEDSDECRCVSGRCVPRPGG AVCECPGGFQLDASRARCVDIDECRELNQRGLLCK SERCVNTSGSFRCVCKAGFARSRPHGACVPQRRR | 35 |
| LTBP3 | CYNO | GPAGERGAGGGGALARERFKVVFAPVICKRTCLK GQCRDSCQQGSNMTLIGENGHSTDTLTGSGFRVVV CPLPCMNGGQCSSRNQCLCPPDFTGRFCQVPAGGA GGGTGGSGPGLSRAGALSTGALPPLAPEGDSVASK HAIYAVQVIADPPGPGEGPPAQHAAFLVPLGPGQIS AEVQAPPPVVNVRVHHPPEASVQVHRIESSNAEGA APSQHLLPHPKPSHPRPPTQKPLGRCFQDTLPKQPC GSNPLPGLTKQEDCCGSIGTAWGQSKCHKCPQLQY TGVQKPGPVRGEVGADCPQGYKRLNSTHCQDINE CAMPGVCRHGDCLNNPGSYRCVCPPGHSLGPSRT QCIADKPEEKSLCFRLVSPEHQCQHPLTTRLTRQLC CCSVGKAWGARCQRCPADGTAAFKEICPAGKGYH ILTSHQTLTIQGESDFSLFLHPDGPPKPQQLPESPSQ APPPEDTEEERGVTTDSPVSEERSVQQSHPTATTSP ARPYPELISRPSPPTMRWFLPDLPPSRSAVEIAPTQV TETDECRLNQNICGHGECVPGPPDYSCHCNPGYRS HPQHRYCVDVNECEAEPCGPGRGICMNTGGSYNC HCNRGYRLHVGAGGRSCVDLNECAKPHLCGDGGF CINFPGHYKCNCYPGYRLKASRPPVCEDIDECRDPS SCPDGKCENKPGSFKCIACQPGYRSQGGGACRDVN ECAEGSPCSPGWCENLPGSFRCTCAQGYAPAPDGR SCVDVDECEAGDVCDNGICTNTPGSFQCQCLSGYH LSRDRSHCEDIDECDFPAACIGGDCINTNGSYRCLC PQGHRLVGGRKCQDIDECTQDPGLCLPHGACKNL QGSYVCVCDEGFTPTQDQHGCEEVEQPHHKKECY LNFDDTVFCDSVLATNVTQQECCCSLGAGWGDHC EIYPCPVYSSAEFHSLCPDGKGYTQDNNIVNYGIPA HRDIDECMLFGAEICKEGKCVNTQPGYECYCKQGF YYDGNLLECVDVDECLDESNCRNGVCENTRGGYR CACTPPAEYSPAQRQCLSPEEMDVDECQDPAACRP | 36 |

TABLE 3-continued

Exemplary LTBP amino acid sequences.

| Protein | Species | Sequence | SEQ ID NO |
|---|---|---|---|
| | | GRCVNLPGSYRCECRPPWVPGPSGRDCQLPESPAE RAPERRDVCWSQRGEDGMCAGPQAGPALTFDDCC CRQGRGWGAQCRPCPPRGAGSQCPTSQSESNSFW DTSPLLLGKPRRDEDSSEEDSDECRCVSGRCVPRPG GAVCECPGGFQLDASRARCVDIDECRELNQRGLLC KSERCVNTSGSFRCVCKAGFARSRPHGACVPQRRR | |
| LTBP3 | Mouse | GPAGERGTGGGGALARERFKVVFAPVICKRTCLKG QCRDSCQQGSNMTLIGENGHSTDTLTGSAFRVVVC PLPCMNGGQCSSRNQCLCPPDFTGRFCQVPAAGTG AGTGSSGPGLARTGAMSTGPLPPLAPEGESVASKH AIYAVQVIADPPGPGEGPPAQHAAFLVPLGPGQISA EVQAPPPVVNVRVHHPPEASVQVHRIEGPNAEGPA SSQHLLPHPKPPHPRPPTQKPLGRCFQDTLPKQPCG SNPLPGLTKQEDCCGSIGTAWGQSKCHKCPQLQYT GVQKPVPVRGEVGADCPQGYKRLNSTHCQDINEC AMPGNVCHGDCLNNPGSYRCVCPPGHSLGPLAAQ CIADKPEEKSLCFRLVSTEHQCQHPLTTRLTRQLCC CSVGKAWGARCQRCPADGTAAFKEICPGKGYHILT SHQTLTIQGESDFSLFLHPDGPPKPQQLPESPSRAPP LEDTEEERGVTMDPPVSEERSVQQSHPTTTTSPPRP YPELISRPSPPTFHRFLPDLPPSRSAVEIAPTQVTETD ECRLNQNICGHGQCVPGPSDYSCHCNAGYRSHPQH RYCVDVNECEAEPCGPGKGICMNTGGSYNCHCNR GYRLHVGAGGRSCVDLNECAKPHLCGDGGFCINFP GHYKCNCYPGYRLKASRPPICEDIDECRDPSTCPDG KCENKPGSFKCIACQPGYRSQGGGACRDVNECSEG TPCSPGWCENLPGSYRCTCAQYEPAQDGLSCIDVD ECEAGKVCQDGICTNTPGSFQCQCLSGYHLSRDRS RCEDIDECDFPAACIGGDCINTNGSYRCLCPLGHRL VGGRKCKKDIDECSQDPGLCLPHACENLQGSYVC VCDEGFTLTQDQHGCEEVEQPHHKKECYLNFDDT VFCDSVLATNVTQQECCCSLGAGWGDHCEIYPCPV YSSAEFHSLVPDGKRLHSGQQHCELCIPAHRDIDEC ILFGAEICKEGKCVNTQPGYECYCKQGFYYDGNLL ECVDVDECLDESNCRNGVCENTRGGYRCACTPPA EYSPAQAQCLIPERWSTPQRDVKCAGASEERTACV WGPWAGPALTFDDCCCRQPRLGTQCRPCPPRGTG SQCPTSQSESNSFWDTSPLLLGKSPRDEDSSEEDSD ECRCVSGRCVPRPGGAVCECPGGFQLDASRARCV DIDECRELNQRGLLCKSERCVNTSGSFRCVCKAGF TRSRPHGPACLSAAADDAAIAHTSVIDHRGYFH | 37 |

In an exemplary embodiment, inhibitors, e.g., antibodies, and antigen-binding portions thereof, that selectively bind LTBP1-TGFβ1 and/or LTBP3-TGFβ1 do not bind to a complex containing TGFβ1 and GARP or LRRC33. In one embodiment, the antibodies, or antigen binding portions thereof, do not bind a GARP protein having a sequence set forth in SEQ ID NO:38 or SEQ ID NO:39, and do not bind to a complex containing said GARP protein. In another embodiment, the inhibitors, e.g., antibodies, or antigen binding portions thereof, do not bind a GARP protein having a sequence set forth in SEQ ID NO:40 or SEQ ID NO:41, and do not bind to a complex containing said GARP protein. In one embodiment, the inhibitors, e.g., antibodies, or antigen binding portions thereof, do not bind a LRRC33 protein having a sequence set forth in SEQ ID NO:42 or SEQ ID NO:43, and do not bind to a complex containing said LRRC33 protein. In one embodiment, the inhibitors, e.g., antibodies, or antigen binding portions thereof, do not bind a GARP/LRRC33 chimera, e.g., the GARP/LRRC33 chimera set forth in SEQ ID NO:44.

TABLE 4

Exemplary GARP and LRRC33 amino acid sequences.

| Protein | Sequence | SEQ ID NO |
|---|---|---|
| GARP | AQHQDKVPCKMVDKKVSCQVLGLLQVPSVLPPDTETLDLS GNQLRSILASPLGFYTALRHLDLSTNEISFLQPGAFQALTHL EHLSLAHNRLAMATALSAGGLGPLPRVTSLDLSGNSLYSG LLERLLGEAPSLHTLSLAENSLTRLTRHTFRDMPALEQLDL HSNVLMDIEDGAFEGLPRLTHLNLSRNSLTCISDFSLQQLRV LDLSCNSIEAFQTASQPQAEFQLTWLDLRENKLLHFPDLAA LPRLIYLNLSNNLIRLPTGPPQDSKGIHAPSEGWSALPLSAPS GNASGRPLSQLLNLDLSYNEIELIPDSFLEHLTSLCFLNLSRN CLRTFEARRLGSLPCLMLLDLSHNALETLELGARALGSLRT | 38 |

TABLE 4-continued

Exemplary GARP and LRRC33 amino acid sequences.

| Protein | Sequence | SEQ ID NO |
|---|---|---|
| | LLLQGNALRDLPPYTFANLASLQRLNLQGNRVSPCGGPDEP<br>GPSGCVAFSGITSLRSLSLVDNEIELLRAGAFLHTPLTELDLS<br>SNPGLEVATGALGGLEASLEVLALQGNGLMVLQVDLPCFI<br>CLKRLNLAENRLSHLPAWTQAVSLEVLDLRNNSFSLLPGSA<br>MGGLETSLRRLYLQGNPLSCCGNGWLAAQLHQGRVDVDA<br>TQDLICRFSSQEEVSLSHVRPEDCEKGGLKNINLIIILTFILVS<br>AILLTTLAACCCVRRQKFNQQYKA | |
| sGARP | AQHQDKVPCKMVDKKVSCQVLGLLQVPSVLPPDTETLDLS<br>GNQLRSILASPLGFYTALRHLDLSTNEISFLQPGAFQALTHL<br>EHLSLAHNRLAMATALSAGGLGPLPRVTSLDLSGNSLYSG<br>LLERLLGEAPSLHTLSLAENSLTRLTRHTFRDMPALEQLDL<br>HSNVLMDIEDGAFEGLPRLTHLNLSRNSLTCISDFSLQQLRV<br>LDLSCNSIEAFQTASQPQAEFQLTWLDLRENKLLHFPDLAA<br>LPRLIYLNLSNNLIRLPTGPPQDSKGIHAPSEGWSALPLSAPS<br>GNASGRPLSQLLNLDLSYNEIELIPDSFLEHLTSLCFLNLSRN<br>CLRTFEARRLGSLPCLMLLDLSHNALETLELGARALGSLRT<br>LLLQGNALRDLPPYTFANLASLQRLNLQGNRVSPCGGPDEP<br>GPSGCVAFSGITSLRSLSLVDNEIELLRAGAFLHTPLTELDLS<br>SNPGLEVATGALGGLEASLEVLALQGNGLMVLQVDLPCFI<br>CLKRLNLAENRLSHLPAWTQAVSLEVLDLRNNSFSLLPGSA<br>MGGLETSLRRLYLQGNPLSCCGNGWLAAQLHQGRVDVDA<br>TQDLICRFSSQEEVSLSHVRPEDCEKGGLKNIN | 39 |
| GARP mouse | ISQRREQVPCRTVNKEALCHGLGLLQVPSVLSLDIQALYLS<br>GNQLQSILVSPLGFYTALRHLDLSDNQISFLQAGVFQALPY<br>LEHLNLAHNRLATGMALNSGGLGRLPLLVSLDLSGNSLHG<br>NLVERLLGETPRLRTLSLAENSLTRLARHTFWGMPAVEQL<br>DLHSNVLMDIEDGAFEALPHLTHLNLSRNSLTCISDFSLQQL<br>QVLDLSCNSIEAFQTAPEPQAQFQLAWLDLRENKLLHFPDL<br>AVFPRLIYLNVSNNLIQLPAGLPRGSEDLHAPSEGWSASPLS<br>NPSRNASTHPLSQLLNLDLSYNEIELVPASFLEHLTSLRFLN<br>LSRNCLRSFEARQVDSLPCLVLLDLSHNVLEALELGTKVLG<br>SLQTLLLQDNALQELPPYTFASLASLQRLNLQGNQVSPCGG<br>PAEPGPPGCVDFSGIPTLHVLNMAGNSMGMLRAGSFLHTP<br>LTELDLSTNPGLDVATGALVGLEASLEVLELQGNGLTVLR<br>VDLPCFLRLKRLNLAENQLSHLPAWTRAVSLEVLDLRNNS<br>FSLLPGNAMGGLETSLRRLYLQGNPLSCCGNGWLAAQLHQ<br>GRVDVDATQDLICRFGSQEELSLSVRPEDCEKGGLKNVN<br>LILLLSFTLVSAIVLTTLATICFLRRQKLSQQYKA | 40 |
| sGARP mouse | ISQRREQVPCRTVNKEALCHGLGLLQVPSVLSLDIQALYLS<br>GNQLQSILVSPLGFYTALRHLDLSDNQISFLQAGVFQALPY<br>LEHLNLAHNRLATGMALNSGGLGRLPLLVSLDLSGNSLHG<br>NLVERLLGETPRLRTLSLAENSLTRLARHTFWGMPAVEQL<br>DLHSNVLMDIEDGAFEALPHLTHLNLSRNSLTCISDFSLQQL<br>QVLDLSCNSIEAFQTAPEPQAQFQLAWLDLRENKLLHFPDL<br>AVFPRLIYLNVSNNLIQLPAGLPRGSEDLHAPSEGWSASPLS<br>NPSRNASTHPLSQLLNLDLSYNEIELVPASFLEHLTSLRFLN<br>LSRNCLRSFEARQVDSLPCLVLLDLSHNVLEALELGTKVLG<br>SLQTLLLQDNALQELPPYTFASLASLQRLNLQGNQVSPCGG<br>PAEPGPPGCVDFSGIPTLHVLNMAGNSMGMLRAGSFLHTP<br>LTELDLSTNPGLDVATGALVGLEASLEVLELQGNGLTVLR<br>VDLPCFLRLKRLNLAENQLSHLPAWTRAVSLEVLDLRNNS<br>FSLLPGNAMGGLETSLRRLYLQGNPLSCCGNGWLAAQLHQ<br>GRVDVDATQDLICRFGSQEELSLSVRPEDCEKGGLKNVN | 41 |
| LRRC33 (also known as NRROS; Uniprot Accession No. Q86YC3) | MELLPLWLCLGFHFLTVGWRNRSGTATAASQGVCKLVG<br>GAADCRGQSLASVPSSLPPHARMLTLDANPLKTLWNHSLQ<br>PYPLLESLSLHSCHLERISRGAFQEQGHLRSLVLGDNCLSEN<br>YEETAAALHALPGLRRLDLSGNALTEDMAALMLQNLSSLR<br>SVSLAGNTIMRLDDSVFEGLERLRELDLQRNYIFEIEGGAFD<br>GLAELRHLNLAFNNLPCIVDFGLTRLRVLNVSYNVLEWFL<br>ATGGEAAFELETLDLSHNQLLFFPLLPQYSKLRTLLLRDNN<br>MGFYRDLYNTSSPREMVAQFLLVDGNVTNITTVSLWEEFS<br>SSDLADLRFLDMSQNQFQYLPDGFLRKMPSLSHLNLHQNC<br>LMTLHIREHEPPGALTELDLSHNQLSELHLAPGLASCLGSL<br>RLFNLSSNQLLGVPPGLFANARNITTLDMSHNQISLCPLPAA<br>SDRVGPPSCVDFRNMASLRSLSLEGCGLGALPDCPFQGTSL<br>TYLDLSSNWGVLNGSLAPLQDVAPMLQVLSLRNMGLHSSF<br>MALDFSGFGNLRDLDLSGNCLTTFPRFGGSLALETLDLRRN | 42 |

TABLE 4-continued

Exemplary GARP and LRRC33 amino acid sequences.

| Protein | Sequence | SEQ ID NO |
|---|---|---|
| | SLTALPQKAVSEQLSRGLRTIYLSQNPYDCCGVDGWGALQ<br>HGQTVADWAMVTCNLSSKIIRVTELPGGVPRDCKWERLDL<br>GLLYLVLILPSCLTLLVACTVIVLTFKKPLLQVIKSRCHWSS<br>VY<br>* Native signal peptide is depicted in bold font. | |
| soluble LRRC33 (sLRRC33) | MDMRVPAQLLGLLLLWFSGVLGWRNRSGTATAASQGV<br>CKLVGGAADCRGQSLASVPSSLPPHARMLTLDANPLKTLW<br>NHSLQPYPLLESLSLHSCHLERISRGAFQEQGHLRSLVLGD<br>NCLSENYEETAAALHALPGLRRLDLSGNALTEDMAALML<br>QNLSSLRSVSLAGNTIMRLDDSVFEGLERLRELDLQRNYIFE<br>IEGGAFDGLAELRHLNLAFNNLPCIVDFGLTRLRVLNVSYN<br>VLEWFLATGGEAAFELETLDLSHNQLLFFPLLPQYSKLRTL<br>LLRDNNMGFYRDLYNTSSPREMVAQFLLVDGNVTNITTVS<br>LWEEFSSSDLADLRFLDMSQNQFQYLPDGFLRKMPSLSHL<br>NLHQNCLMTLHIREHEPPGALTELDLSHNQLSELHLAPGLA<br>SCLGSLRLFNLSSNQLLGVPPGLFANARNITTLDMSHNQISL<br>CPLPAASDRVGPPSCVDFRNMASLRSLSLEGCGLGALPDCP<br>FQGTSLTYLDLSSNWGVLNGSLAPLQDVAPMLQVLSLRNM<br>GLHSSFMALDFSGFGNLRDLDLSGNCLTTFPRFGGSLALET<br>LDLRRNSLTALPQKAVSEQLSRGLRTIYLSQNPYDCCGVDG<br>WGALQHGQTVADWAMVTCNLSSKIIRVTELPGGVPRDCK<br>WERLDLGL<u>HHHHHH</u><br>* Modified human kappa light chain signal peptide is depicted in bold font.<br>** Histidine tag is underlined. | 43 |
| Human LRRC33-GARP chimera | MDMRVPAQLLGLLLLWFSGVLGWRNRSGTATAASQGV<br><u>CKLVGGAADCRGQSLASVPSSLPPHARMLTLDANPLKTLW</u><br><u>NHSLQPYPLLESLSLHSCHLERISRGAFQEQGHLRSLVLGD</u><br><u>NCLSENYEETAAALHALPGLRRLDLSGNALTEDMAALML</u><br><u>QNLSSLRSVSLAGNTIMRLDDSVFEGLERLRELDLQRNYIFE</u><br><u>IEGGAFDGLAELRHLNLAFNNLPCIVDFGLTRLRVLNVSYN</u><br><u>VLEWFLATGGEAAFELETLDLSHNQLLFFPLLPQYSKLRTL</u><br><u>LLRDNNMGFYRDLYNTSSPREMVAQFLLVDGNVTNITTVS</u><br><u>LWEEFSSSDLADLRFLDMSQNQFQYLPDGFLRKMPSLSHL</u><br><u>NLHQNCLMTLHIREHEPPGALTELDLSHNQLSELHLAPGLA</u><br><u>SCLGSLRLFNLSSNQLLGVPPGLFANARNITTLDMSHNQISL</u><br><u>CPLPAASDRVGPPSCVDFRNMASLRSLSLEGCGLGALPDCP</u><br><u>FQGTSLTYLDLSSNWGVLNGSLAPLQDVAPMLQVLSLRNM</u><br><u>GLHSSFMALDFSGFGNLRDLDLSGNCLTTFPRFGGSLALET</u><br><u>LDLRRNSLTALPQKAVSEQLSRGLRTIYLSQNPYDCCGVDG</u><br><u>WGALQHGQTVADWAMVTCNLSSKIIRVTELPGGVPRDCK</u><br><u>WERLDLGL</u>*LIIILTFILVSAILLTTLAACCC*<u>VRRQKFNQQYKA</u><br>* Modified human kappa light chain signal peptide is depicted in bold font.<br>** LRRC33 ectodomain is underlined.<br># GARP transmembrane domain is italicized.<br>## GARP intracellular tail is double underlined. | 44 |

In another aspect, the invention provides methods of inhibiting TGFβ1 activation in the context of LTBP1 and/or LTBP3. In one embodiment, the method comprises exposing a LTBP1-proTGFβ1 complex or a LTBP3-proTGFβ1 complex an inhibitor, an antibody or antigen-binding portion thereof, and/or a pharmaceutical composition described herein. For example, in one embodiment, the inhibitor is an inhibitor of extracellular matrix-associated TGFβ1 activation, which selectively binds a LTBP1/3-presented proTGFβ1 latent complex. In one embodiment, the inhibitor does not inhibit immune cell-associated TGFβ1 activation, for example, immune cell-associated TGFβ1 activation that results from activation of a GARP-presented proTGFβ1 latent complex. In another embodiment, the antibody, or antigen-binding portion thereof, selectively binds an LTBP1-proTGFβ1 latent complex and/or an LTBP3-proTGFβ1 latent complex, thereby modulating release of mature TGFβ1 growth factor from the latent complex, wherein the antibody, or antigen-binding portion thereof, does not bind mature TGFβ1 alone or a GARP-proTGFβ1 latent complex. In one embodiment, the antibody, or antigen-binding portion thereof, inhibits the release of mature TGFβ1 from the LTBP1-proTGFβ1 complex and/or the LTBP3-proTGFβ1 complex. In one embodiment, the antibody, or antigen-binding portion thereof, does not inhibit the release of mature TGFβ1 from a GARP-proTGFβ1 complex or a LRRC33-proTGFβ1 complex.

In one embodiment, the method is performed in vitro. In another embodiment, the method is performed in vivo. In one embodiment, the LTBP1-proTGFβ1 complex or the LTBP3-proTGFβ1 complex is in an extracellular matrix. The extracellular matrix can comprise, for example, fibrillin and/or fibronectin. In some embodiments, the extracellular matrix comprises a protein comprising an RGD motif.

In some embodiments of the foregoing aspects, the antibody, or antigen-binding portion thereof, does not stimulate immune effector cells. In one embodiment, the antibody, or antigen-binding portion thereof, inhibits the release of mature TGFβ1 from a LTBP1-proTGFβ1 complex and/or a LTBP3-proTGFβ1 complex, and does not inhibit the release of mature TGFβ1 from a GARP-proTGFβ1 complex and/or an LRRC33-proTGFβ1 complex.

In some embodiments, inhibitors, e.g., antibodies, of the present disclosure that selectively bind to a LTBP1-TGFβ1 complex and/or a LTBP3-TGFβ1 complex can bind the complex with relatively high affinity, e.g., with a dissociation constant ($K_D$) less than $10^{-6}$ M, $10^{-7}$ M, $10^{-8}$ M, $10^{-9}$ M, $10^{-10}$ M, $10^{-11}$ M or lower. In one embodiment, an antibody, or antigen binding portion thereof, binds a LTBP1-TGFβ1 complex and/or a LTBP3-TGFβ1 complex with a dissociation constant ($K_D$) of about $10^{-8}$M, about $10^{-9}$ M, about $10^{-10}$ M, about $10^{-11}$M, about $10^{-12}$ M, or about $10^{-13}$ M. For example, antibodies that selectively bind to a LTBP1-TGFβ1 complex and/or a LTBP3-TGFβ1 complex can bind the complex with an affinity between 5 pM and 500 nM, e.g., between 50 pM and 100 nM, e.g., between 500 pM and 50 nM. In one embodiment, the antibody, or antigen-binding fragment thereof, can bind a LTBP1-TGFβ1 complex and/or a LTBP3-TGFβ1 complex with an affinity of about 20 nm to about 500 nm. For example, the antibody, or antigen-binding fragment thereof, can bind a LTBP1-TGFβ1 complex and/or a LTBP3-TGFβ1 complex with an affinity of about 50 nm to about 450 nm, from about 100 nm to about 400 nm, about 50 nm to about 300 nm, about 100 nm to about 300 nm, from about 150 nm to about 350 nm, from about 200 nm to about 300 nm, about 50 nm, about 100 nm, about 150 nm, about 200 nm, about 250 nm, about 300 nm, about 350 nm, about 400 nm, about 450 nm, or about 500 nm.

The disclosure also includes antibodies or antigen binding fragments that compete with any of the antibodies described herein for binding to a LTBP1-TGFβ1 complex and/or a LTBP3-TGFβ1 complex. In some embodiments, such antibodies have an affinity for the complex of 50 nM or lower (e.g., 20 nM or lower, 10 nM or lower, 500 pM or lower, 50 pM or lower, or 5 pM or lower). The affinity and binding kinetics of antibodies (or antigen binding fragments thereof) that selectively bind to a LTBP1-TGFβ1 complex and/or a LTBP3-TGFβ1 complex can be tested using any suitable method, including but not limited to biosensor technology (e.g., OCTET or BIACORE).

In one embodiment, the antibodies, or antigen-binding fragments thereof, of the present disclosure do not compete with antibody SR-Ab1 for binding to a human LTBP1-proTGFβ1 complex.

Aspects of the disclosure relate to antibodies that compete or cross-compete with any of the antibodies provided herein. The term "compete", as used herein with regard to an antibody, means that a first antibody binds to an epitope (e.g., an epitope of a LTBP1-TGFβ1 complex and/or an epitope of a LTBP3-TGFβ1 complex) in a manner sufficiently similar to the binding of a second antibody, such that the result of binding of the first antibody with its epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its epitope or ligand, whether to the same, greater, or lesser extent, the antibodies are said to "cross-compete" with each other for binding of their respective epitope(s). Both competing and cross-competing antibodies are within the scope of this disclosure. Regardless of the mechanism by which such competition or cross-competition occurs (e.g., steric hindrance, conformational change, or binding to a common epitope, or portion thereof), the skilled artisan would appreciate that such competing and/or cross-competing antibodies are encompassed and can be useful for the methods and/or compositions provided herein.

Aspects of the disclosure relate to antibodies that compete or cross-compete with any of the specific antibodies, or antigen binding portions thereof, as provided herein, e.g., an antibody having one or more CDR sequences (1, 2, 3, 4, 5, or 6 CDR sequences) set forth in Table 5. In one embodiment, the invention provides antibodies, and antigen-binding fragments thereof, that compete or cross-compete with an antibody having heavy chain CDR sequences comprising SEQ ID NO:1, SEQ ID NO:2, and SEQ ID NO:3 as set forth in Table 5, and/or light chain CDR sequences comprising SEQ ID NO:4, SEQ ID NO:5, and SEQ ID NO:6 as set forth in Table 5. In one embodiment, the invention provides antibodies that compete or cross-compete with an antibody, or antigen binding portion thereof, having a heavy chain variable region sequence comprising SEQ ID NO:7, and/or a light chain variable region sequence comprising SEQ ID NO:8. In some embodiments, an antibody, or antigen binding portion thereof, binds at or near the same epitope as any of the antibodies provided herein. In some embodiments, an antibody, or antigen binding portion thereof, binds near an epitope if it binds within 15 or fewer amino acid residues of the epitope. In some embodiments, any of the antibody, or antigen binding portion thereof, as provided herein, binds within 1, 2, 3, 4, 5, 6, 7, 8, 9, 10, 11, 12, 13, 14 or 15 amino acid residues of an epitope that is bound by any of the antibodies provided herein.

In another embodiment, provided herein is an antibody, or antigen binding portion thereof, competes or cross-competes for binding to any of the antigens provided herein (e.g., a LTBP1-TGFβ1 complex and/or a LTBP3-TGFβ1 complex) with an equilibrium dissociation constant, $K_D$, between the antibody and the protein of less than $10^{-6}$ M. In other embodiments, an antibody competes or cross-competes for binding to any of the antigens provided herein with a $K_D$ in a range from $10^{-11}$ M to $10^{-6}$ M. In some embodiments, provided herein is an anti-TGFβ1 antibody, or antigen binding portion thereof, that competes for binding with an antibody, or antigen binding portion thereof, described herein. In some embodiments, provided herein is an anti-TGFβ1 antibody, or antigen binding portion thereof, that binds to the same epitope as an antibody, or antigen binding portion thereof, described herein. The antibodies provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). In some embodiments, the epitope is a TGFβ1 epitope that is only available for binding by the antibody, or antigen binding portion thereof, described herein, when the TGFβ1 is in a LTBP1-TGFβ1 complex and/or a LTBP3-TGFβ1 complex. In some embodiments, the epitope is present on a LTBP1/3-TGFβ1 complex, and is not present on a GARP-TGFβ1 complex and/or a LRRC33-TGFβ1 complex. In some embodiments, the epitope is available due to a conformational change in LTBP1/3 and/or TGFβ1 that occurs when LTBP1/3 and TGFβ1 form a complex. In this embodiment, the epitope is not present in LTBP1/3 or TGFβ1 when the proteins are not associated in a complex. In one embodiment, the epitope is present on TGFβ1, when TGFβ1 is in a complex with LTBP1 or LTBP3. In another embodiment, the epitope is present on LTBP1, when LTBP1 is in a complex with TGFβ1. In another embodiment, the epitope is present on LTBP3, when LTBP3 is in a complex with TGFβ1. In another embodiment, the epitope comprises residues from both LTBP1 and TGFβ1. In another embodiment, the epitope comprises residues from both LTBP3 and TGFβ1. Peptides of varying lengths (e.g., at least 4-6 amino acids long) can be isolated or synthesized (e.g., recombinantly) and used for binding assays with an antibody. In another example, the epitope to which the antibody binds can be determined in a systematic screen by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the LTBP1-TGFβ1 complex or LTBP3-TGFβ1 complex have been replaced (swapped) with sequences from a closely related, but antigenically distinct protein, such as another member of the TGFβ protein family (e.g., GDF11). By assessing binding of the antibody to the mutant of the LTBP1-TGFβ1 complex and/or LTBP3-TGFβ1 complex, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Further, the interaction of the any of the antibodies provided herein with one or more residues in a LTBP1-TGFβ1 complex and/or a LTBP3-TGFβ1 complex can be determined by routine technology. For example, a crystal structure can be determined, and the distances between the residues in a LTBP1-TGFβ1 complex and/or a LTBP3-TGFβ1 complex, and one or more residues in the antibody, can be determined accordingly. Based on such distance, whether a specific residue in a LTBP1/3-TGFβ1 complex interacts with one or more residues in the antibody can be determined. Further, suitable methods, such as competition assays and target mutagenesis assays, can be applied to determine the preferential binding of a candidate antibody.

In some embodiments, the antibodies, or antigen binding portions thereof, of the present invention that selectively bind to a LTBP1-TGFβ1 complex and/or a LTBP3-TGFβ1 complex include one or more of complementary determining regions (CDRs) shown in Table 5. In some embodiments, the invention provides a nucleic acid molecule that encodes an antibody, or antigen binding portion thereof, that selectively binds to a LTBP1-TGFβ1 complex and/or a LTBP3-TGFβ1 complex, as described herein. In one embodiment, the nucleic acid molecules encode one or more of the CDR sequences shown in Table 5.

TABLE 5

Complementary determining regions of the heavy chain (CDRHs) and the light chain (CDRLs) of SR-AB2 and SR-AB10, as determined using the Kabat numbering scheme.

| Antibody | SR-AB2 |
|---|---|
| CDRH1 | GYTFTSYG (SEQ ID NO: 1) |
| CDRH2 | ISAYNGNT (SEQ ID NO: 2) |
| CDRH3 | ARAPLGNFDS (SEQ ID NO: 3) |
| CDRL1 | SGSIASNY (SEQ ID NO: 4) |
| CDRL2 | EDN (SEQ ID NO: 5) |
| CDRL3 | QSYDSSNHPVV (SEQ ID NO: 6) |

| Antibody | SR-AB10 |
|---|---|
| CDRH1 | FTFNNYPIH (SEQ ID NO: 94) |
| CDRH2 | VMSYDGINKYYADSVKG (SEQ ID NO: 95) |
| CDRH3 | ARPRIAARRGGFDY (SEQ ID NO: 96) |
| CDRL1 | TRSSGNIDNNYVQ (SEQ ID NO: 97) |
| CDRL2 | EDNQRPS (SEQ ID NO: 98) |
| CDRL3 | QSYDSDNQGVV (SEQ ID NO: 99) |

In some embodiments, antibodies of the present invention that selectively bind to a LTBP1-TGFβ1 complex and/or a LTBP3-TGFβ1 complex include any antibody, or antigen binding portion thereof, comprising a CDRH1, CDRH2, CDRH3, CDRL1, CDRL2, or CDRL3, or combinations thereof, as provided in Table 5. In some embodiments, antibodies that selectively bind to a LTBP1-TGFβ1 complex and/or a LTBP3-TGFβ1 complex include CDRH1, CDRH2, CDRH3, CDRL1, CDRL2, and CDRL3 as provided in Table 5.

The present invention also provides a nucleic acid sequence that encodes a molecule comprising CDRH1, CDRH2, CDRH3, CDRL1, CDRL2, or CDRL3, or combinations thereof, as provided in Table 5.

Antibody heavy and light chain CDR3 domains may play a particularly important role in the binding specificity/affinity of an antibody for an antigen. Accordingly, in some embodiments, the antibodies, or antigen binding portions thereof, that selectively bind to a LTBP1-TGFβ1 complex and/or a LTBP3-TGFβ1 complex, or the nucleic acid molecules that encode these antibodies, or antigen binding portions thereof, can include at least the heavy and/or light chain CDR3 of the antibody shown in Table 5.

Aspects of the invention relate to a monoclonal antibody, or antigen binding portion thereof, that binds selectively to a LTBP1-TGFβ1 complex and/or a LTBP3-TGFβ1 complex, and that comprises six complementarity determining regions (CDRs): CDRH1, CDRH2, CDRH3, CDRL1, CDRL2, and CDRL3.

In some embodiments, CDRH1 comprises a sequence as set forth in SEQ ID NO: 1. In some embodiments, CDRH2 comprises a sequence as set forth in SEQ ID NO: 2. In some embodiments, CDRH3 comprises a sequence as set forth in SEQ ID NO: 3. In some embodiments, CDRL1 comprises a sequence as set forth in SEQ ID NO: 4. In some embodiments, CDRL2 comprises a sequence as set forth in SEQ ID NO: 5. In some embodiments, CDRL3 comprises a sequence as set forth in SEQ ID NO: 6.

In some embodiments (e.g., as for antibody SR-AB2, shown in Table 5), the antibody, or antigen binding portion thereof, that selectively binds to a LTBP1-TGFβ1 complex and/or a LTBP3-TGFβ1 complex comprises: a CDRH1 comprising an amino acid sequence as set forth in SEQ ID NO: 1, a CDRH2 comprising an amino acid sequence as set forth in SEQ ID NO: 2, a CDRH3 comprising an amino acid sequence as set forth in SEQ ID NO: 3, a CDRL1 comprising an amino acid sequence as set forth in SEQ ID NO: 4, a CDRL2 comprising an amino acid sequence as set forth in SEQ ID NO: 5, and a CDRL3 comprising an amino acid sequence as set forth in SEQ ID NO: 6.

In some embodiments, the antibody, or antigen binding portion thereof, comprises a heavy chain variable region comprising a complementarity determining region 3 (CDR3) having the amino acid sequence of SEQ ID NO: 3 and a light chain variable region comprising a CDR3 having the amino acid sequence of SEQ ID NO: 6. In some embodiments, the antibody, or antigen binding portion thereof, comprises a heavy chain variable region comprising a complementarity determining region 2 (CDR2) having the amino acid sequence of SEQ ID NO: 2 and a light chain variable region comprising a CDR2 having the amino acid sequence of SEQ ID NO: 5. In some embodiments, the antibody, or antigen binding portion thereof, comprises a heavy chain variable region comprising a complementarity determining region 1 (CDR1) having the amino acid sequence of SEQ ID NO: 1 and a light chain variable region comprising a CDR1 having the amino acid sequence of SEQ ID NO: 4.

The amino acid sequences of the heavy chain variable region (HCVR) and the light chain variable region (LCVR) of the antibody set forth in Table 5 (e.g., SR-AB2) are provided in Table 6.

In some embodiments, CDRH1 comprises a sequence as set forth in SEQ ID NO: 94. In some embodiments, CDRH2 comprises a sequence as set forth in SEQ ID NO: 95. In some embodiments, CDRH3 comprises a sequence as set forth in SEQ ID NO: 96. In some embodiments, CDRL1 comprises a sequence as set forth in SEQ ID NO: 97. In some embodiments, CDRL2 comprises a sequence as set forth in SEQ ID NO: 98. In some embodiments, CDRL3 comprises a sequence as set forth in SEQ ID NO: 99.

In some embodiments (e.g., as for antibody SR-AB10, shown in Table 5), the antibody, or antigen binding portion thereof, that selectively binds to a LTBP1-TGFβ1 complex and/or a LTBP3-TGFβ1 complex comprises: a CDRH1 comprising an amino acid sequence as set forth in SEQ ID NO: 94, a CDRH2 comprising an amino acid sequence as set forth in SEQ ID NO: 95, a CDRH3 comprising an amino acid sequence as set forth in SEQ ID NO: 96, a CDRL1 comprising an amino acid sequence as set forth in SEQ ID NO: 97, a CDRL2 comprising an amino acid sequence as set forth in SEQ ID NO: 98, and a CDRL3 comprising an amino acid sequence as set forth in SEQ ID NO: 99.

In some embodiments, the antibody, or antigen binding portion thereof, comprises a heavy chain variable region comprising a complementarity determining region 3 (CDR3) having the amino acid sequence of SEQ ID NO: 96 and a light chain variable region comprising a CDR3 having the amino acid sequence of SEQ ID NO: 99. In some embodiments, the antibody, or antigen binding portion thereof, comprises a heavy chain variable region comprising a complementarity determining region 2 (CDR2) having the amino acid sequence of SEQ ID NO: 95 and a light chain variable region comprising a CDR2 having the amino acid sequence of SEQ ID NO: 98. In some embodiments, the antibody, or antigen binding portion thereof, comprises a heavy chain variable region comprising a complementarity determining region 1 (CDR1) having the amino acid sequence of SEQ ID NO: 94 and a light chain variable region comprising a CDR1 having the amino acid sequence of SEQ ID NO: 97.

The amino acid sequences of the heavy chain variable region (HCVR) and the light chain variable region (LCVR) of the antibody set forth in Table 5 (e.g., SR-AB10) are provided in Table 6.

Ten additional antibodies were developed that specifically bind to a LTBP1-TGFβ1 complex and/or a LTBP3-TGFβ1 complex, and inhibit release of mature TGFβ1 presented in the context of LTBP1/3. Table 6 also provides the HCVR and LCVR amino acid sequences of these additional LTBP context-specific antibodies.

TABLE 6

Heavy Chain Variable Region Sequence and Light Chain Variable Region Sequence of Antibodies that Specifically Bind a LTBP1/3-TGFβ1 Complex

| Antibody | HCVR Sequence | LCVR Sequence |
| --- | --- | --- |
| SR-AB2 | QVQLVQSGAEVKKPGASVKVSCKA SGYTFTSYGISWVRQAPGQGLEWM GWISAYNGNTNYAQKLQGRVTMTT | NFMLTQPHSVSESPGKTVTISCT RSSGSIASNYVQWYQQRPGSSP TTVIYEDNQRPSGVPDRFSGSID |

TABLE 6-continued

Heavy Chain Variable Region Sequence and Light Chain Variable Region Sequence of Antibodies that Specifically Bind a LTBP1/3-TGFβ1 Complex

| Antibody | HCVR Sequence | LCVR Sequence |
|---|---|---|
|  | DTSTSTAYMELRSLRSDDTAVYYCA RAPLGNFDSWGQGTMVTVSS (SEQ ID NO: 7) | SSSNSASLTISGLKTEDEADYYC QSYDSSNHPVVFGGGTKLTVL (SEQ ID NO: 8) |
| SR-AB3 | QMQLVQSGAEVKKPGASVKVSCKA SGYTFTSYGISWVRQAPGQGLEWMM GWISAYNGNTNYAQKLQGRVTMTT NTSTSTAYMELRSLRSDDTAVYYCA RDDYYYYGMDVWGQGTLVTVSS (SEQ ID NO: 74) | QSGLTQPASVSGSPGQSVTISCT GTSSDVGGYNYASWYQQHPGK APKLMIYDVSKRPSGVPDRFSG SKSGNTASLTISGLQAEDEADY YCSSYTSSSTYVFGTGTKLTVL (SEQ ID NO: 75) |
| SR-AB4 | QVQLQQWGAGLLKPSETLSLTCAV YGGSFSGYYWSWIRQPPGKGLEWI GEIIHSGSTNYNPSLKSRVTISVDTSK NQFSLKLSSVTAADTAVYYCARGV GLGRFDPWGQGTLVTVSS (SEQ ID NO: 76) | QSELTQSPSASGTPGQRVTISCS GSNSNIGTNTVNWYQQFPGTAP KLLIYYNDQRPSGVSDRFSGSRS GTSASLAINGLQSEDEADYYCA TWDDSLSGVVFGGGTKLTVL (SEQ ID NO: 77) |
| SR-AB5 | QVQLQQWGAGLLKPSETLSLTCAV YGGSFSGYYWSWIRQPPGKGLEWI GEINHSGSTNYNPSLKSRVTISVDTS KNQFSLKLSSVTAADTAVYYCARG VGLGRFDPWGQGTLVTVSS (SEQ ID NO: 78) | QSELTQSPSASGTPGQRVTISCS GSNSNIGTNTVNWYQQFPGTAP KLLIYYNDQRPSGVSDRFSGSRS GTSASLAINGLQSEDEADYYCA TWDDSLSGVVFGGGTKLTVL (SEQ ID NO: 79) |
| SR-AB6 | QVQLQQSGPGLVRPSQTLSLTCAISG DSVSSNGAAWNWIRQSPSRGLEWL GRTYYRSKWYNDYAVSVKSRITINP DTSKNQFSLKLTSVTPEDTAVYYCA RGEDWGYAFDIWGQGTLVTVSS (SEQ ID NO: 80) | NFMLTQPHSVSESPGKTVTISCT RSSGSIASNYVQWYQQRPGSAP TTVIYDDKQRPSGIPDRFSGSIDS SSNSASLTISGLKTEDEADYYCQ SYDSSNVVFGGGTKVTVL (SEQ ID NO: 81) |
| SR-AB7 | QVQLVQSGAEVKKPGASVKVSCKA SGYTFTSYGISWVRQAPGQGLEWM GWISAYDGNTNYAQKLQGRVTMTT DTSTSTAYMELSSLRSDDTAVYYCA RNPYYYYMDVWGQGTTVTVSS (SEQ ID NO: 82) | QSELTQAPSVSVAPGQTARITCG GNNIGGRSKSVHWYQHKLGQA PVLIVYDNTDRPSGISERFSGSSS VNAATLTITTAEAGDEGDYYCQ VWDVSTDHVVFGGGTKVTVL (SEQ ID NO: 83) |
| SR-AB8 | QVQLVESGAEVKKPGASVKVSCKA SGYTFTGYYMHWVRQAPGQGLEW MGWINPNGGGTNYAQKFQGRVTM TRDTSISTAYMELSRLRSDDTAVYY CANRRRGSAFDIWGQGTLVTVSS (SEQ ID NO: 84) | NFMLTQPHSVSESPGKTVTISCT GSSGSIASNYVQWYQQRPGSSP TTVIYEDNQRPSGVPDRFSGSID SSSNSASLTISGLKTEDEADYYC QSYDDNYHVIFGGGTKLTVL (SEQ ID NO: 85) |
| SR-AB9 | QVQLVESGGALVQPGGSLRLSCAAS GFTFSSYAMHWVRQAPGKGLEWV AVISYDGSNKYYADSVKGRFTISRD NSKNTLYLQMNSLRAEDTAVYYCA KETGYGFGLFWGQGTMVTVSS (SEQ ID NO: 86) | NFMLTQPHSVSESPGRTLTIPCF RSSGNIGDSYVHWYQQRPGSAP TTVIYRDSQRPSGVPDRFSGSID FSSNSASLTISGLKTEDEAAYYC QSYDRSNQWVFGGGTKLTVL (SEQ ID NO: 87) |
| SR-AB10 | QLQLQESGGGVVQPGRSLRLSCAAS GFTFNNYPIHWVRQAPGKGLEWVA VMSYDGINKYYADSVKGRFTISRDN SKNTLYLQMNSLRAEDTAVYYCAR PRIAARRGGFDYWGQGTLVTVSS (SEQ ID NO: 88) | NFMLTQPHSVSESPGKTVTISCT RSSGNIDNNYVQWYQQRPGSSP TTVIYEDNQRPSGVPDRFSGSID SSSNSASLTISGLKTEDEADYYC QSYDSDNQGVVFGGGTKLTVL (SEQ ID NO: 89) |
| SR-AB11 | QVQLVQSGAEVKKPGASVKVSCKA SGYTFTSYGISWVRQAPGQGLEWM GWISAYNGNTDYAQKLQGRVTMTT DTSTSTAYMELRGLRSDDTAVYYC ARAPLGNFDSWGQGTLVTVSS (SEQ ID NO: 90) | NFMLTQPHSVSESPGKTVTISCT RSSGSIASNYVQWYQQRPGSAP TTVIYEDNQRPSGVPDRFSGSID SSSNSASLTISGLKTEDEADYYC QSYDSSNHVVFGGGTKVTVL (SEQ ID NO: 91) |
| SR-AB12 | EVQLLESGGGVVQPGRSLRLSCAAS GFTFPNYAMSWVRQAPGKGLEWVS AISGSGGSTYYADSVKGRFTISRDNS KNTLYLQMNSLRAEDTAVYYCAKD LEGGYYWDYYYGMDVWGQGTL VTVSS (SEQ ID NO: 92) | NFMLTQPHSVSESPGKTVTISCT RSSGSIASNYVQWYQQRPGSSP TTVIYEDNQRPSGVPDRFSGSID SSSNSASLTISGLKTEDEADYYC QSYDSSIVVFGGGTQLTVL (SEQ ID NO: 93) |

Aspects of the invention relate to a monoclonal antibody, or antigen binding portion thereof, that binds selectively to a LTBP1-TGFβ1 complex and/or a LTBP3-TGFβ1 complex, and that comprises a heavy chain variable region sequence and a light chain variable region sequence.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 7 or SEQ ID NO: 88.

In one embodiment, the antibody, or antigen-binding fragment thereof, comprises a light chain variable region having an amino acid sequence that is at least 90%, 91%, 92%, 93%, 94%, 95%, 96%, 97%, 98% or 99% identical to SEQ ID NO: 8 or SEQ ID NO: 89.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 7 and a light chain variable region having an amino acid sequence that is at least 90%, 91%, 92%, 93%, 94%, 95%, 96%, 97%, 98% or 99% identical to SEQ ID NO: 8.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 88 and a light chain variable region having an amino acid sequence that is at least 90%, 91%, 92%, 93%, 94%, 95%, 96%, 97%, 98% or 99% identical to SEQ ID NO: 89.

In some embodiments, the antibody, or antigen binding portion thereof, comprises a heavy chain variable region comprising an amino acid sequence having at least 70%, 75%, 80%, 85%, 90%, 95%, 96%, 97%, 98%, or 99% identity to the amino acid sequence set forth in SEQ ID NO: 7 and a light chain variable region comprising an amino acid sequence having at least 70%, 75%, 80%, 85%, 90%, 95%, 96%, 97%, 98%, or 99% identity to the amino acid sequence set forth in SEQ ID NO: 8. In some embodiments, the heavy chain variable region and/or the light chain variable region sequences do not vary within any of the CDR sequences provided herein. For example, in some embodiments, the degree of sequence variation (e.g., 80%, 81%, 82%, 83%, 84%, 85%, 86%, 87%, 88%, 89%, 90%, 91%, 92%, 93%, 94%, 95%, 96%, 97%, 98%, or 99%) may occur within a heavy chain variable and/or a light chain variable amino acid sequence excluding any of the CDR sequences provided herein. In some embodiments, the antibody, or antigen binding portion thereof, comprises a heavy chain variable domain comprising an amino acid sequence set forth in SEQ ID NO: 7 and a light chain variable domain comprising an amino acid sequence set forth in SEQ ID NO: 8.

In some embodiments, the antibody, or antigen binding portion thereof, comprises a heavy chain variable domain comprising an amino acid sequence set forth in Table 6, and a light chain variable domain comprising an amino acid sequence set forth in Table 6. For example, in some embodiments, the antibody, or antigen binding portion thereof, comprises a heavy chain variable domain comprising an amino acid sequence set forth in SEQ ID NO: 74 and a light chain variable domain comprising an amino acid sequence set forth in SEQ ID NO: 75. In some embodiments, the antibody, or antigen binding portion thereof, comprises a heavy chain variable domain comprising an amino acid sequence set forth in SEQ ID NO: 76 and a light chain variable domain comprising an amino acid sequence set forth in SEQ ID NO: 77. In some embodiments, the antibody, or antigen binding portion thereof, comprises a heavy chain variable domain comprising an amino acid sequence set forth in SEQ ID NO: 78 and a light chain variable domain comprising an amino acid sequence set forth in SEQ ID NO: 79. In some embodiments, the antibody, or antigen binding portion thereof, comprises a heavy chain variable domain comprising an amino acid sequence set forth in SEQ ID NO: 80 and a light chain variable domain comprising an amino acid sequence set forth in SEQ ID NO: 81. In some embodiments, the antibody, or antigen binding portion thereof, comprises a heavy chain variable domain comprising an amino acid sequence set forth in SEQ ID NO: 82 and a light chain variable domain comprising an amino acid sequence set forth in SEQ ID NO: 83. In some embodiments, the antibody, or antigen binding portion thereof, comprises a heavy chain variable domain comprising an amino acid sequence set forth in SEQ ID NO: 84 and a light chain variable domain comprising an amino acid sequence set forth in SEQ ID NO: 85. In some embodiments, the antibody, or antigen binding portion thereof, comprises a heavy chain variable domain comprising an amino acid sequence set forth in SEQ ID NO: 86 and a light chain variable domain comprising an amino acid sequence set forth in SEQ ID NO: 87. In some embodiments, the antibody, or antigen binding portion thereof, comprises a heavy chain variable domain comprising an amino acid sequence set forth in SEQ ID NO: 88 and a light chain variable domain comprising an amino acid sequence set forth in SEQ ID NO: 89. In some embodiments, the antibody, or antigen binding portion thereof, comprises a heavy chain variable domain comprising an amino acid sequence set forth in SEQ ID NO: 90 and a light chain variable domain comprising an amino acid sequence set forth in SEQ ID NO: 91. In some embodiments, the antibody, or antigen binding portion thereof, comprises a heavy chain variable domain comprising an amino acid sequence set forth in SEQ ID NO: 92 and a light chain variable domain comprising an amino acid sequence set forth in SEQ ID NO: 93.

In some embodiments, the antibody, or antigen binding portion thereof, comprises a heavy chain variable region comprising an amino acid sequence having at least 70%, 75%, 80%, 85%, 90%, 95%, 96%, 97%, 98%, or 99% identity to a heavy chain variable region sequence set forth in Table 6, and/or a light chain variable region comprising an amino acid sequence having at least 70%, 75%, 80%, 85%, 90%, 95%, 96%, 97%, 98%, or 99% identity to a light chain variable region sequence set forth in Table 6. In another embodiment, the antibody, or antigen-binding portion thereof, comprises a heavy chain variable domain comprising a heavy chain amino acid sequence set forth in Table 6, and a light chain variable domain comprising a light chain amino acid sequence set forth in Table 6.

The amino acid sequences of the heavy chain variable region (HCVR) and the light chain variable region (LCVR) of the antibody SR-AB2 set forth in Table 5 are provided below.

SR-AB2 - Heavy chain variable region amino acid sequence (SEQ ID NO: 7)
QVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCARAP

LGNFDSWGQGTMVTVSS

-continued

SR-AB2 - Light chain variable region amino acid
sequence
(SEQ ID NO: 8)
NFMLTQPHSVSESPGKTVTISCTRSSGSIASNYVQWYQQRPGSSPTTVIY

EDNQRPSGVPDRFSGSIDSSSNSASLTISGLKTEDEADYYCQSYDSSNHP

VVFGGGTKLTVL

The amino acid sequences of the heavy chain variable region (HCVR) and the light chain variable region (LCVR) of the antibody SR-AB10 set forth in Table 5 are provided below.

SR-AB10 - Heavy chain variable region amino acid
sequence
(SEQ ID NO: 88)
QLQLQESGGGVVQPGRSLRLSCAASGFTFNNYPIHWVRQAPGKGLEWVAV

MSYDGINKYYADSVKGRFTISRDNSKNTLYLQMNSLRAEDTAVYYCARPR

IAARRGGFDYWGQGTLVTVSS

SR-AB10 - Light chain variable region amino acid
sequence
(SEQ ID NO: 89)
NFMLTQPHSVSESPGKTVTISCTRSSGNIDNNYVQWYQQRPGSSPTTVIY

EDNQRPSGVPDRFSGSIDSSSNSASLTISGLKTEDEADYYCQSYDSDNQG

VVFGGGTKLTVL

In some embodiments, antibodies, or antigen binding portions thereof, of the invention that selectively bind to a LTBP1-TGFβ1 complex and/or a LTBP3-TGFβ1 complex have one or more CDR sequences substantially similar to CDRH1, CDRH2, CDRH3, CDRL1, CDRL2, and/or CDRL3. For example, the antibodies may include one or more CDR sequences as shown in Table 5 (SEQ ID NOs: 1-6 or SEQ ID NOs: 94-99) containing up to 5, 4, 3, 2, or 1 amino acid residue variations as compared to the corresponding CDR region in any one of SEQ ID NOs: 1-6 or SEQ ID NOs: 94-99. In one embodiment, the antibody, or antigen-binding fragment thereof, comprises at least three CDRs selected from the following, optionally comprising up to 3 amino acid changes, for example 1, 2 or 3 amino acid changes, for each of the CDRs CDR-H1: SEQ ID NO: 1; CDR-H2: SEQ ID NO: 2; CDR-H3: SEQ ID NO: 3; CDR-L1: SEQ ID NO: 4; CDR-L2: SEQ ID NO: 5; and, CDR-L3: SEQ ID NO: 6. In one embodiment, the antibody, or antigen-binding fragment thereof, comprises at least three CDRs selected from the following, optionally comprising up to 3 amino acid changes, for example 1, 2 or 3 amino acid changes, for each of the CDRs CDR-H1: SEQ ID NO: 94; CDR-H2: SEQ ID NO: 95; CDR-H3: SEQ ID NO: 96; CDR-L1: SEQ ID NO: 97; CDR-L2: SEQ ID NO: 98; and, CDR-L3: SEQ ID NO: 99.

In one aspect, the invention provides an antibody, or antigen-binding fragment thereof, comprising a heavy chain variable region comprising CDR-H1: SEQ ID NO: 1; CDR-H2: SEQ ID NO: 2; and CDR-H3: SEQ ID NO: 3; and a light chain variable region comprising CDR-L1: SEQ ID NO: 4; CDR-L2: SEQ ID NO: 5; and CDR-L3: SEQ ID NO: 6, optionally comprising up to 3 amino acid changes, for example 1, 2 or 3 amino acid changes, for each of the CDRs.

In one aspect, the invention provides an antibody, or antigen-binding fragment thereof, comprising a heavy chain variable region comprising CDR-H1: SEQ ID NO: 94; CDR-H2: SEQ ID NO: 95; and CDR-H3: SEQ ID NO: 96; and a light chain variable region comprising CDR-L1: SEQ ID NO: 97; CDR-L2: SEQ ID NO: 98; and CDR-L3: SEQ ID NO: 99, optionally comprising up to 3 amino acid changes for each of the CDRs.

In some embodiments, the "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In any of the antibodies or antigen-binding fragments described herein, one or more conservative mutations can be introduced into the CDRs or framework sequences at positions where the residues are not likely to be involved in an antibody-antigen interaction. In some embodiments, such conservative mutation(s) can be introduced into the CDRs or framework sequences at position(s) where the residues are not likely to be involved in interacting with a LTBP1-TGFβ1 complex and/or a LTBP3-TGFβ1 complex, as determined based on the crystal structure. In some embodiments, the likely interface (e.g., residues involved in an antigen-antibody interaction) may be deduced from known structural information on another antigens sharing structural similarities.

As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal et al., "A single amino acid substitution abolishes the heterogeneity of chimeric mouse/human (IgG4) antibody," *Mol Immunol* 30, 105-108; 1993), where serine 228 (EU numbering; residue 241 Kabat numbering) is converted to proline resulting in an IgG1-like (CPPCP (SEQ ID NO: 45)) hinge sequence. Accordingly, any of the antibodies may include a stabilizing 'Adair' mutation or the amino acid sequence CPPCP (SEQ ID NO: 45). In one embodiment, an antibody described herein comprises a heavy chain immunoglobulin constant domain of a human IgG$_4$ having a backbone substitution of Ser to Pro, that produces an IgG$_1$-like hinge and permits formation of inter-chain disulfide bonds.

Antibodies of this disclosure that selectively bind to a LTBP1-TGFβ1 complex and/or a LTBP3-TGFβ1 complex may optionally comprise antibody constant regions or parts thereof. For example, a $V_L$ domain may be attached at its C-terminal end to a light chain constant domain such as CK or a. Similarly, a $V_H$ domain or portion thereof may be attached to all or part of a heavy chain such as IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include $V_H$ and $V_L$ domains, or antigen binding portions thereof, combined with any suitable constant region. In exemplary embodiments, the antibodies, or antigen binding portions thereof, comprise a heavy chain immunoglobulin constant domain containing all or a portion of a human $IgG_1$ or a human $IgG_4$ constant domain. In some embodiments, the antibody, or antigen binding portion thereof, comprises a light chain immunoglobulin constant domain containing all or a portion of a human Ig lambda constant domain or a human Ig kappa constant domain.

In some embodiments, antibodies that selectively bind to a LTBP1-TGFβ1 complex and/or a LTBP3-TGFβ1 complex may or may not include the framework region of the antibodies of SEQ ID NOs: 7 and 8. In some embodiments, antibodies that selectively bind to a LTBP1-TGFβ1 complex and/or a LTBP3-TGFβ1 complex are murine antibodies and include murine framework region sequences. In other embodiments, the antibodies are chimeric antibodies, or antigen binding fragments thereof. In another embodiment, the antibodies are humanized antibodies, or antigen binding fragments thereof. In another embodiment, the antibodies are fully human antibodies, or antigen binding fragments thereof. In one embodiment, the antibody comprises a framework region comprising a human germline amino acid sequence.

The antibodies, and antigen-binding fragments thereof, described herein can have any configuration suitable for binding antigen. For example, in one embodiment, the antibody, or antigen binding portion thereof, comprises four polypeptide chains, including two heavy chain variable regions and two light chain variable regions. In another embodiment, the antibody, or antigen binding portion thereof, comprises one heavy chain variable region and one light chain variable region. In exemplary embodiments, the antibody, or antigen binding portion thereof, is a Fab fragment, a F(ab')2 fragment, a scFab fragment, an scFv, or a diabody.

In one embodiment, the antibody, or antigen-binding portion thereof, comprises a heavy chain immunoglobulin constant domain of a human $IgG_1$ constant domain or a human $IgG_4$ constant domain. In an exemplary embodiment, the heavy chain immunoglobulin constant domain is a human $IgG_4$ constant domain. In one embodiment, the antibody, or antigen-binding portion thereof, binds a conformational epitope. In one embodiment, the antibody, or antigen-binding portion thereof, binds a combinatorial epitope.

In one embodiment, the antibody, or antigen-binding portion thereof, comprises a heavy chain immunoglobulin constant domain of a human $IgG_4$ constant domain having a backbone substitution of Ser to Pro that produces an $IgG_1$-like hinge and permits formation of inter-chain disulfide bonds. In one embodiment, the antibody, or antigen-binding portion thereof, further comprises a light chain immunoglobulin constant domain comprising a human Ig lambda constant domain, or a human Ig kappa constant domain.

In one embodiment, the antibody is an IgG having four polypeptide chains which are two heavy chains and two light chains. In exemplary embodiments, the antibody can be a humanized antibody, a human antibody, or a chimeric antibody. In one embodiment, the antibody comprises a framework having a human germline amino acid sequence.

In one embodiment, the invention provides an antibody, or antigen-binding portion thereof, that competes for binding with an antibody, or antigen-binding portion thereof, described herein. In one embodiment, the invention provides an antibody, or antigen-binding portion thereof, that binds to the same epitope as an antibody, or antigen-binding portion thereof, described herein. In one embodiment, the antibody, or antigen-binding fragment thereof, does not compete with antibody SR-AbI for binding to a human LTBP1-proTGFβ1 complex.

Polypeptides

Some aspects of the disclosure relate to isolated polypeptides. For example, in one embodiment, the invention provides an isolated polypeptide comprising CDRH1, CDRH2, CDRH3, CDRL1, CDRL2, or CDRL3, or combinations thereof, as provided in Table 5. In an exemplary embodiment, the isolated polypeptide can contain CDRH1, CDRH2, and CDRH3 as provided in Table 5. In other embodiments, the isolated polypeptide can contain CDRL1, CDRL2, and CDRL3 as provided in Table 5. In some embodiments, the polypeptide can contain up to 5, 4, 3, 2, or 1 amino acid residue variations as compared to the corresponding CDR region in any one of CDRH1, CDRH2, CDRH3, CDRL1, CDRL2, or CDRL3, or combinations thereof, as provided in Table 5. In one embodiment, the invention provides an isolated polypeptide comprising SEQ ID NO: 7. In another embodiment, the invention provides an isolated polypeptide comprising SEQ ID NO: 8. In another embodiment, the invention provides an isolated polypeptide comprising SEQ ID NO:7 and SEQ ID NO:8. In this embodiment, SEQ ID NO:7 and SEQ ID NO:8 can optionally be connected by a linker peptide. In some embodiments, the polypeptide is a heavy chain variable domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to SEQ ID NO: 7. In some embodiments, the polypeptide is a light chain variable domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to SEQ ID NO: 8.

In another embodiment, the invention provides an isolated polypeptide comprising a heavy chain variable region sequence set forth in Table 6. In one embodiment, the invention provides an isolated polypeptide comprising SEQ ID NO: 7, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, or SEQ ID NO:92. In one embodiment, the invention provides an isolated polypeptide comprising SEQ ID NO: 8, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, or SEQ ID NO:93.

In another embodiment, the invention provides an isolated polypeptide comprising a light chain variable region set forth in Table 6. In another embodiment, the invention provides an isolated polypeptide comprising a heavy chain variable region sequence set forth in Table 6 (e.g., SEQ ID NO: 7, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, or SEQ ID NO:92) and a light chain variable region sequence set forth in Table 6 (e.g., SEQ ID NO: 8, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, or SEQ ID NO:93). In this embodiment, the heavy chain and light chain sequences (e.g., SEQ ID NO:7 and SEQ ID NO:8) can optionally be connected by a linker peptide. In some embodiments, the polypeptide is a heavy chain variable domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to SEQ ID NO: 7, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, or SEQ ID NO:92. In some embodiments, the polypeptide is a light chain variable domain. In some embodiments, the polypeptide is at least 75% (e.g., 80%, 81%, 82%, 83%, 84%, 85%, 86%, 87%, 88%, 89%, 90%, 91%, 92%, 93%, 94%, 95%, 96%, 97%, 98%, or 99%) identical to SEQ ID NO: 8, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, or SEQ ID NO:93.

Nucleic Acids

In some embodiments, antibodies, antigen binding portions thereof, and/or compositions of the present disclosure may be encoded by nucleic acid molecules. Such nucleic acid molecules include, without limitation, DNA molecules, RNA molecules, polynucleotides, oligonucleotides, mRNA molecules, vectors, plasmids and the like. In some embodiments, the present disclosure may comprise cells programmed or generated to express nucleic acid molecules encoding compounds and/or compositions of the present disclosure.

In some embodiments, the invention provides a nucleic acid molecule that encodes the foregoing antibodies, or an antigen-binding portion thereof. For example, in one embodiment, the invention provides a nucleic acid molecule that encodes a polypeptide comprising CDRH1, CDRH2, CDRH3, CDRL1, CDRL2, or CDRL3, or combinations thereof, as provided in Table 5. The nucleic acid molecule can, in some embodiments, encode a polypeptide comprising CDRH1, CDRH2, and CDRH3 as provided in Table 5. In some embodiments, the nucleic acid molecule can encode a polypeptide comprising CDRL1, CDRL2, and CDRL3 as provided in Table 5. In some embodiments, the nucleic acid molecule encodes a polypeptide that can contain up to 5, 4, 3, 2, or 1 amino acid residue variations as compared to the corresponding CDR region in any one of CDRH1, CDRH2, CDRH3, CDRL1, CDRL2, or CDRL3, or combinations thereof, as provided in Table 5. In an exemplary embodiment, the nucleic acid molecule encodes a polypeptide comprising a heavy chain variable domain having at least 70%, 75%, 80%, 85%, 90%, 95%, 96%, 97%, 98%, or 99% identity to the amino acid sequence set forth in SEQ ID NO: 7, and/or a light chain variable domain having at least 70%, 75%, 80%, 85%, 90%, 95%, 96%, 97%, 98%, or 99% identity to the amino acid sequence set forth in SEQ ID NO: 8. In one embodiment, the nucleic acid molecule encodes a polypeptide comprising a heavy chain variable domain having at least 70%, 75%, 80%, 85%, 90%, 95%, 96%, 97%, 98%, or 99% identity to a heavy chain variable region sequence set forth in Table 6, and/or a light chain variable domain having at least 70%, 75%, 80%, 85%, 90%, 95%, 96%, 97%, 98%, or 99% identity to a light chain variable region sequence set forth in Table 6. In an exemplary embodiment, the nucleic acid molecule encodes a polypeptide comprising a heavy chain variable domain having at least 70%, 75%, 80%, 85%, 90%, 95%, 96%, 97%, 98%, or 99% identity to the amino acid sequence set forth in SEQ ID NO: 7, and/or a light chain variable domain having at least 70%, 75%, 80%, 85%, 90%, 95%, 96%, 97%, 98%, or 99% identity to the amino acid sequence set forth in SEQ ID NO: 8. In some embodiments, the nucleic acid molecule encodes an antibody, or antigen binding portion thereof, comprising a heavy chain variable domain amino acid sequence set forth in SEQ ID NO: 7, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, or SEQ ID NO:92, and a light chain variable domain amino acid sequence set forth in SEQ ID NO: 8, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, or SEQ ID NO:93. In some embodiments, the nucleic acid molecule encodes an antibody, or antigen binding portion thereof, comprising a heavy chain variable domain amino acid sequence set forth in SEQ ID NO: 7, and a light chain variable domain amino acid sequence set forth in SEQ ID NO: 8.

In some cases, nucleic acids of the disclosure include codon-optimized nucleic acids. Methods of generating codon-optimized nucleic acids are known in the art and may include, but are not limited to those described in U.S. Pat. Nos. 5,786,464 and 6,114,148, the contents of each of which are herein incorporated by reference in their entirety.

Production of Antibodies that Bind a LTBP1/3-TGFβ1 Complex

Numerous methods may be used for obtaining antibodies, or antigen binding fragments thereof, of the disclosure. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA), and Biolayer Interferometry (e.g., OCTET) and surface plasmon resonance (e.g., BIA-CORE) analysis, to identify one or more hybridomas that produce an antibody that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597; WO 92/18619; WO 91/17271; WO 92/20791; WO 92/15679; WO 93/01288; WO 92/01047; WO 92/09690; and WO 90/02809.

In addition to the use of display libraries, the specified antigen (e.g., a LTBP1-TGFβ1 complex and/or a LTBP3-TGFβ1 complex) can be used to immunize a non-human animal, e g, a rodent, e.g., a mouse, hamster, or rat. In one embodiment, the non-human animal is a mouse.

In one aspect, the invention provides a method for making a composition comprising an antibody, or antigen-binding fragment thereof, that specifically binds a human LTBP1-proTGFβ1 complex and/or a human LTBP3-proTGFβ1 complex, and does not bind a human GARP-proTGFβ1 complex; wherein the antibody, or antigen-binding fragment thereof, inhibits TGFβ1 but does not inhibit TGFβ2 or TGFβ3, the method comprising steps of i) providing at least one antigen comprising LTBP1-proTGFβ1 and/or LTBP3-proTGFβ1, ii) selecting a first pool of antibodies, or antigen-binding fragments thereof, that specifically bind the at least one antigen of step (i) so as to provide specific binders of LTBP1-proTGFβ1 and/or LTBP3-proTGFβ1; iii) selecting a second pool of antibodies, or antigen-binding fragments thereof, that inhibit activation of TGFβ1, so as to generate specific inhibitors of TGFβ1 activation; iv) formulating an antibody, or antigen-binding fragment thereof, that is present in the first pool of antibodies and the second pool of antibodies into a pharmaceutical composition, thereby making the composition comprising the antibody, or antigen-binding fragment thereof.

In one embodiment, the method further comprises a step of removing from the first pool of antibodies, or antigen-binding fragments thereof, any antibodies, or antigen-binding fragments thereof, that bind GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3, mature TGFβ3, or any combinations thereof. In one embodiment, the method further comprises a step of determining or confirming isoform-specificity of the antibodies, or antigen-binding fragments thereof, selected in steps (ii) and/or (iii). In one embodiment, the method further comprises a step of selecting for antibodies, or antigen-binding fragments thereof, that are cross-reactive to human and rodent antigens. In one embodiment, the method further comprises a step of generating a fully human or humanized antibody, or antigen-binding fragment thereof, of the antibody, or antigen-binding fragment thereof, that is present in the first pool of antibodies and the second pool of antibodies. In one embodiment, the method further comprises a step of subjecting the antibody, or antigen-binding fragment thereof, that is present in the first pool of antibodies and the second pool of antibodies to affinity maturation and/or optimization, so as to provide an affinity matured and/or optimized antibody or fragment thereof.

In another embodiment, a monoclonal antibody is obtained from the non-human animal, and then modified, e.g., made chimeric, using suitable recombinant DNA techniques. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see, e.g., Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharo-*

*myces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large scale production of the antibody or antibody fragments.

The transformed host cells can be grown in fermenters and cultured using any suitable techniques to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the β the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in E. coli, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain(s) of the immunoglobulin chains encoding sequences and expression control sequences) can be transferred into the host cell by suitable methods, which vary depending on the type of cellular host.

Modifications

Antibodies, or antigen binding portions thereof, of the disclosure may be modified with a detectable label or detectable moiety, including, but not limited to, an enzyme, prosthetic group, fluorescent material, luminescent material, bioluminescent material, radioactive material, positron emitting metal, nonradioactive paramagnetic metal ion, and affinity label for detection and/or isolation of a LTBP1-TGFβ1 complex or a LTBP3-TGFβ1 complex. The detectable substance or moiety may be coupled or conjugated either directly to the polypeptides of the disclosure or indirectly, through an intermediate (such as, for example, a linker (e.g., a cleavable linker)) using suitable techniques. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115}$mIn, $^{113}$mIn, $^{112}$In, $^{111}$In), and technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Sc, $^{86}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn). The detectable substance may be coupled or conjugated either directly to the antibodies of the disclosure that bind selectively to a LTBP1-TGFβ1 complex and/or a LTBP3-TGFβ1 complex, or indirectly, through an intermediate (such as, for example, a linker) using suitable techniques. Any of the antibodies provided herein that are conjugated to a detectable substance may be used for any suitable diagnostic assays, such as those described herein.

In addition, antibodies, or antigen binding portions thereof, of the disclosure may also be modified with a drug to form, e.g., an antibody-drug conjugate. The drug may be coupled or conjugated either directly to the polypeptides of the disclosure, or indirectly, through an intermediate (such as, for example, a linker (e.g., a cleavable linker)) using suitable techniques.

Targeting Agents

In some embodiments methods of the present disclosure comprise the use of one or more targeting agents to target an antibody, or antigen binding portion thereof, as disclosed herein, to a particular site in a subject for purposes of modulating mature TGFβ release from a LTBP1-TGFβ1 complex and/or a LTBP3-TGFβ1 complex. For example, LTBP1-TGFβ1 and LTBP3-TGFβ1 complexes are typically localized to extracellular matrix. Thus, in some embodiments, antibodies disclosed herein can be conjugated to extracellular matrix targeting agents for purposes of localizing the antibodies to sites where LTBP1-TGFβ1 and LTBP3-TGFβ1 complexes reside. In such embodiments, selective targeting of antibodies leads to selective modulation of LTBP1-TGFβ1 and/or LTBP3-TGFβ1 complexes. In some embodiments, selective targeting of antibodies leads to selective inhibition of LTBP1-TGFβ1 and/or LTBP3-TGFβ1 complexes (e.g., for purposes of treating fibrosis). In some embodiments, extracellular matrix targeting agents include heparin binding agents, matrix metalloproteinase binding agents, lysyl oxidase binding domains, fibrillin-binding agents, hyaluronic acid binding agents, and others.

In some embodiments, bispecific antibodies may be used having a first portion that selectively binds a LTBP1/3-TGFβ1 complex and a second portion that selectively binds a component of a target site, e.g., a component of the ECM (e.g., fibrillin).

Pharmaceutical Compositions

The invention further provides pharmaceutical compositions used as a medicament suitable for administration in human and non-human subjects. One or more antibodies that selectively binds a LTBP1-TGFβ1 complex and/or a LTBP3-TGFβ1 complex can be formulated or admixed with a pharmaceutically acceptable carrier (excipient), including, for example, a buffer, to form a pharmaceutical composition. Such formulations may be used for the treatment of a disease or disorder that involves TGFβ signaling. In some embodiments, such disease or disorder associated with TGFβ signaling involves one or more contexts, i.e., the TGFβ is associated with a particular type or types of presenting molecules. In some embodiments, such context occurs in a cell type-specific and/or tissue-specific manner. In some embodiments, for example, such context-dependent action of TGFβ signaling is mediated in part via GARP, LRRC33, LTBP1 and/or LTBP3.

In some embodiments, the antibody of the present invention binds selectively to a single context of TGFβ, such that the antibody binds TGFβ in a complex with LTBP presenting molecules, e.g., LTBP1 and/or LTBP3. Thus, such pharmaceutical compositions may be administered to patients for alleviating a TGFβ-related indication (e.g., fibrosis) associated with TGFβ1 activation/release from LTBP1 and/or LTBP3.

A pharmaceutically "acceptable" carrier (excipient) means that the carrier is compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. In one example, a pharmaceutical composition described herein contains more than one antibody that selectively binds a LTBP1-TGFβ1 complex and/or a LTBP3-TGFβ1 complex, where the antibodies recognize different epitopes/residues of the LTBP1-TGFβ1 complex and/or LTBP3-TGFβ1 complex.

The pharmaceutical compositions to be used in the present methods can comprise pharmaceutically acceptable carriers, excipients, or stabilizers in the form of lyophilized formulations or aqueous solutions (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing an antibody that selectively binds a LTBP1-TGFβ1 complex and/or a LTBP3-TGFβ1 complex, which can be prepared by any suitable method, such as described in Epstein et al., *Proc. Natl. Acad. Sci. USA* 82:3688 (1985); Hwang et al. *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies that selectively bind a LTBP1-TGFβ1 complex and/or a LTBP3-TGFβ1 complex may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 mg to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. Suitable surface-active agents include, in particular, non-ionic agents, such as polyoxyethylenesorbitans (e.g. TWEEEN™ 20, 40, 60, 80 or 85) and other sorbitans (e.g. SPAN™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™, LIPSYN™, INFONUTROL™, LIPOFUNDIN™ and LIPIPHYSAN™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody that selectively binds a LTBP1-TGFβ1 complex and/or a LTBP3-TGFβ1 complex with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Use of Inhibitors that Selectively Bind a LTBP1/3-TGFβ1 Complex

The inhibitors, e.g., antibodies and antigen binding portions thereof, described herein that selectively bind a LTBP1/3-TGFβ1 complex can be used in a wide variety of applications in which modulation of TGFβ1 activity associated with LTBP1 or LTBP3 is desired.

In one embodiment, the invention provides a method of inhibiting TGFβ1 activation by exposing a LTBP1-TGFβ1 complex and/or a LTBP3-TGFβ1 complex to an inhibitor, e.g., antibody, or antigen binding portion thereof, which selectively binds a LTBP1/3-TGFβ1 complex. The foregoing method can be performed in vitro, e.g., to inhibit TGFβ1 activation in cultured cells. The foregoing method can also be performed in vivo, e.g., in a subject in need of TGFβ1 inhibition, or in an animal model in which the effect of TGFβ1 inhibition is to be assessed.

Any inhibitor, e.g., antibody, or antigen binding portion thereof, described herein which selectively binds a LTBP1-TGFβ1 complex and/or a LTBP3-TGFβ1 complex, and any pharmaceutical composition comprising such antibody, is suitable for use in the methods of the invention. For example, in one embodiment, the inhibitor, e.g., antibody, or antigen-binding portion thereof, selectively binds to a LTBP1-TGFβ1 complex and a LTBP3-TGFβ1 complex, but does not bind to one or more targets selected from LTBP1 alone, mature TGFβ1 alone, a GARP-TGFβ1 complex, a LRRC33-TGFβ1 complex, and combinations thereof. Exemplary inhibitor, e.g., antibodies, can inhibit the release of mature TGFβ1 from a LTBP1-proTGFβ1 complex and/or a LTBP3-proTGFβ1 complex, without inhibiting the release of mature TGFβ1 from a GARP-proTGFβ1 complex and/or a LRRC33-proTGFβ1 complex.

The antibody, or antigen-binding portion thereof, can, in some embodiments, bind a LTBP1-proTGFβ1 complex and/or a LTBP3-proTGFβ1 complex with a dissociation constant ($K_D$) of about $10^{-6}$ M or less, $10^{-7}$ M or less, $10^{-8}$ M or less. In one embodiment, the antibody, or antigen binding portion thereof, comprises at least one (e.g., one, two, or three) heavy chain CDRs shown in Table 5, and/or at least one (e.g., one, two, three) light chain CDRs shown in Table 5. In an exemplary embodiment, the antibody, or antigen binding portion thereof, comprises a heavy chain variable region comprising SEQ ID NO:7, and/or a light chain variable region comprising SEQ ID NO:8. Antibodies and antigen binding portions thereof which bind the same epitope as the foregoing antibodies, and/or which compete for binding with the foregoing antibodies to LTBP1/3-proTGFβ1, are also useful in the methods described herein. Additional features of the antibodies, or antigen-binding portions thereof, that are suitable for practicing the methods of the invention are described herein.

In one embodiment, contacting a LTBP1-TGFβ1 complex and/or a LTBP3-TGFβ1 complex with the inhibitor, e.g., antibody, or antigen binding portion thereof, inhibits the release of mature TGFβ1 from the LTBP1-TGFβ1 complex and/or the LTBP3-TGFβ1 complex. In one embodiment, said contacting does not inhibit the release of mature TGFβ1 from presenting molecules other than LTBP1 and LTBP3. For example, exposing a GARP-TGFβ1 complex or a LRRC33-TGFβ1 complex to a context-specific inhibitor, e.g., antibody, that selectively binds LTBP1/3-TGFβ1 but does not bind TGFβ1 in the context of GARP or LRRC33 will not inhibit the release of mature TGFβ1 from the GARP-TGFβ1 complex or the LRRC33-TGFβ1 complex.

LTBP1 and LTBP3 are generally deposited in the extracellular matrix. Accordingly, in one embodiment, complexes comprising LTBP1-TGFβ1 and/or LTBP3-TGFβ1 are associated with the extracellular matrix, e.g., bound to the extracellular matrix. In some embodiments, the LTBP1/3-TGFβ1 complexes are bound to extracellular matrix comprising fibrillin, and/or a protein containing an RGD motif.

The invention also provides a method of reducing TGFβ1 activation in a subject, by administering to the subject an inhibitor, e.g., antibody, or antigen binding portion thereof, which selectively binds a LTBP1/3-TGFβ1 complex, as described herein. Any antibody, or antigen binding portion thereof, described herein which selectively binds a LTBP1-TGFβ1 complex and/or a LTBP3-TGFβ1 complex, and any pharmaceutical composition comprising such antibody, is suitable for use in the methods of the invention.

Exemplary LTBP1/3 inhibitors, e.g., antibodies, bind a LTBP1/3-TGFβ1 complex, and inhibit TGFβ1 activation in a context-specific manner, by inhibiting release of TGFβ1 presented by LTBP1 and LTBP3, without inhibiting release of TGFβ1 presented by GARP and/or LRRC33. Such antibodies are useful for blocking a particular subset of TGFβ1 activity in vivo. In one embodiment, the context-specific antibodies provided herein can be used to inhibit TGFβ1 localized to the extracellular matrix. In another embodiment, the context-specific antibodies can inhibit TGFβ1 without modulating TGFβ1-associated immune activity or immune response, which is primarily mediated by TGFβ1 presented by GARP and LRRC33. In another embodiment, the context-specific antibodies can be used to inhibit TGFβ1 activity associated with the extracellular matrix (e.g., LTBP1-associated TGFβ1 activity and LTBP3-associated TGFβ1 activity) without modulating TGFβ1 activity associated with hematopoietic cells, e.g., hematopoietic cells that express GARP and/or LRRC33.

Clinical Applications

Applicant previously described so-called "context-independent" inhibitors of TGFβ1 (see, for example: PCT/US2017/021972 and PCT/US2018/012601) which may be useful for treating various diseases and disorders involving TGFβ1 dysregulation, including, but are not limited to, cancer and fibrosis. Unlike traditional TGFβ1 antagonists, these context-independent TGFβ1 inhibitors are capable of selectively targeting the TGFβ1 isoform. Within the multi-faceted biological functions driven by the TGFβ1 isoform, however, the context-independent inhibitors do not discriminate tissue-specific (thus context-specific) proTGFβ1 complexes, such that such inhibitors are capable of binding and thereby inhibiting release of mature growth factor from any of the presenting molecule-proTGFβ1 complexes.

Based at least in part on the recognition that it may be advantageous to provide even greater selectivity in targeting only a subset of TGFβ1 activities, context-selective inhibitors of the present disclosure have been generated. It is contemplated that by further narrowing particular biological contexts in which to inhibit TGFβ1 function, greater safety may be achieved in a subset of disease conditions or patient populations. Specifically, the inventors of the present invention have recognized that in certain conditions, systemic perturbation of immune regulation may be particularly undesirable. Because TGFβ1 plays an important role in mediating immune response and maintaining immune homeostasis, broad inhibition of TGFβ1 activities effectuated in a context-independent manner may lead to unwanted side effects without justifiable benefits. In these circumstances, it is envisaged that it is advantageous to specifically target and inhibit matrix-associated TGFβ1 function using a context-selective inhibitor, such as those encompassed herein, which does not inhibit the immune components of TGFβ1 function.

Accordingly, the context-specific antibodies can be used to inhibit LTBP1/3-associated TGFβ1 activity in applications in which TGFβ1 activation in the context of LTBP1 or LTBP3 is desirable, and in which TGFβ1 activation in the context of GARP and/or or LRRC33 is detrimental.

Rationale for the Development of Matrix-Targeted TGFβ1 Inhibitors that do not Inhibit GARP-Associated TGFβ1

The invention includes context-specific inhibitors of LTBP1-associated and/or LTBP3-associated TGFβ1. Such inhibitors therefore are capable of specifically targeting the ECM-associated latent TGFβ1 complexes (e.g., LTBP1-proTGFβ1 and/or LTBP3-proTGFβ1) thereby inhibiting the release of mature TGFβ1 growth factor from the latent complex at disease environments, e.g., fibrotic tissues. Such inhibitors show no significant binding activities towards a GARP-proTGFβ1 complex, thereby minimizing unwanted systemic immune modulations.

At least three bases for supporting potential benefits of a TGFβ1 inhibitor that does not target the GARP-proTGFβ1 complex expressed on regulatory T cells are discussed below.

First, GARP-expressing T regulatory cells are a component of the immune system that suppress or dampen immune responses of other cells. This notion may be referred to as "tolerance." This is an important "self-check" built into the immune system to prevent excessive reactions that in some situations can result in life-threatening conditions, such as sepsis, cytokine release syndrome and cytokine storm. TGFβ1 inhibition therapies that exert Treg-inhibitory effects may, therefore, pose certain risk when the normal Treg function is impaired, particularly for a prolonged duration of time, e.g., therapeutic regimen involving treatment of six months or longer, and chronic treatment that is administered for an indefinite period of time. For this reason, patients in need of TGFβ1 inhibition therapies, particularly to avoid the risk of eliciting autoimmunity, may benefit from TGFβ1 inhibitors that do not directly perturb the normal Treg function. For example, patient populations in need of a long-term TGFβ1 inhibition therapy may include those with genetic or congenital conditions, such as DMD, CF and others. In addition, patient populations that suffer from conditions that include inflammation may benefit from a context-specific inhibitor that does not perturn the GARP/Treg function so as to minimize the risk of exacerbating the existing inflammatory conditions.

Second, increasing evidence points to a link between disproportionate Th17/Treg ratios and pathologies involving inflammation and/or fibrosis. It is generally accepted that the differentiation of the two cell types, Th17 and Treg, is negatively regulated with an inverse relationship. TGFβ1 appears to be a master gatekeeper of this process, such that, TGFβ1 exposure promotes nave T cells to differentiate into Foxp3+ Tregs, whereas TGFβ1 in combination with IL-6, promotes nave T cells to differentiate into RORγt+Th17 cells instead. In addition, once differentiated, these cell populations negatively regulate each other.

Lines of evidence suggest that an imbalance in Th17/Treg ratios correlates with the pathogenesis and/or progression of fibrotic conditions involving chronic inflammation, or severity thereof.

For example, Shoukry et al. reported that Th17 cytokines drive liver fibrosis by regulating TGFβ signaling. The authors examined ex vivo the frequency of Th17 and Treg populations in liver biopsy samples and found that increased Th17/Treg ratio correlated with advanced fibrosis, as compared to moderate fibrosis or healthy tissue samples. Consistent with the observation, a strong bias towards Th17 cytokins, IL-22 in particular, was also detected in fibrotic livers. These data suggest that increased Th17/Treg ratios lead to an imbalance in pro-fibrotic Th17 cytokines, which correlate with severity of liver fibrosis.

Similar inverse correlations of Th17 and Treg populations are observed in other diseases.

For example, increased muscle expression of IL-17 has been reported in patients with Duchenne muscular dystrophy (DMD), which is a condition that manifests chronic inflammation. De Pasquale et al. (Neurology 78(17): 1309-14) found that DMD muscle biopsy samples contained higher levels of IL-17 (a Th17 marker) and lower levels of Foxp3 (a Treg marker) mRNA compared to control. Elevations in other proinflammatory cytokines, such as TNF-α and MCP-1, were also observed and were found to be associated with worse clinical outcome of patients. The authors concluded that the data point to a possible pathogenic role of IL-17.

Similarly, Jamshidian et al. (J Neuroimmunol 2013, 262 (1-2): 106-12) reported biased Treg/Th17 balance away from regulatory toward inflammatory phenotype in patients with relapsed multiple sclerosis and its correlation with severity of clinical symptoms.

A role of regulatory T cells is also implicated in the pathogenesis of cystic fibrosis (CF). In particular, CF lungs affected by the disease are associated with exaggerated Th17 and Th2 cell responses, indicative of a classic inflammatory phenotype, but also with a deficiency in numbers or function (i.e., impairment) of Treg cells (McGuire (2015) Am J Respir Crit Care Med 191(8): 866-8).

Furthermore, Zhuang et al. (Scientific Reports (2017) 7: 40141) found imbalance of Th17/Treg cells in patients with acute anteir uveitis (anterior segment intraocular inflammation with the positive of human class I major histocompatibility complex), in which both a marked increase in Th17 cells and a marked decrease in Treg cells were seen.

Taken together, the inventors of the present disclosure recognized that what appears to be a common feature in these various diseases associated with elevated Th17/Treg rations is that the patient suffers from a fibrotic condition accompanied by an inflammatory component.

Thus, it is envisaged in the present disclosure that TGFβ1 inhibition therapy that spares the Treg/GARP-arm of the TGFβ1 function may be particularly advantageous for an effective treatment of diseases characterized by an elevated level of Th17/Treg ratios. In this way, the context-selective inhibitors of TGFβ1 according to the invention are aimed to avoid more systemic effects of TGFβ1 inhibition that may interfere with Treg function, which may lead to exacerbation of existing fibrotic/inflammatory conditions in patients. Thus, the isoform-specific, matrix-targeted TGFβ1 inhibitors described herein are used in a method for treating a patient who has or at risk of developing a fibrotic disorder that comprises inflammation. In some embodiments, the patient has an elevated Th17-to-Treg cell ratio. In some embodiments, the elevated Th17/Treg ratio may be predominantly caused by an increased number of Th17 cells, while in other embodiments, the elevated Th17/Treg ratio may be predominantly caused by a decreased number of Treg cells in the patient (or a biological sample collected from the patient). Yet in further embodiments, the elevated Th17/Treg ratio may be caused by a combination of an increased number of Th17 cells and a decreased number of Treg cells. In some embodiments, elevated levels of IL-17 and/or IL-22 detected in patients (or measured in samples collected from the patients) are also indicative of fibrotic conditions accompanied by chronic inflammation. Such patients may be therefore selected as candidates for receiving a context-selective TGFβ1 inhibitor therapy disclosed herein.

The third line of reasoning for keeping the GARP-TGFβ1 axis intact in a TGFβ1 inhibition therapy relates to the benefit of maintaining normal Treg function. As mentioned, GARP is expressed on the cell surface of Tregs and are thought to play a role in TGFβ1-mediated immunomodulation. Because Tregs are indispensable for immune homeostasis and the prevention of autoimmunity, unnecessary perturbation of which may put certain patient populations at higher risk of, for example, infections (reviewed, for example, by: Richert-Spuhler and Lund (2015) Prog Mol Biol Transl Sci. 136:217-243).

The third line of reasoning for keeping the GARP-TGFβ1 axis intact in a TGFβ1 inhibition therapy is that regulatory T cells function as a "break" to modulate or dampen over-reactive immune response. The discovery of Foxp3 as the master regulator of Treg cell development and function was critical for the understanding of Treg cell biology. Inactivating mutations in Foxp3 result in the spontaneous development of severe autoimmunity with a scurfy phenotype in mice and IPEX syndrome ('immune dysregulation, polyendocrinopathy, enteropathy, X-linked') in humans (see Dominguez-Villear and Haler, Nature Immunology 19, 665-673, 2018). Thus, it raises the possibility that TGFb1 therapy that elicits inhibitory effects of the Treg/GARP arm of TGFb1 function, especially in a prolonged treatment, may cause or exacerbate autoimmune response.

Increasing evidence suggests that Tregs not only act to dampen overexuberant effector immune responses, they also have the ability to potentiate appropriate immune responses to pathogens, by participating in pathogen clearance and protection of the host from collateral damage. Such diverse function of Treg cells is particularly apparent in delicate tissues such as the lung, which is constantly exposed to an external environment from which a variety of pathogens and other foreign components (e.g., viral pathogens, bacterial pathogens, fungal pathogens, and allergens) may gain access to host cells.

For example, influenza virus infection elicits a strong proinflammatory cytokine response with abundance immune cell infiltration. In acute and/or severe infections, such response can cause serious sequalae in susceptible individuals. Tregs provide a mechanism for dampening viral infection-associated pathology by controlling the magnitude of immune response in the host. Indeed, pathogen-exposed Tregs retain protective effects in adoptive transfer. Moreover, such adoptive transfer of primed Tregs have been shown to ameliorate influenza virus-associated morbidity and to prolong survival in severe immunocompromised animal models.

Accordingly, the invention provides use of an ECM-targeted, context-selective TGFβ1 inhibitor (e.g., LTBP1-selective or LTBP1/3-selective inhibitors of TGFβ1 activation inhibitors) for the treatment of a disease that involves matrix-associated TGFβ1 dysregulation in a subject. The subject is suffering from or at risk of an infection. The infection can be viral infections (e.g., influenza virus, respiratory syncytial virus or RSV, human immunodeficiency virus or HIV, MARS, SARS, herpes simplex virus or HSV, hepatitis A virus or HAV, hepatitis B virus or HBV, hepatitis C virus or HCV, CMV, Dengue virus, lymphocytic choriomeningitis virus, and West Nile virus), bacterial infections (meningitis, *Mycobacterium tuberculosis, Listeria monocytogenes, Citrobacter rodentium, Salmonoella*, and *E. coli*), and/or fungal infections (e.g., *Candida, Pneumocytis, Aspergillus, Cryptococcus*, and *Coccidioides*).

Typically, high-risk or at-risk populations (individuals that are considered particularly susceptible to severe infections or infection-triggered responses) include pediatric populations (infants, young children, e.g., human individuals under the age of 7); elderly populations (those who are 65 years or older); those with compromised immune system due to medical condition, health status, life styles such as smoking, and/or medications with immunosuppressive effects, etc.

For example, certain medications cause weakened immunity, such as chemotherapy, therapies that target hematopoietic cells such as CD33 therapy, steroids, immunosuppressants, and statins.

In some embodiments, high-risk or at-risk populations are those with existing medical conditions, such as those with chronic infections such as HIV, those with bone marrow transplantation, pre-diabetic individuals, diabetic individuals, those with autoimmune disorders such as RA, asthma and allergy.

Thus, matrix-targeted, context-selective TGFβ1 inhibitors encompassed herein may be particularly advantageous for treating patients who require a long-term or chronic TGFβ1 therapy since in these scenarios it is beneficial to avoid impairment of immune homeostatis and the normal immune function that provides the ability to respond effectively to possible infections caused by a variety of pathogens such as those listed above.

Accordingly, antibodies that selectively bind LTBP-TGFβ1 (e.g., LTBP1-TGFβ1 and LTBP3-TGFβ1), and that do not inhibit TGFβ1 in the context of the immune-associated TGFβ1 presenters GARP and LRRC33, are therapeutic candidates for the treatment of fibrotic indications such as organ fibrosis, and are aimed to avoid TGFβ-related global immune activation. In one embodiment, the context-specific antibodies can be used to inhibit LTBP1/3-associated TGFβ1 activity in applications in which TGFβ1-mediated immune suppression is beneficial, e.g., in a subject who has received a transplant, who is a candidate for receiving a transplant, or who is expected to receive a transplant. In some embodiments, the subject has an advanced stage fibrosis and/or a bone marrow disease.

The foregoing methods can be used to treat a subject having a condition for which inhibition or reduction in LTBP-associated TGFβ1 activity is beneficial. For example, the subject may have or be at risk for developing a disorder in which extracellular matrix-associated TGFβ1 activity has been implicated.

Integrin-mediated activation of latent TGFβ1 in the extracellular matrix is a key contributor to fibrosis. Without wishing to be bound by theory, it is presently understood that integrins, including αVβ6 and αVβ8, can trigger the release of TGFβ1 from presenting molecules including LTBP1 and LTBP3. Inhibiting release of TGFβ1 in this context can reduce or eliminate fibrosis, and/or symptoms associated therewith.

As described, LTBP1 and LTBP3 are produced and are deposited extracellularly as components of the ECM, where they can "present" a proTGFβ1 complex (latent, inactive precursor of TGFβ1) within the ECM. Upon stimulation, the LTBP1/3-proTGFβ1 complex releases the TGFβ1 growth factor (the active, mature form of growth factor) which in turn is thought to be involved in the regulation of the local tissue microenvironment, such as ECM maintenance/remodeling and the process of fibrosis, possibly by responding to various cytokines, chemokines and growth factors, and by interacting with other ECM components, such as fibronectin, Fibrillin, collagen, elastin, and matrix metallopeptidases (MMPs).

In the normal wound healing process that occurs in response to an injury, for example, TGFβ is thought to facilitate granular tissue formation, angiogenesis, and collagen synthesis and production. TGFβ signaling is also implicated in abnormal tissue fibrogenesis (i.e., fibrosis), which results in formation of excess fibrous connective tissue in an organ or tissue in a reparative or reactive process characterized by the pathological accumulation of extracellular matrix (ECM) components, such as collagens. In these and other situations, the TGFβ axis may affect further aspects (in addition to fibrotic aspect), such as inflammation, recruitment and phenotypic switch of various cell types, which may be mediated by its interaction with one or more of the other presenting molecules, such as GARP/LRRC32 and LRRC33. In certain instances, it is advantageous to preferentially inhibit the LTBP1/3-context of TGFβ1 activation, without significantly inhibiting one or more of the other contexts of TGFβ1 activation, in situations where ECM-associated TGFβ1 that drives fibrosis is to be selectively inhibited.

Accordingly, in one embodiment, the invention provides a method of reducing TGFβ1 activation in a subject having, or at risk of developing, a fibrotic disorder by administering to the subject an antibody, or antigen binding portion thereof, which selectively binds a LTBP1/3-TGFβ1 complex, as described herein. In another embodiment, the invention provides a method of treating a fibrotic disorder by administering to the subject an antibody, or antigen binding portion thereof, which selectively binds a LTBP1/3-TGFβ1 complex, as described herein.

In one embodiment, the fibrotic disorder is an organ fibrosis, wherein optionally, the organ fibrosis is an advanced organ fibrosis. In a further embodiment, the organ fibrosis is selected from the group consisting of kidney fibrosis, liver fibrosis, lung fibrosis, cardiac fibrosis, pancreatic fibrosis, skin fibrosis, scleroderma, muscle fibrosis, uterine fibrosis and endometriosis. In another further embodiment, the fibrotic disorder comprising chronic inflammation is a muscular dystrophy, multiple sclerosis (MS), or Cystic Fibrosis (CF). In a further embodiment, the muscular dystrophy is Duchenne muscular dystrophy (DMD). In another further embodiment, the MS comprises perivascular fibrosis. In a further embodiment, the lung fibrosis is idiopathic pulmonary fibrosis (IPF). In another further embodiment, the subject has chronic kidney disease (CKD). In another embodiment, the subject has nonalcoholic steatohepatitis (NASH).

In exemplary embodiments, the fibrotic disorder is fibrosis, Alport syndrome, fibroids, desmoplasia, amyotrophic lateral sclerosis (ALS), or Duchenne muscular dystrophy (DMD).

In one embodiment, the subject has desmoplasia.

In one embodiment, the subject has organ fibrosis, for example, kidney fibrosis (e.g., fibrosis associated with chronic kidney disease (CKD)), liver fibrosis (e.g., fibrosis associated with nonalcoholic steatohepatitis (NASH)), lung fibrosis (e.g., idiopathic pulmonary fibrosis (IPF)), cardiac fibrosis, and/or skin fibrosis (e.g., scleroderma). In some embodiments, the subject can have advanced organ fibrosis.

For example, the subject may be in need of an organ transplant. In one embodiment, the subject may be in need of an organ transplant, and the compounds and compositions described herein are administered to prevent allograft fibrosis from developing in the subject following receipt of the transplant.

A recent study examined whether inhibiting integrin αVβ6 could prevent TGFβ-mediated allograft fibrosis after kidney transplantation (Lo et al., Am. J. Transplant. (2013), 13:3085-3093). Surprisingly, animals treated with an inhibitory anti-αVβ6 antibody experienced a significant decrease in rejection-free survival compared to placebo animals. The authors conclude that this result cautions against TGFβ inhibition in kidney transplantation, because the immunosuppressive properties of TGFβ help prevent allograft rejection. The inhibitors, e.g., antibodies, and antigen binding portions thereof, described herein advantageously inhibit activation of TGFβ1 presented by LTBP1 or LTBP3 in the extracellular matrix, but do not inhibit activation of TGFβ1 presented by GARP or LRRC33 on immune cells. Accordingly, the context-specific LTBP1/3-TGFβ1 inhibitors, e.g., antibodies, described herein can prevent or reduce allograft fibrosis, without eliminating the immunosuppressive properties of TGFβ1 that are useful for preventing allograft rejection. Accordingly, in one aspect, the invention provides a method for treating a fibrotic disorder in a subject, comprising administering to the subject a therapeutically effective amount of an inhibitor of TGFβ1 signaling, wherein the inhibitor is a selective inhibitor of ECM-associated TGFβ1; and, wherein the subject benefits from suppressed immunity. In one embodiment, the subject has a fibrotic condition and would benefit from an allograft transplant, or has received an allograft transplant.

Additional fibrotic conditions for which antibodies and/or compositions of the present disclosure may be used therapeutically include, but are not limited to, lung indications (e.g. idiopathic pulmonary fibrosis (IPF), chronic obstructive pulmonary disorder (COPD), allergic asthma, cystic fibrosis (CF), acute lung injury, eosinophilic esophagitis, pulmonary arterial hypertension and chemical gas-injury), kidney indications (e.g., diabetic glomerulosclerosis, focal segmental glomeruloclerosis (FSGS), chronic kidney disease, fibrosis associated with kidney transplantation and chronic rejection, IgA nephropathy, and hemolytic uremic syndrome), liver fibrosis (e.g., non-alcoholic steatohepatitis (NASH), chronic viral hepatitis, parasitemia, inborn errors of metabolism, toxin-mediated fibrosis, such as alcohol fibrosis, non-alcoholic steatohepatitis-hepatocellular carcinoma (NASH-HCC), primary biliary cirrhosis, and sclerosing cholangitis), cardiovascular fibrosis (e.g., cardiomyopathy, hypertrophic cardiomyopathy, atherosclerosis and restenosis,) systemic sclerosis, skin fibrosis (e.g. skin fibrosis in systemic sclerosis, diffuse cutaneous systemic sclerosis, scleroderma, pathological skin scarring, keloid, post-surgical scarring, scar revision surgery, radiation-induced scarring and chronic wounds), eye-related conditions such as subretinal fibrosis, uveitis syndrome, uveitis associated with idiopathic retroperitoneal fibrosis, extraocular muscle fibrosis, eye diseases associated with the major histocompatibility complex (MHC class I) or histocompatibility antigens, and cancers or secondary fibrosis (e.g. myelofibrosis, head and neck cancer, M7 acute megakaryoblastic leukemia and mucositis). Other diseases, disorders or conditions related to fibrosis that may be treated using compounds and/or compositions of the present disclosure, include, but are not limited to Marfan's syndrome, stiff skin syndrome, scleroderma, rheumatoid arthritis, bone marrow fibrosis, Crohn's disease, ulcerative colitis, systemic lupus erythematosus, muscular dystrophy, (such as DMD), Dupuytren's contracture, Camurati-Engelmann disease, neural scarring, dementia, proliferative vitreoretinopathy, corneal injury, complications after glaucoma drainage surgery, and multiple sclerosis (MS). Many such fibrotic indications are also associated with inflammation of the affected tissue(s), indicating involvement of an immune component. Such inflammation may by accompanied by abbarent immune cell populations, such as increased numbers of Th17 cells, reduced numbers of Treg cells, and/or both. In each case, the affected patient may exhibit increased Th17/Treg cell ratios.

In another aspect, the invention provides a method of selecting an isoform-specific TGFβ1 inhibitor for the treatment of a fibrotic disorder in a subject, comprising: (a) determining whether the subject manifests clinical presentations including fibrosis and one or more of the following: (i) inflammation; (ii) immune suppression; (iii) proliferative dysregulation; (iv) need for an allograft transplant; (v) at risk of severe infection; (vi) in need of a lont-term TGFβ1 inhibition therapy; and (vii) manifestation of an autoimmune conditions(s); and (b) selecting an isoform-specific, context-dependent TGFβ1 inhibitor or an isoform-specific, context-independent TGFβ1 inhibitor for treatment of the fibrotic disorder based on the clinical presentations determined in step (a).

In another aspect, the invention provides a method of treating a subject having a fibrotic disorder, comprising (a) selecting a treatment regimen comprising an isoform-specific TGFβ1 inhibitor for the subject, said selection comprising (i) determining whether the fibrotic disorder manifests clinical presentations including fibrosis and one or more of the following: inflammation, immune suppression, proliferative dysregulation, and need for an allograft transplant; and (ii) selecting a treatment regimen comprising an isoform-specific, context-dependent TGFβ1 inhibitor or an isoform-specific, context-independent TGFβ1 inhibitor, based on the clinical presentations determined in step (i); and (b) administering the selected treatment regimen to the subject.

In one embodiment of the foregoing aspects, the fibrotic disorder manifests clinical presentations comprising fibrosis, inflammation, immune suppression, and proliferative dysregulation. In an exemplary embodiment, the fibrotic disorder is myelofibrosis, and the selected isoform-specific TGFβ1 inhibitor is an isoform-specific, context-independent TGFβ1 inhibitor.

In another embodiment, the fibrotic disorder manifests clinical presentations comprising fibrosis, inflammation, and need for an allograft transplant. In one embodiment, the fibrotic disorder manifests clinical presentations comprising fibrosis and inflammation. In another embodiment, the fibrotic disorder is a degenerative disease.

In one embodiment, the fibrotic disorder manifests clinical presentations comprising immune suppression and proliferative dysregulation. In an exemplary embodiment, the fibrotic disorder is associated with a solid tumor, and the selected isoform-specific TGFβ1 inhibitor is an isoform-specific LTBP1/3-specific inhibitor and/or a GARP-selective inhibitor. In one embodiment, the solid tumor is a malignant tumor. In another embodiment, the tumor is a benign tumor. In one embodiment, the subject has desmoplasia, for example, pancreatic desmoplasia. In another embodiment, the subject has fibroids.

In another aspect, the invention provides a method of treating a subject having a fibrotic disorder with an isoform-specific, LTBP1/3-specific TGFβ1 inhibitor, comprising determining whether the fibrotic disorder manifests clinical presentations including fibrosis and the need for an allograft transplant; and administering an effective amount of an isoform-specific, LTBP1/3-specific TGFβ1 inhibitor to the subject if the fibrotic disorder manifests fibrosis and the need for an allograft transplant.

In another aspect, the invention provides a method of treating a subject having a fibrotic disorder with an isoform-specific, context-independent TGFβ1 inhibitor, comprising determining whether the fibrotic disorder manifests clinical presentations including fibrosis, immune suppression and/or proliferative dysregulation; and administering an effective amount of an isoform-specific, context-independent TGFβ1 inhibitor to the subject if the fibrotic disorder manifests fibrosis in conjunction with immune suppression and/or proliferative dysregulation.

The inhibitors, e.g., antibodies, described herein can be administered to a subject in an amount effective to treat or reduce symptoms of fibrosis. The effective amount of such an inhibitor is an amount effective to achieve both therapeutic efficacy and clinical safety in the subject. In one embodiment, an effective amount is an amount effective to reduce TGFβ1 activity in the extracellular matrix. In another embodiment, an effective amount is an amount effective to reduce fibrosis in a subject. In another embodiment, the effective amount does not inhibit TGFβ1-mediated immune suppression. In some embodiments, such an inhibitor, e.g., antibody, is a context-specific inhibitor that can block activation of TGFβ1 that is mediated by an LTBP-containing, ECM-associated TGFβ1. In some embodiments, the LTBP is LTBP1 and/or LTBP3. Assays useful for determining the efficacy of the inhibitors, e.g., antibodies, and/or compositions of the present disclosure for the alteration of fibrosis include, but are not limited to, histological assays for counting fibroblasts and basic immunohistochemical analyses known in the art.

Diseases Involving Matrix Stiffening and Remodeling

Progression of fibrotic conditions involves increased levels of matrix components deposited into the ECM and/or maintenance/remodeling of the ECM. TGFβ1 at least in part contributes to this process. This is supported, for example, by the observation that increased deposition of ECM components such as collagens can alter the mechanophysical properties of the ECM (e.g., the stiffness of the matrix/substrate) and this phenomenon is associated with TGFβ1 signaling. To confirm this notion, the present inventors have evaluated the role of matrix stiffness in affecting integrin-dependent activation of TGFβ in primary fibroblasts transfected with proTGFβ and LTBP1, and grown on silicon-based substrates with defined stiffness (e.g., 5 kPa, 15 kPa or 100 kPa). Matrices with greater stiffness enhance TGFβ1 activation, and this can be suppressed by antibodies, and antigen binding portions thereof, which are capable of binding and thereby inhibiting TGFβ1 activation associated with LTBP1/3. These observations suggest that TGFβ1 influences ECM properties (such as stiffness), which in turn can further induce TGFβ1 activation, reflective of disease progression. Thus, antibodies, and antigen binding portions thereof, that selectively bind complexes of LTBP1-TGFβ1 and/or LTBP3-TGFβ1, such as those described herein may be used to block this process to counter disease progression involving ECM alterations, such as fibrosis, tumor growth, invasion, metastasis and desmoplasia. Such inhibitors can directly block ECM-associated pro/latent TGFβ complexes which are presented by LTBP1 and/or LTBP3, thereby preventing activation/release of the growth factor from the complex in the disease niche.

Muscle Conditions Associated with Fibrosis

Accumulating evidence indicates that TGFβ plays an important role in muscle homeostasis, repair, and regeneration. Agents, such as monoclonal antibodies described herein, that selectively modulate LTBP-associated TGFβ1 signaling may be effective for treating damaged muscle fibers, such as in chronic/genetic muscular dystrophies, congenital fibrosis of ocular/extraocular muscles, and acute muscle injuries, without the toxicities associated with more broadly-acting TGFβ inhibitors.

Accordingly, the present invention provides methods for treating damaged muscle fibers using an agent that preferentially modulates a subset, but not all, of TGFβ effects in vivo. Such agents can selectively modulate TGFβ1 signaling ("isoform-specific modulation") in a particular context, i.e., when presented by LTBP1 or LTBP3.

In skeletal muscle, TGFβ plays a variety of roles including inhibition of proliferation and differentiation, induction of atrophy, and development of fibrosis. TGFβ reduces satellite cell proliferation and prevents differentiation (via inhibition of MyoD and myogenin) (Allen, R. E. and L. K. J Cell Physiol, 1987. 133(3): p. 567-72; Brennan, T. J., et al., Proc Natl Acad Sci USA, 1991. 88(9): p. 3822-6; Massague, J., et al., Proc Natl Acad Sci USA, 1986. 83(21): p. 8206-10; Olson, E. N., et al., J Cell Biol, 1986. 103(5): p. 1799-805). The isoform of TGFβ (i.e., TGFβ1, 2, or 3) is not specified in these early papers, but is presumed to be TGFβ1. TGFβ also contributes to muscle fibrosis; direct injection of recombinant TGFβ1 results in skeletal muscle fibrosis, and pan-TGFβ inhibition decreases fibrosis in acute and chronically injured muscle (Li, Y., et al., Am J Pathol, 2004. 164(3): p. 1007-19; Mendias, C. L., et al., Muscle Nerve, 2012. 45(1): p. 55-9; Nelson, C. A., et al., Am J Pathol, 2011. 178(6): p. 2611-21). TGFβ1 is expressed by myofibers, macrophages, regulatory T cells, fibroblasts, and fibrocytes within the skeletal muscle (Li, Y., et al., Am J Pathol, 2004. 164(3): p. 1007-19; Lemos, D. R., et al., Nat Med, 2015. 21(7): p. 786-94; Villalta, S. A., et al., Sci Transl Med, 2014. 6(258): p. 258ra142; Wang, X., et al., J Immunol, 2016. 197(12): p. 4750-4761); and expression is increased upon injury and in disease (Li, Y., et al., Am J Pathol, 2004. 164(3): p. 1007-19; Nelson, C. A., et al., Am J Pathol, 2011. 178(6): p. 2611-21; Bernasconi, P., et al., J Clin Invest, 1995. 96(2): p. 1137-44; Ishitobi, M., et al., Neuroreport, 2000. 11(18): p. 4033-5). TGFβ2 and TGFβ3 are also upregulated (at the mRNA level) in mdx muscle (a mouse model of Duchenne muscular dystrophy), although to a lesser extent than TGFβ1 (Nelson, C. A., et al., Am J Pathol, 2011. 178(6): p. 2611-21; Zhou, L., et al., Neuromuscul Disord, 2006. 16(1): p. 32-8). Pessina, et al., recently used lineage tracing experiments to show that cells of multiple origins within dystrophic muscle adopt a fibrogenic fate via a TGFβ-dependent pathway (Pessina, P., et al., Stem Cell Reports, 2015. 4(6): p. 1046-60).

TGFβ1 has been implicated in human muscular dystrophies. Duchenne muscular dystrophy (DMD) is a severe, progressive, and ultimately fatal disease caused by the absence of dystrophin (Bushby, K., et al., Lancet Neurol, 2010. 9(1): p. 77-93). Lack of dystrophin results in increased susceptibility to contraction-induced injury, leading to continual muscle degeneration (Petrof, B. J., et al., Proc Natl Acad Sci USA, 1993. 90(8): p. 3710-4; Dellorusso, C., et al., J Muscle Res Cell Motil, 2001. 22(5): p. 467-75; Pratt, S. J., et al., Cell Mol Life Sci, 2015. 72(1): p. 153-64). Repeated rounds of repair contribute to chronic inflammation, fibrosis, exhaustion of the satellite cell pool, eventual loss of mobility and death (Bushby, K., et al., Lancet Neurol, 2010. 9(1): p. 77-93; McDonald, C. M., et al., Muscle Nerve, 2013. 48(3): p. 343-56). Expression of TGFβ1 is significantly increased in patients with DMD and correlates with the extent of fibrosis observed in these patients (Bernasconi, P., et al., J Clin Invest, 1995. 96(2): p. 1137-44; Chen, Y. W., et al., Neurology, 2005. 65(6): p. 826-34). Excessive ECM deposition has detrimental effects on the contractile properties of the muscle and can limit access to nutrition as the myofibers are isolated from their blood supply (Klingler, W., et al., Acta Myol, 2012. 31(3): p. 184-95). Recently, additional data has further implicated TGFβ1 in muscular dystrophies. Variants in LTBP4 have been found to modify disease severity in mouse and human. In mouse, a variant of LTBP4 is protective in mice lacking dystrophin or γ-sarcoglycan (Coley, W. D., et al., Hum Mol Genet, 2016. 25(1): p. 130-45; Heydemann, A., et al., J Clin Invest, 2009. 119(12): p. 3703-12). In humans, two groups independently identified a variant of LTBP4 as protective in DMD, delaying loss of ambulation by several years (Flanigan, K. M., et al., Ann Neurol, 2013. 73(4): p. 481-8; van den Bergen, J. C., et al., J Neurol Neurosurg Psychiatry, 2015. 86(10): p. 1060-5). Although the nature of the genetic variants in mouse and human differs, in both species the protective variant results in decreased TGFβ signaling (Heydemann, A., et al., J Clin Invest, 2009. 119(12): p. 3703-12); Ceco, E., et al., Sci Transl Med, 2014. 6(259): p. 259ra144). Many of the functions of TGFβ1 in skeletal muscle biology have been inferred from experiments in which purified active growth factor is injected into animals or added to cells in culture (Massague, J., et al., Proc Natl Acad Sci USA, 1986. 83(21): p. 8206-10; Li, Y., et al., Am J Pathol, 2004. 164(3): p. 1007-19; Mendias, C. L., et al., Muscle Nerve, 2012. 45(1): p. 55-9). Given the importance of cellular context for specific functions of TGFβ1 (see, for example, Hinck et al., Cold Spring Harb. Perspect. Biol, 2016. 8(12)) it is possible that some of the effects observed in these experiments do not reflect the endogenous role(s) of the cytokine in vivo. For example, treatment of human dermal fibroblasts with recombinant TGFβ1, myostatin, or GDF11 results in nearly identical changes in gene expression in these cells, although in vivo the roles of these proteins are quite different (Tanner, J. W., Khalil, A., Hill, J., Franti, M., MacDonnell, S. M., Growth Differentiation Factor 11 Potentiates Myofibroblast Activation, in Fibrosis: From Basic Mechanisms to Targeted therapies. 2016: Keystone, Colo.).

Multiple investigators have used inhibitors of TGFβ to clarify the role of the growth factor in vivo. Treatment of mdx mice with the pan-TGFβ neutralizing antibody 1D11 clearly results in reduced fibrosis (by histology and hydroxyproline content), reduced muscle damage (reduced serum creatine kinase and greater myofiber density), and improved muscle function (by plethysmography, force generation of isolated EDL muscles, and increased forelimb grip strength) (Nelson, C. A., et al., Am J Pathol, 2011. 178(6): p. 2611-21; Andreetta, F., et al., J Neuroimmunol, 2006. 175(1-2): p. 77-86; Gumucio, J. P., et al., J Appl Physiol (1985), 2013. 115(4): p. 539-45). In addition, myofiber-specific expression of a dominant negative TGFβ type II receptor protects against muscle damage after cardiotoxin injury and in 6-sarcoglycan-/- mice (Accornero, F., et al., Hum Mol Genet, 2014. 23(25): p. 6903-15). The proteoglycan decorin, which is abundant in skeletal muscle and inhibits TGFβ activity, decreases muscle fibrosis in mdx mice and following laceration injury (Li, Y., et al., Mol Ther, 2007. 15(9): p. 1616-22; Gosselin, L. E., et al., Muscle Nerve, 2004. 30(5): p. 645-53). Other molecules with TGFβ inhibitory activity, such as suramin (an anti-neoplastic agent) and losartan (an angiotensin receptor blocker) have been effective in improving muscle pathology and reducing fibrosis in mouse models of injury, Marfan's syndrome, and muscular dystrophy (Spurney, C. F., et al., J Cardiovasc Pharmacol Ther, 2011. 16(1): p. 87-95; Taniguti, A. P., et al., Muscle Nerve, 2011. 43(1): p. 82-7; Bedair, H. S., et al., Am J Sports Med, 2008. 36(8): p. 1548-54; Cohn, R. D., et al., Nat Med, 2007. 13(2): p. 204-10). While all of the therapeutic agents described above do inhibit TGFβ1 or its signaling, none of them is specific for the TGFβ1 isoform. For example, 1D11 binds to and inhibits the TGFβ1, 2, and 3 isoforms (Dasch, J. R., et al., J Immunol, 1989. 142(5): p. 1536-41). Suramin inhibits the ability of multiple growth factors to bind to their receptors, including PDGF, FGF, and EGF, in addition to TGFβ1 (Hosang, M., J Cell Biochem, 1985. 29(3): p. 265-73; Olivier, S., et al., Eur J Cancer, 1990. 26(8): p. 867-71; Scher, H. I. and W. D. Heston, Cancer Treat Res, 1992. 59: p. 131-51). Decorin also inhibits myostatin activity, both by direct binding and through upregulation of follistatin, a myostatin inhibitor (Miura, T., et al., Biochem Biophys Res Commun, 2006. 340(2): p. 675-80; Brandan, E., C. Cabello-Verrugio, and C. Vial, Matrix Biol, 2008. 27(8): p. 700-8; Zhu, J., et al., J Biol Chem, 2007. 282(35): p. 25852-63). Losartan affects additional signaling pathways through its effects on the renin-angiotensin-aldosterone system, including the IGF-1/AKT/mTOR pathway (Burks, T. N., et al., Sci Transl Med, 2011. 3(82): p. 82ra37; Sabharwal, R. and M. W. Chapleau, Exp Physiol, 2014. 99(4): p. 627-31; McIntyre, M., et al., Pharmacol Ther, 1997. 74(2): p. 181-94). Therefore, all of these therapies inhibit additional molecules which may contribute to their therapeutic effects, as well as toxicities.

Apart from chronic inflammation, the hallmark of DMD is excessive, and progressive, fibrosis. In advanced disease the fibrosis is so severe that it can actually isolate individual muscle fibers from their blood supply. It also alters the contractile properties of the muscle. In human patients, there is a strong correlation between the extent of TGFβ1 upregulation and fibrosis, and a strong link between the extent of fibrosis and negative mobility outcomes. Therefore, in some embodiments, LTBP-proTGFβ1 inhibitors may be administered to dystrophic patients for the prevention and/or reduction of fibrosis to selectively target the ECM-associated TGFβ1 effects in the disease. In some embodiments, various isoform- and/or context-selective agents described herein can be employed to achieve inhibition of TGFβ1 signaling to prevent fibrosis and promote myogenesis, but without having unwanted effects on the immune system (e.g., through GARP or LRRC33).

Administration

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, inhibitors, e.g., antibodies, or antigen binding portions thereof, that selectively bind a LTBP1-TGFβ1 complex and/or a LTBP3-TGFβ1 complex can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a TGFβ-related indication, such as those noted above. A subject having a TGFβ-related indication can be identified by routine medical examination, e.g., laboratory tests, organ functional tests, CT scans, or ultrasounds. A subject suspected of having any of such indication might show one or more symptoms of the indication. A subject at risk for the indication can be a subject having one or more of the risk factors for that indication.

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. For example, in certain embodiments of the present invention, the intended purpose may be to inhibit TGFβ-1 activation in vivo, to achieve clinically meaningful outcome associated with the TGFβ-1 inhibition. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a TGFβ-related indication. Alternatively, sustained continuous release formulations of an antibody that selectively binds a LTBP1-TGFβ1 complex and/or a LTBP3-TGFβ1 complex may be appropriate. Various formulations and devices for achieving sustained release would be apparent to the skilled artisan and are within the scope of this disclosure.

In one example, dosages for an inhibitor, e.g., antibody, that selectively binds a LTBP1-TGFβ1 complex and/or a LTBP3-TGFβ1 complex as described herein may be determined empirically in individuals who have been given one or more administration(s) of the inhibitor. Individuals are given incremental dosages of the inhibitor. To assess efficacy, an indicator of the TGFβ-related indication can be followed. For example, methods for measuring for myofiber damage, myofiber repair, inflammation levels in muscle, and/or fibrosis levels in muscle are well known to one of ordinary skill in the art.

The present invention encompasses the recognition that agents capable of modulating the activation step of TGFβs in an isoform-specific manner, and a context-specific manner, may provide improved safety profiles when used as a medicament. Accordingly, the invention includes inhibitors, e.g., antibodies and antigen-binding fragments thereof, that selectively bind and inhibit activation of TGFβ1, but not TGFβ2 or TGFβ3, thereby conferring specific inhibition of the TGFβ1 signaling in vivo while minimizing unwanted side effects from affecting TGFβ2 and/or TGFβ3 signaling. Likewise, the invention includes inhibitors, e.g., antibodies and antigen-binding fragments thereof, that selectively inhibit activation of TGFβ1 presented by LTBP1 and/or LTBP3, but not TGFβ1 presented by GARP or LRRC33, thereby conferring specific inhibition of LTBP1/3-associated TGFβ1 signaling in vivo while minimizing unwanted side effects caused by modulation of GARP-associated TGFβ1 and/or LRRC33-associated TGFβ1.

In some embodiments, the inhibitors, e.g., antibodies, or antigen binding portions thereof, as described herein, are not toxic when administered to a subject. In some embodiments, the inhibitors, e.g., antibodies, or antigen binding portions thereof, as described herein, exhibit reduced toxicity when administered to a subject as compared to an antibody that binds to both TGFβ1 and TGFβ2. In some embodiments, the inhibitors, e.g., antibodies, or antigen binding portions thereof, as described herein, exhibit reduced toxicity when administered to a subject as compared to an inhibitor that binds to both TGFβ1 and TGFβ3. In some embodiments, the inhibitors, e.g., antibodies, or antigen binding portions thereof, as described herein, exhibit reduced toxicity when administered to a subject as compared to an inhibitor that binds to TGFβ1, TGFβ2 and TGFβ3.

Generally for administration of any of the inhibitors, e.g., antibodies, described herein, an initial candidate dosage can be about 0.5-30 mg/kg per dose, e.g., about 0.5 mg/kg, about 1 mg/kg, about 2 mg/kg, about 5 mg/kg, about 10 mg/kg, about 15 mg/kg, about 20 mg/kg, about 30 mg/kg per dose. Typically, the composition comprising an antibody or a fragment thereof encompassed by the present disclosure is administered to a human patient at the dosage weekly. In some embodiments, frequency of administration may be adjusted to, for example, twice a week, once a week, every two weeks, every three weeks, every four weeks, every six weeks, every eight weeks, etc. For the purpose of the present disclosure, a typical daily dosage might range from about any of 0.1 mg/kg to 5 mg/kg or more, depending on the factors mentioned above. For repeated administrations over several days or longer, depending on the condition, the treatment is sustained until a desired suppression of symptoms occurs or until sufficient therapeutic levels are achieved to alleviate a TGFβ-related indication, or a symptom thereof.

In one embodiment, the antibody, or antigen-binding fragment thereof, is administered to the subject at a dosage of between 0.1 and 30 mg/kg, between 0.5 and 30 mg/kg, between 1 and 30 mg/kg, between 5 and 30 mg/kg, between 10 and 30 mg/kg, between 15 and 30 mg/kg, between 20 and 30 mg/kg, between 25 and 30 mg/kg, between 0.1 and 25 mg/kg, between 0.5 and 25 mg/kg, between 1 and 25 mg/kg, between 5 and 25 mg/kg, between 10 and 25 mg/kg, between 15 and 25 mg/kg, between 20 and 25 mg/kg, between 0.1 and 20 mg/kg, between 0.5 and 20 mg/kg, between 1 and 20 mg/kg, between 5.0 and 20 mg/kg, between 10 and 20 mg/kg, between 15 and 20 mg/kg, between 0.1 and 15 mg/kg, between 0.5 and 15 mg/kg, between 1 and 15 mg/kg, between 5 and 15 mg/kg, between 10 and 15 mg/kg, between 5.0 and 20 mg/kg, between 10 and 20 mg/kg, between 15 and 20 mg/kg, between 0.1 and 10 mg/kg, between 0.5 and 10 mg/kg, between 1 and 10 mg/kg, between 5 and 10 mg/kg, optionally, wherein the subject is administered the antibody, or antigen-binding portion thereof, twice a week, once a week, once every 2 weeks, once every 3 weeks, once a month, or every other month.

An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. Pharmacokinetics experiments have shown that the serum concentration of an inhibitor, e.g., antibody, disclosed herein (e.g., SR-AB2) remains stable for at least 7 days after administration to a preclinical animal model (e.g., a mouse model). Without wishing to be bound by any particular theory, this stability post-administration may be advantageous since the antibody may be administered less frequently while maintaining a clinically effective serum concentration in the subject to whom the antibody is administered (e.g., a human subject). In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

For the purpose of the present disclosure, the appropriate dosage of an inhibitor, e.g., antibody or antigen-binding fragment thereof, that selectively binds a LTBP1-TGFβ1 complex and/or a LTBP3-TGFβ1 complex will depend on the specific antibody (or compositions thereof) employed, the type and severity of the indication, whether the antibody is administered for preventive or therapeutic purposes, previous therapy, the patient's clinical history and response to the inhibitor, and the discretion of the attending physician. In some embodiments, a clinician will administer an inhibitor, e.g., antibody, that selectively binds a LTBP1-TGFβ1 complex and/or a LTBP3-TGFβ1 complex, until a dosage is reached that achieves the desired result. Administration of an inhibitor, e.g., antibody, that selectively binds a LTBP1-TGFβ1 complex and/or a LTBP3-TGFβ1 complex can be continuous or intermittent, depending, for example, upon the recipient's physiological condition, whether the purpose of the administration is therapeutic or prophylactic, and other factors known to skilled practitioners. The administration of an inhibitor, e.g., antibody, that selectively binds a LTBP1-TGFβ1 complex and/or a LTBP3-TGFβ1 complex may be essentially continuous over a preselected period of time or may be in a series of spaced dose, e.g., either before, during, or after developing a TGFβ-related indication.

As used herein, the term "treating" refers to the application or administration of a composition including one or more active agents to a subject, who has a TGFβ-related indication, a symptom of the indication, or a predisposition toward the indication, with the purpose to cure, heal, alleviate, relieve, alter, remedy, ameliorate, improve, or affect the indication, the symptom of the indication, or the predisposition toward the indication.

Alleviating a TGFβ-related indication with an inhibitor, e.g., antibody, that selectively binds a LTBP1-TGFβ1 complex and/or a LTBP3-TGFβ1 complex includes delaying the development or progression of the indication, or reducing indication's severity. Alleviating the indication does not necessarily require curative results. As used therein, "delaying" the development of an indication associated with a TGFβ-related indication means to defer, hinder, slow, retard, stabilize, and/or postpone progression of the indication. This delay can be of varying lengths of time, depending on the history of the indication and/or individuals being treated. A method that "delays" or alleviates the development of an indication, or delays the onset of the indication, is a method that reduces probability of developing one or more symptoms of the indication in a given time frame and/or reduces extent of the symptoms in a given time frame, when compared to not using the method. Such comparisons are typically based on clinical studies, using a number of subjects sufficient to give a statistically significant result.

Selection of a TGFβ1 Inhibitor for Treating a Fibrotic Disorder

The present invention includes specific inhibitors of ECM-associated TGFβ1 activation, e.g., antibodies, and antigen-binding portions thereof, that selectively bind a LTBP1/3-TGFβ1 complex, and which inhibit activation of TGFβ1 presented in the context of LTBP1 or LTBP3. Context-specific antibodies that selectively bind a GARP-TGFβ1 complex and inhibit activation of TGFβ1 presented in the context of GARP have recently been described in U.S. Provisional Applications 62/362,393 and 62/371,355. Isoform-specific, context-independent TGFβ1 inhibitors have also been described, which bind pro/latent TGFβ1 presented by LTBP1/3, GARP, or LRRC33, and inhibit the release of mature TGFβ1 from the presenting molecule complex (see, e.g., PCT/US2017/21972). The entire contents of each of the foregoing applications are incorporated herein by reference.

The present invention encompasses insights into selection of "the right TGFβ1 inhibitor" for "the right patient" to treat a disease condition with certain clinical features. In one aspect, the present invention provides use of preferred TGFβ1 inhibitors suitable for a particular patient population with fibrotic conditions. Accordingly, the invention includes use of an LTBP1/LTBP3-proTGFβ1 inhibitor in the treatment of a fibrotic condition in a subject, wherein the subject benefits from immunosuppression. This is based on the notion that at least a subset of TGFβ1 activities involves immune regulation which is mediated by GARP-associated and/or LRRC33-associated TGFβ1. Thus, the invention includes the recognition that use of TGFβ1 inhibitors that also affect the immune aspect of TGFβ1 effects may be detrimental for treating patients with fibrotic conditions where immunostimulation may cause exacerbation of the disease. The invention therefore aims at least in part to provide means of selectively inhibiting TGFβ1 effects within the ECM context (e.g., LTBP-associated) while sparing TGFβ1 effects associated with non-ECM contexts (e.g., immune cells, leukocytes, etc. expressing GARP or LRRC33 on cell surface), so as to prevent unwanted immunostimulation.

In some embodiments, patient populations who benefit from both: i) inhibition of TGFβ1 signaling, and, ii) immunosuppression, include those who suffer from a severe or late stage organ fibrosis and who are to receive an allograft organ transplant. The severe or late stage organ fibrosis may be associated with IPF, CKD, and/or NASH. Such patients may have already received other therapies for treating the fibrotic disease, yet which may have failed to sufficiently treat or manage the condition. Attending physicians may determine that remaining treatment options may include allograft transplantation. Such patients may be placed in a wait list for an available organ for transplantation. Such patients may be treated with an immunosuppressant. A selective inhibitor of LTBP1/LTBP3-presented TGFβ1 activation, which does not inhibit GARP-presented TGFβ1 activation, can be used to treat such patients, without raising risk of triggering immunostimulation mediated by effector T cells. Similarly, following the transplantation, such patients may continue to receive the selective inhibitor of LTBP1/LTBP3-presented TGFβ1 activation to avoid risk of an organ rejection.

In some embodiments, patient populations who benefit from both: i) inhibition of TGFβ1 signaling, and, ii) immunosuppression, include those who suffer from a fibrotic disorder and who have an inflammatory or autoimmune condition.

In some embodiments, the inflammatory or autoimmune condition is associated with the fibrosis. Non-limiting examples of inflammatory or autoimmune conditions associated with fibrosis include muscular dystrophy, such as DMD.

In other embodiments, where patient populations who benefit from both: i) inhibition of TGFβ1 signaling, and, ii) immunosuppression, include those who suffer from a fibrotic disease and who have an inflammatory or autoimmune condition that is not directly associated with the fibrosis, but rather a discrete disorder.

Such inflammatory or autoimmune conditions, whether or not directly associated with the underlining fibrotic disease or separate condition(s), may be caused by or associated with imbalance of regulatory T cells (Treg) in human autoimmune diseases. For example, such disorders that are linked to Treg dysregulation include, but are not limited to: Juvenile idiopathic arthritis; Rheumatoid arthritis (RA); Spondyloarthritis; Psoriatic arthritis; HCV mixed cryoglobulinaemia; cryoglobulinaemia; Multiple sclerosis; Autoimmune liver disease; Systemic lupus erythematodes; Immune-mediated diabetes; Myasthenia gravis; Primary Sjögren syndrome; Kawasaki disease; and, Inflammatory bowel disease (IBD).

Thus, LTBP1/3-sepective inhibitors of TGFβ1 signaling, such as those described herein, can be used to treat patients who suffer from a fibrotic condition and inflammatory or autoimmune condition such as one or more of the disorders listed above. The LTBP1/3-sepective inhibitors of TGFβ1 signaling used accordingly can treat or alleviate TGFβ1-dependent fibrosis in the ECM, while sparing immune-associated TGFβ1 signaling.

Accordingly, related methods of the invention include methods for selecting an appropriate TGFβ1 inhibitor for treating a fibrotic disorder, based on the clinical manifestations of the fibrotic disorder in a subject. In one embodiment, the invention provides a method of selecting an isoform-specific TGFβ1 inhibitor for treatment of a fibrotic disorder in a subject. The method comprises (a) determining whether the fibrotic disorder manifests clinical presentations including fibrosis and one or more of inflammation, immune suppression, proliferative dysregulation, and need for an allograft transplant, and (b) selecting an isoform-specific, context-dependent TGFβ1 inhibitor or an isoform-specific, context-independent TGFβ1 inhibitor for treatment of the fibrotic disorder based on the clinical presentations determined in step (a). In another embodiment, the invention provides a method of treating a subject having a fibrotic disorder, comprising selecting a treatment regimen including an isoform-specific TGFβ1 inhibitor for the subject, and administering the selected treatment regimen to the subject, wherein the selection comprises (a) determining whether the fibrotic disorder manifests clinical presentations including fibrosis and one or more of the following: inflammation, immune suppression, proliferative dysregulation, and need for an allograft transplant; and (b) selecting a treatment regimen comprising an isoform-specific, context-dependent TGFβ1 inhibitor or an isoform-specific, context-independent TGFβ1 inhibitor, based on the clinical presentations determined in step (a).

Subjects afflicted with fibrotic disorders can display a wide range of symptoms, in addition to fibrosis. The specific combination of clinical manifestations in a subject can guide the selection of an appropriate TGFβ1-inhibitory treatment regimen. For example, a context-independent, isoform-specific TGFβ1 inhibitor can be used to treat the subject if the subject's clinical manifestations indicate a need for inhibition of TGFβ1, without modulating the activity of TGFβ2 or TGFβ3. A treatment regimen including a LTBP context-specific inhibitor can be used to treat the subject if the subject's clinical manifestations indicate that inhibition of TGFβ1 in the extracellular matrix would be beneficial. A LTBP context-specific inhibitor is also advantageous if the subject's clinical manifestations indicate that stimulation of immune effector cells is undesirable. A GARP context-specific inhibitor can be used to treat the subject if the subject's clinical manifestations indicate that blocking the activation/release of TGFβ1 on regulatory T cells (Treg cells) would be beneficial, e.g., to prevent Treg cells from suppressing effector T cell activity. A LRRC33 context-specific inhibitor can be used to treat the subject if the subject's clinical manifestations indicate that blocking the activation/release of TGFβ1 on myeloid cells, monocytes, macrophages, dendritic cells and/or microglia would be beneficial, e.g., to reverse or reduce immune suppression in the subject.

By way of example, a subject having a fibrotic disorder may display clinical manifestations including fibrosis, inflammation, immune suppression, and proliferative dysregulation. Fibrotic disorders which commonly present with the foregoing combination of symptoms include, e.g., myelofibrosis. In this embodiment, an isoform-specific, context-independent TGFβ1 inhibitor can be selected for treating the subject.

A subject having a fibrotic disorder may display clinical manifestations including fibrosis, inflammation, and need for an allograft transplant. Fibrotic disorders which commonly present with the foregoing combination of symptoms include, e.g., organ fibrosis, such as kidney fibrosis (e.g., fibrosis associated with chronic kidney disease), liver fibrosis (e.g., fibrosis associated with nonalcoholic steatohepatitis (NASH)), or lung fibrosis (e.g., fibrosis associated with idiopathic pulmonary fibrosis (IPF)). In this embodiment, a context-specific LTBP1/3-specific inhibitor is selected for treating the subject.

In another example, a subject having a fibrotic disorder may display clinical manifestations including fibrosis and inflammation. Fibrotic disorders which commonly present with the foregoing combination of symptoms include, e.g., scleroderma. In this embodiment, a context-specific LTBP1/3-specific inhibitor is selected for treating the subject. Additional fibrotic disorders which commonly present with the foregoing combination of symptoms include, e.g., degenerative diseases, such as muscular dystrophy, e.g., Duchenne muscular dystrophy (DMD). In this embodiment, a context-specific LTBP1/3-specific inhibitor is selected for treating the subject.

A subject having a fibrotic disorder may display clinical manifestations including immune suppression and proliferative dysregulation. Fibrotic disorders which commonly present with the foregoing combination of symptoms include, e.g., solid tumors. In some embodiments, the solid tumor is a malignant tumor. In other embodiments, the solid tumor is a benign tumor. In an exemplary embodiment, the subject has desmoplasia (e.g., pancreatic desmoplasia). In some embodiments, patients may have a solid tumor that has been assessed as "inoperable" or not suitable for surgical resection. Thus, in some embodiments, patients are not candidates for surgical resection of the tumor. However, TGFβ1 inhibition therapy comprising a context-selective TGFβ1 inhibitor of the present invention may reverse such non-candidate patients to be more suited for receiving a surgery. In some embodiments, subjects having a solid tumor are poorly responsive to cancer therapy (e.g., the tumor is resistant to the cancer therapy), such as chemotherapy, radiation therapy, CAR-T therapy and checkpoint inhibitor therapy. TGFβ1 inhibition therapy comprising a context-selective TGFβ1 inhibitor of the present invention may at least in part reverse the resistance to render the patient more responsive to the cancer therapy. In some embodiments, a combination therapy comprising both the context-selective TGFβ1 inhibition therapy and the cancer therapy may synergistically treat the cancer. In some embodiments, the context-selective TGFβ1 inhibition therapy administered in conjunction with the cancer therapy may reduce the required dosage of the cancer therapy to produce equivalent or improved clinical effects.

In another exemplary embodiment, the subject has fibroids. In the foregoing embodiments, in which the fibrotic disorder displays clinical manifestations including immune suppression and proliferative dysregulation, a context-specific LTBP1/3-specific inhibitor and/or a context-specific GARP-specific inhibitor are selected for treating the subject.

In another aspect, the invention provides a method of treating a subject having a fibrotic disorder with an isoform-specific, LTBP1/3-specific TGFβ1 inhibitor, by selecting a subject having a fibrotic disorder manifesting clinical presentations including fibrosis and the need for an allograft transplant, and administering an effective amount of an isoform-specific, LTBP1/3-specific TGFβ1 inhibitor to the subject. In one embodiment, the method comprises determining whether the fibrotic disorder manifests clinical presentations including fibrosis and the need for an allograft transplant. The LTBP1/3-specific TGFβ1 inhibitor is administered to the subject if the subject exhibits symptoms including fibrosis and the need for an allograft transplant.

In another aspect, the invention provides a method of treating a subject having a fibrotic disorder with an isoform-specific, context-independent TGFβ1 inhibitor, by selecting a subject having a fibrotic disorder manifesting clinical presentations including fibrosis, immune suppression, and/or proliferative dysregulation, and administering an effective amount of an isoform-specific, context-independent TGFβ1 inhibitor to the subject. In one embodiment, the method comprises determining whether the fibrotic disorder manifests clinical presentations including fibrosis, immune suppression, and/or proliferative dysregulation. The isoform-specific, context-independent TGFβ1 inhibitor is administered to the subject if the subject inhibits symptoms including fibrosis, immune suppression, and/or proliferative dysregulation.

Clinical manifestations including inflammation, immune suppression, proliferative dysregulation, and/or the need for an allograft transplant can be determined in a subject having a fibrotic disorder using methods and practices known in the art. Such methods include, for example, physical examination and standard diagnostic tests. In one embodiment, inflammation can be assessed by determining if a subject displays an elevated level of inflammatory biomarkers in plasma, blood, or serum. Such inflammatory biomarkers include, for example, C-reactive protein, interleukin 1 (IL-1), interleukin 6 (IL-6), tumor necrosis factor α (TNF-α), or combinations thereof. Blood tests including erythrocyte sedimentation rate (ESR) and plasma viscosity (PV) can also indicate the presence of inflammation in a subject with a fibrotic disorder. In another embodiment, immune suppression can be assessed by determining the number and composition of a subject's blood cells, e.g., T cells, B cells, NK cells, monocytes, macrophages, etc. Immune suppression can also be assessed by determining if the subject is taking or has a history of taking immunosuppressant medications, or determining if the subject has a condition associated with immune suppression (e.g., hematological malignancies, HIV/AIDS, etc.). In another embodiment, proliferative dysregulation can be assessed using standard tests including blood tests, biopsy, and/or imaging procedures such as CT scan, ultrasound, and MRI. Other standard tests for diagnosing cancer (e.g., biomarker tests, etc.) can also be used to assess proliferative dysregulation. The need for an allograft transplant can be determined by a clinician using standard procedures. In one embodiment, the loss or partial loss of organ function, or an increased likelihood of loss of organ function, indicates the need for a transplant.

As mentioned, the present invention provides selective targeting of the ECM-associated TGFβ1 complexes enabled by the use of antibodies that are capable of specifically binding LTBP-presented TGFβ1 precursors. While some antibodies of the present invention are capable of binding and inhibiting both LTBP1- and LTBP3-associated proTGFβ1 complexes, others show even greater selectivity in that they only bind either LTBP1-proTGFβ1 or LTBP3-proTGFβ1.

The invention therefore encompasses the recognition that certain patient populations may benefit from TGFβ1 inhibition therapy comprising a context-selective inhibitor that is specific to LTBP1-proTGFβ1.

LTBP1 and LTBP3 are both components of the ECM, where they can display or "present" a latent TGFβ1 precursor complex. Some observations from expression studies raise the possibility that deletion, ablation or functional inhibition of LTBP3 may cause certain toxicities. LTBP3−/− mice (as well as some human mutations) have short stature, as well as bone and dental anomalies. These phenotypes are likely associated with disruptions in development, however, but it is possible that LTBP3 plays a role in homeostasis of these tissues in adults (expression in adult bone is reported). Based on these observations, in certain clinical situations (where the disease manifests in a tissue known to express LTBP3 and associated with toxicities) or in certain patient populations, such as pediatric patients who are still in active development, it may be advisable to avoid potential toxicities of LTBP3-related inhibition. Loss of LTBP1 function does appear to be sufficient to protect against at least some forms of fibrosis, as LTBP1−/− KO mice are protected against liver fibrosis (induced by bile duct ligation). Taken together, these data raise the possibility that LTBP1-specific TGFβ1 inhibition could have a superior safety profile as compared to LTBP1/3-TGFβ1 inhibitors in certain situations.

Combination Therapies

The disclosure further encompasses pharmaceutical compositions and related methods used as combination therapies for treating subjects who may benefit from TGFβ1 inhibition in vivo. In any of these embodiments, such subjects may receive combination therapies that include a first composition comprising at least one TGFβ1 inhibitor, e.g., antibody or antigen-binding portion thereof, described herein, in conjunction with a second composition comprising at least one additional therapeutic intended to treat the same or overlapping disease or clinical condition. The first and second compositions may both act on the same cellular target, or discrete cellular targets. In some embodiments, the first and second compositions may treat or alleviate the same or overlapping set of symptoms or aspects of a disease or clinical condition. In some embodiments, the first and second compositions may treat or alleviate a separate set of symptoms or aspects of a disease or clinical condition. To give but one example, the first composition may treat a disease or condition associated with TGFβ1 signaling, while the second composition may treat inflammation or fibrosis associated with the same disease, etc. Such combination therapies may be administered in conjunction with each other. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

In preferred embodiments, combination therapies produce synergistic effects in the treatment of a disease. The term "synergistic" refers to effects that are greater than additive effects (e.g., greater efficacy) of each monotherapy in aggregate.

In some embodiments, combination therapies comprising a pharmaceutical composition described herein produce efficacy that is overall equivalent to that produced by another therapy (such as monotherapy of a second agent) but are associated with fewer unwanted adverse effect or less severe toxicity associated with the second agent, as compared to the monotherapy of the second agent. In some embodiments, such combination therapies allow lower dosage of the second agent but maintain overall efficacy. Such combination therapies may be particularly suitable for patient populations where a long-term treatment is warranted and/or involving pediatric patients.

Accordingly, the invention provides pharmaceutical compositions and methods for use in combination therapies for the reduction of TGFβ1 protein activation and the treatment or prevention of diseases or conditions associated with TGFβ1 signaling, as described herein. Accordingly, the methods or the pharmaceutical compositions further comprise a second therapy. In some embodiments, the second therapy may be useful in treating or preventing diseases or conditions associated with TGFβ1 signaling. The second therapy may diminish or treat at least one symptom(s) associated with the targeted disease. The first and second therapies may exert their biological effects by similar or unrelated mechanisms of action; or either one or both of the first and second therapies may exert their biological effects by a multiplicity of mechanisms of action.

It should be understood that the pharmaceutical compositions described herein may have the first and second therapies in the same pharmaceutically acceptable carrier or in a different pharmaceutically acceptable carrier for each described embodiment. It further should be understood that the first and second therapies may be administered simultaneously or sequentially within described embodiments.

In one embodiment, the inhibitors, e.g., antibodies, described herein that selectively binds a LTBP1-TGFβ1 complex and/or a LTBP3-TGFβ1 complex can be administered with another agent that inhibits TGFβ1 activity. For example, the second agent can be another context-specific TGFβ1 inhibitor. In one embodiment, the combination therapy comprises (i) an inhibitor, e.g., antibody or antigen binding portion thereof, that selectively binds a LTBP1-TGFβ1 complex and/or a LTBP3-TGFβ1 complex, and (ii) an inhibitor, e.g., antibody or antigen binding portion thereof, that selectively binds a GARP-TGFβ1 complex. In another embodiment, the combination therapy comprises (i) an inhibitor, e.g., antibody or antigen binding portion thereof, that selectively binds a LTBP1-TGFβ1 complex and/or a LTBP3-TGFβ1 complex, and (ii) an inhibitor, e.g., antibody or antigen binding portion thereof, that selectively binds a LRRC33-TGFβ1 complex. Context-specific antibodies that selectively bind LRRC33-TGFβ1 are described, for example, in U.S. 62/503,785, and context-specific antibodies that selectively bind GARP-TGFβ1 are described, above. The entire contents of the foregoing applications are incorporated by reference herein. In one embodiment, the combination therapy comprises (i) an inhibitor, e.g., antibody or antigen binding portion thereof, that selectively binds a LTBP1-TGFβ1 complex and/or a LTBP3-TGFβ1 complex, and (ii) an context-independent inhibitor, e.g., antibody or antigen binding portion thereof, that selectively binds pro/latent TGFβ1 in a complex with a presenting molecule (e.g., LTBP, GARP, and/or LRRC33). Context-independent inhibitors of TGFβ1 are described, for example, in PCT/US2017/21972, the entire contents of which are incorporated herein by reference.

The one or more anti-TGFβ1 inhibitors, e.g., antibodies, or antigen binding portions thereof, of the invention may be used in combination with one or more additional therapeutic agents. Examples of the additional therapeutic agents which can be used with an anti-TGFβ antibody of the invention include, but are not limited to, a myostatin inhibitor, a VEGF agonist, an IGF1 agonist, an FXR agonist, a CCR2 inhibitor, a CCR5 inhibitor, a dual CCR2/CCR5 inhibitor, a lysyl oxidase-like-2 inhibitor, an ASK1 inhibitor, an Acetyl-CoA Carboxylase (ACC) inhibitor, a p38 kinase inhibitor, Pirfenidone, Nintedanib, a GDF11 inhibitor, and the like.

In some embodiments, the additional agent is a checkpoint inhibitor. In some embodiments, the additional agent is selected from the group consisting of a PD-1 antagonist, a PDL1 antagonist, a PD-L1 or PDL2 fusion protein, a CTLA4 antagonist, a GITR agonist, an anti-ICOS antibody, an anti-ICOSL antibody, an anti-B7H3 antibody, an anti-B7H4 antibody, an anti-TIM3 antibody, an anti-LAG3 antibody, an anti-OX40 antibody, an anti-CD27 antibody, an anti-CD70 antibody, an anti-CD47 antibody, an anti-41BB antibody, an anti-PD-1 antibody, an oncolytic virus, and a PARP inhibitor. In some embodiments, the additional therapy is radiation. In some embodiments, the additional agent is a chemotherapeutic agent. In some embodiments, the chemotherapeutic agent is Taxol. In some embodiments, the additional agent is an anti-inflammatory agent. In some embodiments, the additional agent inhibits the process of monocyte/macrophage recruitment and/or tissue infiltration. In some embodiments, the additional agent is an inhibitor of hepatic stellate cell activation. In some embodiments, the additional agent is a chemokine receptor antagonist, e.g., CCR2 antagonists and CCR5 antagonists. In some embodiments, such chemokine receptor antagonist is a dual specific antagonist, such as a CCR2/CCR5 antagonist. In some embodiments, the additional agent to be administered as combination therapy is or comprises a member of the TGFβ superfamily of growth factors or regulators thereof. In some embodiments, such agent is selected from modulators (e.g., inhibitors and activators) of GDF8/myostatin and GDF11. In some embodiments, such agent is an inhibitor of GDF8/myostatin signaling. In some embodiments, such agent is a monoclonal antibody that binds a pro/latent myostatin complex and blocks activation of myostatin. In some embodiments, the monoclonal antibody that binds a pro/latent myostatin complex and blocks activation of myostatin does not bind free, mature myostatin.

Such combination therapies may advantageously utilize lower dosages of the administered therapeutic agents, thus avoiding possible toxicities or complications associated with the various monotherapies.

Assays for Detecting a LTBP1-TGFβ1 Complex and/or a LTBP3-TGFβ1 Complex

In some embodiments, methods and compositions provided herein relate to a method for detecting a LTBP1-TGFβ1 complex and/or a LTBP3-TGFβ1 complex in a sample obtained from a subject. As used herein, a "subject" refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, poultry, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is a patient or a healthy volunteer.

In some embodiments, a method for detecting a LTBP1-TGFβ1 complex and/or a LTBP3-TGFβ1 complex in a sample obtained from a subject involves (a) contacting the sample with an antibody that selectively binds a LTBP1-TGFβ1 complex and/or a LTBP3-TGFβ1 complex under conditions suitable for binding of the antibody to the antigen, if the antigen is present in the sample, thereby forming binding complexes; and (b) determining the level of the antibody bound to the antigen (e.g., determining the level of the binding complexes).

In one embodiment, a screening assay that utilizes biotinylated latent TGFβ1 complexes immobilized onto a surface is utilized, which allows for the activation of latent TGFβ by integrins, e.g., by providing a tether. Other, non-integrin activators could also be tested in that system. A readout can be measured through reporter cells or other TGFβ-dependent cellular responses.

Cell-Based Assays for Measuring TGFβ Activation

Activation of TGFβ (and inhibition thereof by a TGFβ test inhibitor, such as an antibody) may be measured by any suitable method known in the art. For example, integrin-mediated activation of TGFβ can be utilized in a cell-based assay, such as the "CAGA12" luciferase assay, described in more detail herein. Such an assay system may comprise the following components: i) a source of TGFβ (recombinant, endogenous or transfected); ii) a source of integrin (recombinant, endogenous, or transfected); and iii) a reporter system that responds to TGFβ activation, such as cells expressing TGFβ receptors capable of responding to TGFβ and translating the signal into a readable output (e.g., luciferase activity in CAGA12 cells or other reporter cell lines). In some embodiments, the reporter cell line comprises a reporter gene (e.g., a luciferase gene) under the control of a TGFβ-responsive promoter (e.g., a PAI-1 promoter). In some embodiments, certain promoter elements that confer sensitivity may be incorporated into the reporter system. In some embodiments, such promoter element is the CAGA12 element. Reporter cell lines that may be used in the assay have been described, for example, in Abe et al. (1994) *Anal Biochem.* 216(2): 276-84, incorporated herein by reference. In some embodiments, each of the aforementioned assay components are provided from the same source (e.g., the same cell). In some embodiments, two of the aforementioned assay components are provided from the same source, and a third assay component is provided from a different source. In some embodiments, all three assay components are provided from different sources. For example, in some embodiments, the integrin and the latent TGFβ complex (proTGFβ and a presenting molecule) are provided for the assay from the same source (e.g., the same transfected cell line). In some embodiments, the integrin and the TGF are provided for the assay from separate sources (e.g., two different cell lines, a combination of purified integrin and a transfected cell). When cells are used as the source of one or more of the assay components, such components of the assay may be endogenous to the cell, stably expressed in the cell, transiently transfected, or any combination thereof.

A skilled artisan could readily adapt such assays to various suitable configurations. For instance, a variety of sources of TGFβ may be considered. In some embodiments, the source of TGFβ is a cell that expresses and deposits TGFβ (e.g., a primary cell, a propagated cell, an immortalized cell or cell line, etc.). In some embodiments, the source of TGFβ is purified and/or recombinant TGFβ immobilized in the assay system using suitable means. In some embodiments, TGFβ immobilized in the assay system is presented within an extracellular matrix (ECM) composition on the assay plate, with or without de-cellularization, which mimics fibroblast-originated TGFβ. In some embodiments, TGFβ is presented on the cell surface of a cell used in the assay. Additionally, a presenting molecule of choice may be included in the assay system to provide suitable latent-TGFβ complex. One of ordinary skill in the art can readily determine which presenting molecule(s) may be present or expressed in certain cells or cell types. Using such assay systems, relative changes in TGFβ activation in the presence or absence of a test agent (such as an antibody) may be readily measured to evaluate the effects of the test agent on TGFβ activation in vitro.

Such cell-based assays may be modified or tailored in a number of ways depending on the TGFβ isoform being studied, the type of latent complex (e.g., presenting molecule), and the like. In some embodiments, a cell known to express integrin capable of activating TGFβ may be used as the source of integrin in the assay. Such cells include SW480/136 cells (e.g., clone 1E7). In some embodiments, integrin-expressing cells may be co-transfected with a plasmid encoding a presenting molecule of interest (such as GARP, LRRC33, LTBP (e.g., LTBP1 or LTBP3), etc.) and a plasmid encoding a pro-form of the TGFβ isoform of interest (such as proTGFβ1). After transfection, the cells are incubated for sufficient time to allow for the expression of the transfected genes (e.g., about 24 hours), cells are washed, and incubated with serial dilutions of a test agent (e.g., an antibody). Then, a reporter cell line (e.g., CAGA12 cells) is added to the assay system, followed by appropriate incubation time to allow TGFβ signaling. After an incubation period (e.g., about 18-20 hours) following the addition of the test agent, signal/read-out (e.g., luciferase activity) is detected using suitable means (e.g., for luciferase-expressing reporter cell lines, the Bright-Glo reagent (Promega) can be used). In some embodiments, Luciferase fluorescence may be detected using a BioTek (Synergy H1) plate reader, with autogain settings.

Kits for Use in Alleviating Diseases/Disorders Associated with LTBP1/3-TGFβ

The present disclosure also provides kits for use in alleviating diseases/disorders associated with a TGFβ-related indication. Such kits can include one or more containers comprising an inhibitor, e.g., antibody, or antigen binding portion thereof, that selectively binds to a LTBP1-TGFβ1 complex and/or a LTBP3-TGFβ1 complex, e.g., any of those described herein.

In some embodiments, the kit can comprise instructions for use in accordance with any of the methods described herein. The included instructions can comprise a description of administration of the inhibitor, e.g., antibody, or antigen binding portion thereof, that selectively binds a LTBP1-TGFβ1 complex and/or a LTBP3-TGFβ1 complex to treat, delay the onset, or alleviate a target disease as those described herein. The kit may further comprise a description of selecting an individual suitable for treatment based on identifying whether that individual has the target disease. In still other embodiments, the instructions comprise a description of administering an antibody, or antigen binding portion thereof, to an individual at risk of the target disease.

The instructions relating to the use of inhibitors, e.g., antibodies, or antigen binding portions thereof, that selectively bind a LTBP1-TGFβ1 complex and/or a LTBP3-TGFβ1 complex generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable. The label or package insert can indicate that the composition is used for treating, delaying the onset and/or alleviating a disease or disorder associated with a TGFβ-related indication. Instructions may be provided for practicing any of the methods described herein.

The kits of this disclosure can be provided in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an inhibitor, e.g., antibody, or antigen binding portion thereof, that selectively binds a LTBP1-TGFβ1 complex and/or a LTBP3-TGFβ1 complex, as described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The present invention is further illustrated by the following examples, which are not intended to be limiting in any

EXAMPLES

Transforming growth factor beta 1 (TGFβ1) is expressed as a pro-protein that is proteolytically cleaved into a C-terminal growth factor and an N-terminal prodomain. After cleavage, the prodomain remains noncovalently associated with the growth factor, preventing receptor binding. This latent TGFβ1 forms a large latent complex (LLC) through disulfide bonds that link the prodomain to presenting molecules, and these large latent complexes are then deposited into the extracellular matrix (ECM) or brought to the cell surface. These presenting molecules provide an anchor for specific αVβ integrins to exert traction force on latent TGFβ1, thus releasing the growth factor from the complex to allow signaling. Four TGFβ1 presenting proteins have been identified: Latent TGFβ Binding Protein-1 (LTBP1) and LTBP3 are deposited in the extracellular matrix, while Glycoprotein-A Repetitions Predominant (GARP/LRRC32) and Leucine-Rich Repeat-Containing Protein 33 (LRRC33) present latent TGFβ1 on the surface of immune cells. TGFβ1 is involved in tissue homeostasis processes and regulation of immune responses, and dysregulation of its activation is a key driver of organ fibrosis, cancer, and autoimmunity.

However, non-selective targeting of TGFβ activity for therapeutic purposes has been challenging due to dose-limiting toxicities reported for pan-TGFβ pathway inhibitors, as well as immune system activation through chronic TGFβ suppression. In an effort to address this therapeutic need for both isoform- and context-selectivity for TGFβ1 targeting, provided herein are isoform-specific monoclonal antibodies that bind the latent TGFβ1 prodomain, with no detectable binding to latent TGFβ2 or TGFβ3, and that inhibit integrin-mediated activation of latent TGFβ1 in vitro with context-selectivity. In order to facilitate antibody discovery and characterization efforts, context-dependent cell-based assays of TGFβ1 activation were developed.

Example 1: Development of Context-Specific Inhibitors that Bind a LTBP1/3-TGBβ1 Complex A control antibody, SR-AB1, was used as a control. SR-AB1 binds latent TGBβ1 independent of the presenting molecule (see FIG. 2A).

Antibodies that are selective for TGFβ1-containing large latent complexes were developed. SR-AB2 was selected for further analysis using the functional assays described in the below examples. The heavy and light chain variable regions of SR-AB2 were sequenced (FIG. 8); complementarity determining regions are underlined. It was demonstrated that SR-AB2 binds LTBP-presented latent TGFβ1 complexes but does not bind GARP-TGFβ1 or proTGFβ1 alone (FIG. 2B). However, as described below, the functional effect of such selective binding was unknown and could not be determined using currently known techniques without the further development of novel functional assays.

Example 2: Functional Assays to Detect Inhibition of Activated Recombinant Latent TGFβ1

In order to identify isoform-specific inhibitors that bind the latent TGFβ1 prodomain, with no detectable binding to latent TGFβ2 or TGFβ3, and that inhibit integrin-mediated activation of latent TGFβ1 in vitro with context-dependency, new functional assays were required. Prior to the instant invention, assays were not available which could detect isoform-specific TGFβ1 antibodies that bound only to LTBPs. Specifically, previous assay formats could not differentiate between the activation of proTGFβ1 presented by endogenous presenting molecules and the activation of proTGFβ1 presented by exogenous LTBPs. By directly transfecting integrin-expressing cells, the novel assays disclosed herein establish a window between endogenous presenter-proTGFβ1 activity and exogenous LTBP-proTGFβ1 activity. As LTBP-proTGFβ1 complexes are embedded in the extracellular matrix, the assay plate coating is also an important component of the assay. The use of high binding plates, coated with the ECM protein Fibronectin, made the LTBP assays more robust. In other words, prior to the instant disclosure, there was no assay window between proTGFβ1 transfection and co-transfection of LTBP1/3+proTGFβ1. Prior to the instant invention, the only available assay format was a triple co-culture system: transfectants (latent TGFβ presenting cells)+integrin expressing cells (activator)+CAGA cells (reporter). By removing the third cell population from the system, and directly transfecting the integrin expressing cells, a window for LTBP-proTGFβ1 activation was established herein. The issue of 'bulk transfection' vs 'direct transfection' protocol and whether an assay window is seen for LTBP complexes seems to be cell dependent—the bulk transfection protocol is used for the SW480/b6 cells, but the direct transfection protocol can be used for LN229 cells. Thus, the discovery and characterization of LTBP1/3-TGFβ1 inhibitors, e.g., antibodies and antigen-binding portions thereof, would not have been possible without the development of context-dependent cell-based assays of TGFβ1 activation described herein (see also FIGS. 3A and 3B).

Specifically, to determine if the antibodies developed in Example 1 were functional, cell-based assays of αVβ integrin activation of TGFβ1 large latent complex (LLC) were developed, which are specific for each known presenting molecule: LTBP1, LTBP3, GARP and LRRC33. Through the process of assay development and optimization, it was determined that fibronectin is a critical ECM protein for the integrin-dependent in vitro activation of LTBP presented TGFβ1 LLCs. The context-independent and LTBP-specific TGFβ1 LLC antibodies were also validated as inhibitors of integrin-dependent activation using the below assays. Thus, the antibodies developed in Example 1 can be divided into 2 classes: antibodies which bind all TGFβ1 containing complexes (isoform-specific and context independent), and antibodies which only bind LTBP presented TGFβ1 LLC. As described in more detail herein, the development of an LTBP-specific class of inhibitor, which was not capable of being identified prior to the assays developed and described herein, enables a therapeutic approach for treating fibrotic indications, and could allow for chronic dosing while avoiding immune system activation due to TGFβ1 inhibition of immune suppressive cells.

Assay I. Activation of Latent TGFβ1 Deposited in the ECM

For the assay depicted in FIG. 3A, the following protocol was developed. This assay is optimal for extracellular matrix (LTBP presented) activation by integrin cells.

Materials:
- MvLu1-CAGA12 cells (Clone 4A4)
- SW480/136 cells (Clone 1E7) (αV subunit is endogenously expressed at high levels; β6 subunit is stably overexpressed)
- LN229 cell line (high levels of endogenous αVβ8 integrin)
- Costar white walled TC treated 96 well assay plate #3903
- Greiner Bio-One High Binding white uclear 96 well assay plate #655094
- Human Fibronectin (Corning #354008)
- P200 multichannel pipet
- P20, P200, and P1000 pipets with sterile filter tips for each
- Sterile microfuge tubes and rack
- Sterile reagent reservoirs
- 0.4% trypan blue
- 2 mL, 5 mL, 10 mL, and 25 mL sterile pipets
- Tissue culture treated 100 mm or 150 mm plates
- 70% Ethanol
- Opti-MEM reduced serum media (Life Tech #31985-070)
- Lipofectamine 3000 (Life Tech #L3000015)
- Bright-Glo luciferase assay reagent (Promega #E2620)
- 0.25% Tryspin+0.53 mM EDTA
- proTGFb1 expression plasmid, human (SR005)
- LTBP1S expression plasmid, human (SR044)
- LTBP3 expression plasmid, human (SR117)
- LRRC32 (GARP) expression plasmid, human (SR116)
- LRRC33 expression plasmid, human (SR386)

Equipment:
- BioTek Synergy H1 plate reader
- TC hood
- Bench top centrifuge
- CO2 incubator 37 C 5% CO2
- 37C water/bead bath
- Platform shaker
- Microscope
- Hemocytometer/countess Definitions:
- CAGA12 4A4 cells: Derivative of MvLu1 cells (Mink Lung Epithelial Cells), stably transfected with CAGA12 synthetic promoter, driving luciferase gene expression
- DMEM-0.1% BSA: Assay media; base media is DMEM (Gibco Cat #11995-065), media also contains BSA diluted to 0.1% w/v, penicillin/streptinomycin, and 4 mM glutamine
- D10: DMEM 10% FBS, P/S, 4 mM glutamine, 1% NEAA, 1× GlutaMAX (Gibco Cat #35050061)
- SW480/136 Media: D10+1000 ug/mL G-418
- CAGA12 (4A4) media: D10+0.75 ug/mL puromycin Procedure:

On Day 0, cells were seeded for transfection. SW480/136 (clone 1E7) cells were detached with trypsin and pellet (spin 5 min @ 200×g). Cell pellet was resuspended in D10 media and viable cells per ml were counted. Cells were seeded at 5.0e6 cells/12 ml/100 mm TC dish. For CAGA12 cells, cells were passaged at a density of 1.0 million per T75 flask, to be used for the assay on Day 3. Cultures were incubated at 37° C. and 5% $CO_2$.

On Day 1, integrin-expressing cells were transfected. Manufacturer's protocol for transfection with Lipofectamine 3000 reagent was followed. Briefly, the following were diluted into OptiMEM I, for 125 ul per well: 7.5 ug DNA (presenting molecule)+7.5 ug DNA (proTGFβ1), 30 ul P3000, and Up to 125 ul with OptiMEM I. The well was mixed by pipetting DNA together, then OptiMEM was added. P3000 was added, and everything was mixed well by pipetting. A master mix of Lipofectamine3000 was made, to be added to DNA mixes: for the LTBP1 assay: 15 ul Lipofectamine3000, up to 125 ul in OptiMEM I, per well; for the LTBP3 assay: 45 ul Lipofectamine3000, up to 125 ul in OptiMEM I, per well. Diluted Lipofectamine3000 was added to DNA, mixed well by pipetting, and incubated at room temp for 15 min After the incubation, the solution was mixed a few times by pipetting, and then 250 ul of DNA: Lipofectamine3000 (2×125 ul) per dish was added dropwise. Each dish was gently swirled to mix and the dish was returned to the tissue culture incubator for 24 hrs.

On Days 1-2, the assay plates were coated with human fibronectin. Specifically, lyophilized fibronectin was diluted to 1 mg/ml in ultra-pure distilled water (sterile). 1 mg/ml stock solution was diluted to 19.2 ug/ml in PBS (sterile). Added 50 ul/well to assay plate (high binding) and incubated 0/N in tissue culture incubator (37° C. and 5% CO2). Final concentration was 3.0 $ug/cm^2$.

On Day 2, transfected cells were plated for assay and inhibitor addition. First, the fibronecting coating was washed by adding 200 ul/well PBS to the fibronectin solution already in the assay plate. Removed wash manually with multichannel pipette. Wash was repeated for two washes total. The plate was allowed to dry at room temperature with lid off prior to cell addition. The cells were then plated by detaching with trypsin and pellet (spin 5 min @ 200×g.). The pellet was resuspended in assay media and viable cells were counted per ml. For the LTBP1 assay cells were diluted to 0.10e6 cells/ml and seed 50 ul per well (5,000 cells per well). For the LTBP3 assay, cells were diluted to 0.05e6 cells/ml and seed 50 ul per well (2,500 cells per well). To prepare functional antibody dilutions, antibodies were prediluted to a consistent working concentration in vehicle. Stock antibodies were serially diluted in vehicle (PBS is optimal, avoid sodium citrate buffer). Each point of serial dilution was diluted into assay media for a 4× final concentration of antibody. Added 25 ul per well of 4× antibody and incubated cultures at 37° C. and 5% $CO_2$ for ~24 hours.

On Day 3, the TGFβ reporter cells were added. CAGA12 (clone 4A4) cells for the assay were detached with trypsin and pellet (spin 5 min @ 200×g.). The pellet was resuspended in assay media and count viable cells per ml. Cells were diluted to $0.4e^6$ cells/ml and seed 50 ul per well (20,000 cells per well). Cells were returned to incubator.

On Day 4, the assay was read (16-20 hours after antibody and/or reporter cell addition). Bright-Glo reagent and test plate were allowed to come to room temperature before reading. Read settings on BioTek Synergy H1 were set using TMLC_std protocol this method has an auto-gain setting. Selected positive control wells for autoscale (high). 100 uL of Bright-Glo reagent was added per well. Incubated for 2 min with shaking, at room temperature, protected plate from light. The plate was read on BioTek Synergy H1.

Results:

Data generated from this assay reflected TGFβ1 activity in cell supernatants (FIG. 3A). Raw data units were relative light units (RLU). FIG. 3A depicts that the assay depicts LTBP1-TGFβ1 and/or LTBP3-TGFβ1 binding.

Figure 4A:
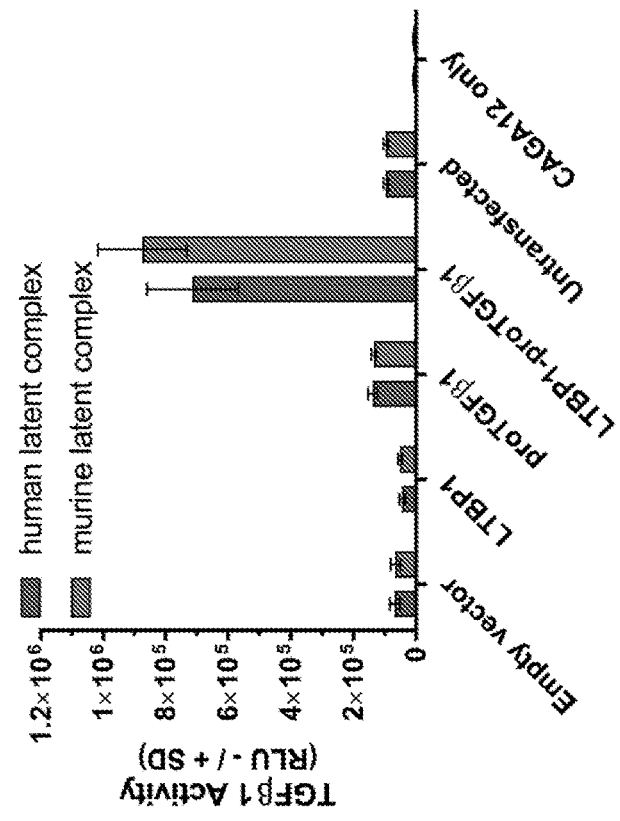

The assay was further optimized as described in FIG. 4. Specifically, the relative contribution of presenting molecule and/or proTGFβ1 to latent TGFβ1 activation was determined. A significant increase in latent TGFβ1 activation upon co-transfection of presenting molecule and proTGFβ1 was observed in FIG. 4A. FIG. 4B depicts the optimization of co-transfection by changing the ratio of plasmid DNAs for presenting molecule and proTGFβ1. Equivalent amounts of each plasmid were found to be optimal for co-transfection.

FIG. 5 demonstrates that fibronecting promotes integrin activation of LTBP-presented latent TGFβ1. In this assay, plates were pre-coated with fibronectin purified from human plasma. Fibronectin increased activation of latent TGFβ1 presented by LTBP1 and LTBP3.

Assay II. Activation of Latent TGFβ1 Presented on the Cell Surface

For the assay depicted in FIG. 3B, the following protocol was developed. This assay, or "direct-transfection" protocol, is optimal for cell-surface presented TGFβ1 (GARP or LRRC33 presenter) activation by integrin cells.

Material:
  MvLu1-CAGA12 cells (Clone 4A4)
  SW480/136 cells (Clone 1E7) (αV subunit is endogenously expressed at high levels; β6 subunit is stably overexpressed)
  LN229 cell line (high levels of endogenous αVβ8 integrin)
  Costar white walled TC treated 96 well assay plate #3903
  Greiner Bio-One High Binding white uclear 96 well assay plate #655094
  Human Fibronectin (Corning #354008)
  P200 multichannel pipet
  P20, P200, and P1000 pipets with sterile filter tips for each
  Sterile microfuge tubes and rack
  Sterile reagent reservoirs
  0.4% trypan blue
  2 mL, 5 mL, 10 mL, and 25 mL sterile pipets
  Tissue culture treated 100 mm or 150 mm plates
  70% Ethanol
  Opti-MEM reduced serum media (Life Tech #31985-070)
  Lipofectamine 3000 (Life Tech #L3000015)
  Bright-Glo luciferase assay reagent (Promega #E2620)
  0.25% Tryspin+0.53 mM EDTA
  proTGFb1 expression plasmid, human (SR005)
  LTBP1S expression plasmid, human (SR044)
  LTBP3 expression plasmid, human (SR117)
  LRRC32 (GARP) expression plasmid, human (SR116)
  LRRC33 expression plasmid, human (SR386)

Equipment:
  BioTek Synergy H1 plate reader
  TC hood
  Bench top centrifuge
  $CO_2$ incubator 37C 5% CO2
  37° C. water/bead bath
  Platform shaker
  Microscope
  Hemocytometer/countess Definitions:
  CAGA12 4A4 cells: Derivative of MvLu1 cells (Mink Lung Epithelial Cells), stably transfected with CAGA12 synthetic promoter, driving luciferase gene expression
  DMEM-0.1% BSA: Assay media; base media is DMEM (Gibco Cat #11995-065), media also contains BSA diluted to 0.1% w/v, penicillin/streptomycin, and 4 mM glutamine
  D10: DMEM 10% FBS, P/S, 4 mM glutamine, 1% NEAA, 1× GlutaMAX (Gibco Cat #35050061)
  SW480/136 Media: D10+1000 ug/mL G-418
  CAGA12 (4A4) media: D10+0.75 ug/mL puromycin Methods:

On Day 0, integrin expressing cells were seeded for transfection. Cells were detached with trypsin and pelleted (spin 5 min @ 200×g). Cell pellet was resuspended in D10 media and count viable cells per ml. Cells were diluted to $0.1e^6$ cells/ml and seeded 100 ul per well (10,000 cells per well) in an assay plate. For CAGA12 cells, passaged at a density of 1.5 million per T75 flask, to be used for the assay on Day 2. Cultures were incubated at 37° C. and 5% $CO_2$.

On Day 1, cells were transfected. The manufacturer's protocol was followed for transfection with Lipofectamine 3000 reagent. Briefly, the following was diluted into OptiMEM I, for 5 ul per well: 0.1 ug DNA (presenting molecule)+0.1 ug DNA (proTGFβ1), 0.4 ul P3000, and up to 5 ul with OptiMEM I. The well was mixed by pipetting DNA together, then add OptiMEM. Add P3000 and mix everything well by pipetting. A master mix was made with Lipofectamine3000, to be added to DNA mixes: 0.2 ul Lipofectamine3000, up to 5 ul in OptiMEM I, per well. Diluted Lipofectamine3000 was added to DNA, mixed well by pipetting, and incubated at room temp for 15 min. After the incubation, the solution was mixed a few times by pipetting, and then 10 ul per well of DNA:Lipofectamine3000 (2×5 ul) was added. The cell plate was returned to the tissue culture incubator for 24 hrs.

On Day 2, the antibody and TGFβ reporter cells were added. In order to prepare functional antibody dilutions, stock antibody in vehicle (PBS is optimal) was serially diluted. Then each point was diluted into assay media for 2× final concentration of antibody. After preparing antibodies, the cell plate was wished twice with assay media, by aspirating (vacuum aspirator) followed by the addition of 100 ul per well assay media. After second wash, the assay media was replaced with 50 ul per well of 2× antibody. The cell plate was returned to the incubator for ~15-20 min.

In order to prepare the CAGA12 (clone 4A4) cells for the assay, the cells were detached with trypsin and pelleted (spin 5 min @ 200×g.). The pellet was resuspended in assay media and viable cells per ml were counted. Cells were diluted to $0.3e^6$ cells/ml and seeded 50 ul per well (15,000 cells per well). Cells were returned to incubator.

On Day 3, the assay was read about 16-20 hours after the antibody and/or reporter cell addition. Bright-Glo reagent and test plate were allowed to come to room temperature before reading. The read settings on BioTek Synergy H1 were set to use TMLC_std protocol this method has an auto-gain setting. Positive control wells were set for autoscale (high). 100 uL of Bright-Glo reagent was added per well. Incubated for 2 min with shaking, at room temperature, protected plate from light. The plate was read on BioTek Synergy H1.

Data generated from this assay reflects TGFβ1 activity in cell supernatants (FIG. 3B). Raw data units are relative light units (RLU). Samples with high RLU values contained high amounts of free TGFβ1, samples with low RLU values contained low levels of TGFβ1.

Example 3. SR-AB2 is a Complex-Specific Inhibitor of LTBP-proTGFβ1

SR-AB2 was selected for further analysis. It was demonstrated that SR-AB2 specifically binds to proTGFβ1:LTBP1 & 3 complexes (FIG. 9).

As discussed above, LTBP1 and LTBP3 are deposited in the extracellular matrix, while GARP/LRRC32 and LRRC33 present latent TGFβ1 on the surface of immune cells. It was demonstrated that SR-AB2 inhibits LTBP-proTGFβ1 signaling, but does not affect GARP-proTGFβ1

(FIG. 10A and FIG. 10B). FIG. 10A demonstrates that SR-AB2 inhibits LTBP-proTGFβ. This assay was performed in LN229 cells, which express high LTBP1 & 3, undetectable GARP and LRRC33. FIG. 10B demonstrates that SR-AB2 does not inhibit GARP-proTGFβ. SR-AB1 binds latent TGBβ1 independent of the presenting molecule. proTGFβ1 is presented by overexpressed GARP. This assay was performed in LN229 cells, which express high levels of LTBP1 & 3, and undetectable levels of GARP and LRRC33.

Inhibition of LTBP-proTGFβ1 by SR-AB2 was also shown in αVβ6 Integrin-dependent activation of LTBP1-presented TGFβ1 in cell-based assays (human and mouse, data not shown). SR-AB2 showed no inhibitory effects on overexpressed LRRC33-proTGFβ1.

Example 4: Octet Binning of LTBP1-proTGF81 Antibodies 500 nM of human LTBP1-proTGFb1 complex was pre-incubated with 1 µM of each test antibody. After an overnight incubation, the LTBP1-proTGFβ1+first antibody was tested for binding to a second antibody which was immobilized to an Anti-Human IgG Fc Capture (AHC) sensor tip at 67 nM. The sensor tip was also blocked with HuNeg before seeing the LTBP1-proTGFβ1+first antibody.

Binding of the complex to a specific second antibody was normalized to the uninhibited interaction, that is the complex in the presence of HuNeg control antibody. Normalized responses less than 70% or 0.7 of the uninhibited interaction were considered antibodies that cross block. A response greater than 1 indicated that both antibodies were bound simultaneously. The results are shown in Table 7, below.

TABLE 7

|  | SR-AB13 | SR-AB10 | SR-AB2 | SR-AB1 | Second Antibody |
| --- | --- | --- | --- | --- | --- |
| SR-AB13 | 0.47 | 1.38 | 1.29 | 1.08 |  |
| SR-AB10 | 1.27 | 0.51 | 1.53 | 0.82 |  |
| SR-AB2 | 1.31 | 1.54 | 0.47 | 1.11 |  |
| SR-AB1 | 1.43 | 0.76 | 1.38 | 0.69 |  |
| HuNeg | 1 | 1 | 1 | 1 |  |
| First Antibody |  |  |  |  |  |

As shown in Table 7, antibodies SR-AB13, SR-AB10, SR-AB2 and SR-AB1 do not cross block each other, and therefore each antibody occupies a distinct epitope on the surface of human LTBP1-proTGFβ1.

Example 5: In Vitro Binding Profile and Affinity Data

The affinity of SR-AB10, SR-AB2 and SR-AB13 was measured by Octet assay. The protocol used to measure the affinity of the antibodies to the complexes provided herein is summarized in Table 8.

TABLE 8

Protocol for performing Octet binding assay

Materials:
- 96 well black polypropylene plates
- Streptavidin-coated tips for Octet
- 10x kinetics buffer (diluted 1:10 in PBS)
1. Soak required amount of streptavidin tips in 1X kinetics buffer; place in machine to equilibrate
2. Load sample plate:
    - 200 µl of buffer or antibody dilution to each well
        a. Column 1 – baseline (buffer)
        b. Column 2 – biotinylated protein (e.g., sGARP-proTGFβ1 or LTBP1-proTGFβ1); diluted to 5 µg/mL
        c. Column 3 - baseline 2 (buffer)
        d. Column 4 - antibody association for Ab
        e. Column 5 - antibody association for Ab
        f. Column 6 - dissociation Ab (buffer)
        g. Column 7 - dissociation Ab (buffer)
3. Make dilutions in the 96 well plate:
        a. Dilute both antibodies to 50 µg/mL in 300 µl of 1x buffer in row A.
        b. Add 200 µl of buffer to the rest of each column
        c. Transfer 100 µl down the column to make 3-fold dilutions
4. Place the sample plate in the machine next to the tips plate
5. Set up the software
        a. Indicate buffer, load, sample (one assay per antibody tested)
        b. Indicate steps of the protocol (baseline, load, association, dissociation) for set amounts of time:
            • Baseline: 60 seconds
            • Loading: 300 seconds
            • Baseline 2: 60 seconds
            • Association: 300 seconds
            • Dissociation: 600 seconds
6. Analyze data
        a. Subtract baseline from reference well
        b. Set normalization to last five seconds of baseline
        c. Align to dissociation
        d. Analyze to association and dissociation (1:1 binding model, fit curves)
        e. Determine the best $R^2$ values; include concentrations with best $R^2$ values
        f. Select global fit
        g. Set colors of samples by sensor type
        h. Analyze
        i. Save table and export FIG. 11 presents the binding profile and affinity data for LTBP-specific antibodies SR-AB10, SR-AB2, and SR-AB13. Notably, SR-AB13 binds both LTBP1 and LTBP3 complexed, while SR-AB2 and SR-AB10 are specific to LTBP1.

What is claimed is:

1. A method for making a composition comprising an antibody, or an antigen-binding fragment thereof, that specifically binds a human LTBP1-proTGFβ1 complex, and does not bind a GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3 and mature TGFβ3; wherein the antibody, or the antigen-binding fragment thereof, inhibits TGFβ1 but does not inhibit TGFβ2 or TGFβ3, the method comprising steps of:
  i) providing an antigen comprising human LTBP1-proTGFβ1,
  ii) selecting antibodies, or antigen-binding fragments thereof, that specifically bind the antigen of step (i), and do not bind GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3, and mature TGFβ3, so as to provide specific binders of human LTBP1-proTGFβ1;
  iii) selecting from the antibodies, or the antigen-binding fragments thereof, of step ii), antibodies, or antigen-binding fragments thereof, that inhibit activation of TGFβ1, so as to identify specific inhibitors of TGFβ1 activation, wherein the selection step comprises a cell-based assay to measure TGFβ activation, wherein the cell-based assay comprises:
    transfecting αVβ integrin-expressing cells with a plasmid encoding human LTBP1 and a plasmid encoding proTGFβ1;
    coating an assay plate with fibronectin;
    plating the transfected cells expressing human LTBP1 and proTGFβ1 on the assay plate coated with fibronectin, wherein the expressed human LTBP1-proTGFβ1 complex binds to the fibronectin;
    incubating in the presence of the antibody or the antigen-binding fragment thereof;
    adding reporter cells expressing a TGFβ-responsive promoter element, wherein the reporter cells further comprise a reporter gene under the control of the TGFβ-responsive promoter element, wherein the reporter gene comprises a luciferase gene;
    reading the results from the reporter cells, wherein the data generated reflects levels of TGFβ activation; and
    identifying the antibodies or the antigen-binding fragments thereof that inhibit TGFβ1 activation; and
  iv) formulating an antibody or an antigen-binding fragment thereof, selected from the previous step into a pharmaceutical composition,
thereby making the composition comprising the antibody, or the antigen-binding fragment thereof.

2. The method of claim 1, wherein the reporter cells are CAGA12 cells.

3. A method for making a composition comprising an antibody, or an antigen-binding fragment thereof, that specifically binds a human LTBP3-proTGFβ1 complex, and does not bind a GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3 and mature TGFβ3; wherein the antibody, or the antigen-binding fragment thereof, inhibits TGFβ1 but does not inhibit TGFβ2 or TGFβ3, the method comprising steps of:
  i) providing an antigen comprising human LTBP3-proTGFβ1,
  ii) selecting antibodies, or antigen-binding fragments thereof, that specifically bind the antigen of step (i), and do not bind GARP-proTGFβ1, LRRC33-proTGFβ1, mature TGFβ1, GARP-proTGFβ2, LRRC33-proTGFβ2, mature TGFβ2, GARP-proTGFβ3, LRRC33-proTGFβ3, and mature TGFβ3, so as to provide specific binders of human LTBP3-proTGFβ1;
  iii) selecting from the antibodies, or the antigen-binding fragments thereof, of step ii), antibodies, or antigen-binding fragments thereof, that inhibit activation of TGFβ1, so as to identify specific inhibitors of TGFβ1 activation, wherein the selection step comprises a cell-based assay to measure TGFβ activation, wherein the cell-based assay comprises:
    transfecting αVβ integrin-expressing cells with a plasmid encoding human LTBP3 and a plasmid encoding proTGFβ1;
    coating an assay plate with fibronectin;

plating the transfected cells expressing human LTBP3 and proTGFβ1 on the assay plate coated with fibronectin, wherein the expressed human LTBP3-proTGFβ1 complex binds to the fibronectin;

incubating in the presence of the antibody or the antigen-binding fragment thereof;

adding reporter cells expressing a TGFβ-responsive promoter element, wherein the reporter cells further comprise a reporter gene under the control of the TGFβ-responsive promoter element, wherein the reporter gene comprises a luciferase gene;

reading the results from the reporter cells, wherein the data generated reflects levels of TGFβ activation; and identifying the antibodies or the antigen-binding fragments thereof that inhibit TGFβ1 activation; and iv) formulating an antibody or an antigen-binding fragment thereof, selected from the previous step into a pharmaceutical composition, thereby making the composition comprising the antibody, or the antigen-binding fragment thereof.

4. The method of claim 3, wherein the reporter cells are CAGA12 cells.

* * * * *

SEQUENCE LISTING

```
<160> NUMBER OF SEQ ID NOS: 99

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1
```

```
Gly Tyr Thr Phe Thr Ser Tyr Gly
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ile Ser Ala Tyr Asn Gly Asn Thr
1               5

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ala Arg Ala Pro Leu Gly Asn Phe Asp Ser
1               5                   10

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Gly Ser Ile Ala Ser Asn Tyr
1               5

<210> SEQ ID NO 5
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Asp Asn
1

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Ser Tyr Asp Ser Ser Asn His Pro Val Val
1               5                   10
```

<210> SEQ ID NO 7
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Pro Leu Gly Asn Phe Asp Ser Trp Gly Gln Gly Thr Met
            100                 105                 110

Val Thr Val Ser Ser
        115

<210> SEQ ID NO 8
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Pro Val Val Phe Gly Gly Gly Thr Lys Leu Thr Val Leu
            100                 105                 110

<210> SEQ ID NO 9
<211> LENGTH: 361
<212> TYPE: PRT
<213> ORGANISM: Homo sapiens

<400> SEQUENCE: 9

Leu Ser Thr Cys Lys Thr Ile Asp Met Glu Leu Val Lys Arg Lys Arg
1               5                   10                  15

-continued

Ile Glu Ala Ile Arg Gly Gln Ile Leu Ser Lys Leu Arg Leu Ala Ser
         20                  25                  30

Pro Pro Ser Gln Gly Glu Val Pro Gly Pro Leu Pro Glu Ala Val
         35                  40                  45

Leu Ala Leu Tyr Asn Ser Thr Arg Asp Arg Val Ala Gly Glu Ser Ala
 50                  55                  60

Glu Pro Glu Pro Glu Pro Glu Ala Asp Tyr Tyr Ala Lys Glu Val Thr
 65                  70                  75                  80

Arg Val Leu Met Val Glu Thr His Asn Glu Ile Tyr Asp Lys Phe Lys
                 85                  90                  95

Gln Ser Thr His Ser Ile Tyr Met Phe Phe Asn Thr Ser Glu Leu Arg
                100                 105                 110

Glu Ala Val Pro Glu Pro Val Leu Leu Ser Arg Ala Glu Leu Arg Leu
                115                 120                 125

Leu Arg Leu Lys Leu Lys Val Glu Gln His Val Glu Leu Tyr Gln Lys
 130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
                180                 185                 190

His Cys Ser Cys Asp Ser Arg Asp Asn Thr Leu Gln Val Asp Ile Asn
                195                 200                 205

Gly Phe Thr Thr Gly Arg Arg Gly Asp Leu Ala Thr Ile His Gly Met
 210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
                260                 265                 270

Phe Arg Lys Asp Leu Gly Trp Lys Trp Ile His Glu Pro Lys Gly Tyr
                275                 280                 285

His Ala Asn Phe Cys Leu Gly Pro Cys Pro Tyr Ile Trp Ser Leu Asp
                290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
                340                 345                 350

Met Ile Val Arg Ser Cys Lys Cys Ser
                355                 360

<210> SEQ ID NO 10
<211> LENGTH: 395
<212> TYPE: PRT
<213> ORGANISM: Homo sapiens

<400> SEQUENCE: 10

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr

```
            20                  25                  30
Ser Pro Pro Glu Asp Tyr Pro Glu Pro Glu Val Pro Pro Glu Val
            35                  40                  45
Ile Ser Ile Tyr Asn Ser Thr Arg Asp Leu Leu Gln Glu Lys Ala Ser
 50                  55                  60
Arg Arg Ala Ala Ala Cys Glu Arg Glu Arg Ser Asp Glu Glu Tyr Tyr
 65                  70                  75                  80
Ala Lys Glu Val Tyr Lys Ile Asp Met Pro Pro Phe Phe Pro Ser Glu
                 85                  90                  95
Asn Ala Ile Pro Pro Thr Phe Tyr Arg Pro Tyr Phe Arg Ile Val Arg
                100                 105                 110
Phe Asp Val Ser Ala Met Glu Lys Asn Ala Ser Asn Leu Val Lys Ala
                115                 120                 125
Glu Phe Arg Val Phe Arg Leu Gln Asn Pro Lys Ala Arg Val Pro Glu
                130                 135                 140
Gln Arg Ile Glu Leu Tyr Gln Ile Leu Lys Ser Lys Asp Leu Thr Ser
145                 150                 155                 160
Pro Thr Gln Arg Tyr Ile Asp Ser Lys Val Val Lys Thr Arg Ala Glu
                165                 170                 175
Gly Glu Trp Leu Ser Phe Asp Val Thr Asp Ala Val His Glu Trp Leu
                180                 185                 190
His His Lys Asp Arg Asn Leu Gly Phe Lys Ile Ser Leu His Cys Pro
                195                 200                 205
Cys Cys Thr Phe Val Pro Ser Asn Asn Tyr Ile Ile Pro Asn Lys Ser
                210                 215                 220
Glu Glu Leu Glu Ala Arg Phe Ala Gly Ile Asp Gly Thr Ser Thr Tyr
225                 230                 235                 240
Thr Ser Gly Asp Gln Lys Thr Ile Lys Ser Thr Arg Lys Lys Asn Ser
                245                 250                 255
Gly Lys Thr Pro His Leu Leu Leu Met Leu Leu Pro Ser Tyr Arg Leu
                260                 265                 270
Glu Ser Gln Gln Thr Asn Arg Arg Lys Lys Arg Ala Leu Asp Ala Ala
                275                 280                 285
Tyr Cys Phe Arg Asn Val Gln Asp Asn Cys Cys Leu Arg Pro Leu Tyr
                290                 295                 300
Ile Asp Phe Lys Arg Asp Leu Gly Trp Lys Trp Ile His Glu Pro Lys
305                 310                 315                 320
Gly Tyr Asn Ala Asn Phe Cys Ala Gly Ala Cys Pro Tyr Leu Trp Ser
                325                 330                 335
Ser Asp Thr Gln His Ser Arg Val Leu Ser Leu Tyr Asn Thr Ile Asn
                340                 345                 350
Pro Glu Ala Ser Ala Ser Pro Cys Cys Val Ser Gln Asp Leu Glu Pro
                355                 360                 365
Leu Thr Ile Leu Tyr Tyr Ile Gly Lys Thr Pro Lys Ile Glu Gln Leu
                370                 375                 380
Ser Asn Met Ile Val Lys Ser Cys Lys Cys Ser
385                 390                 395

<210> SEQ ID NO 11
<211> LENGTH: 392
<212> TYPE: PRT
<213> ORGANISM: Homo sapiens

<400> SEQUENCE: 11
```

```
Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
            20                  25                  30

Leu Thr Ser Pro Pro Glu Pro Thr Val Met Thr His Val Pro Tyr Gln
        35                  40                  45

Val Leu Ala Leu Tyr Asn Ser Thr Arg Glu Leu Leu Glu Glu Met His
50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
            115                 120                 125

Ala Glu Phe Arg Val Leu Arg Val Pro Asn Pro Ser Ser Lys Arg Asn
            130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
            195                 200                 205

Cys His Thr Phe Gln Pro Asn Gly Asp Ile Leu Glu Asn Ile His Glu
            210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Lys Arg Ala Leu Asp Thr Asn Tyr Cys Phe
            275                 280                 285

Arg Asn Leu Glu Glu Asn Cys Cys Val Arg Pro Leu Tyr Ile Asp Phe
            290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335

Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
            355                 360                 365

Leu Tyr Tyr Val Gly Arg Thr Pro Lys Val Glu Gln Leu Ser Asn Met
370                 375                 380

Val Val Lys Ser Cys Lys Cys Ser
385                 390

<210> SEQ ID NO 12
<211> LENGTH: 361
<212> TYPE: PRT
```

<213> ORGANISM: Homo sapiens

<400> SEQUENCE: 12

```
Leu Ser Thr Cys Lys Thr Ile Asp Met Glu Leu Val Lys Arg Lys Arg
1               5                  10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360
```

<210> SEQ ID NO 13
<211> LENGTH: 361
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 13

| | | | | | | | | | | | | | | |
|---|---|---|---|---|---|---|---|---|---|---|---|---|---|---|
| Leu | Ser | Thr | Ser | Lys | Thr | Ile | Asp | Met | Glu | Leu | Val | Lys | Arg | Lys | Arg |
| 1 | | | | 5 | | | | | 10 | | | | | 15 | |
| Ile | Glu | Ala | Ile | Arg | Gly | Gln | Ile | Leu | Ser | Lys | Leu | Arg | Leu | Ala | Ser |
| | | | 20 | | | | | 25 | | | | | 30 | | |
| Pro | Pro | Ser | Gln | Gly | Glu | Val | Pro | Pro | Gly | Pro | Leu | Pro | Glu | Ala | Val |
| | | 35 | | | | 40 | | | | | 45 | | | | |
| Leu | Ala | Leu | Tyr | Asn | Ser | Thr | Arg | Asp | Arg | Val | Ala | Gly | Glu | Ser | Ala |
| | 50 | | | | | 55 | | | | | 60 | | | | |
| Glu | Pro | Glu | Pro | Glu | Pro | Glu | Ala | Asp | Tyr | Tyr | Ala | Lys | Glu | Val | Thr |
| 65 | | | | | 70 | | | | | 75 | | | | | 80 |
| Arg | Val | Leu | Met | Val | Glu | Thr | His | Asn | Glu | Ile | Tyr | Asp | Lys | Phe | Lys |
| | | | | 85 | | | | | 90 | | | | | 95 | |
| Gln | Ser | Thr | His | Ser | Ile | Tyr | Met | Phe | Phe | Asn | Thr | Ser | Glu | Leu | Arg |
| | | | 100 | | | | | 105 | | | | | 110 | | |
| Glu | Ala | Val | Pro | Glu | Pro | Val | Leu | Leu | Ser | Arg | Ala | Glu | Leu | Arg | Leu |
| | | 115 | | | | 120 | | | | | 125 | | | | |
| Leu | Arg | Leu | Lys | Leu | Lys | Val | Glu | Gln | His | Val | Glu | Leu | Tyr | Gln | Lys |
| | 130 | | | | | 135 | | | | | 140 | | | | |
| Tyr | Ser | Asn | Asn | Ser | Trp | Arg | Tyr | Leu | Ser | Asn | Arg | Leu | Leu | Ala | Pro |
| 145 | | | | | 150 | | | | | 155 | | | | | 160 |
| Ser | Asp | Ser | Pro | Glu | Trp | Leu | Ser | Phe | Asp | Val | Thr | Gly | Val | Val | Arg |
| | | | | 165 | | | | | 170 | | | | | 175 | |
| Gln | Trp | Leu | Ser | Arg | Gly | Gly | Glu | Ile | Glu | Gly | Phe | Arg | Leu | Ser | Ala |
| | | | 180 | | | | | 185 | | | | | 190 | | |
| His | Cys | Ser | Cys | Asp | Ser | Arg | Asp | Asn | Thr | Leu | Gln | Val | Asp | Ile | Asn |
| | | 195 | | | | 200 | | | | | 205 | | | | |
| Gly | Phe | Thr | Thr | Gly | Arg | Arg | Gly | Asp | Leu | Ala | Thr | Ile | His | Gly | Met |
| | 210 | | | | | 215 | | | | | 220 | | | | |
| Asn | Arg | Pro | Phe | Leu | Leu | Leu | Met | Ala | Thr | Pro | Leu | Glu | Arg | Ala | Gln |
| 225 | | | | | 230 | | | | | 235 | | | | | 240 |
| His | Leu | Gln | Ser | Ser | Arg | His | Arg | Arg | Ala | Leu | Asp | Thr | Asn | Tyr | Cys |
| | | | | 245 | | | | | 250 | | | | | 255 | |
| Phe | Ser | Ser | Thr | Glu | Lys | Asn | Cys | Cys | Val | Arg | Gln | Leu | Tyr | Ile | Asp |
| | | | 260 | | | | | 265 | | | | | 270 | | |
| Phe | Arg | Lys | Asp | Leu | Gly | Trp | Lys | Trp | Ile | His | Glu | Pro | Lys | Gly | Tyr |
| | | 275 | | | | 280 | | | | | 285 | | | | |
| His | Ala | Asn | Phe | Cys | Leu | Gly | Pro | Cys | Pro | Tyr | Ile | Trp | Ser | Leu | Asp |
| | 290 | | | | | 295 | | | | | 300 | | | | |
| Thr | Gln | Tyr | Ser | Lys | Val | Leu | Ala | Leu | Tyr | Asn | Gln | His | Asn | Pro | Gly |
| 305 | | | | | 310 | | | | | 315 | | | | | 320 |
| Ala | Ser | Ala | Ala | Pro | Cys | Cys | Val | Pro | Gln | Ala | Leu | Glu | Pro | Leu | Pro |
| | | | | 325 | | | | | 330 | | | | | 335 | |
| Ile | Val | Tyr | Tyr | Val | Gly | Arg | Lys | Pro | Lys | Val | Glu | Gln | Leu | Ser | Asn |
| | | | 340 | | | | | 345 | | | | | 350 | | |
| Met | Ile | Val | Arg | Ser | Cys | Lys | Cys | Ser | | | | | | | |
| | | | 355 | | | | | 360 | | | | | | | |

<210> SEQ ID NO 14
<211> LENGTH: 360
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
        355                 360
```

<210> SEQ ID NO 15

```
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
    290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
        355                 360
```

```
<210> SEQ ID NO 16
<211> LENGTH: 395
<212> TYPE: PRT
<213> ORGANISM: Homo sapiens

<400> SEQUENCE: 16

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
                20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
    50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
    115                 120                 125

Glu Phe Arg Val Phe Arg Leu Gln Asn Pro Lys Ala Arg Val Pro Glu
130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
    195                 200                 205

Cys Cys Thr Phe Val Pro Ser Asn Asn Tyr Ile Ile Pro Asn Lys Ser
210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Lys Arg Ala Leu Asp Ala Ala
    275                 280                 285

Tyr Cys Phe Arg Asn Val Gln Asp Asn Cys Cys Leu Arg Pro Leu Tyr
290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335

Ser Asp Thr Gln His Ser Arg Val Leu Ser Leu Tyr Asn Thr Ile Asn
            340                 345                 350

Pro Glu Ala Ser Ala Ser Pro Cys Cys Val Ser Gln Asp Leu Glu Pro
    355                 360                 365

Leu Thr Ile Leu Tyr Tyr Ile Gly Lys Thr Pro Lys Ile Glu Gln Leu
370                 375                 380
```

```
Ser Asn Met Ile Val Lys Ser Cys Lys Cys Ser
385                 390                 395

<210> SEQ ID NO 17
<211> LENGTH: 395
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ser Leu Ser Thr Ser Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
                20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
            115                 120                 125

Glu Phe Arg Val Phe Arg Leu Gln Asn Pro Lys Ala Arg Val Pro Glu
130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
            195                 200                 205

Cys Cys Thr Phe Val Pro Ser Asn Asn Tyr Ile Ile Pro Asn Lys Ser
            210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Lys Arg Ala Leu Asp Ala Ala
            275                 280                 285

Tyr Cys Phe Arg Asn Val Gln Asp Asn Cys Cys Leu Arg Pro Leu Tyr
290                 295                 300

Ile Asp Phe Lys Arg Asp Leu Gly Trp Lys Trp Ile His Glu Pro Lys
305                 310                 315                 320

Gly Tyr Asn Ala Asn Phe Cys Ala Gly Ala Cys Pro Tyr Leu Trp Ser
                325                 330                 335
```

-continued

```
Ser Asp Thr Gln His Ser Arg Val Leu Ser Leu Tyr Asn Thr Ile Asn
            340                 345                 350

Pro Glu Ala Ser Ala Ser Pro Cys Cys Val Ser Gln Asp Leu Glu Pro
            355                 360                 365

Leu Thr Ile Leu Tyr Tyr Ile Gly Lys Thr Pro Lys Ile Glu Gln Leu
            370                 375                 380

Ser Asn Met Ile Val Lys Ser Cys Lys Cys Ser
385                 390                 395

<210> SEQ ID NO 18
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ser Leu Ser Thr Ser Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
            20                  25                  30

Ser Pro Pro Glu Asp Tyr Pro Glu Pro Glu Glu Val Pro Pro Glu Val
            35                  40                  45

Ile Ser Ile Tyr Asn Ser Thr Arg Asp Leu Leu Gln Glu Lys Ala Ser
        50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
            100                 105                 110

Phe Asp Val Ser Ala Met Glu Lys Asn Ala Ser Asn Leu Val Lys Ala
            115                 120                 125

Glu Phe Arg Val Phe Arg Leu Gln Asn Pro Lys Ala Arg Val Pro Glu
            130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
            195                 200                 205

Cys Cys Thr Phe Val Pro Ser Asn Asn Tyr Ile Ile Pro Asn Lys Ser
            210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255

Gly Lys Thr Pro His Leu Leu Leu Met Leu Leu Pro Ser Tyr Arg Leu
            260                 265                 270

Glu Ser Gln Gln Thr Asn Arg Arg Lys Gly Ala Leu Asp Ala Ala Tyr
            275                 280                 285

Cys Phe Arg Asn Val Gln Asp Asn Cys Cys Leu Arg Pro Leu Tyr Ile
```

```
                290                 295                 300
Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
                340                 345                 350

Glu Ala Ser Ala Ser Pro Cys Cys Val Ser Gln Asp Leu Glu Pro Leu
                355                 360                 365

Thr Ile Leu Tyr Tyr Ile Gly Lys Thr Pro Lys Ile Glu Gln Leu Ser
                370                 375                 380

Asn Met Ile Val Lys Ser Cys Lys Cys Ser
385                 390

<210> SEQ ID NO 19
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ser Leu Ser Thr Cys Ser Thr Leu Asp Met Asp Gln Phe Met Arg Lys
1               5                   10                  15

Arg Ile Glu Ala Ile Arg Gly Gln Ile Leu Ser Lys Leu Lys Leu Thr
                20                  25                  30

Ser Pro Pro Glu Asp Tyr Pro Glu Pro Glu Val Pro Pro Glu Val
            35                  40                  45

Ile Ser Ile Tyr Asn Ser Thr Arg Asp Leu Leu Gln Glu Lys Ala Ser
    50                  55                  60

Arg Arg Ala Ala Ala Cys Glu Arg Glu Arg Ser Asp Glu Glu Tyr Tyr
65                  70                  75                  80

Ala Lys Glu Val Tyr Lys Ile Asp Met Pro Pro Phe Phe Pro Ser Glu
                85                  90                  95

Asn Ala Ile Pro Pro Thr Phe Tyr Arg Pro Tyr Phe Arg Ile Val Arg
                100                 105                 110

Phe Asp Val Ser Ala Met Glu Lys Asn Ala Ser Asn Leu Val Lys Ala
            115                 120                 125

Glu Phe Arg Val Phe Arg Leu Gln Asn Pro Lys Ala Arg Val Pro Glu
            130                 135                 140

Gln Arg Ile Glu Leu Tyr Gln Ile Leu Lys Ser Lys Asp Leu Thr Ser
145                 150                 155                 160

Pro Thr Gln Arg Tyr Ile Asp Ser Lys Val Val Lys Thr Arg Ala Glu
                165                 170                 175

Gly Glu Trp Leu Ser Phe Asp Val Thr Asp Ala Val His Glu Trp Leu
            180                 185                 190

His His Lys Asp Arg Asn Leu Gly Phe Lys Ile Ser Leu His Cys Pro
        195                 200                 205

Cys Cys Thr Phe Val Pro Ser Asn Asn Tyr Ile Ile Pro Asn Lys Ser
    210                 215                 220

Glu Glu Leu Glu Ala Arg Phe Ala Gly Ile Asp Gly Thr Ser Thr Tyr
225                 230                 235                 240

Thr Ser Gly Asp Gln Lys Thr Ile Lys Ser Thr Arg Lys Lys Asn Ser
                245                 250                 255
```

```
Gly Lys Thr Pro His Leu Leu Met Leu Leu Pro Ser Tyr Arg Leu
            260                 265                 270

Glu Ser Gln Gln Thr Asn Arg Arg Lys Gly Ala Leu Asp Ala Ala Tyr
            275                 280                 285

Cys Phe Arg Asn Val Gln Asp Asn Cys Cys Leu Arg Pro Leu Tyr Ile
290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
            355                 360                 365

Thr Ile Leu Tyr Tyr Ile Gly Lys Thr Pro Lys Ile Glu Gln Leu Ser
            370                 375                 380

Asn Met Ile Val Lys Ser Cys Lys Cys Ser
385                 390

<210> SEQ ID NO 20
<211> LENGTH: 392
<212> TYPE: PRT
<213> ORGANISM: Homo sapiens

<400> SEQUENCE: 20

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
                20                  25                  30

Leu Thr Ser Pro Pro Glu Pro Thr Val Met Thr His Val Pro Tyr Gln
            35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
        115                 120                 125

Ala Glu Phe Arg Val Leu Arg Val Pro Asn Pro Ser Ser Lys Arg Asn
    130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
```

```
225                 230                 235                 240
Arg Gly Asp Leu Gly Arg Leu Lys Lys Gln Lys Asp His His Asn Pro
                245                 250                 255
His Leu Ile Leu Met Met Ile Pro Pro His Arg Leu Asp Asn Pro Gly
                260                 265                 270
Gln Gly Gly Gln Arg Lys Lys Arg Ala Leu Asp Thr Asn Tyr Cys Phe
                275                 280                 285
Arg Asn Leu Glu Glu Asn Cys Cys Val Arg Pro Leu Tyr Ile Asp Phe
            290                 295                 300
Arg Gln Asp Leu Gly Trp Lys Trp Val His Glu Pro Lys Gly Tyr Tyr
305                 310                 315                 320
Ala Asn Phe Cys Ser Gly Pro Cys Pro Tyr Leu Arg Ser Ala Asp Thr
                325                 330                 335
Thr His Ser Thr Val Leu Gly Leu Tyr Asn Thr Leu Asn Pro Glu Ala
                340                 345                 350
Ser Ala Ser Pro Cys Cys Val Pro Gln Asp Leu Glu Pro Leu Thr Ile
                355                 360                 365
Leu Tyr Tyr Val Gly Arg Thr Pro Lys Val Glu Gln Leu Ser Asn Met
    370                 375                 380
Val Val Lys Ser Cys Lys Cys Ser
385                 390

<210> SEQ ID NO 21
<211> LENGTH: 392
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ser Leu Ser Leu Ser Thr Ser Thr Thr Leu Asp Phe Gly His Ile Lys
1               5                   10                  15
Lys Lys Arg Val Glu Ala Ile Arg Gly Gln Ile Leu Ser Lys Leu Arg
                20                  25                  30
Leu Thr Ser Pro Pro Glu Pro Thr Val Met Thr His Val Pro Tyr Gln
                35                  40                  45
Val Leu Ala Leu Tyr Asn Ser Thr Arg Glu Leu Leu Glu Glu Met His
            50                  55                  60
Gly Glu Arg Glu Glu Gly Cys Thr Gln Glu Asn Thr Glu Ser Glu Tyr
65                  70                  75                  80
Tyr Ala Lys Glu Ile His Lys Phe Asp Met Ile Gln Gly Leu Ala Glu
                85                  90                  95
His Asn Glu Leu Ala Val Cys Pro Lys Gly Ile Thr Ser Lys Val Phe
                100                 105                 110
Arg Phe Asn Val Ser Ser Val Glu Lys Asn Arg Thr Asn Leu Phe Arg
            115                 120                 125
Ala Glu Phe Arg Val Leu Arg Val Pro Asn Pro Ser Ser Lys Arg Asn
        130                 135                 140
Glu Gln Arg Ile Glu Leu Phe Gln Ile Leu Arg Pro Asp Glu His Ile
145                 150                 155                 160
Ala Lys Gln Arg Tyr Ile Gly Gly Lys Asn Leu Pro Thr Arg Gly Thr
                165                 170                 175
Ala Glu Trp Leu Ser Phe Asp Val Thr Asp Thr Val Arg Glu Trp Leu
                180                 185                 190
```

Leu Arg Arg Glu Ser Asn Leu Gly Leu Glu Ile Ser Ile His Cys Pro
    195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
                260                 265                 270

Gln Gly Gln Arg Lys Lys Arg Ala Leu Asp Thr Asn Tyr Cys Phe
            275                 280                 285

Arg Asn Leu Glu Glu Asn Cys Cys Val Arg Pro Leu Tyr Ile Asp Phe
    290                 295                 300

Arg Gln Asp Leu Gly Trp Lys Trp Val His Glu Pro Lys Gly Tyr Tyr
305                 310                 315                 320

Ala Asn Phe Cys Ser Gly Pro Cys Pro Tyr Leu Arg Ser Ala Asp Thr
                325                 330                 335

Thr His Ser Thr Val Leu Gly Leu Tyr Asn Thr Leu Asn Pro Glu Ala
            340                 345                 350

Ser Ala Ser Pro Cys Cys Val Pro Gln Asp Leu Glu Pro Leu Thr Ile
            355                 360                 365

Leu Tyr Tyr Val Gly Arg Thr Pro Lys Val Glu Gln Leu Ser Asn Met
    370                 375                 380

Val Val Lys Ser Cys Lys Cys Ser
385                 390

<210> SEQ ID NO 22
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 22

Ser Leu Ser Leu Ser Thr Ser Thr Thr Leu Asp Phe Gly His Ile Lys
1               5                   10                  15

Lys Lys Arg Val Glu Ala Ile Arg Gly Gln Ile Leu Ser Lys Leu Arg
                20                  25                  30

Leu Thr Ser Pro Pro Glu Pro Thr Val Met Thr His Val Pro Tyr Gln
            35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe
            100                 105                 110

Arg Phe Asn Val Ser Ser Val Glu Lys Asn Arg Thr Asn Leu Phe Arg
    115                 120                 125

Ala Glu Phe Arg Val Leu Arg Val Pro Asn Pro Ser Ser Lys Arg Asn
            130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
            180                 185                 190

Leu Arg Arg Glu Ser Asn Leu Gly Leu Glu Ile Ser Ile His Cys Pro
        195                 200                 205

Cys His Thr Phe Gln Pro Asn Gly Asp Ile Leu Glu Asn Ile His Glu
    210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
            260                 265                 270

Gln Gly Gly Gln Arg Lys Gly Ala Leu Asp Thr Asn Tyr Cys Phe Arg
        275                 280                 285

Asn Leu Glu Glu Asn Cys Cys Val Arg Pro Leu Tyr Ile Asp Phe Arg
    290                 295                 300

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
                325                 330                 335

His Ser Thr Val Leu Gly Leu Tyr Asn Thr Leu Asn Pro Glu Ala Ser
            340                 345                 350

Ala Ser Pro Cys Cys Val Pro Gln Asp Leu Glu Pro Leu Thr Ile Leu
        355                 360                 365

Tyr Tyr Val Gly Arg Thr Pro Lys Val Glu Gln Leu Ser Asn Met Val
    370                 375                 380

Val Lys Ser Cys Lys Cys Ser
385                 390

<210> SEQ ID NO 23
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ser Leu Ser Leu Ser Thr Cys Thr Thr Leu Asp Phe Gly His Ile Lys
1               5                   10                  15

Lys Lys Arg Val Glu Ala Ile Arg Gly Gln Ile Leu Ser Lys Leu Arg
                20                  25                  30

Leu Thr Ser Pro Pro Glu Pro Thr Val Met Thr His Val Pro Tyr Gln
            35                  40                  45

Val Leu Ala Leu Tyr Asn Ser Thr Arg Glu Leu Leu Glu Glu Met His
    50                  55                  60

Gly Glu Arg Glu Glu Gly Cys Thr Gln Glu Asn Thr Glu Ser Glu Tyr
65                  70                  75                  80

Tyr Ala Lys Glu Ile His Lys Phe Asp Met Ile Gln Gly Leu Ala Glu
                85                  90                  95

His Asn Glu Leu Ala Val Cys Pro Lys Gly Ile Thr Ser Lys Val Phe

```
                100                 105                 110
Arg Phe Asn Val Ser Val Glu Lys Asn Arg Thr Asn Leu Phe Arg
            115                 120                 125

Ala Glu Phe Arg Val Leu Arg Val Pro Asn Pro Ser Ser Lys Arg Asn
130                 135                 140

Glu Gln Arg Ile Glu Leu Phe Gln Ile Leu Arg Pro Asp Glu His Ile
145                 150                 155                 160

Ala Lys Gln Arg Tyr Ile Gly Gly Lys Asn Leu Pro Thr Arg Gly Thr
                165                 170                 175

Ala Glu Trp Leu Ser Phe Asp Val Thr Asp Thr Val Arg Glu Trp Leu
                180                 185                 190

Leu Arg Arg Glu Ser Asn Leu Gly Leu Glu Ile Ser Ile His Cys Pro
            195                 200                 205

Cys His Thr Phe Gln Pro Asn Gly Asp Ile Leu Glu Asn Ile His Glu
        210                 215                 220

Val Met Glu Ile Lys Phe Lys Gly Val Asp Asn Glu Asp Asp His Gly
225                 230                 235                 240

Arg Gly Asp Leu Gly Arg Leu Lys Lys Gln Lys Asp His His Asn Pro
                245                 250                 255

His Leu Ile Leu Met Met Ile Pro Pro His Arg Leu Asp Asn Pro Gly
                260                 265                 270

Gln Gly Gly Gln Arg Lys Gly Ala Leu Asp Thr Asn Tyr Cys Phe Arg
            275                 280                 285

Asn Leu Glu Glu Asn Cys Cys Val Arg Pro Leu Tyr Ile Asp Phe Arg
        290                 295                 300

Gln Asp Leu Gly Trp Lys Trp Val His Glu Pro Lys Gly Tyr Tyr Ala
305                 310                 315                 320

Asn Phe Cys Ser Gly Pro Cys Pro Tyr Leu Arg Ser Ala Asp Thr Thr
                325                 330                 335

His Ser Thr Val Leu Gly Leu Tyr Asn Thr Leu Asn Pro Glu Ala Ser
                340                 345                 350

Ala Ser Pro Cys Cys Val Pro Gln Asp Leu Glu Pro Leu Thr Ile Leu
            355                 360                 365

Tyr Tyr Val Gly Arg Thr Pro Lys Val Glu Gln Leu Ser Asn Met Val
        370                 375                 380

Val Lys Ser Cys Lys Cys Ser
385                 390

<210> SEQ ID NO 24
<211> LENGTH: 361
<212> TYPE: PRT
<213> ORGANISM: Mus sp.

<400> SEQUENCE: 24

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80
```

```
Arg Val Leu Met Val Asp Arg Asn Asn Ala Ile Tyr Glu Lys Thr Lys
                85                  90                  95
Asp Ile Ser His Ser Ile Tyr Met Phe Phe Asn Thr Ser Asp Ile Arg
            100                 105                 110
Glu Ala Val Pro Glu Pro Leu Leu Ser Arg Ala Glu Leu Arg Leu
            115                 120                 125
Gln Arg Leu Lys Ser Ser Val Glu Gln His Val Glu Leu Tyr Gln Lys
        130                 135                 140
Tyr Ser Asn Asn Ser Trp Arg Tyr Leu Gly Asn Arg Leu Leu Thr Pro
145                 150                 155                 160
Thr Asp Thr Pro Glu Trp Leu Ser Phe Asp Val Thr Gly Val Val Arg
                165                 170                 175
Gln Trp Leu Asn Gln Gly Asp Gly Ile Gln Gly Phe Arg Phe Ser Ala
            180                 185                 190
His Cys Ser Cys Asp Ser Lys Asp Asn Lys Leu His Val Glu Ile Asn
            195                 200                 205
Gly Ile Ser Pro Lys Arg Arg Gly Asp Leu Gly Thr Ile His Asp Met
        210                 215                 220
Asn Arg Pro Phe Leu Leu Leu Met Ala Thr Pro Leu Glu Arg Ala Gln
225                 230                 235                 240
His Leu His Ser Ser Arg His Arg Arg Ala Leu Asp Thr Asn Tyr Cys
                245                 250                 255
Phe Ser Ser Thr Glu Lys Asn Cys Cys Val Arg Gln Leu Tyr Ile Asp
                260                 265                 270
Phe Arg Lys Asp Leu Gly Trp Lys Trp Ile His Glu Pro Lys Gly Tyr
            275                 280                 285
His Ala Asn Phe Cys Leu Gly Pro Cys Pro Tyr Ile Trp Ser Leu Asp
        290                 295                 300
Thr Gln Tyr Ser Lys Val Leu Ala Leu Tyr Asn Gln His Asn Pro Gly
305                 310                 315                 320
Ala Ser Ala Ser Pro Cys Cys Val Pro Gln Ala Leu Glu Pro Leu Pro
                325                 330                 335
Ile Val Tyr Tyr Val Gly Arg Lys Pro Lys Val Glu Gln Leu Ser Asn
            340                 345                 350
Met Ile Val Arg Ser Cys Lys Cys Ser
            355                 360

<210> SEQ ID NO 25
<211> LENGTH: 361
<212> TYPE: PRT
<213> ORGANISM: Macaca fascicularis

<400> SEQUENCE: 25

Leu Ser Thr Cys Lys Thr Ile Asp Met Glu Leu Val Lys Arg Lys Arg
1               5                   10                  15
Ile Glu Ala Ile Arg Gly Gln Ile Leu Ser Lys Leu Arg Leu Ala Ser
            20                  25                  30
Pro Pro Ser Gln Gly Glu Val Pro Pro Gly Pro Leu Pro Glu Ala Val
            35                  40                  45
Leu Ala Leu Tyr Asn Ser Thr Arg Asp Arg Val Ala Gly Glu Ser Ala
        50                  55                  60
Glu Pro Glu Pro Glu Pro Glu Ala Asp Tyr Tyr Ala Lys Glu Val Thr
65                  70                  75                  80
Arg Val Leu Met Val Glu Thr His Asn Glu Ile Tyr Asp Lys Phe Lys
                85                  90                  95
```

Gln Ser Thr His Ser Ile Tyr Met Phe Phe Asn Thr Ser Glu Leu Arg
                100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360

<210> SEQ ID NO 26
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

```
Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
            115                 120                 125

Gln Arg Leu Lys Ser Ser Val Glu Gln His Val Glu Leu Tyr Gln Lys
            130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
            195                 200                 205

Gly Ile Ser Pro Lys Arg Arg Gly Asp Leu Gly Thr Ile His Asp Met
            210                 215                 220

Asn Arg Pro Phe Leu Leu Leu Met Ala Thr Pro Leu Glu Arg Ala Gln
225                 230                 235                 240

His Leu His Ser Ser Arg His Arg Arg
                245

<210> SEQ ID NO 27
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
        50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
            130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
```

```
                    180                 185                 190
His Cys Ser Cys Asp Ser Lys Asp Asn Thr Leu Gln Val Asp Ile Asn
                195                 200                 205

Gly Phe Thr Thr Gly Arg Arg Gly Asp Leu Ala Thr Ile His Gly Met
            210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg
                245

<210> SEQ ID NO 28
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Gly Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285
```

Ala Asn Phe Cys Leu Gly Pro Cys Pro Tyr Ile Trp Ser Leu Asp Thr
    290                 295                 300

Gln Tyr Ser Lys Val Leu Ala Leu Tyr Asn Gln His Asn Pro Gly Ala
305                 310                 315                 320

Ser Ala Ser Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
            355                 360

<210> SEQ ID NO 29
<211> LENGTH: 361
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190

His Cys Ser Cys Asp Ser Lys Asp Asn Lys Leu His Val Glu Ile Asn
        195                 200                 205

Gly Ile Ser Pro Lys Arg Arg Gly Asp Leu Gly Thr Ile His Asp Met
    210                 215                 220

Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

```
Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
        290                 295                 300

Thr Gln Tyr Ser Lys Val Leu Ala Leu Tyr Asn Gln His Asn Pro Gly
305                 310                 315                 320

Ala Ser Ala Ser Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
                340                 345                 350

Met Ile Val Arg Ser Cys Lys Cys Ser
            355                 360

<210> SEQ ID NO 30
<211> LENGTH: 361
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Leu Ser Thr Ser Lys Thr Ile Asp Met Glu Leu Val Lys Arg Lys Arg
1               5                  10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
```

```
                    260                 265                 270
Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
            290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
            325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360
```

<210> SEQ ID NO 31
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Leu Ser Thr Ser Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
        50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
            85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
        130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
            165                 170                 175

Gln Trp Leu Ser Arg Gly Gly Glu Ile Glu Gly Phe Arg Leu Ser Ala
            180                 185                 190

His Cys Ser Cys Asp Ser Lys Asp Asn Thr Leu Gln Val Asp Ile Asn
            195                 200                 205

Gly Phe Thr Thr Gly Arg Arg Gly Asp Leu Ala Thr Ile His Gly Met
        210                 215                 220

Asn Arg Pro Phe Leu Leu Leu Met Ala Thr Pro Leu Glu Arg Ala Gln
225                 230                 235                 240

His Leu Gln Ser Ser Arg His Gly Ala Leu Asp Thr Asn Tyr Cys Phe
            245                 250                 255
```

```
Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
            275                 280                 285

Ala Asn Phe Cys Leu Gly Pro Cys Pro Tyr Ile Trp Ser Leu Asp Thr
            290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
            355                 360

<210> SEQ ID NO 32
<211> LENGTH: 1375
<212> TYPE: PRT
<213> ORGANISM: Homo sapiens

<400> SEQUENCE: 32

Asn His Thr Gly Arg Ile Lys Val Val Phe Thr Pro Ser Ile Cys Lys
1               5                   10                  15

Val Thr Cys Thr Lys Gly Ser Cys Gln Asn Ser Cys Glu Lys Gly Asn
            20                  25                  30

Thr Thr Thr Leu Ile Ser Glu Asn Gly His Ala Ala Asp Thr Leu Thr
            35                  40                  45

Ala Thr Asn Phe Arg Val Val Ile Cys His Leu Pro Cys Met Asn Gly
50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val His Gly Ala Ser Val Pro Lys Leu
                85                  90                  95

Tyr Gln His Ser Gln Gln Pro Gly Lys Ala Leu Gly Thr His Val Ile
            100                 105                 110

His Ser Thr His Thr Leu Pro Leu Thr Val Thr Ser Gln Gln Gly Val
            115                 120                 125

Lys Val Lys Phe Pro Pro Asn Ile Val Asn Ile His Val Lys His Pro
            130                 135                 140

Pro Glu Ala Ser Val Gln Ile His Gln Val Ser Arg Ile Asp Gly Pro
145                 150                 155                 160

Thr Gly Gln Lys Thr Lys Glu Ala Gln Pro Gly Gln Ser Gln Val Ser
                165                 170                 175

Tyr Gln Gly Leu Pro Val Gln Lys Thr Gln Thr Ile His Ser Thr Tyr
            180                 185                 190

Ser His Gln Gln Val Ile Pro His Val Tyr Pro Val Ala Ala Lys Thr
            195                 200                 205

Gln Leu Gly Arg Cys Phe Gln Glu Thr Ile Gly Ser Gln Cys Gly Lys
            210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Pro Ser
                245                 250                 255

Tyr His Gly Tyr Asn Gln Met Met Glu Cys Leu Pro Gly Tyr Lys Arg
```

-continued

```
                260                 265                 270
Val Asn Asn Thr Phe Cys Gln Asp Ile Asn Glu Cys Gln Leu Gln Gly
            275                 280                 285

Val Cys Pro Asn Gly Glu Cys Leu Asn Thr Met Gly Ser Tyr Arg Cys
            290                 295                 300

Thr Cys Lys Ile Gly Phe Gly Pro Asp Pro Thr Phe Ser Ser Cys Val
305                 310                 315                 320

Pro Asp Pro Pro Val Ile Ser Glu Glu Lys Gly Pro Cys Tyr Arg Leu
                325                 330                 335

Val Ser Ser Gly Arg Gln Cys Met His Pro Leu Ser Val His Leu Thr
            340                 345                 350

Lys Gln Leu Cys Cys Cys Ser Val Gly Lys Ala Trp Gly Pro His Cys
            355                 360                 365

Glu Lys Cys Pro Leu Pro Gly Thr Ala Ala Phe Lys Glu Ile Cys Pro
            370                 375                 380

Gly Gly Met Gly Tyr Thr Val Ser Gly Val His Arg Arg Pro Ile
385                 390                 395                 400

His His His Val Gly Lys Gly Pro Val Phe Val Lys Pro Lys Asn Thr
                405                 410                 415

Gln Pro Val Ala Lys Ser Thr His Pro Pro Leu Pro Ala Lys Glu
            420                 425                 430

Glu Pro Val Glu Ala Leu Thr Phe Ser Arg Glu His Gly Pro Gly Val
            435                 440                 445

Ala Glu Pro Glu Val Ala Thr Ala Pro Pro Glu Lys Glu Ile Pro Ser
450                 455                 460

Leu Asp Gln Glu Lys Thr Lys Leu Glu Pro Gly Gln Pro Gln Leu Ser
465                 470                 475                 480

Pro Gly Ile Ser Thr Ile His Leu His Pro Gln Phe Pro Val Val Ile
            485                 490                 495

Glu Lys Thr Ser Pro Pro Val Pro Val Glu Val Ala Pro Glu Ala Ser
            500                 505                 510

Thr Ser Ser Ala Ser Gln Val Ile Ala Pro Thr Gln Val Thr Glu Ile
            515                 520                 525

Asn Glu Cys Thr Val Asn Pro Asp Ile Cys Gly Ala Gly His Cys Ile
            530                 535                 540

Asn Leu Pro Val Arg Tyr Thr Cys Ile Cys Tyr Glu Gly Tyr Arg Phe
545                 550                 555                 560

Ser Glu Gln Gln Arg Lys Cys Val Asp Ile Asp Glu Cys Thr Gln Val
                565                 570                 575

Gln His Leu Cys Ser Gln Gly Arg Cys Glu Asn Thr Glu Gly Ser Phe
            580                 585                 590

Leu Cys Ile Cys Pro Ala Gly Phe Met Ala Ser Glu Glu Gly Thr Asn
            595                 600                 605

Cys Ile Asp Val Asp Glu Cys Leu Arg Pro Asp Val Cys Gly Glu Gly
            610                 615                 620

His Cys Val Asn Thr Val Gly Ala Phe Arg Cys Glu Tyr Cys Asp Ser
625                 630                 635                 640

Gly Tyr Arg Met Thr Gln Arg Gly Arg Cys Glu Asp Ile Asp Glu Cys
                645                 650                 655

Leu Asn Pro Ser Thr Cys Pro Asp Glu Gln Cys Val Asn Ser Pro Gly
            660                 665                 670

Ser Tyr Gln Cys Val Pro Cys Thr Glu Gly Phe Arg Gly Trp Asn Gly
            675                 680                 685
```

```
Gln Cys Leu Asp Val Asp Glu Cys Leu Glu Pro Asn Val Cys Ala Asn
    690                 695                 700
Gly Asp Cys Ser Asn Leu Glu Gly Ser Tyr Met Cys Ser Cys His Lys
705                 710                 715                 720
Gly Tyr Thr Arg Thr Pro Asp His Lys His Cys Arg Asp Ile Asp Glu
                725                 730                 735
Cys Gln Gln Gly Asn Leu Cys Val Asn Gly Gln Cys Lys Asn Thr Glu
            740                 745                 750
Gly Ser Phe Arg Cys Thr Cys Gly Gln Gly Tyr Gln Leu Ser Ala Ala
        755                 760                 765
Lys Asp Gln Cys Glu Asp Ile Asp Glu Cys Gln His Arg His Leu Cys
770                 775                 780
Ala His Gly Gln Cys Arg Asn Thr Glu Gly Ser Phe Gln Cys Val Cys
785                 790                 795                 800
Asp Gln Gly Tyr Arg Ala Ser Gly Leu Gly Asp His Cys Glu Asp Ile
                805                 810                 815
Asn Glu Cys Leu Glu Asp Lys Ser Val Cys Gln Arg Gly Asp Cys Ile
            820                 825                 830
Asn Thr Ala Gly Ser Tyr Asp Cys Thr Cys Pro Asp Gly Phe Gln Leu
        835                 840                 845
Asp Asp Asn Lys Thr Cys Gln Asp Ile Asn Glu Cys Glu His Pro Gly
850                 855                 860
Leu Cys Gly Pro Gln Gly Glu Cys Leu Asn Thr Glu Gly Ser Phe His
865                 870                 875                 880
Cys Val Cys Gln Gln Gly Phe Ser Ile Ser Ala Asp Gly Arg Thr Cys
                885                 890                 895
Glu Asp Ile Asp Glu Cys Val Asn Asn Thr Val Cys Asp Ser His Gly
            900                 905                 910
Phe Cys Asp Asn Thr Ala Gly Ser Phe Arg Cys Leu Cys Tyr Gln Gly
        915                 920                 925
Phe Gln Ala Pro Gln Asp Gly Gln Gly Cys Val Asp Val Asn Glu Cys
930                 935                 940
Glu Leu Leu Ser Gly Val Cys Gly Glu Ala Phe Cys Glu Asn Val Glu
945                 950                 955                 960
Gly Ser Phe Leu Cys Val Cys Ala Asp Glu Asn Gln Glu Tyr Ser Pro
                965                 970                 975
Met Thr Gly Gln Cys Arg Ser Arg Thr Ser Thr Asp Leu Asp Val Asp
            980                 985                 990
Val Asp Gln Pro Lys Glu Glu Lys  Lys Glu Cys Tyr Tyr  Asn Leu Asn
        995                 1000                1005
Asp Ala  Ser Leu Cys Asp Asn  Val Leu Ala Pro Asn  Val Thr Lys
        1010                1015                1020
Gln Glu  Cys Cys Cys Thr Ser  Gly Val Gly Trp Gly  Asp Asn Cys
        1025                1030                1035
Glu Ile  Phe Pro Cys Pro Val  Leu Gly Thr Ala Glu  Phe Thr Glu
        1040                1045                1050
Met Cys  Pro Lys Gly Lys Gly  Phe Val Pro Ala Gly  Glu Ser Ser
        1055                1060                1065
Ser Glu  Ala Gly Gly Glu Asn  Tyr Lys Asp Ala Asp  Glu Cys Leu
        1070                1075                1080
Leu Phe  Gly Gln Glu Ile Cys  Lys Asn Gly Phe Cys  Leu Asn Thr
        1085                1090                1095
```

```
Arg Pro Gly Tyr Glu Cys Tyr Cys Lys Gln Gly Thr Tyr Tyr Asp
    1100            1105                1110

Pro Val Lys Leu Gln Cys Phe Asp Met Asp Glu Cys Gln Asp Pro
    1115            1120                1125

Ser Ser Cys Ile Asp Gly Gln Cys Val Asn Thr Glu Gly Ser Tyr
    1130            1135                1140

Asn Cys Phe Cys Thr His Pro Met Val Leu Asp Ala Ser Glu Lys
    1145            1150                1155

Arg Cys Ile Arg Pro Ala Glu Ser Asn Glu Gln Ile Glu Glu Thr
    1160            1165                1170

Asp Val Tyr Gln Asp Leu Cys Trp Glu His Leu Ser Asp Glu Tyr
    1175            1180                1185

Val Cys Ser Arg Pro Leu Val Gly Lys Gln Thr Thr Tyr Thr Glu
    1190            1195                1200

Cys Cys Cys Leu Tyr Gly Glu Ala Trp Gly Met Gln Cys Ala Leu
    1205            1210                1215

Cys Pro Leu Lys Asp Ser Asp Tyr Ala Gln Leu Cys Asn Ile
    1220            1225                1230

Pro Val Thr Gly Arg Arg Gln Pro Tyr Gly Arg Asp Ala Leu Val
    1235            1240                1245

Asp Phe Ser Glu Gln Tyr Thr Pro Glu Ala Asp Pro Tyr Phe Ile
    1250            1255                1260

Gln Asp Arg Phe Leu Asn Ser Phe Glu Glu Leu Gln Ala Glu Glu
    1265            1270                1275

Cys Gly Ile Leu Asn Gly Cys Glu Asn Gly Arg Cys Val Arg Val
    1280            1285                1290

Gln Glu Gly Tyr Thr Cys Asp Cys Phe Asp Gly Tyr His Leu Asp
    1295            1300                1305

Thr Ala Lys Met Thr Cys Val Asp Val Asn Glu Cys Asp Glu Leu
    1310            1315                1320

Asn Asn Arg Met Ser Leu Cys Lys Asn Ala Lys Cys Ile Asn Thr
    1325            1330                1335

Asp Gly Ser Tyr Lys Cys Leu Cys Leu Pro Gly Tyr Val Pro Ser
    1340            1345                1350

Asp Lys Pro Asn Tyr Cys Thr Pro Leu Asn Thr Ala Leu Asn Leu
    1355            1360                1365

Glu Lys Asp Ser Asp Leu Glu
    1370            1375

<210> SEQ ID NO 33
<211> LENGTH: 1373
<212> TYPE: PRT
<213> ORGANISM: Macaca fascicularis

<400> SEQUENCE: 33

Asn His Thr Gly Arg Ile Lys Val Val Phe Thr Pro Ser Ile Cys Lys
1               5                   10                  15

Val Thr Cys Thr Lys Gly Ser Cys Gln Asn Ser Cys Glu Lys Gly Asn
                20                  25                  30

Thr Thr Thr Leu Ile Ser Glu Asn Gly His Ala Ala Asp Thr Leu Thr
            35                  40                  45

Ala Thr Asn Phe Arg Val Val Leu Cys His Leu Pro Cys Met Asn Gly
        50                  55                  60

Gly Gln Cys Ser Ser Arg Asp Lys Cys Gln Cys Pro Pro Asn Phe Thr
65                  70                  75                  80
```

```
Gly Lys Leu Cys Gln Ile Pro Val His Gly Ala Ser Val Pro Lys Leu
                85                  90                  95
Tyr Gln His Ser Gln Gln Pro Gly Lys Ala Leu Gly Thr His Val Ile
                100                 105                 110
His Ser Thr His Thr Leu Pro Leu Thr Val Thr Ser Gln Gln Gly Val
                115                 120                 125
Lys Val Lys Phe Pro Pro Asn Ile Val Asn Ile His Val Lys His Pro
    130                 135                 140
Pro Glu Ala Ser Val Gln Ile His Gln Val Ser Arg Ile Asp Gly Pro
145                 150                 155                 160
Thr Gly Gln Lys Thr Lys Glu Ala Gln Pro Gly Gln Ser Gln Val Ser
                165                 170                 175
Tyr Gln Gly Leu Pro Val Gln Lys Thr Gln Thr Ile His Ser Thr Tyr
                180                 185                 190
Ser His Gln Gln Val Ile Pro His Val Tyr Pro Val Ala Ala Lys Thr
                195                 200                 205
Gln Leu Gly Arg Cys Phe Gln Glu Thr Ile Gly Ser Gln Cys Gly Lys
                210                 215                 220
Ala Leu Pro Gly Leu Ser Lys Gln Glu Asp Cys Cys Gly Thr Val Gly
225                 230                 235                 240
Thr Ser Trp Gly Phe Asn Lys Cys Gln Lys Cys Pro Lys Lys Pro Ser
                245                 250                 255
Tyr His Gly Tyr Asn Gln Met Met Glu Cys Leu Pro Gly Tyr Lys Arg
                260                 265                 270
Val Asn Asn Thr Phe Cys Gln Asp Ile Asn Glu Cys Gln Leu Gln Gly
                275                 280                 285
Val Cys Pro Asn Gly Glu Cys Leu Asn Thr Met Gly Ser Tyr Arg Cys
                290                 295                 300
Thr Cys Lys Ile Gly Phe Gly Pro Asp Pro Thr Phe Ser Ser Cys Val
305                 310                 315                 320
Pro Asp Pro Pro Val Ile Ser Glu Glu Lys Gly Pro Cys Tyr Arg Leu
                325                 330                 335
Val Ser Ser Gly Arg Gln Cys Met His Pro Leu Ser Val His Leu Thr
                340                 345                 350
Lys Gln Leu Cys Cys Cys Ser Val Gly Lys Ala Trp Gly Pro His Cys
                355                 360                 365
Glu Lys Cys Pro Leu Pro Gly Thr Ala Ala Phe Lys Glu Ile Cys Pro
                370                 375                 380
Gly Gly Met Gly Tyr Thr Val Ser Gly Val His Arg Arg Arg Pro Ile
385                 390                 395                 400
His His His Val Gly Lys Gly Pro Val Phe Val Lys Pro Lys Asn Thr
                405                 410                 415
Gln Pro Val Ala Lys Ser Thr His Pro Pro Leu Pro Ala Lys Glu
                420                 425                 430
Glu Pro Val Glu Ala Leu Thr Phe Ser Arg Glu His Gly Pro Gly Val
                435                 440                 445
Ala Glu Pro Glu Val Ala Thr Ala Pro Pro Glu Lys Glu Ile Pro Ser
450                 455                 460
Leu Asp Gln Glu Lys Thr Lys Leu Glu Pro Gly Gln Pro Gln Leu Ser
465                 470                 475                 480
Pro Gly Ile Ser Thr Ile His Leu His Pro Gln Phe Pro Val Val Ile
                485                 490                 495
```

```
Glu Lys Thr Ser Pro Pro Val Pro Glu Val Ala Pro Glu Ala Ser
            500             505             510
Thr Ser Ser Ala Ser Gln Val Ile Ala Pro Thr Gln Val Thr Glu Ile
        515                 520             525
Asn Glu Cys Thr Val Asn Pro Asp Ile Cys Gly Ala Gly His Cys Ile
    530                 535                 540
Asn Leu Pro Val Arg Tyr Thr Cys Ile Cys Tyr Glu Gly Tyr Lys Phe
545                 550                 555                 560
Ser Glu Gln Gln Arg Lys Cys Val Asp Ile Asp Glu Cys Thr Gln Val
                565                 570                 575
Gln His Leu Cys Ser Gln Gly Arg Cys Glu Asn Thr Glu Gly Ser Phe
            580                 585                 590
Leu Cys Ile Cys Pro Ala Gly Phe Met Ala Ser Glu Glu Gly Thr Asn
        595                 600                 605
Cys Ile Asp Val Asp Glu Cys Leu Arg Pro Asp Val Cys Gly Glu Gly
    610                 615                 620
His Cys Val Asn Thr Val Gly Ala Phe Arg Cys Glu Tyr Cys Asp Ser
625                 630                 635                 640
Gly Tyr Arg Met Thr Gln Arg Gly Arg Cys Glu Asp Ile Asp Glu Cys
                645                 650                 655
Leu Asn Pro Ser Thr Cys Pro Asp Glu Gln Cys Val Asn Ser Pro Gly
            660                 665                 670
Ser Tyr Gln Cys Val Pro Cys Thr Glu Gly Phe Arg Gly Trp Asn Gly
        675                 680                 685
Gln Cys Leu Asp Val Asp Glu Cys Leu Glu Pro Asn Val Cys Thr Asn
    690                 695                 700
Gly Asp Cys Ser Asn Leu Glu Gly Ser Tyr Met Cys Ser Cys His Lys
705                 710                 715                 720
Gly Tyr Thr Arg Thr Pro Asp His Lys His Cys Lys Asp Ile Asp Glu
                725                 730                 735
Cys Gln Gln Gly Asn Leu Cys Val Asn Gly Gln Cys Lys Asn Thr Glu
            740                 745                 750
Gly Ser Phe Arg Cys Thr Cys Gly Gln Gly Tyr Gln Leu Ser Ala Ala
        755                 760                 765
Lys Asp Gln Cys Glu Asp Ile Asp Glu Cys Gln His His Leu Cys
770                 775                 780
Ala His Gly Gln Cys Arg Asn Thr Glu Gly Ser Phe Gln Cys Val Cys
785                 790                 795                 800
Asp Gln Gly Tyr Arg Ala Ser Gly Leu Gly Asp His Cys Glu Asp Ile
                805                 810                 815
Asn Glu Cys Leu Glu Asp Lys Ser Val Cys Gln Arg Gly Asp Cys Ile
            820                 825                 830
Asn Thr Ala Gly Ser Tyr Asp Cys Thr Cys Pro Asp Gly Phe Gln Leu
        835                 840                 845
Asp Asp Asn Lys Thr Cys Gln Asp Ile Asn Glu Cys Glu His Pro Gly
    850                 855                 860
Leu Cys Gly Pro Gln Gly Glu Cys Leu Asn Thr Glu Gly Ser Phe His
865                 870                 875                 880
Cys Val Cys Gln Gln Gly Phe Ser Ile Ser Ala Asp Gly Arg Thr Cys
                885                 890                 895
Glu Asp Ile Asp Glu Cys Val Asn Asn Thr Val Cys Asp Ser His Gly
            900                 905                 910
Phe Cys Asp Asn Thr Ala Gly Ser Phe Arg Cys Leu Cys Tyr Gln Gly
```

```
              915                 920                 925
Phe Gln Ala Pro Gln Asp Gly Gln Gly Cys Val Asp Val Asn Glu Cys
    930                 935                 940
Glu Leu Leu Ser Gly Val Cys Gly Glu Ala Phe Cys Glu Asn Val Glu
945                 950                 955                 960
Gly Ser Phe Leu Cys Val Cys Ala Asp Glu Asn Gln Glu Tyr Ser Pro
                965                 970                 975
Met Thr Gly Gln Cys Arg Ser Arg Thr Ser Thr Asp Leu Asp Val Glu
            980                 985                 990
Gln Pro Lys Glu Glu Lys Lys Glu  Cys Tyr Tyr Asn Leu  Asn Asp Ala
        995                 1000                 1005
Ser Leu  Cys Asp Asn Val Leu  Ala Pro Asn Val Thr  Lys Gln Glu
    1010                1015                1020
Cys Cys  Cys Thr Ser Gly Ala  Gly Trp Gly Asp Asn  Cys Glu Ile
    1025                1030                1035
Phe Pro  Cys Pro Val Leu Gly  Thr Ala Glu Phe Thr  Glu Met Cys
    1040                1045                1050
Pro Lys  Gly Lys Gly Phe Val  Pro Ala Gly Glu Ser  Ser Ser Glu
    1055                1060                1065
Ala Gly  Gly Glu Asn Tyr Lys  Asp Ala Asp Glu Cys  Leu Leu Phe
    1070                1075                1080
Gly Gln  Glu Ile Cys Lys Asn  Gly Phe Cys Leu Asn  Thr Arg Pro
    1085                1090                1095
Gly Tyr  Glu Cys Tyr Cys Lys  Gln Gly Thr Tyr Tyr  Asp Pro Val
    1100                1105                1110
Lys Leu  Gln Cys Phe Asp Met  Asp Glu Cys Gln Asp  Pro Ser Ser
    1115                1120                1125
Cys Ile  Asp Gly Gln Cys Val  Asn Thr Glu Gly Ser  Tyr Asn Cys
    1130                1135                1140
Phe Cys  Thr His Pro Met Val  Leu Asp Ala Ser Glu  Lys Arg Cys
    1145                1150                1155
Ile Arg  Pro Ala Glu Ser Asn  Glu Gln Ile Glu Glu  Thr Asp Val
    1160                1165                1170
Tyr Gln  Asp Leu Cys Trp Glu  His Leu Ser Asp Glu  Tyr Val Cys
    1175                1180                1185
Ser Arg  Pro Leu Val Gly Lys  Gln Thr Thr Tyr Thr  Glu Cys Cys
    1190                1195                1200
Cys Leu  Tyr Gly Glu Ala Trp  Gly Met Gln Cys Ala  Leu Cys Pro
    1205                1210                1215
Met Lys  Asp Ser Asp Asp Tyr  Ala Gln Leu Cys Asn  Ile Pro Val
    1220                1225                1230
Thr Gly  Arg Arg Gln Pro Tyr  Gly Arg Asp Ala Leu  Val Asp Phe
    1235                1240                1245
Ser Glu  Gln Tyr Ala Pro Glu  Ala Asp Pro Tyr Phe  Ile Gln Asp
    1250                1255                1260
Arg Phe  Leu Asn Ser Phe Glu  Glu Leu Gln Ala Glu  Glu Cys Gly
    1265                1270                1275
Ile Leu  Asn Gly Cys Glu Asn  Gly Arg Cys Val Arg  Val Gln Glu
    1280                1285                1290
Gly Tyr  Thr Cys Asp Cys Phe  Asp Gly Tyr His Leu  Asp Thr Ala
    1295                1300                1305
Lys Met  Thr Cys Val Asp Val  Asn Glu Cys Asp Glu  Leu Asn Asn
    1310                1315                1320
```

```
Arg Met Ser Leu Cys Lys Asn Ala Lys Cys Ile Asn Thr Glu Gly
    1325              1330                1335

Ser Tyr Lys Cys Leu Cys Leu Pro Gly Tyr Val Pro Ser Asp Lys
    1340              1345                1350

Pro Asn Tyr Cys Thr Pro Leu Asn Thr Ala Leu Asn Leu Glu Lys
    1355              1360                1365

Asp Ser Asp Leu Glu
    1370

<210> SEQ ID NO 34
<211> LENGTH: 1374
<212> TYPE: PRT
<213> ORGANISM: Mus sp.

<400> SEQUENCE: 34

Asn His Thr Gly Arg Ile Lys Val Val Phe Thr Pro Ser Ile Cys Lys
1               5                   10                  15

Val Thr Cys Thr Lys Gly Asn Cys Gln Asn Ser Cys Gln Lys Gly Asn
            20                  25                  30

Thr Thr Thr Leu Ile Ser Glu Asn Gly His Ala Ala Asp Thr Leu Thr
        35                  40                  45

Ala Thr Asn Phe Arg Val Val Ile Cys His Leu Pro Cys Met Asn Gly
50                  55                  60

Gly Gln Cys Ser Ser Arg Asp Lys Cys Gln Cys Pro Pro Asn Phe Thr
65                  70                  75                  80

Gly Lys Leu Cys Gln Ile Pro Val Leu Gly Ala Ser Met Pro Lys Leu
                85                  90                  95

Tyr Gln His Ala Gln Gln Gln Gly Lys Ala Leu Gly Ser His Val Ile
            100                 105                 110

His Ser Thr His Thr Leu Pro Leu Thr Met Thr Ser Gln Gln Gly Val
        115                 120                 125

Lys Val Lys Phe Pro Pro Asn Ile Val Asn Ile His Val Lys His Pro
    130                 135                 140

Pro Glu Ala Ser Val Gln Ile His Gln Val Ser Arg Ile Asp Ser Pro
145                 150                 155                 160

Gly Gly Gln Lys Val Lys Glu Ala Gln Pro Gly Gln Ser Gln Val Ser
                165                 170                 175

Tyr Gln Gly Leu Pro Val Gln Lys Thr Gln Thr Val His Ser Thr Tyr
            180                 185                 190

Ser His Gln Gln Leu Ile Pro His Val Tyr Pro Val Ala Ala Lys Thr
        195                 200                 205

Gln Leu Gly Arg Cys Phe Gln Glu Thr Ile Gly Ser Gln Cys Gly Lys
    210                 215                 220

Ala Leu Pro Gly Leu Ser Lys Gln Glu Asp Cys Cys Gly Thr Val Gly
225                 230                 235                 240

Thr Ser Trp Gly Phe Asn Lys Cys Gln Lys Cys Pro Lys Lys Gln Ser
                245                 250                 255

Tyr His Gly Tyr Thr Gln Met Met Glu Cys Leu Gln Gly Tyr Lys Arg
            260                 265                 270

Val Asn Asn Thr Phe Cys Gln Asp Ile Asn Glu Cys Gln Leu Gln Gly
        275                 280                 285

Val Cys Pro Asn Gly Glu Cys Leu Asn Thr Met Gly Ser Tyr Arg Cys
    290                 295                 300

Ser Cys Lys Met Gly Phe Gly Pro Asp Pro Thr Phe Ser Ser Cys Val
```

```
          305                 310                 315                 320
Pro Asp Pro Pro Val Ile Ser Glu Glu Lys Gly Pro Cys Tyr Arg Leu
                    325                 330                 335

Val Ser Pro Gly Arg His Cys Met His Pro Leu Ser Val His Leu Thr
                340                 345                 350

Lys Gln Ile Cys Cys Ser Val Gly Lys Ala Trp Gly Pro His Cys
            355                 360                 365

Glu Lys Cys Pro Leu Pro Gly Thr Ala Ala Phe Lys Glu Ile Cys Pro
        370                 375                 380

Gly Gly Met Gly Tyr Thr Val Ser Gly Val His Arg Arg Pro Ile
385                 390                 395                 400

His Gln His Ile Gly Lys Glu Ala Val Tyr Val Lys Pro Lys Asn Thr
                405                 410                 415

Gln Pro Val Ala Lys Ser Thr His Pro Pro Leu Pro Ala Lys Glu
            420                 425                 430

Glu Pro Val Glu Ala Leu Thr Ser Ser Trp Glu His Gly Pro Arg Gly
        435                 440                 445

Ala Glu Pro Glu Val Val Thr Ala Pro Pro Glu Lys Glu Ile Pro Ser
    450                 455                 460

Leu Asp Gln Glu Lys Thr Arg Leu Glu Pro Gly Gln Pro Gln Leu Ser
465                 470                 475                 480

Pro Gly Val Ser Thr Ile His Leu His Pro Gln Phe Pro Val Val Val
                485                 490                 495

Glu Lys Thr Ser Pro Pro Val Pro Val Glu Val Ala Pro Glu Ala Ser
            500                 505                 510

Thr Ser Ser Ala Ser Gln Val Ile Ala Pro Thr Gln Val Thr Glu Ile
        515                 520                 525

Asn Glu Cys Thr Val Asn Pro Asp Ile Cys Gly Ala Gly His Cys Ile
    530                 535                 540

Asn Leu Pro Val Arg Tyr Thr Cys Ile Cys Tyr Glu Gly Tyr Lys Phe
545                 550                 555                 560

Ser Glu Gln Leu Arg Lys Cys Val Asp Ile Asp Glu Cys Ala Gln Val
                565                 570                 575

Arg His Leu Cys Ser Gln Gly Arg Cys Glu Asn Thr Glu Gly Ser Phe
            580                 585                 590

Leu Cys Val Cys Pro Ala Gly Phe Met Ala Ser Glu Glu Gly Thr Asn
        595                 600                 605

Cys Ile Asp Val Asp Glu Cys Leu Arg Pro Asp Met Cys Arg Asp Gly
    610                 615                 620

Arg Cys Ile Asn Thr Ala Gly Ala Phe Arg Cys Glu Tyr Cys Asp Ser
625                 630                 635                 640

Gly Tyr Arg Met Ser Arg Arg Gly Tyr Cys Glu Asp Ile Asp Glu Cys
                645                 650                 655

Leu Lys Pro Ser Thr Cys Pro Glu Glu Gln Cys Val Asn Thr Pro Gly
            660                 665                 670

Ser Tyr Gln Cys Val Pro Cys Thr Glu Gly Phe Arg Gly Trp Asn Gly
        675                 680                 685

Gln Cys Leu Asp Val Asp Glu Cys Leu Gln Pro Lys Val Cys Thr Asn
    690                 695                 700

Gly Ser Cys Thr Asn Leu Glu Gly Ser Tyr Met Cys Ser Cys His Arg
705                 710                 715                 720

Gly Tyr Ser Pro Thr Pro Asp His Arg His Cys Gln Asp Ile Asp Glu
                725                 730                 735
```

-continued

Cys Gln Gln Gly Asn Leu Cys Met Asn Gly Gln Cys Arg Asn Thr Asp
              740                 745                 750

Gly Ser Phe Arg Cys Thr Cys Gly Gln Gly Tyr Gln Leu Ser Ala Ala
            755                 760                 765

Lys Asp Gln Cys Glu Asp Ile Asp Glu Cys Glu His His His Leu Cys
        770                 775                 780

Ser His Gly Gln Cys Arg Asn Thr Glu Gly Ser Phe Gln Cys Val Cys
785             790                 795                 800

Asn Gln Gly Tyr Arg Ala Ser Val Leu Gly Asp His Cys Glu Asp Ile
                805                 810                 815

Asn Glu Cys Leu Glu Asp Ser Ser Val Cys Gln Gly Gly Asp Cys Ile
            820                 825                 830

Asn Thr Ala Gly Ser Tyr Asp Cys Thr Cys Pro Asp Gly Phe Gln Leu
                835                 840                 845

Asn Asp Asn Lys Gly Cys Gln Asp Ile Asn Glu Cys Ala Gln Pro Gly
        850                 855                 860

Leu Cys Gly Ser His Gly Glu Cys Leu Asn Thr Gln Gly Ser Phe His
865             870                 875                 880

Cys Val Cys Glu Gln Gly Phe Ser Ile Ser Ala Asp Gly Arg Thr Cys
                885                 890                 895

Glu Asp Ile Asp Glu Cys Val Asn Asn Thr Val Cys Asp Ser His Gly
            900                 905                 910

Phe Cys Asp Asn Thr Ala Gly Ser Phe Arg Cys Leu Cys Tyr Gln Gly
        915                 920                 925

Phe Gln Ala Pro Gln Asp Gly Gln Gly Cys Val Asp Val Asn Glu Cys
        930                 935                 940

Glu Leu Leu Ser Gly Val Cys Gly Glu Ala Phe Cys Glu Asn Val Glu
945             950                 955                 960

Gly Ser Phe Leu Cys Val Cys Ala Asp Glu Asn Gln Glu Tyr Ser Pro
                965                 970                 975

Met Thr Gly Gln Cys Arg Ser Arg Val Thr Glu Asp Ser Gly Val Asp
                980                 985                 990

Arg Gln Pro Arg Glu Glu Lys Lys Glu Cys Tyr Tyr Asn Leu Asn Asp
        995                 1000                1005

Ala Ser Leu Cys Asp Asn Val Leu Ala Pro Asn Val Thr Lys Gln
        1010                1015                1020

Glu Cys Cys Cys Thr Ser Gly Ala Gly Trp Gly Asp Asn Cys Glu
        1025                1030                1035

Ile Phe Pro Cys Pro Val Gln Gly Thr Ala Glu Phe Thr Glu Met
        1040                1045                1050

Cys Pro Arg Gly Lys Gly Leu Val Pro Ala Gly Glu Ser Ser Tyr
        1055                1060                1065

Asp Thr Gly Gly Glu Asn Tyr Lys Asp Ala Asp Glu Cys Leu Leu
        1070                1075                1080

Phe Gly Glu Glu Ile Cys Lys Asn Gly Tyr Cys Leu Asn Thr Gln
        1085                1090                1095

Pro Gly Tyr Glu Cys Tyr Cys Lys Gln Gly Thr Tyr Tyr Asp Pro
        1100                1105                1110

Val Lys Leu Gln Cys Phe Asp Met Asp Glu Cys Gln Asp Pro Asn
        1115                1120                1125

Ser Cys Ile Asp Gly Gln Cys Val Asn Thr Glu Gly Ser Tyr Asn
        1130                1135                1140

```
Cys Phe Cys Thr His Pro Met Val Leu Asp Ala Ser Glu Lys Arg
    1145                1150                1155

Cys Val Gln Pro Thr Glu Ser Asn Glu Gln Ile Glu Glu Thr Asp
    1160                1165                1170

Val Tyr Gln Asp Leu Cys Trp Glu His Leu Ser Glu Glu Tyr Val
    1175                1180                1185

Cys Ser Arg Pro Leu Val Gly Lys Gln Thr Thr Tyr Thr Glu Cys
    1190                1195                1200

Cys Cys Leu Tyr Gly Glu Ala Trp Gly Met Gln Cys Ala Leu Cys
    1205                1210                1215

Pro Met Lys Asp Ser Asp Tyr Ala Gln Leu Cys Asn Ile Pro
    1220                1225                1230

Val Thr Gly Arg Arg Pro Tyr Gly Arg Asp Ala Leu Val Asp
    1235                1240                1245

Phe Ser Glu Gln Tyr Gly Pro Glu Thr Asp Pro Tyr Phe Ile Gln
    1250                1255                1260

Asp Arg Phe Leu Asn Ser Phe Glu Glu Leu Gln Ala Glu Glu Cys
    1265                1270                1275

Gly Ile Leu Asn Gly Cys Glu Asn Gly Arg Cys Val Arg Val Gln
    1280                1285                1290

Glu Gly Tyr Thr Cys Asp Cys Phe Asp Gly Tyr His Leu Asp Met
    1295                1300                1305

Ala Lys Met Thr Cys Val Asp Val Asn Glu Cys Ser Glu Leu Asn
    1310                1315                1320

Asn Arg Met Ser Leu Cys Lys Asn Ala Lys Cys Ile Asn Thr Glu
    1325                1330                1335

Gly Ser Tyr Lys Cys Leu Cys Leu Pro Gly Tyr Ile Pro Ser Asp
    1340                1345                1350

Lys Pro Asn Tyr Cys Thr Pro Leu Asn Ser Ala Leu Asn Leu Asp
    1355                1360                1365

Lys Glu Ser Asp Leu Glu
    1370

<210> SEQ ID NO 35
<211> LENGTH: 1260
<212> TYPE: PRT
<213> ORGANISM: Homo sapiens

<400> SEQUENCE: 35

Gly Pro Ala Gly Glu Arg Gly Ala Gly Gly Gly Ala Leu Ala Arg
1               5                   10                  15

Glu Arg Phe Lys Val Val Phe Ala Pro Val Ile Cys Lys Arg Thr Cys
                20                  25                  30

Leu Lys Gly Gln Cys Arg Asp Ser Cys Gln Gln Gly Ser Asn Met Thr
                35                  40                  45

Leu Ile Gly Glu Asn Gly His Ser Thr Asp Thr Leu Thr Gly Ser Gly
        50                  55                  60

Phe Arg Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Gly Gly Ala Gly Gly Gly Thr Gly Gly Ser Gly
                100                 105                 110

Pro Gly Leu Ser Arg Thr Gly Ala Leu Ser Thr Gly Ala Leu Pro Pro
        115                 120                 125
```

```
Leu Ala Pro Glu Gly Asp Ser Val Ala Ser Lys His Ala Ile Tyr Ala
    130                 135                 140
Val Gln Val Ile Ala Asp Pro Pro Gly Pro Gly Glu Pro Pro Ala
145                 150                 155                 160
Gln His Ala Ala Phe Leu Val Pro Leu Gly Pro Gly Gln Ile Ser Ala
                    165                 170                 175
Glu Val Gln Ala Pro Pro Val Val Asn Val Arg Val His His Pro
                180                 185                 190
Pro Glu Ala Ser Val Gln Val His Arg Ile Glu Ser Ser Asn Ala Glu
            195                 200                 205
Ser Ala Ala Pro Ser Gln His Leu Leu Pro His Pro Lys Pro Ser His
210                 215                 220
Pro Arg Pro Pro Thr Gln Lys Pro Leu Gly Arg Cys Phe Gln Asp Thr
225                 230                 235                 240
Leu Pro Lys Gln Pro Cys Gly Ser Asn Pro Leu Pro Gly Leu Thr Lys
                    245                 250                 255
Gln Glu Asp Cys Cys Gly Ser Ile Gly Thr Ala Trp Gly Gln Ser Lys
                260                 265                 270
Cys His Lys Cys Pro Gln Leu Gln Tyr Thr Gly Val Gln Lys Pro Gly
            275                 280                 285
Pro Val Arg Gly Glu Val Gly Ala Asp Cys Pro Gln Gly Tyr Lys Arg
290                 295                 300
Leu Asn Ser Thr His Cys Gln Asp Ile Asn Glu Cys Ala Met Pro Gly
305                 310                 315                 320
Val Cys Arg His Gly Asp Cys Leu Asn Asn Pro Gly Ser Tyr Arg Cys
                    325                 330                 335
Val Cys Pro Pro Gly His Ser Leu Gly Pro Ser Arg Thr Gln Cys Ile
                340                 345                 350
Ala Asp Lys Pro Glu Glu Lys Ser Leu Cys Phe Arg Leu Val Ser Pro
            355                 360                 365
Glu His Gln Cys Gln His Pro Leu Thr Thr Arg Leu Thr Arg Gln Leu
370                 375                 380
Cys Cys Cys Ser Val Gly Lys Ala Trp Gly Ala Arg Cys Gln Arg Cys
385                 390                 395                 400
Pro Thr Asp Gly Thr Ala Ala Phe Lys Glu Ile Cys Pro Ala Gly Lys
                    405                 410                 415
Gly Tyr His Ile Leu Thr Ser His Gln Thr Leu Thr Ile Gln Gly Glu
                420                 425                 430
Ser Asp Phe Ser Leu Phe Leu His Pro Asp Gly Pro Pro Lys Pro Gln
            435                 440                 445
Gln Leu Pro Glu Ser Pro Ser Gln Ala Pro Pro Glu Asp Thr Glu
450                 455                 460
Glu Glu Arg Gly Val Thr Thr Asp Ser Pro Val Ser Glu Glu Arg Ser
465                 470                 475                 480
Val Gln Gln Ser His Pro Thr Ala Thr Thr Pro Ala Arg Pro Tyr
                    485                 490                 495
Pro Glu Leu Ile Ser Arg Pro Ser Pro Pro Thr Met Arg Trp Phe Leu
                500                 505                 510
Pro Asp Leu Pro Pro Ser Arg Ser Ala Val Glu Ile Ala Pro Thr Gln
            515                 520                 525
Val Thr Glu Thr Asp Glu Cys Arg Leu Asn Gln Asn Ile Cys Gly His
530                 535                 540
```

-continued

```
Gly Glu Cys Val Pro Gly Pro Pro Asp Tyr Ser Cys His Cys Asn Pro
545                 550                 555                 560

Gly Tyr Arg Ser His Pro Gln His Arg Tyr Cys Val Asp Val Asn Glu
            565                 570                 575

Cys Glu Ala Glu Pro Cys Gly Pro Gly Arg Gly Ile Cys Met Asn Thr
        580                 585                 590

Gly Gly Ser Tyr Asn Cys His Cys Asn Arg Gly Tyr Arg Leu His Val
    595                 600                 605

Gly Ala Gly Arg Ser Cys Val Asp Leu Asn Glu Cys Ala Lys Pro
610                 615                 620

His Leu Cys Gly Asp Gly Gly Phe Cys Ile Asn Phe Pro Gly His Tyr
625                 630                 635                 640

Lys Cys Asn Cys Tyr Pro Gly Tyr Arg Leu Lys Ala Ser Arg Pro Pro
                645                 650                 655

Val Cys Glu Asp Ile Asp Glu Cys Arg Asp Pro Ser Ser Cys Pro Asp
            660                 665                 670

Gly Lys Cys Glu Asn Lys Pro Gly Ser Phe Lys Cys Ile Ala Cys Gln
    675                 680                 685

Pro Gly Tyr Arg Ser Gln Gly Gly Ala Cys Arg Asp Val Asn Glu
690                 695                 700

Cys Ala Glu Gly Ser Pro Cys Ser Pro Gly Trp Cys Glu Asn Leu Pro
705                 710                 715                 720

Gly Ser Phe Arg Cys Thr Cys Ala Gln Gly Tyr Ala Pro Ala Pro Asp
                725                 730                 735

Gly Arg Ser Cys Leu Asp Val Asp Glu Cys Glu Ala Gly Asp Val Cys
            740                 745                 750

Asp Asn Gly Ile Cys Ser Asn Thr Pro Gly Ser Phe Gln Cys Gln Cys
        755                 760                 765

Leu Ser Gly Tyr His Leu Ser Arg Asp Arg Ser His Cys Glu Asp Ile
770                 775                 780

Asp Glu Cys Asp Phe Pro Ala Ala Cys Ile Gly Gly Asp Cys Ile Asn
785                 790                 795                 800

Thr Asn Gly Ser Tyr Arg Cys Leu Cys Pro Gln Gly His Arg Leu Val
                805                 810                 815

Gly Gly Arg Lys Cys Gln Asp Ile Asp Glu Cys Ser Gln Asp Pro Ser
            820                 825                 830

Leu Cys Leu Pro His Gly Ala Cys Lys Asn Leu Gln Gly Ser Tyr Val
        835                 840                 845

Cys Val Cys Asp Glu Gly Phe Thr Pro Thr Gln Asp Gln His Gly Cys
850                 855                 860

Glu Glu Val Glu Gln Pro His His Lys Lys Glu Cys Tyr Leu Asn Phe
865                 870                 875                 880

Asp Asp Thr Val Phe Cys Asp Ser Val Leu Ala Thr Asn Val Thr Gln
                885                 890                 895

Gln Glu Cys Cys Cys Ser Leu Gly Ala Gly Trp Gly Asp His Cys Glu
            900                 905                 910

Ile Tyr Pro Cys Pro Val Tyr Ser Ser Ala Glu Phe His Ser Leu Cys
        915                 920                 925

Pro Asp Gly Lys Gly Tyr Thr Gln Asp Asn Asn Ile Val Asn Tyr Gly
930                 935                 940

Ile Pro Ala His Arg Asp Ile Asp Glu Cys Met Leu Phe Gly Ser Glu
945                 950                 955                 960

Ile Cys Lys Glu Gly Lys Cys Val Asn Thr Gln Pro Gly Tyr Glu Cys
```

-continued

```
                965                 970                 975
Tyr Cys Lys Gln Gly Phe Tyr Tyr Asp Gly Asn Leu Leu Glu Cys Val
                    980                 985                 990
Asp Val Asp Glu Cys Leu Asp Glu Ser Asn Cys Arg Asn Gly Val Cys
            995                 1000                1005
Glu Asn Thr Arg Gly Gly Tyr Arg Cys Ala Cys Thr Pro Pro Ala
    1010                1015                1020
Glu Tyr Ser Pro Ala Gln Arg Gln Cys Leu Ser Pro Glu Glu Met
    1025                1030                1035
Asp Val Asp Glu Cys Gln Asp Pro Ala Ala Cys Arg Pro Gly Arg
    1040                1045                1050
Cys Val Asn Leu Pro Gly Ser Tyr Arg Cys Glu Cys Arg Pro Pro
    1055                1060                1065
Trp Val Pro Gly Pro Ser Gly Arg Asp Cys Gln Leu Pro Glu Ser
    1070                1075                1080
Pro Ala Glu Arg Ala Pro Glu Arg Arg Asp Val Cys Trp Ser Gln
    1085                1090                1095
Arg Gly Glu Asp Gly Met Cys Ala Gly Pro Leu Ala Gly Pro Ala
    1100                1105                1110
Leu Thr Phe Asp Asp Cys Cys Cys Arg Gln Gly Arg Gly Trp Gly
    1115                1120                1125
Ala Gln Cys Arg Pro Cys Pro Pro Arg Gly Ala Gly Ser His Cys
    1130                1135                1140
Pro Thr Ser Gln Ser Glu Ser Asn Ser Phe Trp Asp Thr Ser Pro
    1145                1150                1155
Leu Leu Leu Gly Lys Pro Pro Arg Asp Glu Asp Ser Ser Glu Glu
    1160                1165                1170
Asp Ser Asp Glu Cys Arg Cys Val Ser Gly Arg Cys Val Pro Arg
    1175                1180                1185
Pro Gly Gly Ala Val Cys Glu Cys Pro Gly Gly Phe Gln Leu Asp
    1190                1195                1200
Ala Ser Arg Ala Arg Cys Val Asp Ile Asp Glu Cys Arg Glu Leu
    1205                1210                1215
Asn Gln Arg Gly Leu Leu Cys Lys Ser Glu Arg Cys Val Asn Thr
    1220                1225                1230
Ser Gly Ser Phe Arg Cys Val Cys Lys Ala Gly Phe Ala Arg Ser
    1235                1240                1245
Arg Pro His Gly Ala Cys Val Pro Gln Arg Arg Arg
    1250                1255                1260

<210> SEQ ID NO 36
<211> LENGTH: 1260
<212> TYPE: PRT
<213> ORGANISM: Macaca fascicularis

<400> SEQUENCE: 36

Gly Pro Ala Gly Glu Arg Gly Ala Gly Gly Gly Ala Leu Ala Arg
1               5                   10                  15

Glu Arg Phe Lys Val Val Phe Ala Pro Val Ile Cys Lys Arg Thr Cys
            20                  25                  30

Leu Lys Gly Gln Cys Arg Asp Ser Cys Gln Gln Gly Ser Asn Met Thr
                35                  40                  45

Leu Ile Gly Glu Asn Gly His Ser Thr Asp Leu Thr Gly Ser Gly
        50                  55                  60
```

```
Phe Arg Val Val Val Cys Pro Leu Pro Cys Met Asn Gly Gly Gln Cys
 65                  70                  75                  80

Ser Ser Arg Asn Gln Cys Leu Cys Pro Pro Asp Phe Thr Gly Arg Phe
                 85                  90                  95

Cys Gln Val Pro Ala Gly Gly Ala Gly Gly Thr Gly Gly Ser Gly
            100                 105                 110

Pro Gly Leu Ser Arg Ala Gly Ala Leu Ser Thr Gly Ala Leu Pro Pro
            115                 120                 125

Leu Ala Pro Glu Gly Asp Ser Val Ala Ser Lys His Ala Ile Tyr Ala
130                 135                 140

Val Gln Val Ile Ala Asp Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Val Val Asn Val Arg Val His His Pro
            180                 185                 190

Pro Glu Ala Ser Val Gln Val His Arg Ile Glu Ser Ser Asn Ala Glu
            195                 200                 205

Gly Ala Ala Pro Ser Gln His Leu Leu Pro His Pro Lys Pro Ser His
210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
            260                 265                 270

Cys His Lys Cys Pro Gln Leu Gln Tyr Thr Gly Val Gln Lys Pro Gly
            275                 280                 285

Pro Val Arg Gly Glu Val Gly Ala Asp Cys Pro Gln Gly Tyr Lys Arg
            290                 295                 300

Leu Asn Ser Thr His Cys Gln Asp Ile Asn Glu Cys Ala Met Pro Gly
305                 310                 315                 320

Val Cys Arg His Gly Asp Cys Leu Asn Asn Pro Gly Ser Tyr Arg Cys
                325                 330                 335

Val Cys Pro Pro Gly His Ser Leu Gly Pro Ser Arg Thr Gln Cys Ile
            340                 345                 350

Ala Asp Lys Pro Glu Glu Lys Ser Leu Cys Phe Arg Leu Val Ser Pro
            355                 360                 365

Glu His Gln Cys Gln His Pro Leu Thr Thr Arg Leu Thr Arg Gln Leu
            370                 375                 380

Cys Cys Cys Ser Val Gly Lys Ala Trp Gly Ala Arg Cys Gln Arg Cys
385                 390                 395                 400

Pro Ala Asp Gly Thr Ala Ala Phe Lys Glu Ile Cys Pro Ala Gly Lys
                405                 410                 415

Gly Tyr His Ile Leu Thr Ser His Gln Thr Leu Thr Ile Gln Gly Glu
            420                 425                 430

Ser Asp Phe Ser Leu Phe Leu His Pro Asp Gly Pro Pro Lys Pro Gln
            435                 440                 445

Gln Leu Pro Glu Ser Pro Ser Gln Ala Pro Pro Glu Asp Thr Glu
            450                 455                 460

Glu Glu Arg Gly Val Thr Thr Asp Ser Pro Val Ser Glu Glu Arg Ser
465                 470                 475                 480

Val Gln Gln Ser His Pro Thr Ala Thr Thr Ser Pro Ala Arg Pro Tyr
```

```
            485                 490                 495
Pro Glu Leu Ile Ser Arg Pro Ser Pro Thr Met Arg Trp Phe Leu
            500                 505                 510

Pro Asp Leu Pro Pro Ser Arg Ser Ala Val Glu Ile Ala Pro Thr Gln
            515                 520                 525

Val Thr Glu Thr Asp Glu Cys Arg Leu Asn Gln Asn Ile Cys Gly His
            530                 535                 540

Gly Glu Cys Val Pro Gly Pro Asp Tyr Ser Cys His Cys Asn Pro
545                 550                 555                 560

Gly Tyr Arg Ser His Pro Gln His Arg Tyr Cys Val Asp Val Asn Glu
            565                 570                 575

Cys Glu Ala Glu Pro Cys Gly Pro Arg Gly Ile Cys Met Asn Thr
            580                 585                 590

Gly Gly Ser Tyr Asn Cys His Cys Asn Arg Gly Tyr Arg Leu His Val
            595                 600                 605

Gly Ala Gly Gly Arg Ser Cys Val Asp Leu Asn Glu Cys Ala Lys Pro
            610                 615                 620

His Leu Cys Gly Asp Gly Gly Phe Cys Ile Asn Phe Pro Gly His Tyr
625                 630                 635                 640

Lys Cys Asn Cys Tyr Pro Gly Tyr Arg Leu Lys Ala Ser Arg Pro Pro
                645                 650                 655

Val Cys Glu Asp Ile Asp Glu Cys Arg Asp Pro Ser Ser Cys Pro Asp
            660                 665                 670

Gly Lys Cys Glu Asn Lys Pro Gly Ser Phe Lys Cys Ile Ala Cys Gln
            675                 680                 685

Pro Gly Tyr Arg Ser Gln Gly Gly Ala Cys Arg Asp Val Asn Glu
690                 695                 700

Cys Ala Glu Gly Ser Pro Cys Ser Pro Gly Trp Cys Glu Asn Leu Pro
705                 710                 715                 720

Gly Ser Phe Arg Cys Thr Cys Ala Gln Gly Tyr Ala Pro Ala Pro Asp
            725                 730                 735

Gly Arg Ser Cys Val Asp Val Asp Glu Cys Glu Ala Gly Asp Val Cys
            740                 745                 750

Asp Asn Gly Ile Cys Thr Asn Thr Pro Gly Ser Phe Gln Cys Gln Cys
            755                 760                 765

Leu Ser Gly Tyr His Leu Ser Arg Asp Arg Ser His Cys Glu Asp Ile
            770                 775                 780

Asp Glu Cys Asp Phe Pro Ala Ala Cys Ile Gly Gly Asp Cys Ile Asn
785                 790                 795                 800

Thr Asn Gly Ser Tyr Arg Cys Leu Cys Pro Gln Gly His Arg Leu Val
            805                 810                 815

Gly Gly Arg Lys Cys Gln Asp Ile Asp Glu Cys Thr Gln Asp Pro Gly
            820                 825                 830

Leu Cys Leu Pro His Gly Ala Cys Lys Asn Leu Gln Gly Ser Tyr Val
            835                 840                 845

Cys Val Cys Asp Glu Gly Phe Thr Pro Thr Gln Asp Gln His Gly Cys
            850                 855                 860

Glu Glu Val Glu Gln Pro His His Lys Lys Glu Cys Tyr Leu Asn Phe
865                 870                 875                 880

Asp Asp Thr Val Phe Cys Asp Ser Val Leu Ala Thr Asn Val Thr Gln
            885                 890                 895

Gln Glu Cys Cys Cys Ser Leu Gly Ala Gly Trp Gly Asp His Cys Glu
            900                 905                 910
```

```
Ile Tyr Pro Cys Pro Val Tyr Ser Ser Ala Glu Phe His Ser Leu Cys
            915                 920                 925

Pro Asp Gly Lys Gly Tyr Thr Gln Asp Asn Asn Ile Val Asn Tyr Gly
930                 935                 940

Ile Pro Ala His Arg Asp Ile Asp Glu Cys Met Leu Phe Gly Ala Glu
945                 950                 955                 960

Ile Cys Lys Glu Gly Lys Cys Val Asn Thr Gln Pro Gly Tyr Glu Cys
            965                 970                 975

Tyr Cys Lys Gln Gly Phe Tyr Tyr Asp Gly Asn Leu Leu Glu Cys Val
            980                 985                 990

Asp Val Asp Glu Cys Leu Asp Glu Ser Asn Cys Arg Asn Gly Val Cys
            995                1000                1005

Glu Asn Thr Arg Gly Gly Tyr Arg Cys Ala Cys Thr Pro Pro Ala
       1010                1015                1020

Glu Tyr Ser Pro Ala Gln Arg Gln Cys Leu Ser Pro Glu Glu Met
       1025                1030                1035

Asp Val Asp Glu Cys Gln Asp Pro Ala Ala Cys Arg Pro Gly Arg
       1040                1045                1050

Cys Val Asn Leu Pro Gly Ser Tyr Arg Cys Glu Cys Arg Pro Pro
       1055                1060                1065

Trp Val Pro Gly Pro Ser Gly Arg Asp Cys Gln Leu Pro Glu Ser
       1070                1075                1080

Pro Ala Glu Arg Ala Pro Glu Arg Arg Asp Val Cys Trp Ser Gln
       1085                1090                1095

Arg Gly Glu Asp Gly Met Cys Ala Gly Pro Gln Ala Gly Pro Ala
       1100                1105                1110

Leu Thr Phe Asp Asp Cys Cys Arg Gln Gly Arg Gly Trp Gly
       1115                1120                1125

Ala Gln Cys Arg Pro Cys Pro Pro Arg Gly Ala Gly Ser Gln Cys
       1130                1135                1140

Pro Thr Ser Gln Ser Glu Ser Asn Ser Phe Trp Asp Thr Ser Pro
       1145                1150                1155

Leu Leu Leu Gly Lys Pro Arg Arg Asp Glu Asp Ser Ser Glu Glu
       1160                1165                1170

Asp Ser Asp Glu Cys Arg Cys Val Ser Gly Arg Cys Val Pro Arg
       1175                1180                1185

Pro Gly Gly Ala Val Cys Glu Cys Pro Gly Gly Phe Gln Leu Asp
       1190                1195                1200

Ala Ser Arg Ala Arg Cys Val Asp Ile Asp Glu Cys Arg Glu Leu
       1205                1210                1215

Asn Gln Arg Gly Leu Leu Cys Lys Ser Glu Arg Cys Val Asn Thr
       1220                1225                1230

Ser Gly Ser Phe Arg Cys Val Cys Lys Ala Gly Phe Ala Arg Ser
       1235                1240                1245

Arg Pro His Gly Ala Cys Val Pro Gln Arg Arg Arg
       1250                1255                1260

<210> SEQ ID NO 37
<211> LENGTH: 1228
<212> TYPE: PRT
<213> ORGANISM: Mus sp.

<400> SEQUENCE: 37

Gly Pro Ala Gly Glu Arg Gly Thr Gly Gly Gly Gly Ala Leu Ala Arg
```

-continued

```
1               5                   10                  15
Glu Arg Phe Lys Val Val Phe Ala Pro Val Ile Cys Lys Arg Thr Cys
                20                  25                  30

Leu Lys Gly Gln Cys Arg Asp Ser Cys Gln Gln Gly Ser Asn Met Thr
                35                  40                  45

Leu Ile Gly Glu Asn Gly His Ser Thr Asp Thr Leu Thr Gly Ser Ala
                50                  55                  60

Phe Arg Val Val Val Cys Pro Leu Pro Cys Met Asn Gly Gly Gln Cys
65                  70                  75                  80

Ser Ser Arg Asn Gln Cys Leu Cys Pro Pro Asp Phe Thr Gly Arg Phe
                85                  90                  95

Cys Gln Val Pro Ala Ala Gly Thr Gly Ala Gly Thr Gly Ser Ser Gly
                100                 105                 110

Pro Gly Leu Ala Arg Thr Gly Ala Met Ser Thr Gly Pro Leu Pro Pro
                115                 120                 125

Leu Ala Pro Glu Gly Glu Ser Val Ala Ser Lys His Ala Ile Tyr Ala
                130                 135                 140

Val Gln Val Ile Ala Asp Pro Pro Gly Pro Gly Glu Gly Pro Pro Ala
145                 150                 155                 160

Gln His Ala Ala Phe Leu Val Pro Leu Gly Pro Gly Gln Ile Ser Ala
                165                 170                 175

Glu Val Gln Ala Pro Pro Val Val Asn Val Arg Val His His Pro
                180                 185                 190

Pro Glu Ala Ser Val Gln Val His Arg Ile Glu Gly Pro Asn Ala Glu
                195                 200                 205

Gly Pro Ala Ser Ser Gln His Leu Leu Pro His Pro Lys Pro Pro His
                210                 215                 220

Pro Arg Pro Pro Thr Gln Lys Pro Leu Gly Arg Cys Phe Gln Asp Thr
225                 230                 235                 240

Leu Pro Lys Gln Pro Cys Gly Ser Asn Pro Leu Pro Gly Leu Thr Lys
                245                 250                 255

Gln Glu Asp Cys Cys Gly Ser Ile Gly Thr Ala Trp Gly Gln Ser Lys
                260                 265                 270

Cys His Lys Cys Pro Gln Leu Gln Tyr Thr Gly Val Gln Lys Pro Val
                275                 280                 285

Pro Val Arg Gly Glu Val Gly Ala Asp Cys Pro Gln Gly Tyr Lys Arg
                290                 295                 300

Leu Asn Ser Thr His Cys Gln Asp Ile Asn Glu Cys Ala Met Pro Gly
305                 310                 315                 320

Asn Val Cys His Gly Asp Cys Leu Asn Asn Pro Gly Ser Tyr Arg Cys
                325                 330                 335

Val Cys Pro Pro Gly His Ser Leu Gly Pro Leu Ala Ala Gln Cys Ile
                340                 345                 350

Ala Asp Lys Pro Glu Glu Lys Ser Leu Cys Phe Arg Leu Val Ser Thr
                355                 360                 365

Glu His Gln Cys Gln His Pro Leu Thr Thr Arg Leu Thr Arg Gln Leu
                370                 375                 380

Cys Cys Cys Ser Val Gly Lys Ala Trp Gly Ala Arg Cys Gln Arg Cys
385                 390                 395                 400

Pro Ala Asp Gly Thr Ala Ala Phe Lys Glu Ile Cys Pro Gly Lys Gly
                405                 410                 415

Tyr His Ile Leu Thr Ser His Gln Thr Leu Thr Ile Gln Gly Glu Ser
                420                 425                 430
```

```
Asp Phe Ser Leu Phe Leu His Pro Asp Gly Pro Pro Lys Pro Gln Gln
            435                 440                 445
Leu Pro Glu Ser Pro Ser Arg Ala Pro Pro Leu Glu Asp Thr Glu Glu
    450                 455                 460
Glu Arg Gly Val Thr Met Asp Pro Pro Val Ser Glu Glu Arg Ser Val
465                 470                 475                 480
Gln Gln Ser His Pro Thr Thr Thr Ser Pro Pro Arg Pro Tyr Pro
                485                 490                 495
Glu Leu Ile Ser Arg Pro Ser Pro Pro Thr Phe His Arg Phe Leu Pro
                500                 505                 510
Asp Leu Pro Pro Ser Arg Ser Ala Val Glu Ile Ala Pro Thr Gln Val
            515                 520                 525
Thr Glu Thr Asp Glu Cys Arg Leu Asn Gln Asn Ile Cys Gly His Gly
    530                 535                 540
Gln Cys Val Pro Gly Pro Ser Asp Tyr Ser Cys His Cys Asn Ala Gly
545                 550                 555                 560
Tyr Arg Ser His Pro Gln His Arg Tyr Cys Val Asp Val Asn Glu Cys
                565                 570                 575
Glu Ala Glu Pro Cys Gly Pro Gly Lys Gly Ile Cys Met Asn Thr Gly
            580                 585                 590
Gly Ser Tyr Asn Cys His Cys Asn Arg Gly Tyr Arg Leu His Val Gly
    595                 600                 605
Ala Gly Gly Arg Ser Cys Val Asp Leu Asn Glu Cys Ala Lys Pro His
610                 615                 620
Leu Cys Gly Asp Gly Gly Phe Cys Ile Asn Phe Pro Gly His Tyr Lys
625                 630                 635                 640
Cys Asn Cys Tyr Pro Gly Tyr Arg Leu Lys Ala Ser Arg Pro Pro Ile
                645                 650                 655
Cys Glu Asp Ile Asp Glu Cys Arg Asp Pro Ser Thr Cys Pro Asp Gly
            660                 665                 670
Lys Cys Glu Asn Lys Pro Gly Ser Phe Lys Cys Ile Ala Cys Gln Pro
    675                 680                 685
Gly Tyr Arg Ser Gln Gly Gly Gly Ala Cys Arg Asp Val Asn Glu Cys
690                 695                 700
Ser Glu Gly Thr Pro Cys Ser Pro Gly Trp Cys Glu Asn Leu Pro Gly
705                 710                 715                 720
Ser Tyr Arg Cys Thr Cys Ala Gln Tyr Glu Pro Ala Gln Asp Gly Leu
                725                 730                 735
Ser Cys Ile Asp Val Asp Glu Cys Glu Ala Gly Lys Val Cys Gln Asp
            740                 745                 750
Gly Ile Cys Thr Asn Thr Pro Gly Ser Phe Gln Cys Gln Cys Leu Ser
    755                 760                 765
Gly Tyr His Leu Ser Arg Asp Arg Ser Arg Cys Glu Asp Ile Asp Glu
770                 775                 780
Cys Asp Phe Pro Ala Ala Cys Ile Gly Gly Asp Cys Ile Asn Thr Asn
785                 790                 795                 800
Gly Ser Tyr Arg Cys Leu Cys Pro Leu Gly His Arg Leu Val Gly Gly
                805                 810                 815
Arg Lys Cys Lys Lys Asp Ile Asp Glu Cys Ser Gln Asp Pro Gly Leu
            820                 825                 830
Cys Leu Pro His Ala Cys Glu Asn Leu Gln Gly Ser Tyr Val Cys Val
    835                 840                 845
```

Cys Asp Glu Gly Phe Thr Leu Thr Gln Asp Gln His Gly Cys Glu Glu
         850                 855                 860

Val Glu Gln Pro His His Lys Lys Glu Cys Tyr Leu Asn Phe Asp Asp
865                 870                 875                 880

Thr Val Phe Cys Asp Ser Val Leu Ala Thr Asn Val Thr Gln Gln Glu
                885                 890                 895

Cys Cys Cys Ser Leu Gly Ala Gly Trp Gly Asp His Cys Glu Ile Tyr
            900                 905                 910

Pro Cys Pro Val Tyr Ser Ser Ala Glu Phe His Ser Leu Val Pro Asp
        915                 920                 925

Gly Lys Arg Leu His Ser Gly Gln Gln His Cys Glu Leu Cys Ile Pro
    930                 935                 940

Ala His Arg Asp Ile Asp Glu Cys Ile Leu Phe Gly Ala Glu Ile Cys
945                 950                 955                 960

Lys Glu Gly Lys Cys Val Asn Thr Gln Pro Gly Tyr Glu Cys Tyr Cys
                965                 970                 975

Lys Gln Gly Phe Tyr Tyr Asp Gly Asn Leu Leu Glu Cys Val Asp Val
            980                 985                 990

Asp Glu Cys Leu Asp Glu Ser Asn Cys Arg Asn Gly Val Cys Glu Asn
        995                 1000                1005

Thr Arg Gly Gly Tyr Arg Cys Ala Cys Thr Pro Pro Ala Glu Tyr
    1010                1015                1020

Ser Pro Ala Gln Ala Gln Cys Leu Ile Pro Glu Arg Trp Ser Thr
    1025                1030                1035

Pro Gln Arg Asp Val Lys Cys Ala Gly Ala Ser Glu Glu Arg Thr
    1040                1045                1050

Ala Cys Val Trp Gly Pro Trp Ala Gly Pro Ala Leu Thr Phe Asp
    1055                1060                1065

Asp Cys Cys Cys Arg Gln Pro Arg Leu Gly Thr Gln Cys Arg Pro
    1070                1075                1080

Cys Pro Pro Arg Gly Thr Gly Ser Gln Cys Pro Thr Ser Gln Ser
    1085                1090                1095

Glu Ser Asn Ser Phe Trp Asp Thr Ser Pro Leu Leu Leu Gly Lys
    1100                1105                1110

Ser Pro Arg Asp Glu Asp Ser Ser Glu Glu Asp Ser Asp Glu Cys
    1115                1120                1125

Arg Cys Val Ser Gly Arg Cys Val Pro Arg Pro Gly Gly Ala Val
    1130                1135                1140

Cys Glu Cys Pro Gly Gly Phe Gln Leu Asp Ala Ser Arg Ala Arg
    1145                1150                1155

Cys Val Asp Ile Asp Glu Cys Arg Glu Leu Asn Gln Arg Gly Leu
    1160                1165                1170

Leu Cys Lys Ser Glu Arg Cys Val Asn Thr Ser Gly Ser Phe Arg
    1175                1180                1185

Cys Val Cys Lys Ala Gly Phe Thr Arg Ser Arg Pro His Gly Pro
    1190                1195                1200

Ala Cys Leu Ser Ala Ala Ala Asp Asp Ala Ala Ile Ala His Thr
    1205                1210                1215

Ser Val Ile Asp His Arg Gly Tyr Phe His
    1220                1225

<210> SEQ ID NO 38
<211> LENGTH: 645
<212> TYPE: PRT

<213> ORGANISM: Homo sapiens

<400> SEQUENCE: 38

```
Ala Gln His Gln Asp Lys Val Pro Cys Lys Met Val Asp Lys Lys Val
 1               5                  10                  15
Ser Cys Gln Val Leu Gly Leu Leu Gln Val Pro Ser Val Leu Pro Pro
            20                  25                  30
Asp Thr Glu Thr Leu Asp Leu Ser Gly Asn Gln Leu Arg Ser Ile Leu
        35                  40                  45
Ala Ser Pro Leu Gly Phe Tyr Thr Ala Leu Arg His Leu Asp Leu Ser
    50                  55                  60
Thr Asn Glu Ile Ser Phe Leu Gln Pro Gly Ala Phe Gln Ala Leu Thr
65                  70                  75                  80
His Leu Glu His Leu Ser Leu Ala His Asn Arg Leu Ala Met Ala Thr
                85                  90                  95
Ala Leu Ser Ala Gly Gly Leu Gly Pro Leu Pro Arg Val Thr Ser Leu
            100                 105                 110
Asp Leu Ser Gly Asn Ser Leu Tyr Ser Gly Leu Leu Glu Arg Leu Leu
        115                 120                 125
Gly Glu Ala Pro Ser Leu His Thr Leu Ser Leu Ala Glu Asn Ser Leu
    130                 135                 140
Thr Arg Leu Thr Arg His Thr Phe Arg Asp Met Pro Ala Leu Glu Gln
145                 150                 155                 160
Leu Asp Leu His Ser Asn Val Leu Met Asp Ile Glu Asp Gly Ala Phe
                165                 170                 175
Glu Gly Leu Pro Arg Leu Thr His Leu Asn Leu Ser Arg Asn Ser Leu
            180                 185                 190
Thr Cys Ile Ser Asp Phe Ser Leu Gln Gln Leu Arg Val Leu Asp Leu
        195                 200                 205
Ser Cys Asn Ser Ile Glu Ala Phe Gln Thr Ala Ser Gln Pro Gln Ala
    210                 215                 220
Glu Phe Gln Leu Thr Trp Leu Asp Leu Arg Glu Asn Lys Leu Leu His
225                 230                 235                 240
Phe Pro Asp Leu Ala Ala Leu Pro Arg Leu Ile Tyr Leu Asn Leu Ser
                245                 250                 255
Asn Asn Leu Ile Arg Leu Pro Thr Gly Pro Pro Gln Asp Ser Lys Gly
            260                 265                 270
Ile His Ala Pro Ser Glu Gly Trp Ser Ala Leu Pro Leu Ser Ala Pro
        275                 280                 285
Ser Gly Asn Ala Ser Gly Arg Pro Leu Ser Gln Leu Leu Asn Leu Asp
    290                 295                 300
Leu Ser Tyr Asn Glu Ile Glu Leu Ile Pro Asp Ser Phe Leu Glu His
305                 310                 315                 320
Leu Thr Ser Leu Cys Phe Leu Asn Leu Ser Arg Asn Cys Leu Arg Thr
                325                 330                 335
Phe Glu Ala Arg Arg Leu Gly Ser Leu Pro Cys Leu Met Leu Leu Asp
            340                 345                 350
Leu Ser His Asn Ala Leu Glu Thr Leu Glu Leu Gly Ala Arg Ala Leu
        355                 360                 365
Gly Ser Leu Arg Thr Leu Leu Leu Gln Gly Asn Ala Leu Arg Asp Leu
    370                 375                 380
Pro Pro Tyr Thr Phe Ala Asn Leu Ala Ser Leu Gln Arg Leu Asn Leu
385                 390                 395                 400
```

```
Gln Gly Asn Arg Val Ser Pro Cys Gly Gly Pro Asp Glu Pro Gly Pro
                405                 410                 415

Ser Gly Cys Val Ala Phe Ser Gly Ile Thr Ser Leu Arg Ser Leu Ser
            420                 425                 430

Leu Val Asp Asn Glu Ile Glu Leu Leu Arg Ala Gly Ala Phe Leu His
        435                 440                 445

Thr Pro Leu Thr Glu Leu Asp Leu Ser Ser Asn Pro Gly Leu Glu Val
    450                 455                 460

Ala Thr Gly Ala Leu Gly Leu Glu Ala Ser Leu Glu Val Leu Ala
465                 470                 475                 480

Leu Gln Gly Asn Gly Leu Met Val Leu Gln Val Asp Leu Pro Cys Phe
                485                 490                 495

Ile Cys Leu Lys Arg Leu Asn Leu Ala Glu Asn Arg Leu Ser His Leu
            500                 505                 510

Pro Ala Trp Thr Gln Ala Val Ser Leu Glu Val Leu Asp Leu Arg Asn
        515                 520                 525

Asn Ser Phe Ser Leu Leu Pro Gly Ser Ala Met Gly Gly Leu Glu Thr
    530                 535                 540

Ser Leu Arg Arg Leu Tyr Leu Gln Gly Asn Pro Leu Ser Cys Cys Gly
545                 550                 555                 560

Asn Gly Trp Leu Ala Ala Gln Leu His Gln Gly Arg Val Asp Val Asp
                565                 570                 575

Ala Thr Gln Asp Leu Ile Cys Arg Phe Ser Ser Gln Glu Glu Val Ser
            580                 585                 590

Leu Ser His Val Arg Pro Glu Asp Cys Glu Lys Gly Gly Leu Lys Asn
        595                 600                 605

Ile Asn Leu Ile Ile Ile Leu Thr Phe Ile Leu Val Ser Ala Ile Leu
    610                 615                 620

Leu Thr Thr Leu Ala Ala Cys Cys Cys Val Arg Arg Gln Lys Phe Asn
625                 630                 635                 640

Gln Gln Tyr Lys Ala
                645

<210> SEQ ID NO 39
<211> LENGTH: 610
<212> TYPE: PRT
<213> ORGANISM: Homo sapiens

<400> SEQUENCE: 39

Ala Gln His Gln Asp Lys Val Pro Cys Lys Met Val Asp Lys Lys Val
1               5                   10                  15

Ser Cys Gln Val Leu Gly Leu Leu Gln Val Pro Ser Val Leu Pro Pro
            20                  25                  30

Asp Thr Glu Thr Leu Asp Leu Ser Gly Asn Gln Leu Arg Ser Ile Leu
        35                  40                  45

Ala Ser Pro Leu Gly Phe Tyr Thr Ala Leu Arg His Leu Asp Leu Ser
    50                  55                  60

Thr Asn Glu Ile Ser Phe Leu Gln Pro Gly Ala Phe Gln Ala Leu Thr
65                  70                  75                  80

His Leu Glu His Leu Ser Leu Ala His Asn Arg Leu Ala Met Ala Thr
                85                  90                  95

Ala Leu Ser Ala Gly Gly Leu Gly Pro Leu Pro Arg Val Thr Ser Leu
            100                 105                 110

Asp Leu Ser Gly Asn Ser Leu Tyr Ser Gly Leu Leu Glu Arg Leu Leu
        115                 120                 125
```

```
Gly Glu Ala Pro Ser Leu His Thr Leu Ser Leu Ala Glu Asn Ser Leu
    130                 135                 140

Thr Arg Leu Thr Arg His Thr Phe Arg Asp Met Pro Ala Leu Glu Gln
145                 150                 155                 160

Leu Asp Leu His Ser Asn Val Leu Met Asp Ile Glu Asp Gly Ala Phe
                165                 170                 175

Glu Gly Leu Pro Arg Leu Thr His Leu Asn Leu Ser Arg Asn Ser Leu
            180                 185                 190

Thr Cys Ile Ser Asp Phe Ser Leu Gln Gln Leu Arg Val Leu Asp Leu
        195                 200                 205

Ser Cys Asn Ser Ile Glu Ala Phe Gln Thr Ala Ser Gln Pro Gln Ala
    210                 215                 220

Glu Phe Gln Leu Thr Trp Leu Asp Leu Arg Glu Asn Lys Leu Leu His
225                 230                 235                 240

Phe Pro Asp Leu Ala Ala Leu Pro Arg Leu Ile Tyr Leu Asn Leu Ser
                245                 250                 255

Asn Asn Leu Ile Arg Leu Pro Thr Gly Pro Pro Gln Asp Ser Lys Gly
            260                 265                 270

Ile His Ala Pro Ser Glu Gly Trp Ser Ala Leu Pro Leu Ser Ala Pro
        275                 280                 285

Ser Gly Asn Ala Ser Gly Arg Pro Leu Ser Gln Leu Leu Asn Leu Asp
    290                 295                 300

Leu Ser Tyr Asn Glu Ile Glu Leu Ile Pro Asp Ser Phe Leu Glu His
305                 310                 315                 320

Leu Thr Ser Leu Cys Phe Leu Asn Leu Ser Arg Asn Cys Leu Arg Thr
                325                 330                 335

Phe Glu Ala Arg Arg Leu Gly Ser Leu Pro Cys Leu Met Leu Leu Asp
            340                 345                 350

Leu Ser His Asn Ala Leu Glu Thr Leu Glu Leu Gly Ala Arg Ala Leu
        355                 360                 365

Gly Ser Leu Arg Thr Leu Leu Leu Gln Gly Asn Ala Leu Arg Asp Leu
    370                 375                 380

Pro Pro Tyr Thr Phe Ala Asn Leu Ala Ser Leu Gln Arg Leu Asn Leu
385                 390                 395                 400

Gln Gly Asn Arg Val Ser Pro Cys Gly Gly Pro Asp Glu Pro Gly Pro
                405                 410                 415

Ser Gly Cys Val Ala Phe Ser Gly Ile Thr Ser Leu Arg Ser Leu Ser
            420                 425                 430

Leu Val Asp Asn Glu Ile Glu Leu Leu Arg Ala Gly Ala Phe Leu His
        435                 440                 445

Thr Pro Leu Thr Glu Leu Asp Leu Ser Ser Asn Pro Gly Leu Glu Val
    450                 455                 460

Ala Thr Gly Ala Leu Gly Gly Leu Glu Ala Ser Leu Glu Val Leu Ala
465                 470                 475                 480

Leu Gln Gly Asn Gly Leu Met Val Leu Gln Val Asp Leu Pro Cys Phe
                485                 490                 495

Ile Cys Leu Lys Arg Leu Asn Leu Ala Glu Asn Arg Leu Ser His Leu
            500                 505                 510

Pro Ala Trp Thr Gln Ala Val Ser Leu Glu Val Leu Asp Leu Arg Asn
        515                 520                 525

Asn Ser Phe Ser Leu Leu Pro Gly Ser Ala Met Gly Gly Leu Glu Thr
    530                 535                 540
```

```
Ser Leu Arg Arg Leu Tyr Leu Gln Gly Asn Pro Leu Ser Cys Cys Gly
545                 550                 555                 560

Asn Gly Trp Leu Ala Ala Gln Leu His Gln Gly Arg Val Asp Val Asp
            565                 570                 575

Ala Thr Gln Asp Leu Ile Cys Arg Phe Ser Ser Gln Glu Glu Val Ser
            580                 585                 590

Leu Ser His Val Arg Pro Glu Asp Cys Glu Lys Gly Gly Leu Lys Asn
            595                 600                 605

Ile Asn
    610

<210> SEQ ID NO 40
<211> LENGTH: 646
<212> TYPE: PRT
<213> ORGANISM: Mus sp.

<400> SEQUENCE: 40

Ile Ser Gln Arg Arg Glu Gln Val Pro Cys Arg Thr Val Asn Lys Glu
1               5                   10                  15

Ala Leu Cys His Gly Leu Gly Leu Leu Gln Val Pro Ser Val Leu Ser
            20                  25                  30

Leu Asp Ile Gln Ala Leu Tyr Leu Ser Gly Asn Gln Leu Gln Ser Ile
        35                  40                  45

Leu Val Ser Pro Leu Gly Phe Tyr Thr Ala Leu Arg His Leu Asp Leu
    50                  55                  60

Ser Asp Asn Gln Ile Ser Phe Leu Gln Ala Gly Val Phe Gln Ala Leu
65                  70                  75                  80

Pro Tyr Leu Glu His Leu Asn Leu Ala His Asn Arg Leu Ala Thr Gly
                85                  90                  95

Met Ala Leu Asn Ser Gly Gly Leu Gly Arg Leu Pro Leu Leu Val Ser
            100                 105                 110

Leu Asp Leu Ser Gly Asn Ser Leu His Gly Asn Leu Val Glu Arg Leu
        115                 120                 125

Leu Gly Glu Thr Pro Arg Leu Arg Thr Leu Ser Leu Ala Glu Asn Ser
    130                 135                 140

Leu Thr Arg Leu Ala Arg His Thr Phe Trp Gly Met Pro Ala Val Glu
145                 150                 155                 160

Gln Leu Asp Leu His Ser Asn Val Leu Met Asp Ile Glu Asp Gly Ala
                165                 170                 175

Phe Glu Ala Leu Pro His Leu Thr His Leu Asn Leu Ser Arg Asn Ser
            180                 185                 190

Leu Thr Cys Ile Ser Asp Phe Ser Leu Gln Gln Leu Gln Val Leu Asp
        195                 200                 205

Leu Ser Cys Asn Ser Ile Glu Ala Phe Gln Thr Ala Pro Glu Pro Gln
    210                 215                 220

Ala Gln Phe Gln Leu Ala Trp Leu Asp Leu Arg Glu Asn Lys Leu Leu
225                 230                 235                 240

His Phe Pro Asp Leu Ala Val Phe Pro Arg Leu Ile Tyr Leu Asn Val
                245                 250                 255

Ser Asn Asn Leu Ile Gln Leu Pro Ala Gly Leu Pro Arg Gly Ser Glu
            260                 265                 270

Asp Leu His Ala Pro Ser Glu Gly Trp Ser Ala Ser Pro Leu Ser Asn
        275                 280                 285

Pro Ser Arg Asn Ala Ser Thr His Pro Leu Ser Gln Leu Leu Asn Leu
    290                 295                 300
```

Asp Leu Ser Tyr Asn Glu Ile Glu Leu Val Pro Ala Ser Phe Leu Glu
305                 310                 315                 320

His Leu Thr Ser Leu Arg Phe Leu Asn Leu Ser Arg Asn Cys Leu Arg
            325                 330                 335

Ser Phe Glu Ala Arg Gln Val Asp Ser Leu Pro Cys Leu Val Leu Leu
        340                 345                 350

Asp Leu Ser His Asn Val Leu Glu Ala Leu Glu Leu Gly Thr Lys Val
    355                 360                 365

Leu Gly Ser Leu Gln Thr Leu Leu Gln Asp Asn Ala Leu Gln Glu
370                 375                 380

Leu Pro Pro Tyr Thr Phe Ala Ser Leu Ala Ser Leu Gln Arg Leu Asn
385                 390                 395                 400

Leu Gln Gly Asn Gln Val Ser Pro Cys Gly Gly Pro Ala Glu Pro Gly
            405                 410                 415

Pro Pro Gly Cys Val Asp Phe Ser Gly Ile Pro Thr Leu His Val Leu
        420                 425                 430

Asn Met Ala Gly Asn Ser Met Gly Met Leu Arg Ala Gly Ser Phe Leu
    435                 440                 445

His Thr Pro Leu Thr Glu Leu Asp Leu Ser Thr Asn Pro Gly Leu Asp
450                 455                 460

Val Ala Thr Gly Ala Leu Val Gly Leu Glu Ala Ser Leu Glu Val Leu
465                 470                 475                 480

Glu Leu Gln Gly Asn Gly Leu Thr Val Leu Arg Val Asp Leu Pro Cys
            485                 490                 495

Phe Leu Arg Leu Lys Arg Leu Asn Leu Ala Glu Asn Gln Leu Ser His
        500                 505                 510

Leu Pro Ala Trp Thr Arg Ala Val Ser Leu Glu Val Leu Asp Leu Arg
    515                 520                 525

Asn Asn Ser Phe Ser Leu Leu Pro Gly Asn Ala Met Gly Gly Leu Glu
530                 535                 540

Thr Ser Leu Arg Arg Leu Tyr Leu Gln Gly Asn Pro Leu Ser Cys Cys
545                 550                 555                 560

Gly Asn Gly Trp Leu Ala Ala Gln Leu His Gln Gly Arg Val Asp Val
            565                 570                 575

Asp Ala Thr Gln Asp Leu Ile Cys Arg Phe Gly Ser Gln Glu Glu Leu
        580                 585                 590

Ser Leu Ser Leu Val Arg Pro Glu Asp Cys Glu Lys Gly Gly Leu Lys
    595                 600                 605

Asn Val Asn Leu Ile Leu Leu Ser Phe Thr Leu Val Ser Ala Ile
    610                 615                 620

Val Leu Thr Thr Leu Ala Thr Ile Cys Phe Leu Arg Arg Gln Lys Leu
625                 630                 635                 640

Ser Gln Gln Tyr Lys Ala
            645

<210> SEQ ID NO 41
<211> LENGTH: 611
<212> TYPE: PRT
<213> ORGANISM: Mus sp.

<400> SEQUENCE: 41

Ile Ser Gln Arg Arg Glu Gln Val Pro Cys Arg Thr Val Asn Lys Glu
1               5                   10                  15

Ala Leu Cys His Gly Leu Gly Leu Leu Gln Val Pro Ser Val Leu Ser

```
            20                  25                  30
Leu Asp Ile Gln Ala Leu Tyr Leu Ser Gly Asn Gln Leu Gln Ser Ile
            35                  40                  45
Leu Val Ser Pro Leu Gly Phe Tyr Thr Ala Leu Arg His Leu Asp Leu
        50                  55                  60
Ser Asp Asn Gln Ile Ser Phe Leu Gln Ala Gly Val Phe Gln Ala Leu
65                  70                  75                  80
Pro Tyr Leu Glu His Leu Asn Leu Ala His Asn Arg Leu Ala Thr Gly
                85                  90                  95
Met Ala Leu Asn Ser Gly Leu Gly Arg Leu Pro Leu Leu Val Ser
            100                 105                 110
Leu Asp Leu Ser Gly Asn Ser Leu His Gly Asn Leu Val Glu Arg Leu
            115                 120                 125
Leu Gly Glu Thr Pro Arg Leu Arg Thr Leu Ser Leu Ala Glu Asn Ser
            130                 135                 140
Leu Thr Arg Leu Ala Arg His Thr Phe Trp Gly Met Pro Ala Val Glu
145                 150                 155                 160
Gln Leu Asp Leu His Ser Asn Val Leu Met Asp Ile Glu Asp Gly Ala
                165                 170                 175
Phe Glu Ala Leu Pro His Leu Thr His Leu Asn Leu Ser Arg Asn Ser
            180                 185                 190
Leu Thr Cys Ile Ser Asp Phe Ser Leu Gln Gln Leu Gln Val Leu Asp
            195                 200                 205
Leu Ser Cys Asn Ser Ile Glu Ala Phe Gln Thr Ala Pro Glu Pro Gln
            210                 215                 220
Ala Gln Phe Gln Leu Ala Trp Leu Asp Leu Arg Glu Asn Lys Leu Leu
225                 230                 235                 240
His Phe Pro Asp Leu Ala Val Phe Pro Arg Leu Ile Tyr Leu Asn Val
                245                 250                 255
Ser Asn Asn Leu Ile Gln Leu Pro Ala Gly Leu Pro Arg Gly Ser Glu
            260                 265                 270
Asp Leu His Ala Pro Ser Glu Gly Trp Ser Ala Ser Pro Leu Ser Asn
            275                 280                 285
Pro Ser Arg Asn Ala Ser Thr His Pro Leu Ser Gln Leu Leu Asn Leu
            290                 295                 300
Asp Leu Ser Tyr Asn Glu Ile Glu Leu Val Pro Ala Ser Phe Leu Glu
305                 310                 315                 320
His Leu Thr Ser Leu Arg Phe Leu Asn Leu Ser Arg Asn Cys Leu Arg
                325                 330                 335
Ser Phe Glu Ala Arg Gln Val Asp Ser Leu Pro Cys Leu Val Leu Leu
            340                 345                 350
Asp Leu Ser His Asn Val Leu Glu Ala Leu Glu Leu Gly Thr Lys Val
            355                 360                 365
Leu Gly Ser Leu Gln Thr Leu Leu Leu Gln Asp Asn Ala Leu Gln Glu
            370                 375                 380
Leu Pro Pro Tyr Thr Phe Ala Ser Leu Ala Ser Leu Gln Arg Leu Asn
385                 390                 395                 400
Leu Gln Gly Asn Gln Val Ser Pro Cys Gly Gly Pro Ala Glu Pro Gly
                405                 410                 415
Pro Pro Gly Cys Val Asp Phe Ser Gly Ile Pro Thr Leu His Val Leu
            420                 425                 430
Asn Met Ala Gly Asn Ser Met Gly Met Leu Arg Ala Gly Ser Phe Leu
            435                 440                 445
```

His Thr Pro Leu Thr Glu Leu Asp Leu Ser Thr Asn Pro Gly Leu Asp
    450                 455                 460

Val Ala Thr Gly Ala Leu Val Gly Leu Glu Ala Ser Leu Glu Val Leu
465                 470                 475                 480

Glu Leu Gln Gly Asn Gly Leu Thr Val Leu Arg Val Asp Leu Pro Cys
                485                 490                 495

Phe Leu Arg Leu Lys Arg Leu Asn Leu Ala Glu Asn Gln Leu Ser His
                500                 505                 510

Leu Pro Ala Trp Thr Arg Ala Val Ser Leu Glu Val Leu Asp Leu Arg
                515                 520                 525

Asn Asn Ser Phe Ser Leu Leu Pro Gly Asn Ala Met Gly Gly Leu Glu
530                 535                 540

Thr Ser Leu Arg Arg Leu Tyr Leu Gln Gly Asn Pro Leu Ser Cys Cys
545                 550                 555                 560

Gly Asn Gly Trp Leu Ala Ala Gln Leu His Gln Gly Arg Val Asp Val
                565                 570                 575

Asp Ala Thr Gln Asp Leu Ile Cys Arg Phe Gly Ser Gln Glu Glu Leu
                580                 585                 590

Ser Leu Ser Leu Val Arg Pro Glu Asp Cys Glu Lys Gly Gly Leu Lys
                595                 600                 605

Asn Val Asn
    610

<210> SEQ ID NO 42
<211> LENGTH: 692
<212> TYPE: PRT
<213> ORGANISM: Homo sapiens

<400> SEQUENCE: 42

Met Glu Leu Leu Pro Leu Trp Leu Cys Leu Gly Phe His Phe Leu Thr
1               5                   10                  15

Val Gly Trp Arg Asn Arg Ser Gly Thr Ala Thr Ala Ala Ser Gln Gly
                20                  25                  30

Val Cys Lys Leu Val Gly Gly Ala Ala Asp Cys Arg Gly Gln Ser Leu
                35                  40                  45

Ala Ser Val Pro Ser Ser Leu Pro Pro His Ala Arg Met Leu Thr Leu
50                  55                  60

Asp Ala Asn Pro Leu Lys Thr Leu Trp Asn His Ser Leu Gln Pro Tyr
65                  70                  75                  80

Pro Leu Leu Glu Ser Leu Ser Leu His Ser Cys His Leu Glu Arg Ile
                85                  90                  95

Ser Arg Gly Ala Phe Gln Glu Gln Gly His Leu Arg Ser Leu Val Leu
                100                 105                 110

Gly Asp Asn Cys Leu Ser Glu Asn Tyr Glu Glu Thr Ala Ala Ala Leu
                115                 120                 125

His Ala Leu Pro Gly Leu Arg Arg Leu Asp Leu Ser Gly Asn Ala Leu
                130                 135                 140

Thr Glu Asp Met Ala Ala Leu Met Leu Gln Asn Leu Ser Ser Leu Arg
145                 150                 155                 160

Ser Val Ser Leu Ala Gly Asn Thr Ile Met Arg Leu Asp Asp Ser Val
                165                 170                 175

Phe Glu Gly Leu Glu Arg Leu Arg Glu Leu Asp Leu Gln Arg Asn Tyr
                180                 185                 190

Ile Phe Glu Ile Glu Gly Gly Ala Phe Asp Gly Leu Ala Glu Leu Arg

```
              195                 200                 205
His Leu Asn Leu Ala Phe Asn Leu Pro Cys Ile Val Asp Phe Gly
    210                 215                 220

Leu Thr Arg Leu Arg Val Leu Asn Val Ser Tyr Asn Val Leu Glu Trp
225                 230                 235                 240

Phe Leu Ala Thr Gly Glu Ala Ala Phe Glu Leu Glu Thr Leu Asp
                    245                 250                 255

Leu Ser His Asn Gln Leu Leu Phe Phe Pro Leu Leu Pro Gln Tyr Ser
            260                 265                 270

Lys Leu Arg Thr Leu Leu Arg Asp Asn Asn Met Gly Phe Tyr Arg
        275                 280                 285

Asp Leu Tyr Asn Thr Ser Ser Pro Arg Glu Met Val Ala Gln Phe Leu
    290                 295                 300

Leu Val Asp Gly Asn Val Thr Asn Ile Thr Thr Val Ser Leu Trp Glu
305                 310                 315                 320

Glu Phe Ser Ser Ser Asp Leu Ala Asp Leu Arg Phe Leu Asp Met Ser
                    325                 330                 335

Gln Asn Gln Phe Gln Tyr Leu Pro Asp Gly Phe Leu Arg Lys Met Pro
            340                 345                 350

Ser Leu Ser His Leu Asn Leu His Gln Asn Cys Leu Met Thr Leu His
        355                 360                 365

Ile Arg Glu His Glu Pro Pro Gly Ala Leu Thr Glu Leu Asp Leu Ser
370                 375                 380

His Asn Gln Leu Ser Glu Leu His Leu Ala Pro Gly Leu Ala Ser Cys
385                 390                 395                 400

Leu Gly Ser Leu Arg Leu Phe Asn Leu Ser Ser Asn Gln Leu Leu Gly
                    405                 410                 415

Val Pro Pro Gly Leu Phe Ala Asn Ala Arg Asn Ile Thr Thr Leu Asp
            420                 425                 430

Met Ser His Asn Gln Ile Ser Leu Cys Pro Leu Pro Ala Ala Ser Asp
        435                 440                 445

Arg Val Gly Pro Pro Ser Cys Val Asp Phe Arg Asn Met Ala Ser Leu
450                 455                 460

Arg Ser Leu Ser Leu Glu Gly Cys Gly Leu Gly Ala Leu Pro Asp Cys
465                 470                 475                 480

Pro Phe Gln Gly Thr Ser Leu Thr Tyr Leu Asp Leu Ser Ser Asn Trp
                    485                 490                 495

Gly Val Leu Asn Gly Ser Leu Ala Pro Leu Gln Asp Val Ala Pro Met
            500                 505                 510

Leu Gln Val Leu Ser Leu Arg Asn Met Gly Leu His Ser Ser Phe Met
        515                 520                 525

Ala Leu Asp Phe Ser Gly Phe Gly Asn Leu Arg Asp Leu Asp Leu Ser
530                 535                 540

Gly Asn Cys Leu Thr Thr Phe Pro Arg Phe Gly Gly Ser Leu Ala Leu
545                 550                 555                 560

Glu Thr Leu Asp Leu Arg Arg Asn Ser Leu Thr Ala Leu Pro Gln Lys
                    565                 570                 575

Ala Val Ser Glu Gln Leu Ser Arg Gly Leu Arg Thr Ile Tyr Leu Ser
            580                 585                 590

Gln Asn Pro Tyr Asp Cys Cys Gly Val Asp Gly Trp Gly Ala Leu Gln
        595                 600                 605

His Gly Gln Thr Val Ala Asp Trp Ala Met Val Thr Cys Asn Leu Ser
610                 615                 620
```

```
Ser Lys Ile Ile Arg Val Thr Glu Leu Pro Gly Gly Val Pro Arg Asp
625                 630                 635                 640

Cys Lys Trp Glu Arg Leu Asp Leu Gly Leu Tyr Leu Val Leu Ile
            645                 650                 655

Leu Pro Ser Cys Leu Thr Leu Leu Val Ala Cys Thr Val Ile Val Leu
        660                 665                 670

Thr Phe Lys Lys Pro Leu Leu Gln Val Ile Lys Ser Arg Cys His Trp
        675                 680                 685

Ser Ser Val Tyr
    690

<210> SEQ ID NO 43
<211> LENGTH: 660
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Met Asp Met Arg Val Pro Ala Gln Leu Leu Gly Leu Leu Leu Leu Trp
1               5                   10                  15

Phe Ser Gly Val Leu Gly Trp Arg Asn Arg Ser Gly Thr Ala Thr Ala
            20                  25                  30

Ala Ser Gln Gly Val Cys Lys Leu Val Gly Gly Ala Ala Asp Cys Arg
        35                  40                  45

Gly Gln Ser Leu Ala Ser Val Pro Ser Ser Leu Pro Pro His Ala Arg
    50                  55                  60

Met Leu Thr Leu Asp Ala Asn Pro Leu Lys Thr Leu Trp Asn His Ser
65                  70                  75                  80

Leu Gln Pro Tyr Pro Leu Leu Glu Ser Leu Ser Leu His Ser Cys His
                85                  90                  95

Leu Glu Arg Ile Ser Arg Gly Ala Phe Gln Glu Gln Gly His Leu Arg
            100                 105                 110

Ser Leu Val Leu Gly Asp Asn Cys Leu Ser Glu Asn Tyr Glu Glu Thr
        115                 120                 125

Ala Ala Ala Leu His Ala Leu Pro Gly Leu Arg Arg Leu Asp Leu Ser
    130                 135                 140

Gly Asn Ala Leu Thr Glu Asp Met Ala Ala Leu Met Leu Gln Asn Leu
145                 150                 155                 160

Ser Ser Leu Arg Ser Val Ser Leu Ala Gly Asn Thr Ile Met Arg Leu
                165                 170                 175

Asp Asp Ser Val Phe Glu Gly Leu Glu Arg Leu Arg Glu Leu Asp Leu
            180                 185                 190

Gln Arg Asn Tyr Ile Phe Glu Ile Glu Gly Gly Ala Phe Asp Gly Leu
        195                 200                 205

Ala Glu Leu Arg His Leu Asn Leu Ala Phe Asn Asn Leu Pro Cys Ile
    210                 215                 220

Val Asp Phe Gly Leu Thr Arg Leu Arg Val Leu Asn Val Ser Tyr Asn
225                 230                 235                 240

Val Leu Glu Trp Phe Leu Ala Thr Gly Gly Glu Ala Ala Phe Glu Leu
                245                 250                 255

Glu Thr Leu Asp Leu Ser His Asn Gln Leu Leu Phe Phe Pro Leu Leu
            260                 265                 270
```

```
Pro Gln Tyr Ser Lys Leu Arg Thr Leu Leu Arg Asp Asn Asn Met
            275                 280                 285
Gly Phe Tyr Arg Asp Leu Tyr Asn Thr Ser Ser Pro Arg Glu Met Val
290                 295                 300
Ala Gln Phe Leu Leu Val Asp Gly Asn Val Thr Asn Ile Thr Thr Val
305                 310                 315                 320
Ser Leu Trp Glu Glu Phe Ser Ser Asp Leu Ala Asp Leu Arg Phe
                325                 330                 335
Leu Asp Met Ser Gln Asn Gln Phe Gln Tyr Leu Pro Asp Gly Phe Leu
            340                 345                 350
Arg Lys Met Pro Ser Leu Ser His Leu Asn Leu His Gln Asn Cys Leu
            355                 360                 365
Met Thr Leu His Ile Arg Glu His Glu Pro Pro Gly Ala Leu Thr Glu
370                 375                 380
Leu Asp Leu Ser His Asn Gln Leu Ser Glu Leu His Leu Ala Pro Gly
385                 390                 395                 400
Leu Ala Ser Cys Leu Gly Ser Leu Arg Leu Phe Asn Leu Ser Ser Asn
                405                 410                 415
Gln Leu Leu Gly Val Pro Pro Gly Leu Phe Ala Asn Ala Arg Asn Ile
            420                 425                 430
Thr Thr Leu Asp Met Ser His Asn Gln Ile Ser Leu Cys Pro Leu Pro
435                 440                 445
Ala Ala Ser Asp Arg Val Gly Pro Pro Ser Cys Val Asp Phe Arg Asn
450                 455                 460
Met Ala Ser Leu Arg Ser Leu Ser Leu Glu Gly Cys Gly Leu Gly Ala
465                 470                 475                 480
Leu Pro Asp Cys Pro Phe Gln Gly Thr Ser Leu Thr Tyr Leu Asp Leu
                485                 490                 495
Ser Ser Asn Trp Gly Val Leu Asn Gly Ser Leu Ala Pro Leu Gln Asp
            500                 505                 510
Val Ala Pro Met Leu Gln Val Leu Ser Leu Arg Asn Met Gly Leu His
            515                 520                 525
Ser Ser Phe Met Ala Leu Asp Phe Ser Gly Phe Gly Asn Leu Arg Asp
530                 535                 540
Leu Asp Leu Ser Gly Asn Cys Leu Thr Thr Phe Pro Arg Phe Gly Gly
545                 550                 555                 560
Ser Leu Ala Leu Glu Thr Leu Asp Leu Arg Arg Asn Ser Leu Thr Ala
                565                 570                 575
Leu Pro Gln Lys Ala Val Ser Glu Gln Leu Ser Arg Gly Leu Arg Thr
            580                 585                 590
Ile Tyr Leu Ser Gln Asn Pro Tyr Asp Cys Cys Gly Val Asp Gly Trp
            595                 600                 605
Gly Ala Leu Gln His Gly Gln Thr Val Ala Asp Trp Ala Met Val Thr
610                 615                 620
Cys Asn Leu Ser Ser Lys Ile Ile Arg Val Thr Glu Leu Pro Gly Gly
625                 630                 635                 640
Val Pro Arg Asp Cys Lys Trp Glu Arg Leu Asp Leu Gly Leu His His
                645                 650                 655
His His His His
        660

<210> SEQ ID NO 44
<211> LENGTH: 689
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44
```

| | | | | | | | | | | | | | | | |
|---|---|---|---|---|---|---|---|---|---|---|---|---|---|---|---|
| Met | Asp | Met | Arg | Val | Pro | Ala | Gln | Leu | Leu | Gly | Leu | Leu | Leu | Leu | Trp |
| 1 | | | | 5 | | | | | 10 | | | | | 15 | |
| Phe | Ser | Gly | Val | Leu | Gly | Trp | Arg | Asn | Arg | Ser | Gly | Thr | Ala | Thr | Ala |
| | | | 20 | | | | | 25 | | | | | 30 | | |
| Ala | Ser | Gln | Gly | Val | Cys | Lys | Leu | Val | Gly | Gly | Ala | Ala | Asp | Cys | Arg |
| | | 35 | | | | | 40 | | | | | 45 | | | |
| Gly | Gln | Ser | Leu | Ala | Ser | Val | Pro | Ser | Ser | Leu | Pro | Pro | His | Ala | Arg |
| | 50 | | | | | 55 | | | | | 60 | | | | |
| Met | Leu | Thr | Leu | Asp | Ala | Asn | Pro | Leu | Lys | Thr | Leu | Trp | Asn | His | Ser |
| 65 | | | | | 70 | | | | | 75 | | | | | 80 |
| Leu | Gln | Pro | Tyr | Pro | Leu | Leu | Glu | Ser | Leu | Ser | Leu | His | Ser | Cys | His |
| | | | | 85 | | | | | 90 | | | | | 95 | |
| Leu | Glu | Arg | Ile | Ser | Arg | Gly | Ala | Phe | Gln | Glu | Gln | Gly | His | Leu | Arg |
| | | | 100 | | | | | 105 | | | | | 110 | | |
| Ser | Leu | Val | Leu | Gly | Asp | Asn | Cys | Leu | Ser | Glu | Asn | Tyr | Glu | Glu | Thr |
| | | 115 | | | | | 120 | | | | | 125 | | | |
| Ala | Ala | Ala | Leu | His | Ala | Leu | Pro | Gly | Leu | Arg | Arg | Leu | Asp | Leu | Ser |
| | 130 | | | | | 135 | | | | | 140 | | | | |
| Gly | Asn | Ala | Leu | Thr | Glu | Asp | Met | Ala | Ala | Leu | Met | Leu | Gln | Asn | Leu |
| 145 | | | | | 150 | | | | | 155 | | | | | 160 |
| Ser | Ser | Leu | Arg | Ser | Val | Ser | Leu | Ala | Gly | Asn | Thr | Ile | Met | Arg | Leu |
| | | | | 165 | | | | | 170 | | | | | 175 | |
| Asp | Asp | Ser | Val | Phe | Glu | Gly | Leu | Glu | Arg | Leu | Arg | Glu | Leu | Asp | Leu |
| | | | 180 | | | | | 185 | | | | | 190 | | |
| Gln | Arg | Asn | Tyr | Ile | Phe | Glu | Ile | Glu | Gly | Gly | Ala | Phe | Asp | Gly | Leu |
| | | 195 | | | | | 200 | | | | | 205 | | | |
| Ala | Glu | Leu | Arg | His | Leu | Asn | Leu | Ala | Phe | Asn | Asn | Leu | Pro | Cys | Ile |
| | 210 | | | | | 215 | | | | | 220 | | | | |
| Val | Asp | Phe | Gly | Leu | Thr | Arg | Leu | Arg | Val | Leu | Asn | Val | Ser | Tyr | Asn |
| 225 | | | | | 230 | | | | | 235 | | | | | 240 |
| Val | Leu | Glu | Trp | Phe | Leu | Ala | Thr | Gly | Gly | Glu | Ala | Ala | Phe | Glu | Leu |
| | | | | 245 | | | | | 250 | | | | | 255 | |
| Glu | Thr | Leu | Asp | Leu | Ser | His | Asn | Gln | Leu | Leu | Phe | Phe | Pro | Leu | Leu |
| | | | 260 | | | | | 265 | | | | | 270 | | |
| Pro | Gln | Tyr | Ser | Lys | Leu | Arg | Thr | Leu | Leu | Leu | Arg | Asp | Asn | Asn | Met |
| | | 275 | | | | | 280 | | | | | 285 | | | |
| Gly | Phe | Tyr | Arg | Asp | Leu | Tyr | Asn | Thr | Ser | Ser | Pro | Arg | Glu | Met | Val |
| | 290 | | | | | 295 | | | | | 300 | | | | |
| Ala | Gln | Phe | Leu | Leu | Val | Asp | Gly | Asn | Val | Thr | Asn | Ile | Thr | Thr | Val |
| 305 | | | | | 310 | | | | | 315 | | | | | 320 |
| Ser | Leu | Trp | Glu | Glu | Phe | Ser | Ser | Asp | Leu | Ala | Asp | Leu | Arg | Phe | |
| | | | | 325 | | | | | 330 | | | | | 335 | |
| Leu | Asp | Met | Ser | Gln | Asn | Gln | Phe | Gln | Tyr | Leu | Pro | Asp | Gly | Phe | Leu |
| | | | 340 | | | | | 345 | | | | | 350 | | |
| Arg | Lys | Met | Pro | Ser | Leu | Ser | His | Leu | Asn | Leu | His | Gln | Asn | Cys | Leu |
| | | 355 | | | | | 360 | | | | | 365 | | | |
| Met | Thr | Leu | His | Ile | Arg | Glu | His | Glu | Pro | Pro | Gly | Ala | Leu | Thr | Glu |
| | 370 | | | | | 375 | | | | | 380 | | | | |

```
Leu Asp Leu Ser His Asn Gln Leu Ser Glu Leu His Leu Ala Pro Gly
385                 390                 395                 400

Leu Ala Ser Cys Leu Gly Ser Leu Arg Leu Phe Asn Leu Ser Ser Asn
            405                 410                 415

Gln Leu Leu Gly Val Pro Pro Gly Leu Phe Ala Asn Ala Arg Asn Ile
        420                 425                 430

Thr Thr Leu Asp Met Ser His Asn Gln Ile Ser Leu Cys Pro Leu Pro
            435                 440                 445

Ala Ala Ser Asp Arg Val Gly Pro Pro Ser Cys Val Asp Phe Arg Asn
        450                 455                 460

Met Ala Ser Leu Arg Ser Leu Ser Leu Glu Gly Cys Gly Leu Gly Ala
465                 470                 475                 480

Leu Pro Asp Cys Pro Phe Gln Gly Thr Ser Leu Thr Tyr Leu Asp Leu
                485                 490                 495

Ser Ser Asn Trp Gly Val Leu Asn Gly Ser Leu Ala Pro Leu Gln Asp
            500                 505                 510

Val Ala Pro Met Leu Gln Val Leu Ser Leu Arg Asn Met Gly Leu His
        515                 520                 525

Ser Ser Phe Met Ala Leu Asp Phe Ser Gly Phe Gly Asn Leu Arg Asp
        530                 535                 540

Leu Asp Leu Ser Gly Asn Cys Leu Thr Thr Phe Pro Arg Phe Gly Gly
545                 550                 555                 560

Ser Leu Ala Leu Glu Thr Leu Asp Leu Arg Arg Asn Ser Leu Thr Ala
                565                 570                 575

Leu Pro Gln Lys Ala Val Ser Glu Gln Leu Ser Arg Gly Leu Arg Thr
            580                 585                 590

Ile Tyr Leu Ser Gln Asn Pro Tyr Asp Cys Cys Gly Val Asp Gly Trp
            595                 600                 605

Gly Ala Leu Gln His Gly Gln Thr Val Ala Asp Trp Ala Met Val Thr
        610                 615                 620

Cys Asn Leu Ser Ser Lys Ile Ile Arg Val Thr Glu Leu Pro Gly Gly
625                 630                 635                 640

Val Pro Arg Asp Cys Lys Trp Glu Arg Leu Asp Leu Gly Leu Leu Ile
                645                 650                 655

Ile Ile Leu Thr Phe Ile Leu Val Ser Ala Ile Leu Leu Thr Thr Leu
            660                 665                 670

Ala Ala Cys Cys Cys Val Arg Arg Gln Lys Phe Asn Gln Gln Tyr Lys
        675                 680                 685

Ala

<210> SEQ ID NO 45
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Cys Pro Pro Cys Pro
1               5

<210> SEQ ID NO 46
<211> LENGTH: 13
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ala Ser Thr Lys Gly Pro Ser Val Phe Pro Leu Ala Pro
1               5                   10

<210> SEQ ID NO 47
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Ser Thr Lys Gly Pro
1               5

<210> SEQ ID NO 48
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Thr Val Ala Ala Pro Ser Val Phe Ile Phe Pro Pro
1               5                   10

<210> SEQ ID NO 49
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Thr Val Ala Ala Pro
1               5

<210> SEQ ID NO 50
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ala Lys Thr Thr Pro Lys Leu Glu Glu Gly Glu Phe Ser Glu Ala Arg
1               5                   10                  15

<210> SEQ ID NO 51
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 51

Ala Lys Thr Thr Pro Lys Leu Glu Glu Gly Glu Phe Ser Glu Ala Arg
1               5                   10                  15
Val

<210> SEQ ID NO 52
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ala Lys Thr Thr Pro Lys Leu Gly Gly
1               5

<210> SEQ ID NO 53
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ser Ala Lys Thr Thr Pro Lys Leu Gly Gly
1               5                   10

<210> SEQ ID NO 54
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ser Ala Lys Thr Thr Pro
1               5

<210> SEQ ID NO 55
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Arg Ala Asp Ala Ala Pro
1               5

<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 56

Arg Ala Asp Ala Ala Pro Thr Val Ser
1               5

<210> SEQ ID NO 57
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Arg Ala Asp Ala Ala Ala Ala Gly Gly Pro Gly Ser
1               5                   10

<210> SEQ ID NO 58
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 59
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Ser Ala Lys Thr Thr Pro Lys Leu Glu Glu Gly Glu Phe Ser Glu Ala
1               5                   10                  15

Arg Val

<210> SEQ ID NO 60
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ala Asp Ala Ala Pro
1               5

<210> SEQ ID NO 61
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 61

Ala Asp Ala Ala Pro Thr Val Ser Ile Phe Pro Pro
1               5                   10

<210> SEQ ID NO 62
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gln Pro Lys Ala Ala Pro
1               5

<210> SEQ ID NO 63
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gln Pro Lys Ala Ala Pro Ser Val Thr Leu Phe Pro Pro
1               5                   10

<210> SEQ ID NO 64
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ala Lys Thr Thr Pro Pro
1               5

<210> SEQ ID NO 65
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ala Lys Thr Thr Pro Pro Ser Val Thr Pro Leu Ala Pro
1               5                   10

<210> SEQ ID NO 66
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Ala Lys Thr Thr Ala Pro
```

```
<210> SEQ ID NO 67
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ala Lys Thr Thr Ala Pro Ser Val Tyr Pro Leu Ala Pro
1               5                   10

<210> SEQ ID NO 68
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Gly Gly Gly Gly Ser Gly Gly Gly Gly Ser Gly Gly Gly Gly Ser
1               5                   10                  15

<210> SEQ ID NO 69
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Glu Asn Lys Val Glu Tyr Ala Pro Ala Leu Met Ala Leu Ser
1               5                   10                  15

<210> SEQ ID NO 70
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gly Pro Ala Lys Glu Leu Thr Pro Leu Lys Glu Ala Lys Val Ser
1               5                   10                  15

<210> SEQ ID NO 71
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gly His Glu Ala Ala Ala Val Met Gln Val Gln Tyr Pro Ala Ser
1               5                   10                  15

<210> SEQ ID NO 72
```

<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 72

Thr Val Ala Ala Pro Ser Val Phe Ile Phe Pro Pro Thr Val Ala Ala
1               5                   10                  15

Pro Ser Val Phe Ile Phe Pro Pro
            20

<210> SEQ ID NO 73
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 73

Ala Ser Thr Lys Gly Pro Ser Val Phe Pro Leu Ala Pro Ala Ser Thr
1               5                   10                  15

Lys Gly Pro Ser Val Phe Pro Leu Ala Pro
            20                  25

<210> SEQ ID NO 74
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 74

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asn Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Asp Tyr Tyr Tyr Gly Met Asp Val Trp Gly Gln Gly
            100                 105                 110

Thr Leu Val Thr Val Ser Ser
        115

<210> SEQ ID NO 75
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 75

Gln Ser Gly Leu Thr Gln Pro Ala Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Ala Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Leu Thr Val Leu
            100                 105                 110

<210> SEQ ID NO 76
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Ile His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Val Gly Leu Gly Arg Phe Asp Pro Trp Gly Gln Gly Thr Leu
            100                 105                 110

Val Thr Val Ser Ser
        115

<210> SEQ ID NO 77
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Gln Ser Glu Leu Thr Gln Ser Pro Ser Ala Ser Gly Thr Pro Gly Gln
1               5                   10                  15

Arg Val Thr Ile Ser Cys Ser Gly Ser Asn Ser Asn Ile Gly Thr Asn
            20                  25                  30

Thr Val Asn Trp Tyr Gln Gln Phe Pro Gly Thr Ala Pro Lys Leu Leu

```
                35                  40                  45
Ile Tyr Tyr Asn Asp Gln Arg Pro Ser Gly Val Ser Asp Arg Phe Ser
 50                  55                  60

Gly Ser Arg Ser Gly Thr Ser Ala Ser Leu Ala Ile Asn Gly Leu Gln
 65                  70                  75                  80

Ser Glu Asp Glu Ala Asp Tyr Tyr Cys Ala Thr Trp Asp Asp Ser Leu
                 85                  90                  95

Ser Gly Val Val Phe Gly Gly Gly Thr Lys Leu Thr Val Leu
                100                 105                 110

<210> SEQ ID NO 78
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
                 35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Val Gly Leu Gly Arg Phe Asp Pro Trp Gly Gln Gly Thr Leu
                100                 105                 110

Val Thr Val Ser Ser
        115

<210> SEQ ID NO 79
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Gln Ser Glu Leu Thr Gln Ser Pro Ser Ala Ser Gly Thr Pro Gly Gln
 1               5                  10                  15

Arg Val Thr Ile Ser Cys Ser Gly Ser Asn Ser Asn Ile Gly Thr Asn
                 20                  25                  30

Thr Val Asn Trp Tyr Gln Gln Phe Pro Gly Thr Ala Pro Lys Leu Leu
                 35                  40                  45

Ile Tyr Tyr Asn Asp Gln Arg Pro Ser Gly Val Ser Asp Arg Phe Ser
 50                  55                  60

Gly Ser Arg Ser Gly Thr Ser Ala Ser Leu Ala Ile Asn Gly Leu Gln
 65                  70                  75                  80

Ser Glu Asp Glu Ala Asp Tyr Tyr Cys Ala Thr Trp Asp Asp Ser Leu
                 85                  90                  95
```

Ser Gly Val Val Phe Gly Gly Gly Thr Lys Leu Thr Val Leu
            100                 105                 110

<210> SEQ ID NO 80
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Gln Val Gln Leu Gln Gln Ser Gly Pro Gly Leu Val Arg Pro Ser Gln
1               5                   10                  15

Thr Leu Ser Leu Thr Cys Ala Ile Ser Gly Asp Ser Val Ser Ser Asn
            20                  25                  30

Gly Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Lys Leu Thr Ser Val Thr Pro Glu Asp Thr Ala Val
                85                  90                  95

Tyr Tyr Cys Ala Arg Gly Glu Asp Trp Gly Tyr Ala Phe Asp Ile Trp
            100                 105                 110

Gly Gln Gly Thr Leu Val Thr Val Ser Ser
            115                 120

<210> SEQ ID NO 81
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Asp Asp Lys Gln Arg Pro Ser Gly Ile Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Val Val Phe Gly Gly Gly Thr Lys Val Thr Val Leu
            100                 105                 110

<210> SEQ ID NO 82
<211> LENGTH: 118
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asp Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asn Pro Tyr Tyr Tyr Met Asp Val Trp Gly Gln Gly Thr
                100                 105                 110

Thr Val Thr Val Ser Ser
            115

<210> SEQ ID NO 83
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Gln Ser Glu Leu Thr Gln Ala Pro Ser Val Ser Val Ala Pro Gly Gln
1               5                   10                  15

Thr Ala Arg Ile Thr Cys Gly Gly Asn Asn Ile Gly Gly Arg Ser Lys
                20                  25                  30

Ser Val His Trp Tyr Gln His Lys Leu Gly Gln Ala Pro Val Leu Ile
            35                  40                  45

Val Tyr Asp Asn Thr Asp Arg Pro Ser Gly Ile Ser Glu Arg Phe Ser
        50                  55                  60

Gly Ser Ser Ser Val Asn Ala Ala Thr Leu Thr Ile Thr Thr Ala Glu
65                  70                  75                  80

Ala Gly Asp Glu Gly Asp Tyr Tyr Cys Gln Val Trp Asp Val Ser Thr
                85                  90                  95

Asp His Val Val Phe Gly Gly Gly Thr Lys Val Thr Val Leu
                100                 105                 110

<210> SEQ ID NO 84
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
```

```
            20                  25                  30
Tyr Met His Trp Val Arg Gln Ala Pro Gly Gln Gly Leu Glu Trp Met
        35                  40                  45

Gly Trp Ile Asn Pro Asn Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Asn Arg Arg Arg Gly Ser Ala Phe Asp Ile Trp Gly Gln Gly Thr
            100                 105                 110

Leu Val Thr Val Ser Ser
            115

<210> SEQ ID NO 85
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asp
                85                  90                  95

Asn Tyr His Val Ile Phe Gly Gly Gly Thr Lys Leu Thr Val Leu
            100                 105                 110

<210> SEQ ID NO 86
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys Glu Thr Gly Tyr Gly Phe Gly Leu Phe Trp Gly Gln Gly Thr
            100                 105                 110

Met Val Thr Val Ser Ser
        115

<210> SEQ ID NO 87
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Asn Phe Met Leu Thr Gln Pro His Ser Val Ser Glu Ser Pro Gly Arg
1               5                   10                  15

Thr Leu Thr Ile Pro Cys Phe Arg Ser Ser Gly Asn Ile Gly Asp Ser
            20                  25                  30

Tyr Val His Trp Tyr Gln Gln Arg Pro Gly Ser Ala Pro Thr Thr Val
        35                  40                  45

Ile Tyr Arg Asp Ser Gln Arg Pro Ser Gly Val Pro Asp Arg Phe Ser
50                  55                  60

Gly Ser Ile Asp Phe Ser Ser Asn Ser Ala Ser Leu Thr Ile Ser Gly
65                  70                  75                  80

Leu Lys Thr Glu Asp Glu Ala Ala Tyr Tyr Cys Gln Ser Tyr Asp Arg
                85                  90                  95

Ser Asn Gln Trp Val Phe Gly Gly Gly Thr Lys Leu Thr Val Leu
            100                 105                 110

<210> SEQ ID NO 88
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Pro Ile His Trp Val Arg Gln Ala Pro Gly Lys Gly Leu Glu Trp Val
        35                  40                  45

Ala Val Met Ser Tyr Asp Gly Ile Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ile Ala Ala Arg Arg Gly Gly Phe Asp Tyr Trp Gly
            100                 105                 110

Gln Gly Thr Leu Val Thr Val Ser Ser
        115                 120

<210> SEQ ID NO 89
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Asn Phe Met Leu Thr Gln Pro His Ser Val Ser Glu Ser Pro Gly Lys
1               5                   10                  15

Thr Val Thr Ile Ser Cys Thr Arg Ser Ser Gly Asn Ile Asp Asn Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asp Asn Gln Gly Val Val Phe Gly Gly Gly Thr Lys Leu Thr Val Leu
            100                 105                 110

<210> SEQ ID NO 90
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asp Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Gly Leu Arg Ser Asp Asp Thr Ala Val Tyr Tyr Cys
                85                  90                  95

Ala Arg Ala Pro Leu Gly Asn Phe Asp Ser Trp Gly Gln Gly Thr Leu
            100                 105                 110

Val Thr Val Ser Ser
        115

<210> SEQ ID NO 91
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

<400> SEQUENCE: 91

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Val Val Phe Gly Gly Gly Thr Lys Val Thr Val Leu
            100                 105                 110

<210> SEQ ID NO 92
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Pro Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Glu Gly Gly Tyr Tyr Trp Tyr Tyr Tyr Gly
            100                 105                 110

Met Asp Val Trp Gly Gln Gly Thr Leu Val Thr Val Ser Ser
        115                 120                 125

<210> SEQ ID NO 93
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

-continued

Ile Tyr Glu Asp Asn Gln Arg Pro Ser Gly Val Pro Asp Arg Phe Ser
            50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Ile Val Val Phe Gly Gly Gly Thr Gln Leu Thr Val Leu
            100                 105                 110

<210> SEQ ID NO 94
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Phe Thr Phe Asn Asn Tyr Pro Ile His
1               5

<210> SEQ ID NO 95
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Val Met Ser Tyr Asp Gly Ile Asn Lys Tyr Tyr Ala Asp Ser Val Lys
1               5                   10                  15

Gly

<210> SEQ ID NO 96
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ala Arg Pro Arg Ile Ala Ala Arg Arg Gly Gly Phe Asp Tyr
1               5                   10

<210> SEQ ID NO 97
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Thr Arg Ser Ser Gly Asn Ile Asp Asn Asn Tyr Val Gln
1               5                   10

<210> SEQ ID NO 98
<211> LENGTH: 7
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Glu Asp Asn Gln Arg Pro Ser
1               5

<210> SEQ ID NO 99
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gln Ser Tyr Asp Ser Asp Asn Gln Gly Val Val
1               5                   10
```